US012527216B2

(12) United States Patent
So et al.

(10) Patent No.: US 12,527,216 B2
(45) Date of Patent: Jan. 13, 2026

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Ki Ho So, Cheonan-si (KR); Sang Don Choi, Cheonan-si (KR); Sun Hee Lee, Cheonan-si (KR); Won Sam Kim, Cheonan-si (KR); Soung Yun Mun, Cheonan-si (KR); Jung Wook Lee, Cheonan-si (KR); Hyung Dong Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 1007 days.

(21) Appl. No.: 17/457,510

(22) Filed: Dec. 3, 2021

(65) Prior Publication Data

US 2022/0278284 A1 Sep. 1, 2022

(30) Foreign Application Priority Data

Dec. 29, 2020 (KR) ........................ 10-2020-0186342
Feb. 9, 2021 (KR) ........................ 10-2021-0018564

(51) Int. Cl.

| | |
|---|---|
| ***C07D 409/12*** | (2006.01) |
| ***C07D 307/91*** | (2006.01) |
| ***C07D 333/76*** | (2006.01) |
| ***C07D 409/14*** | (2006.01) |
| ***C09K 11/06*** | (2006.01) |

(Continued)

(52) U.S. Cl.

CPC ......... *H10K 85/636* (2023.02); *C07D 307/91* (2013.01); *C07D 333/76* (2013.01); *C07D 409/12* (2013.01); *C07D 409/14* (2013.01); *C09K 11/06* (2013.01); *H10K 85/633* (2023.02); *C07B 2200/05* (2013.01); *C09K 2211/1022* (2013.01); *H10K 50/13* (2023.02); *H10K 85/615* (2023.02); *H10K 85/626* (2023.02); *H10K 85/6574* (2023.02); *H10K 85/6576* (2023.02)

(58) Field of Classification Search

None

See application file for complete search history.

(56) References Cited

U.S. PATENT DOCUMENTS

2020/0176685 A1* 6/2020 Kang .................. C07D 307/91
2021/0300888 A1* 9/2021 Park .................. H10K 85/6572

(Continued)

FOREIGN PATENT DOCUMENTS

CN 106207000 A 12/2016
CN 110669025 A * 1/2020 ............ C07D 13/38

(Continued)

OTHER PUBLICATIONS

Machine translation of CN-110669025, translation generated Oct. 2024, 12 pages. (Year: 2024).*

*Primary Examiner* — Robert S Loewe

(74) *Attorney, Agent, or Firm* — Vorys, Sater, Seymour and Pease LLP; Mih Suhn Koh

(57) ABSTRACT

Provided herein are an organic electronic compound capable of improving luminous efficiency, stability and lifespan of an electronic device, an organic electronic element employing the same, and an electronic device thereof.

17 Claims, 4 Drawing Sheets

(51) Int. Cl.
*H10K 85/60* (2023.01)
*H10K 50/13* (2023.01)

(56) References Cited

U.S. PATENT DOCUMENTS

| | | | | |
|---|---|---|---|---|
| 2021/0380568 | A1* | 12/2021 | Kim | H10K 85/615 |
| 2022/0246856 | A1* | 8/2022 | Park | H10K 85/615 |
| 2023/0048456 | A1* | 2/2023 | Kwon | H10K 85/615 |

FOREIGN PATENT DOCUMENTS

| | | | | |
|---|---|---|---|---|
| CN | 111354873 A | 6/2020 | | |
| CN | 111511734 A | 8/2020 | | |
| CN | 111747938 A | 10/2020 | | |
| CN | 112209921 A | 1/2021 | | |
| CN | 113321589 A | 8/2021 | | |
| CN | 114824144 A | 7/2022 | | |
| CN | 115943749 A | 4/2023 | | |
| CN | 116134032 A | 5/2023 | | |
| CN | 116583507 A | 8/2023 | | |
| KR | 10-2018-0031874 A | 3/2018 | | |
| KR | 10-2019-0098020 A | 8/2019 | | |
| WO | 2015/041492 A1 | 3/2015 | | |
| WO | WO-2018056649 A1 * | 3/2018 | | C07D 307/91 |
| WO | WO-2020085797 A1 * | 4/2020 | | C07D 333/76 |

* cited by examiner

| Comparative compound C | Compound P-55 of the present invention |
|---|---|
|  |  |

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

Lifespan and efficiency are the most problematic in organic electroluminescent device, and as displays become larger, these problems of efficiency and lifespan must be solved. Efficiency, lifespan, and driving voltage are related to each other, and when the efficiency is increased, the driving voltage is relatively decreased, and as the driving voltage is decreased, crystallization of the organic material due to Joule heating generated during driving decreases, and as a result, the lifespan tends to increase.

However, the efficiency cannot be maximized simply by improving the organic material layer. This is because, when the energy level and T1 value between each organic material layer, and the intrinsic properties of the material (mobility, interfacial properties, etc.) are optimally combined, a long lifespan and high efficiency can be achieved at the same time.

Also, in order to solve the problem of light emission in the hole transport layer in recent organic electroluminescent devices, an emitting-auxiliary layer must exist between the hole transport layer and the emitting layer, and it is time to develop different emitting-auxiliary layers according to each emitting layer (R, G, B).

In general, electrons are transferred from the electron transport layer to the emitting layer, and holes are transferred from the hole transport layer to the emitting layer, and excitons are generated by recombination.

However, since the material used for the hole transport layer should have a low HOMO value, most have a low T1 value. As a result, excitons generated in the emitting layer are transferred to the hole transport layer, resulting in charge unbalance in the emitting layer to emit light at the hole transport layer interface.

When light is emitted at the hole transport layer interface, the color purity and efficiency of the organic electronic element are lowered, and the lifespan is shortened. Therefore, it is urgently required to develop an emitting-auxiliary layer having a high T1 value and having a HOMO level between the HOMO energy level of the hole transport layer and the HOMO energy level of the emitting layer.

Furthermore, it is necessary to develop a hole injection layer material that delays the penetration and diffusion of metal oxides from the anode electrode (ITO) into the organic layer, which is one of the causes of shortening the lifespan of organic electronic element, and that has stable characteristics, that is, a high glass transition temperature, even against Joule heating generated during device driving. The low glass transition temperature of the hole transport layer material has a characteristic of lowering the uniformity of the thin film surface during device driving, which is reported to have a significant effect on device lifespan. Moreover, OLED devices are mainly formed by a deposition method, and it is necessary to develop a material that can withstand a long time during deposition, that is, a material with strong heat resistance.

In other words, in order to fully exhibit the excellent characteristics of an organic electronic element, the material constituting the organic material layer in the device, such as a hole injection material, a hole transport material, a light emitting material, an electron transport material, an electron injection material, emitting auxiliary layer material, etc., is supported by a stable and efficient material. should take precedence, but the development of a stable and efficient organic material layer material for an organic electronic device has not yet been sufficiently made. Therefore, the development of new materials is continuously required.

DETAILED DESCRIPTION OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the device can be significantly improved.

Accordingly, an object of the present invention is to provide a novel compound, an organic electronic element using the same, and an electronic device thereof.

Technical Solution

The present invention provides a compound represented by Formula 1.

Formula 1

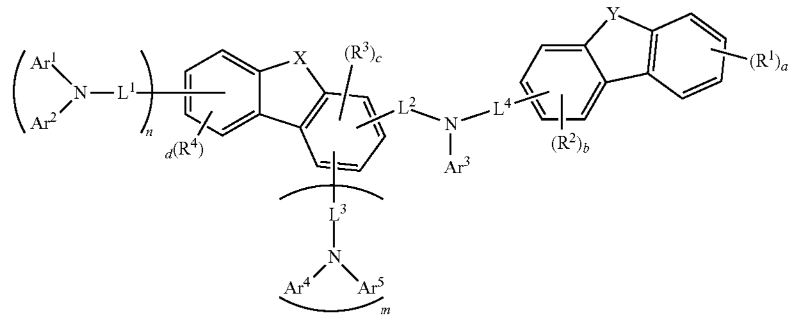

In another aspect, the present invention provides an organic electronic element comprising the compound represented by Formula 1 and an electronic device thereof.

Effects of the Invention

By using the compound according to the present invention, high luminous efficiency, low driving voltage and high heat resistance of the device can be achieved, and color purity and lifespan of the device can be greatly improved.

Figure 1:
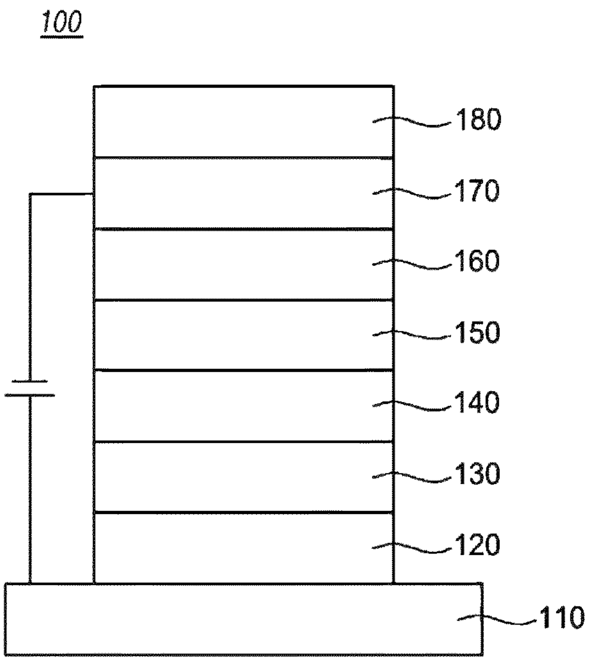
FIG. 1 to FIG. 3 are each an exemplary view of an organic electroluminescent device according to the present invention.

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting-auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being “connected”, “coupled”, or “connected” to another component, the component may be directly connected or connected to the other component, but another component may be “connected “,” coupled” or “connected” between each component.

As used in the specification and the accompanying claims, unless otherwise stated, the following is the meaning of the term as follows.

Unless otherwise stated, the term “halo” or “halogen”, as used herein, includes fluorine, bromine, chlorine, or iodine.

Unless otherwise stated, the term “alkyl” or “alkyl group”, as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term “alkenyl” or “alkynyl”, as used herein, has double or triple bonds of 2 to 60 carbon atoms, but is not limited thereto, and includes a linear or a branched chain group.

Unless otherwise stated, the term “cycloalkyl”, as used herein, means alkyl forming a ring having 3 to 60 carbon atoms, but is not limited thereto.

Unless otherwise stated, the term “alkoxyl group”, “alkoxy group” or “alkyloxy group”, as used herein, means an oxygen radical attached to an alkyl group, but is not limited thereto, and has 1 to 60 carbon atoms.

Unless otherwise stated, the term “aryloxyl group” or “aryloxy group”, as used herein, means an oxygen radical attached to an aryl group, but is not limited thereto, and has 6 to 60 carbon atoms.

The terms “aryl group” and “arylene group” used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix “aryl” or “ar” means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

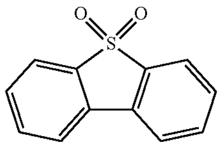 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

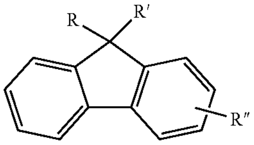

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

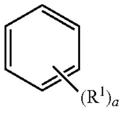

Here, when a is an integer of zero, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

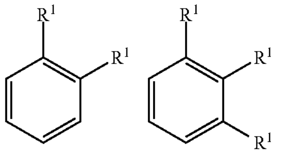

(a=2) (a=3)

Hereinafter, a compound according to an aspect of the present invention and an organic electronic element including the same will be described.

The present invention provides a compound represented by Formula 1.

Formula 1

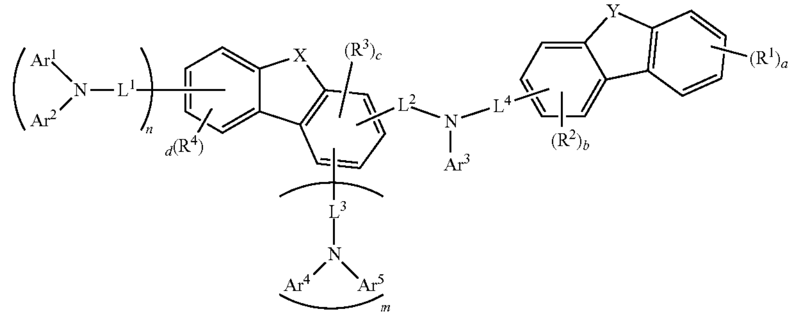

wherein, each symbol may be defined as follows.

1) $R^1$, $R^2$, $R^3$ and $R^4$ are the same or different from each other, and are each independently selected from the group consisting of a hydrogen; deuterium; halogen; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; or an adjacent plurality of $R^1$s, or a plurality of $R^2$s, or a plurality of $R^3$s, or a plurality of $R^4$s may be bonded to each other to form a ring.

When $R^1$, $R^2$, $R^3$ and $R^4$ are an aryl group, it may be preferably a $C_6$-$C_{30}$ aryl group, and more preferably a $C_6$-$C_{25}$ aryl group, for example, it may be phenyl, biphenyl, naphthyl, terphenyl, etc.

When $R^1$, $R^2$, $R^3$ and $R^4$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-blindole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

When $R^1$, $R^2$, $R^3$ and $R^4$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^1$, $R^2$, $R^3$ and $R^4$ are an alkyl group, it may be preferably a $C_1$-$C_{30}$ alkyl group, and more preferably a $C_1$-$C_{24}$ alkyl group.

When $R^1$, $R^2$, $R^3$ and $R^4$ are an alkoxy group, it may be preferably a $C_1$-$C_{24}$ alkoxy group.

When $R^1$, $R^2$, $R^3$ and $R^4$ are an aryloxy group, it may be preferably a $C_1$-$C_{24}$ aryloxy group.

2) X and Y are independently of each other are O or S,

3) $L^1$, $L^2$ and $L^3$ are each independently selected from the group consisting of single bond; a $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

4) $L^4$ is selected from the group consisting of a $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

Wherein $L^1$, $L^2$, $L^3$ and $L^4$ are an arylene group, it may be preferably a $C_6$-$C_{30}$ arylene group, more preferably a $C_6$-$C_{24}$ arylene group, for example, phenylene, biphenyl, naphthalene, terphenyl, etc.

Wherein $L^1$, $L^2$, $L^3$ and $L^4$ are a heterocyclic group, it may be preferably a $C_2$~$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

Wherein $L^1$, $L^2$, $L^3$ and $L^4$ are fused ring groups, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

5) $Ar^1$, $Ar^2$, $Ar^3$, $Ar^4$ and $Ar^5$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; an $C_2$~$C_{30}$ alkenyl group; a $C_2$-$C_{20}$ alkynyl group; a $C_1$-$C_{30}$ alkoxy group; a $C_6$-$C_{30}$ aryloxy group;

Wherein $Ar^1$, $Ar^2$, $Ar^3$, $Ar^4$ and $Ar^5$ are an aryl group, they may be preferably a $C_6$-$C_{30}$ aryl group, most preferably a $C_6$-$C_{25}$ aryl group, exemplarily, they may be phenyl, biphenyl, naphthyl, terphenyl, and the like.

Wherein $Ar^1$, $Ar^2$, $Ar^3$, $Ar^4$ and $Ar^5$ are a heterocyclic group, they may be preferably a $C_2$-$C_{30}$ heterocyclic group, and more preferably a $C_2$-$C_{24}$ heterocyclic group, for example, they may be pyrazine, thiophene, pyridine, pyrimidoindole, 5-phenyl-5H-pyrimido[5,4-b]indole, quinazoline, benzoquinazoline, carbazole, dibenzoquinazole, dibenzofuran, dibenzothiophene, benzothienopyrimidine, benzofuropyrimidine, phenothiazine, phenylphenothiazine, etc.

Wherein $Ar^1$, $Ar^2$, $Ar^3$, $Ar^4$ and $Ar^5$ are a fused ring group, they may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

Wherein $Ar^1$, $Ar^2$, $Ar^3$, Art and $Ar^5$ are an alkyl group, they may be preferably an $C_1$~$C_{30}$ alkyl group, more preferably an $C_1$~$C_{24}$ alkyl group.

Wherein $Ar^1$, $Ar^2$, $Ar^3$, $Ar^4$ and $Ar^5$ are an alkoxy group, they may be preferably a $C_1$-$C_{24}$ alkoxy group.

Wherein $Ar^1$, $Ar^2$, $Ar^3$, $Ar^4$ and $Ar^5$ are an aryloxy group, they may be preferably a $C_1$-$C_{24}$ aryloxy group.

6) a and d are each independently an integer of 0 to 4, b and c are each independently an integer of 0 to 3, m and n are each independently 0 or 1, provided that $m+n \geq 1$;

7) provided that the compound of Formula 1 excludes is a compound represented by Formula 7:

Formula 7

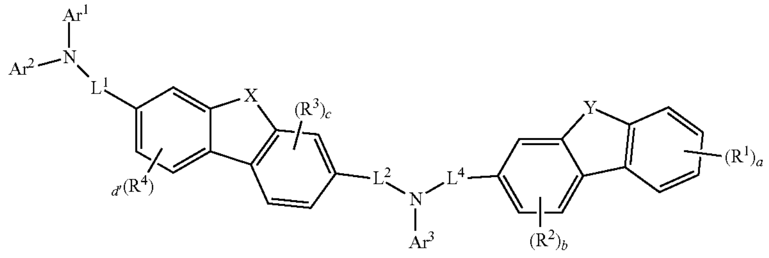

8) wherein $R^1$, $R^2$, $R^3$, $R^4$, X, Y, $L^1$, $L^2$, $L^4$, $Ar^1$, $Ar^2$, $Ar^3$, a, b and c are the same as defined in Formula 1, d' is an integer from 0 to 3, 9) wherein the aryl group, arylene group, heterocyclic group, fluorenyl group, fluorenylene group, aliphatic ring group, fused ring group, alkyl group, alkenyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the present invention provides a compound wherein $L^1$, $L^2$, $L^3$ and $L^4$ are represented by any one of Formulas b-1 to b-13.

Formula b-1

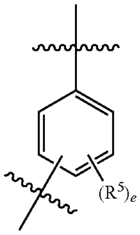

Formula b-2

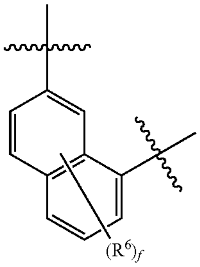

-continued

Formula b-3

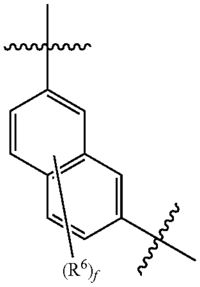

Formula b-4

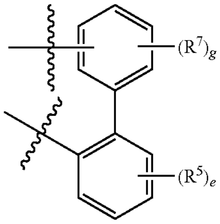

Formula b-5

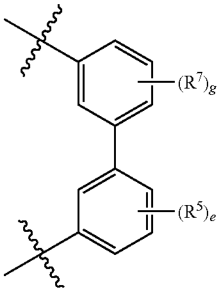

Formula b-6

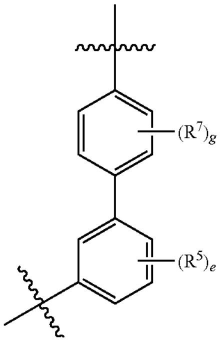

-continued

Formula b-7

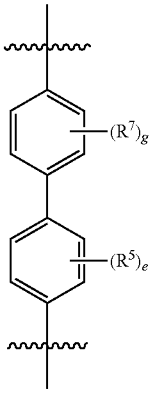

Formula b-8

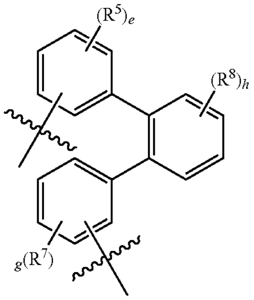

Formula b-9

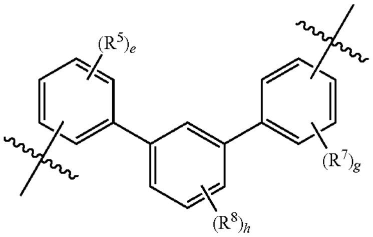

Formula b-10

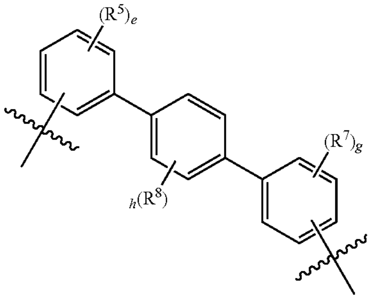

-continued

Formula b-11

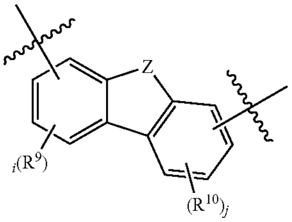

Formula b-12

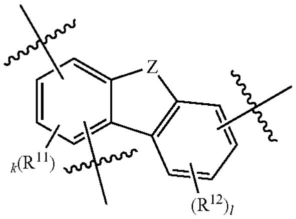

Formula b-13

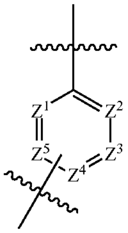

{wherein

1) Z is O, S, $C(R^{13})(R^{14})$ or $N-L^5-Ar^6$,

2) $Z^1$, $Z^2$, $z^3$, $Z^4$ and $Z^5$ are each independently N or $C(R^{15})$, provided that at least one of $Z^1$, $Z^2$, $Z^3$, $Z^4$ and $Z^5$ is $C(R^{15})$, at least one is N;

3) $R^5$, $R^6$, $R^7$, $R^8$, $R^9$, $R^{10}$, $R^{11}$, $R^{12}$, $R^{13}$, $R^{14}$ and $R^{15}$ are the same as the definition of $R^1$ in Formula 1, or adjacent groups may combine with each other to form a ring, 4) e, g, h and l are each independently an integer of 0 to 4, f is an integer of 0 to 6, i and j are each independently an integer of 0 to 3, k is an integer of 0 to 2, 5) $Ar^6$ is the same as the definition of $Ar^1$ in Formula 1, 6) $L^6$ is the same as the definition of $L^1$ in Formula 1, 7) un indicates the binding position.}

Also, the compound represented by Formula 1 is represented by any one of Formulas 1-1 to 1-3

Formula 1-1

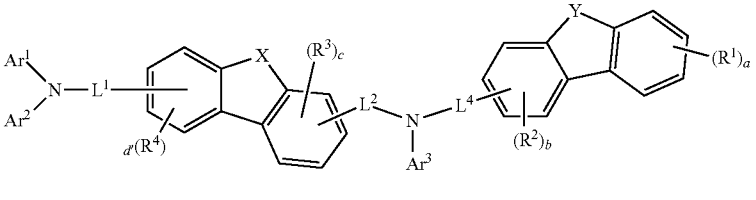

-continued
Formula 1-2
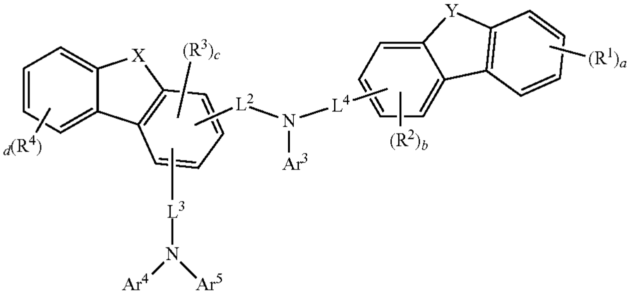
Formula 1-3
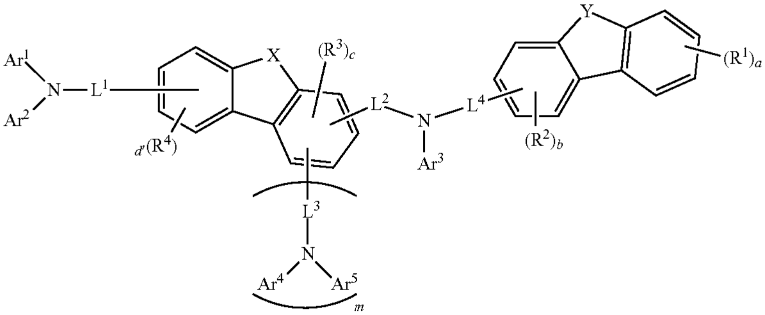
{wherein
1) $R^1$, $R^2$, $R^3$, $R^4$, X, Y, $L^1$, $L^2$, $L^3$, $L^4$, $Ar^1$, $Ar^2$, $Ar^3$, $Ar^4$, $Ar^5$, a, b, c and d are the same as defined in Formula 1,
2) c' is an integer from 0 to 2, and d' is an integer from 0 to 3.}
Also, the compound represented by Formula 1 is represented by any one of Formulas 2-1 to 2-4.
Formula 2-1
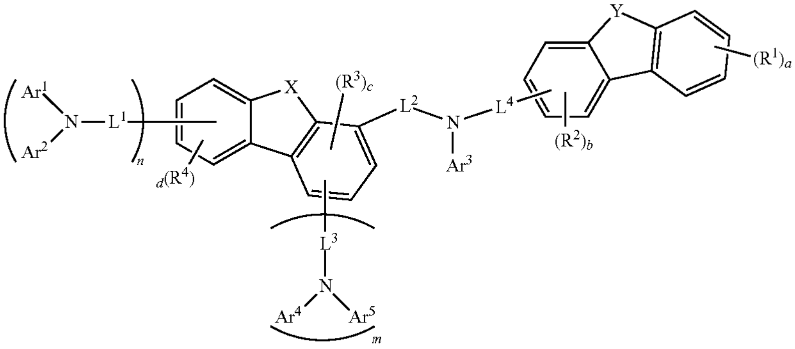
Formula 2-2
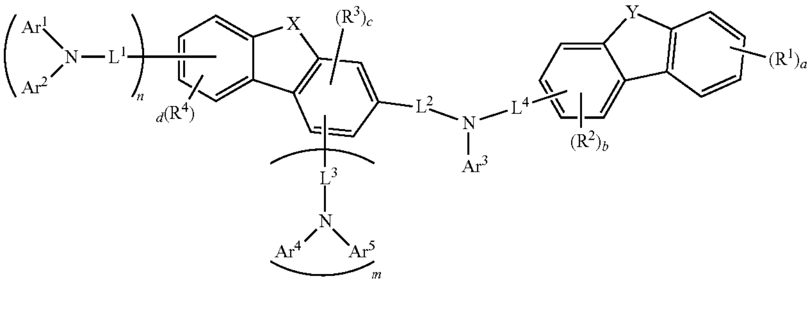

-continued
Formula 2-3
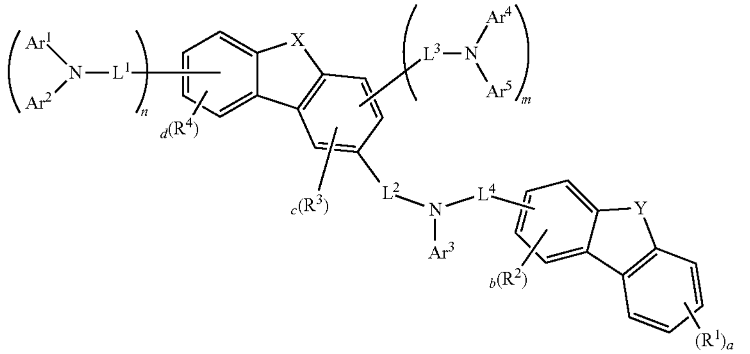
Formula 2-4
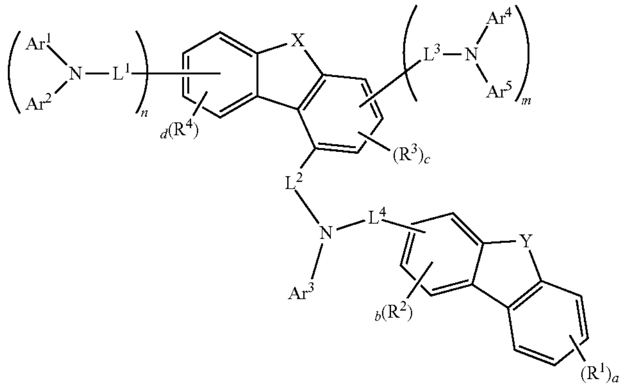
{wherein
$R^1$, $R^2$, $R^3$, $R^4$, X, Y, $L^1$, $L^2$, $L^3$, $L^4$, $Ar^1$, $Ar^2$, $Ar^3$, Art, $Ar^5$, a, b, c, d, m and n are the same as defined in Formula 1}
Also, the compound represented by Formula 1 is represented by any one of Formulas 3-1 to 3-14
Formula 3-1
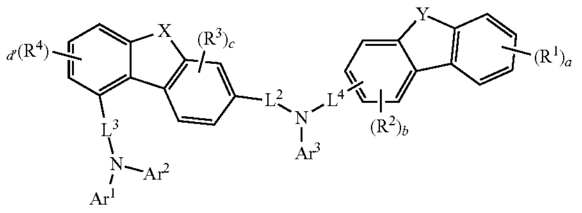
Formula 3-2
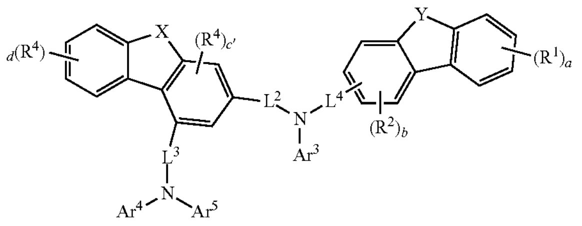
-continued
Formula 3-3
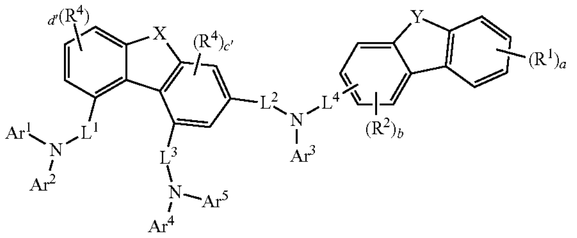
Formula 3-4
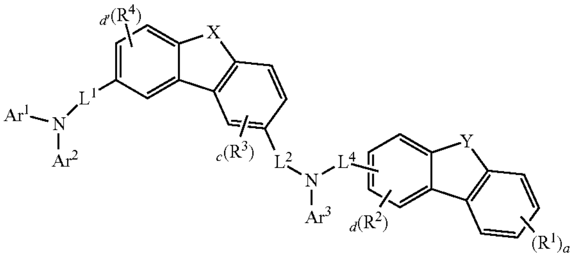

-continued
Formula 3-5
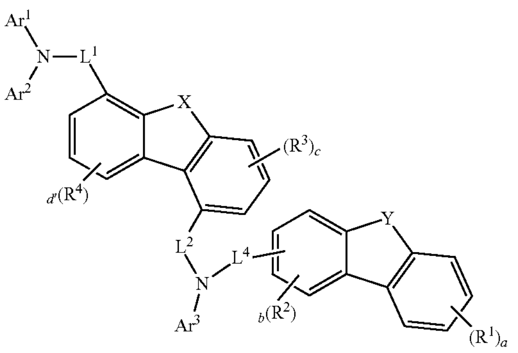
Formula 3-6
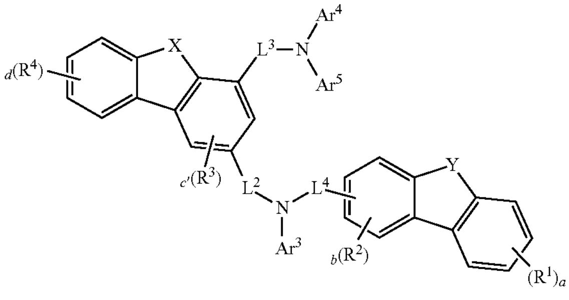
Formula 3-7
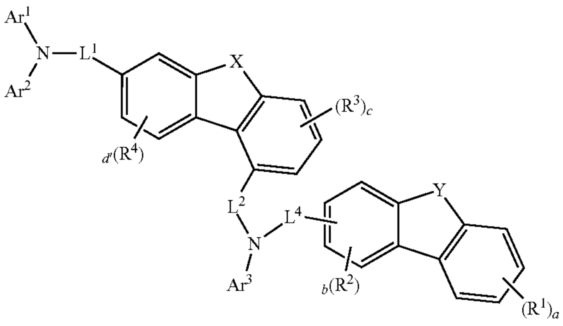
Formula 3-8
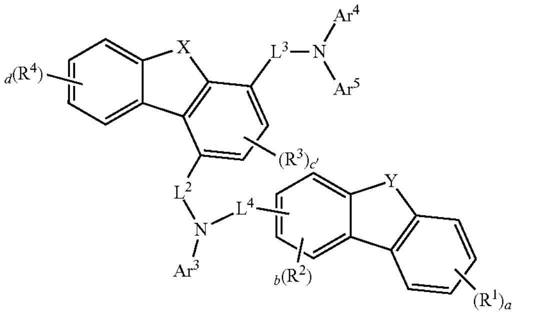
Formula 3-9
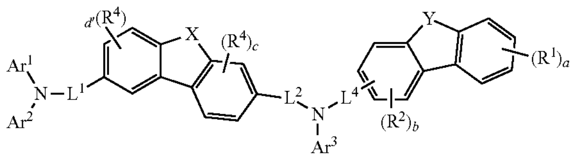
-continued
Formula 3-10
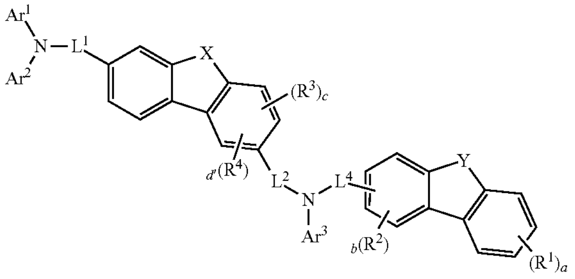
Formula 3-11
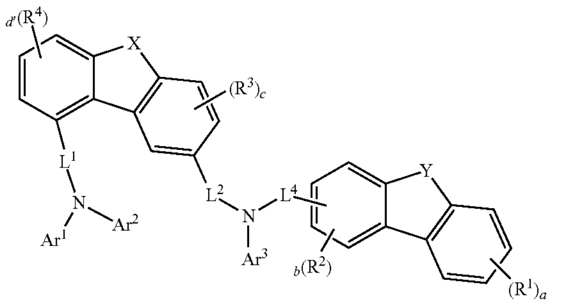
Formula 3-12
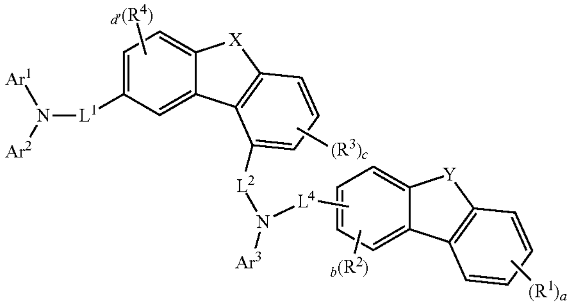
Formula 3-13
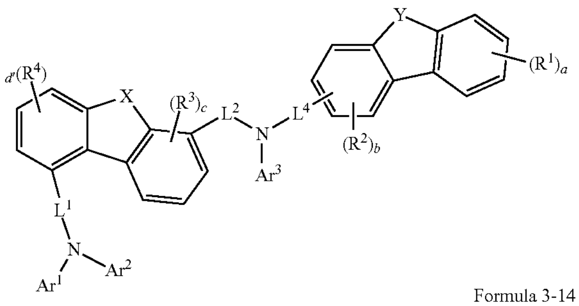
Formula 3-14
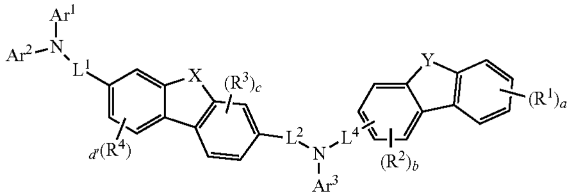
{wherein
1) $R^1$, $R^2$, $R^3$, $R^4$, X, Y, $L^1$, $L^2$, $L^3$, $L^4$, $Ar^1$, $Ar^2$, $Ar^3$, $Ar^4$, $Ar^5$, a, b, c and d are the same as defined in Formula 1,
2) c' is an integer from 0 to 2, and d' is an integer from 0 to 3}
Also, the compound represented by Formula 1 is represented by any one of Formulas 4-1 to 4-6.

Formula 4-1
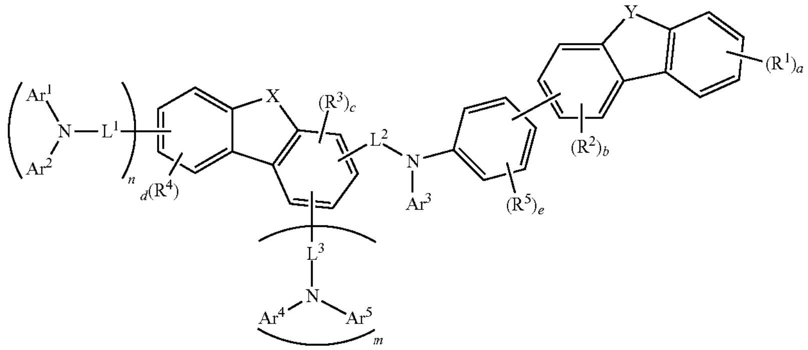
Formula 4-2
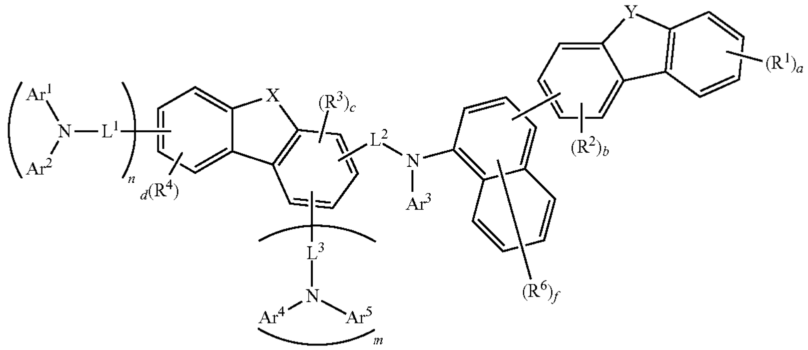
Formula 4-3
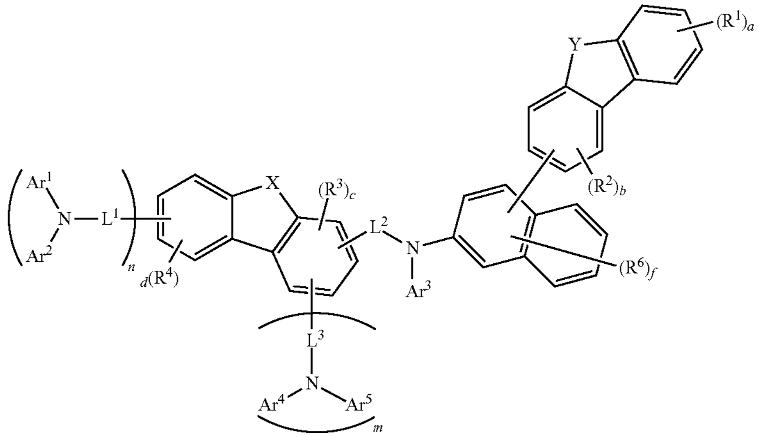
Formula 4-4
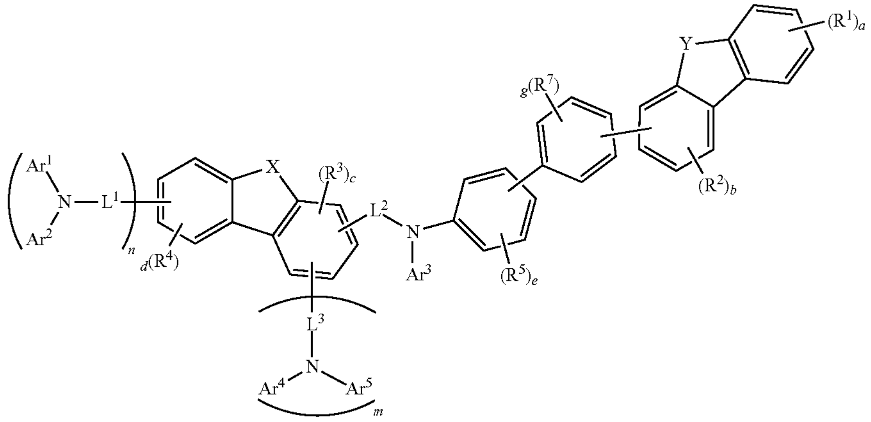

-continued
Formula 4-5
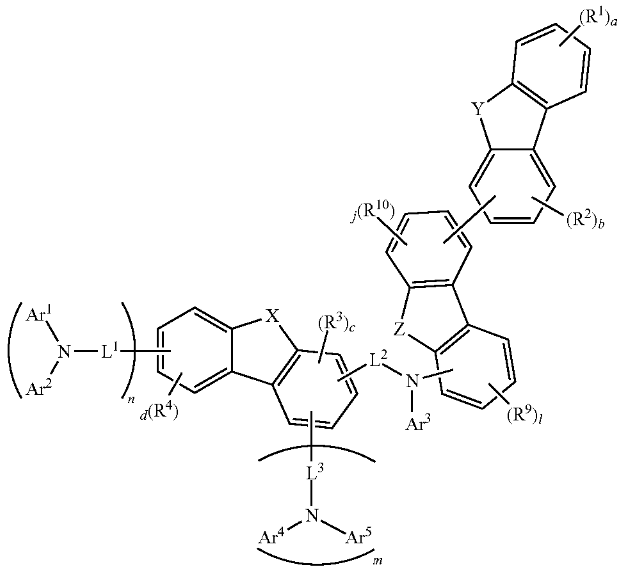
Formula 4-6
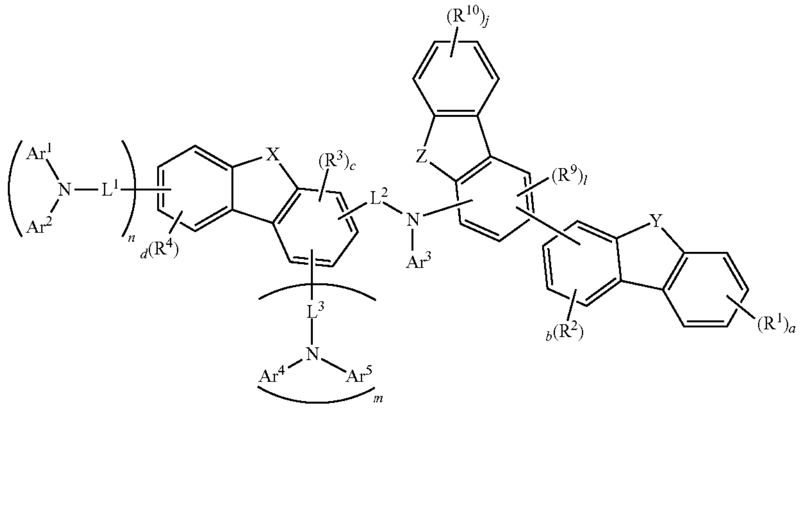

{wherein

1) $R^1$, $R^2$, $R^3$, $R^4$, X, Y, $L^1$, $L^2$, $L^3$, $Ar^1$, $Ar^2$, $Ar^3$, $Ar^4$, $Ar^5$, a, b, c, d, m and n are the same as defined in Formula 1, 2) $R^5$, $R^6$, $R^7$, $R^9$, $R^{10}$, $R^{11}$, $R^{12}$, e, f, g, i, j, k, l and Z are the same as defined in Formulas b-1 to b-13.}

Also, the compound represented by Formula 1 is represented by any one of Formulas 5-1 to 5-4

Formula 5-1

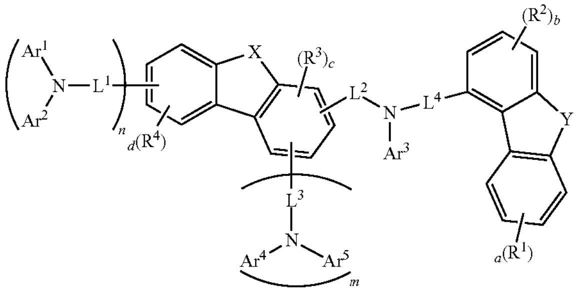

Formula 5-2

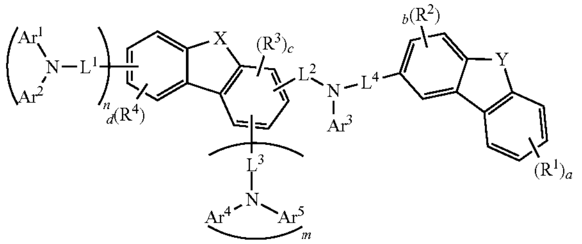

Formula 5-3

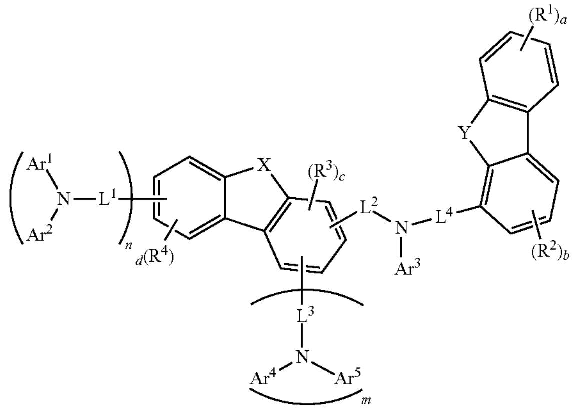

Formula 5-4

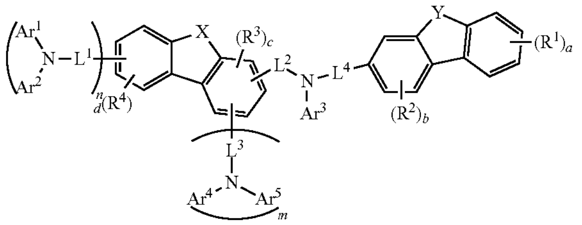

{wherein $R^1$, $R^2$, $R^3$, $R^4$, X, Y, $L^1$, $L^2$, $L^3$, $L^4$, $Ar^1$, $Ar^2$, $Ar^3$, $Ar^4$, $Ar^5$, a, b, c, d, m and n are the same as defined in Formula 1.}

Also, the compound represented by Formula 1 is represented by any one of Formulas 6-1 to 6-40

Formula 6-1

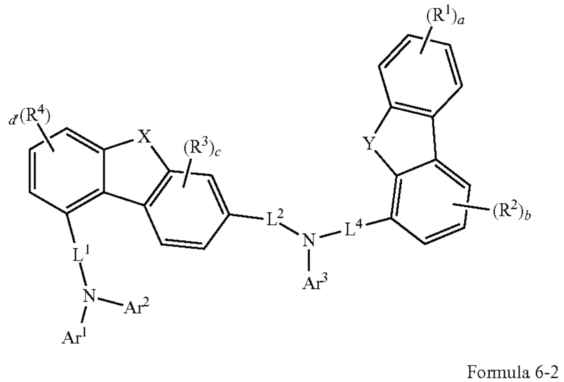

Formula 6-2

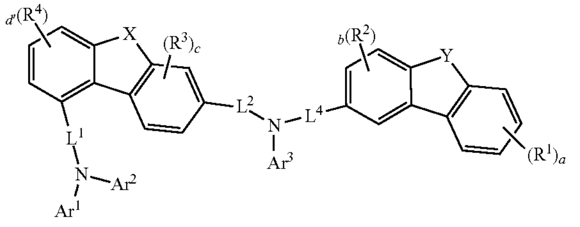

Formula 6-3

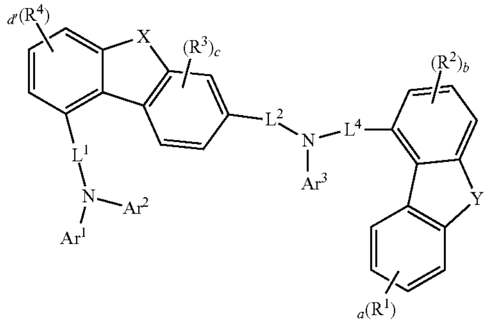

Formula 6-4

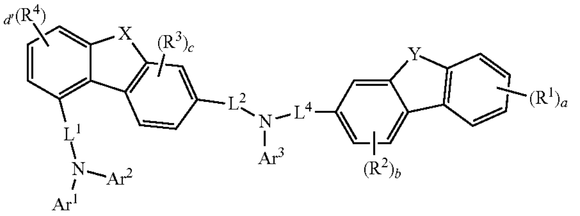

Formula 6-5

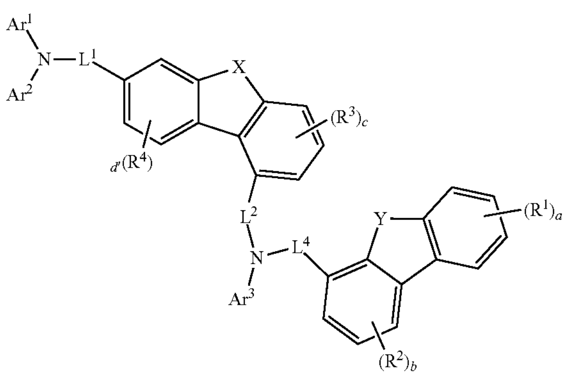

-continued
Formula 6-6
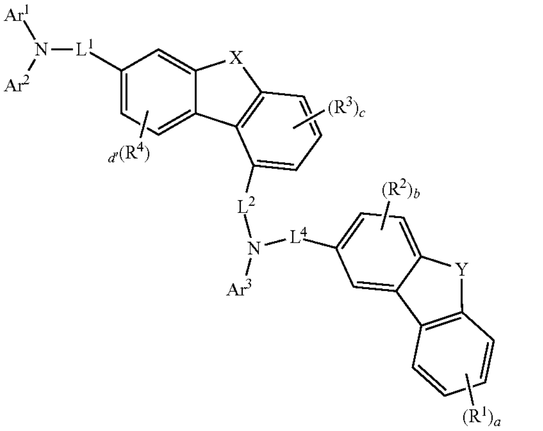
Formula 6-7
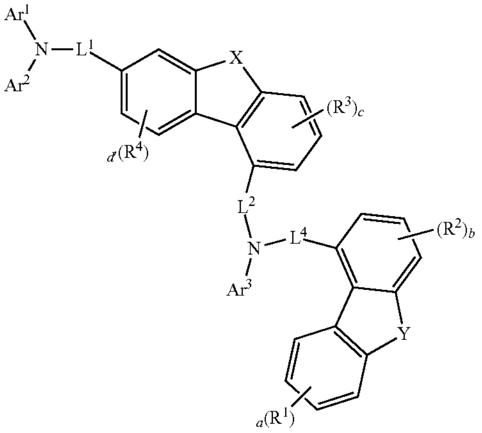
Formula 6-8
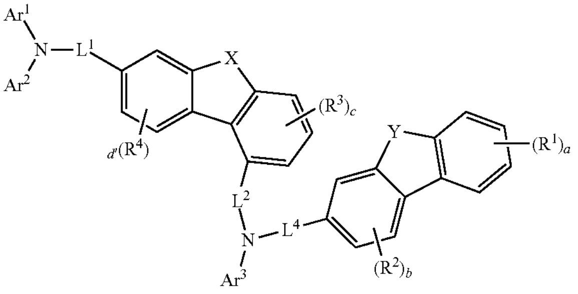
Formula 6-9
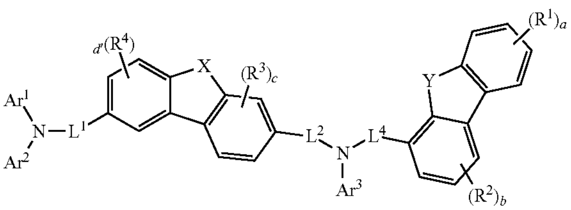
Formula 6-10
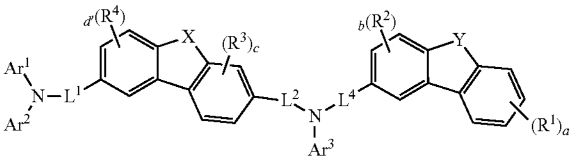
-continued
Formula 6-11
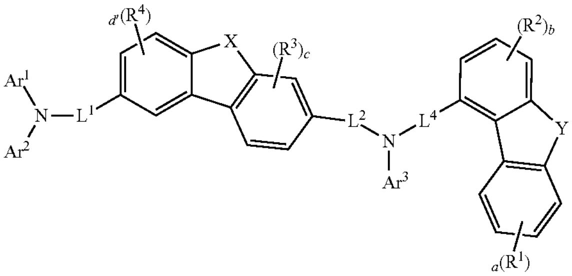
Formula 6-12
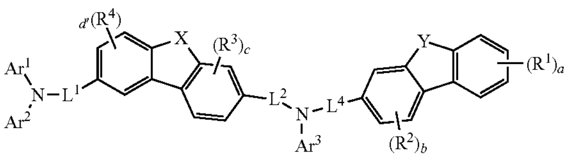
Formula 6-13
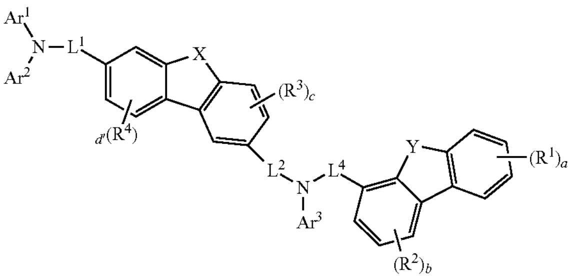
Formula 6-14
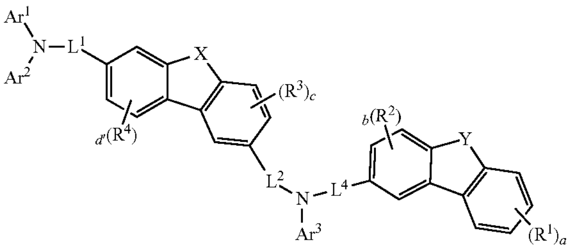
Formula 6-15
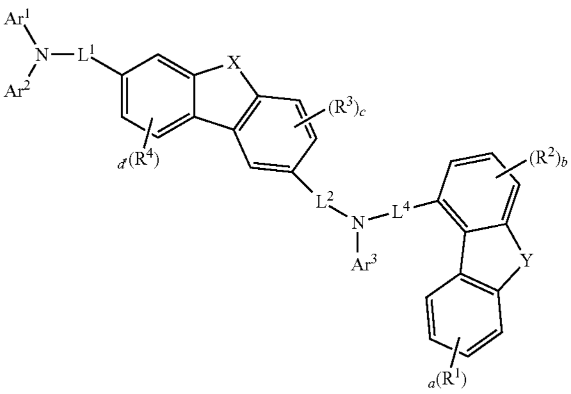

-continued
Formula 6-16
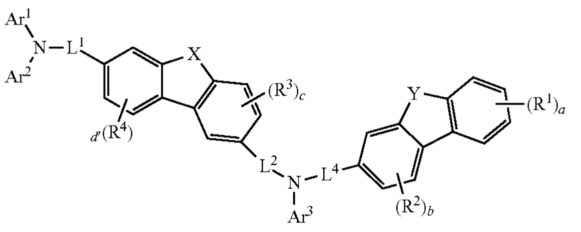
Formula 6-17
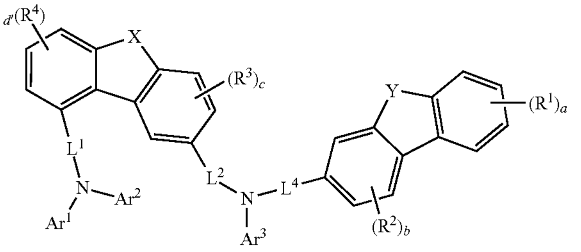
Formula 6-18
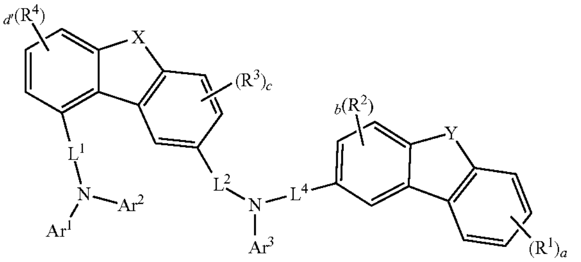
Formula 6-19
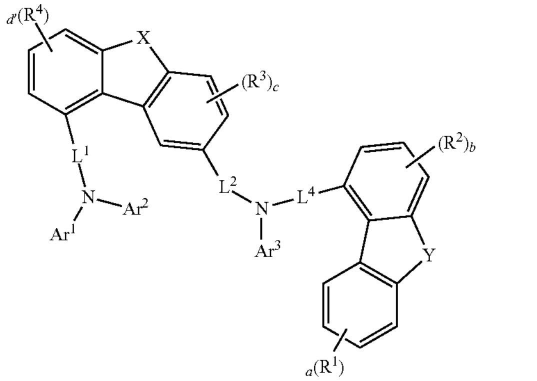
Formula 6-20
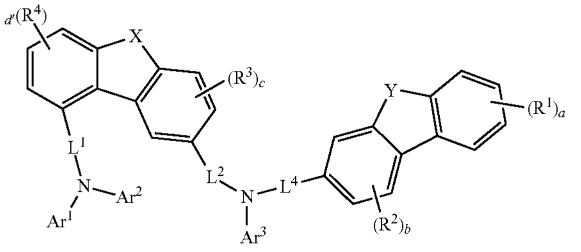
-continued
Formula 6-21
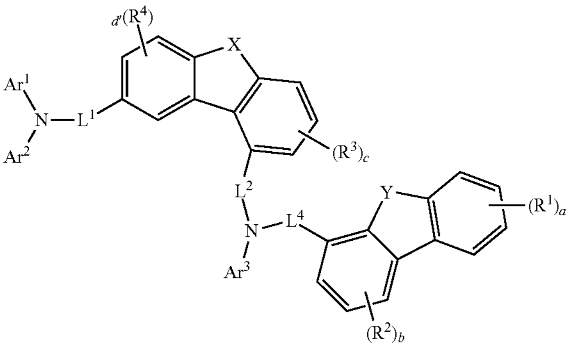
Formula 6-22
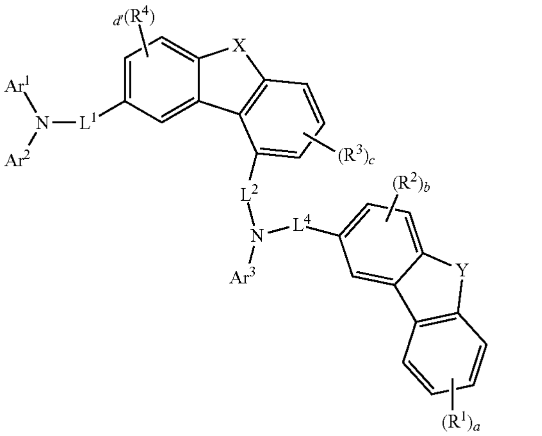
Formula 6-23
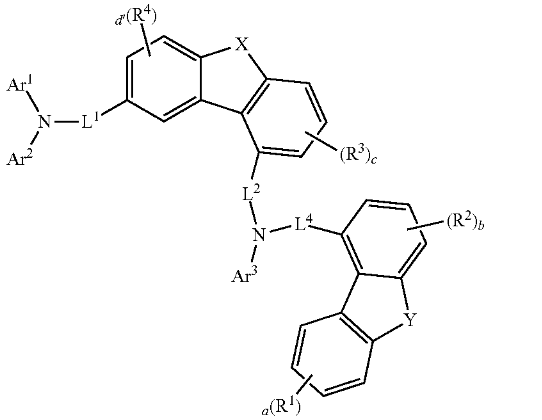
Formula 6-24
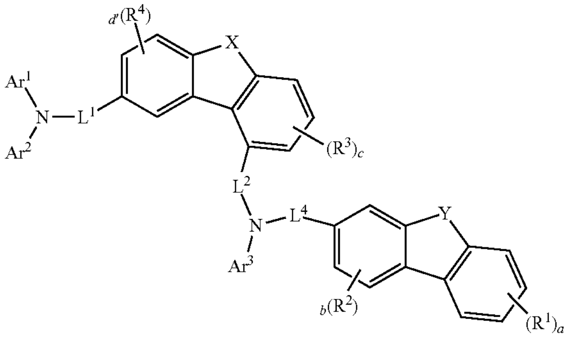

-continued
Formula 6-25
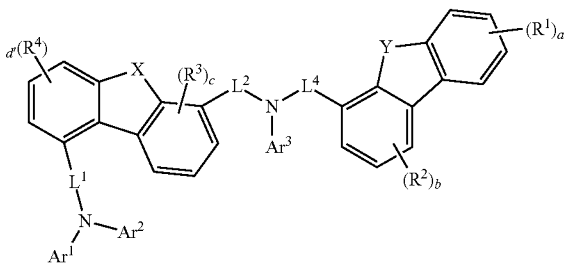
Formula 6-26
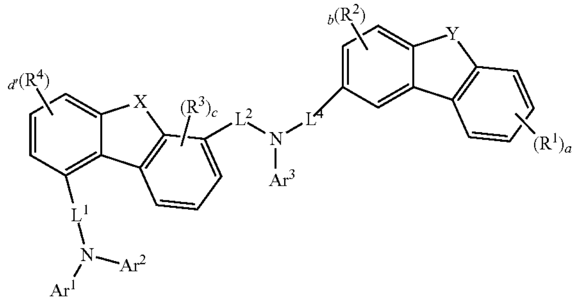
Formula 6-27
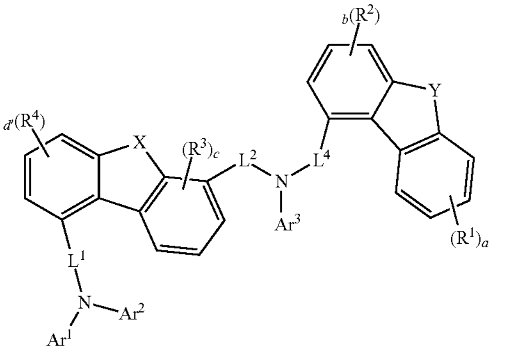
Formula 6-28
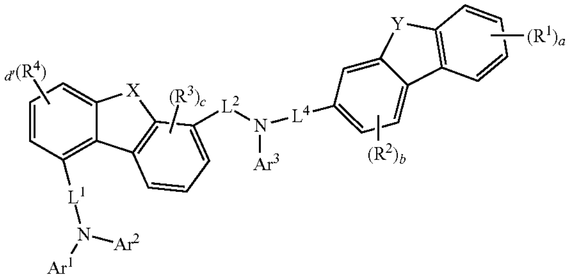
-continued
Formula 6-29
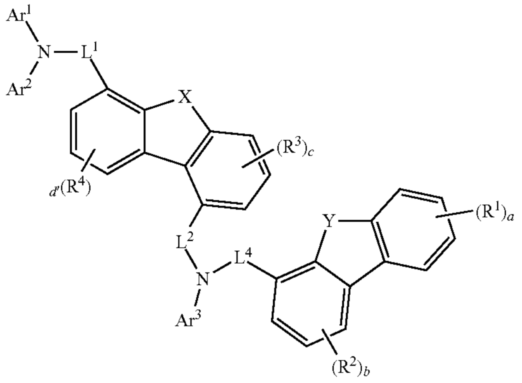
Formula 6-30
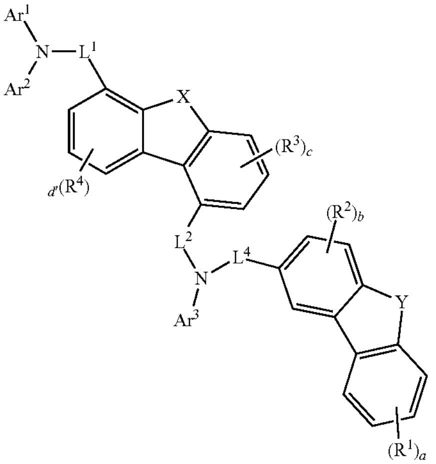
Formula 6-31
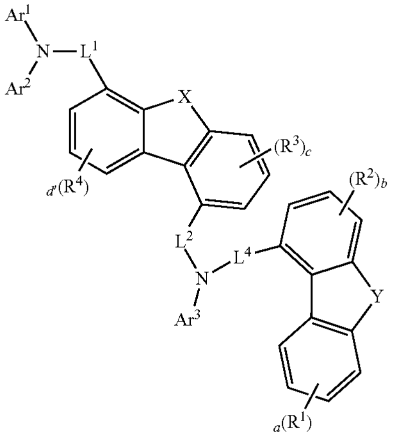

-continued

Formula 6-32

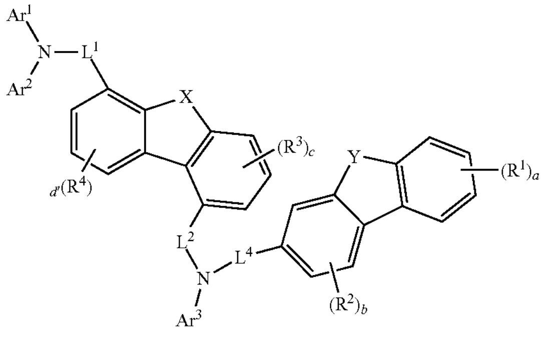

Formula 6-33

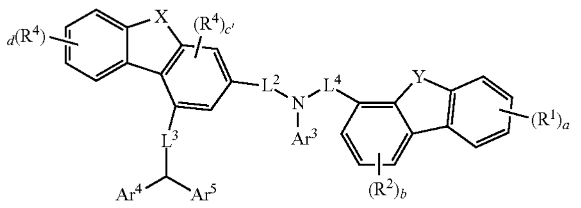

Formula 6-34

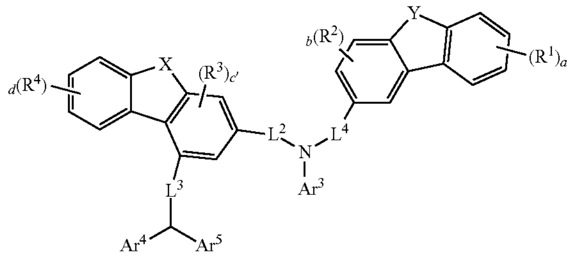

Formula 6-35

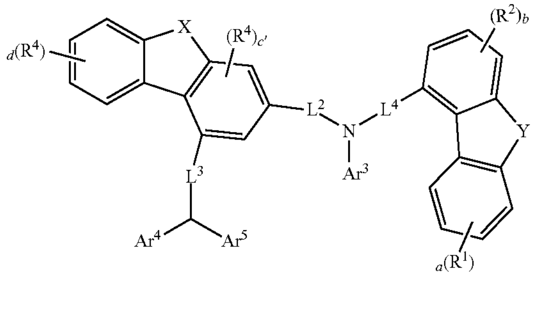

Formula 6-36

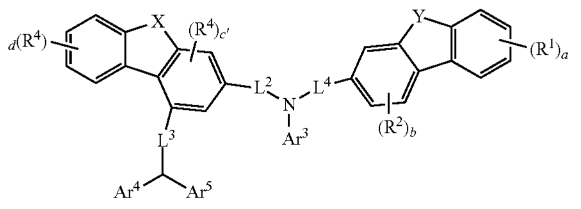

-continued

Formula 6-37

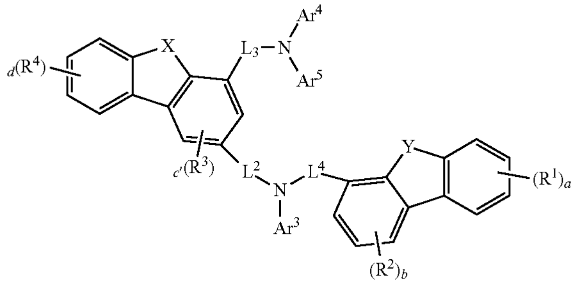

Formula 6-38

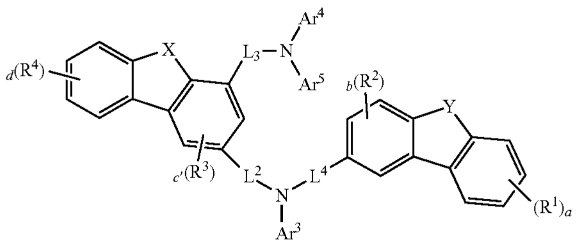

Formula 6-39

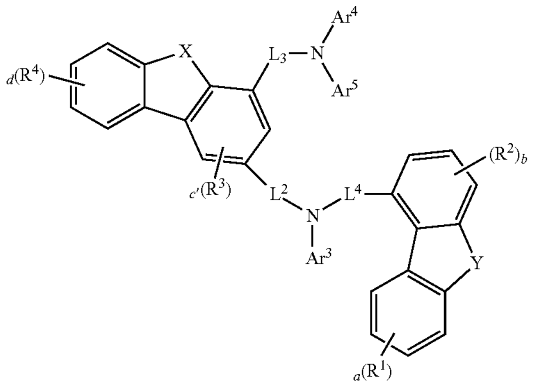

Formula 6-40

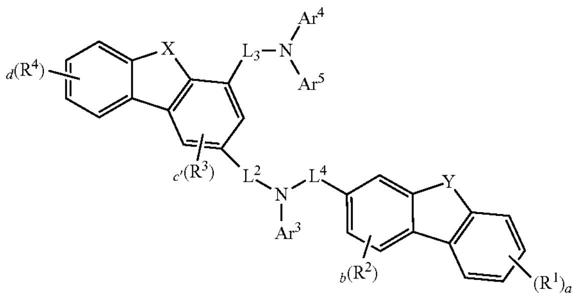

{wherein,

1) $R^1$, $R^2$, $R^3$, $R^4$, X, Y, $L^1$, $L^2$, $L^3$, $L^4$, $Ar^1$, $Ar^2$, $Ar^3$, $Ar^4$, $Ar^5$, a, b, c and d are the same as defined in Formula 1.}

2) c' is an integer from 0 to 2, and d' is an integer from 0 to 3.}

Also, the compound represented by Formula 1 is represented by any one of the following compounds P-1 to P-152.

P-1
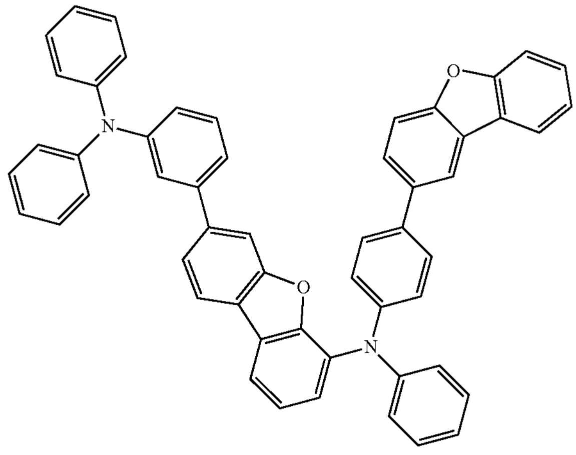
P-2
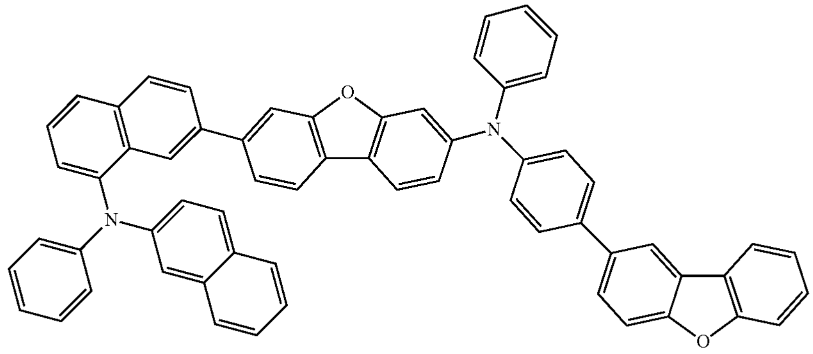
P-3
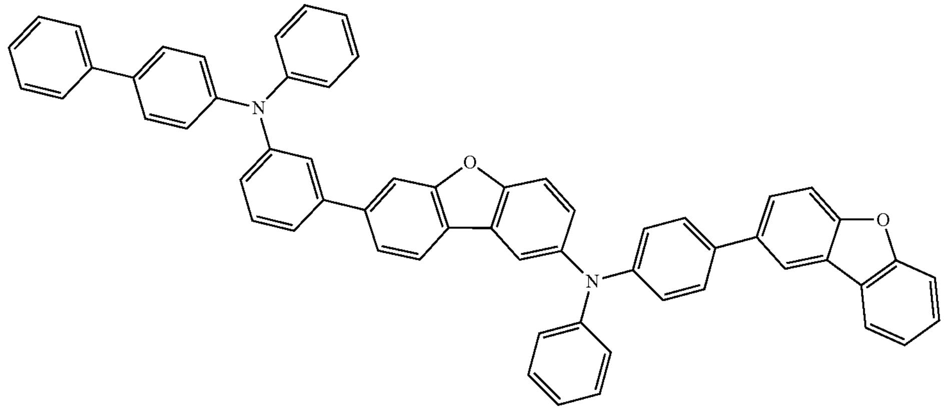

-continued
P-4
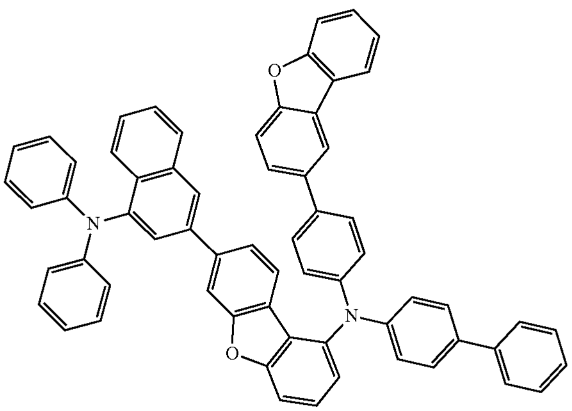
P-5
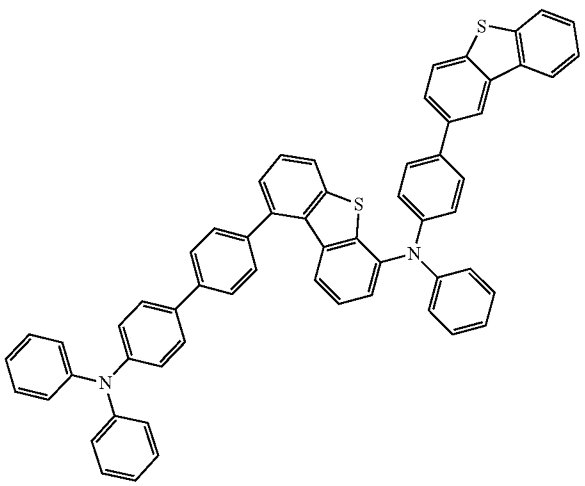
P-6
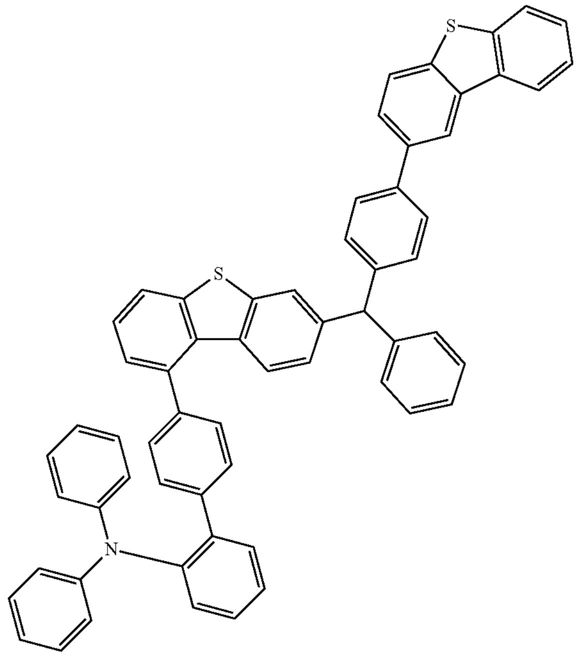
P-7
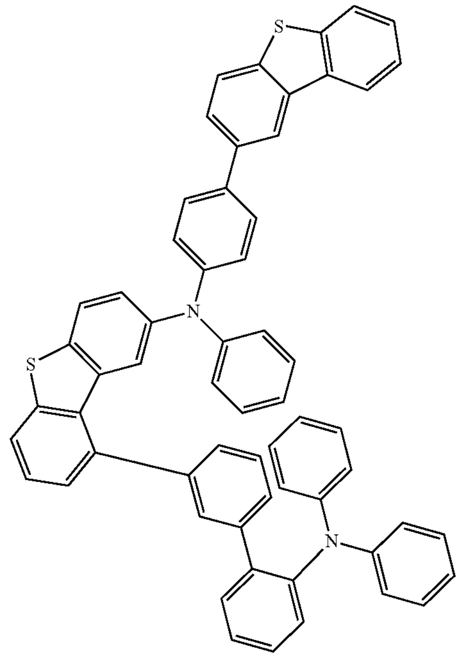
P-8
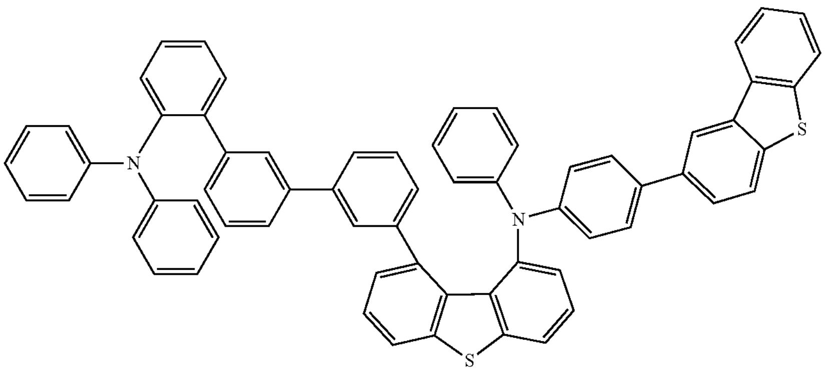

-continued
P-9
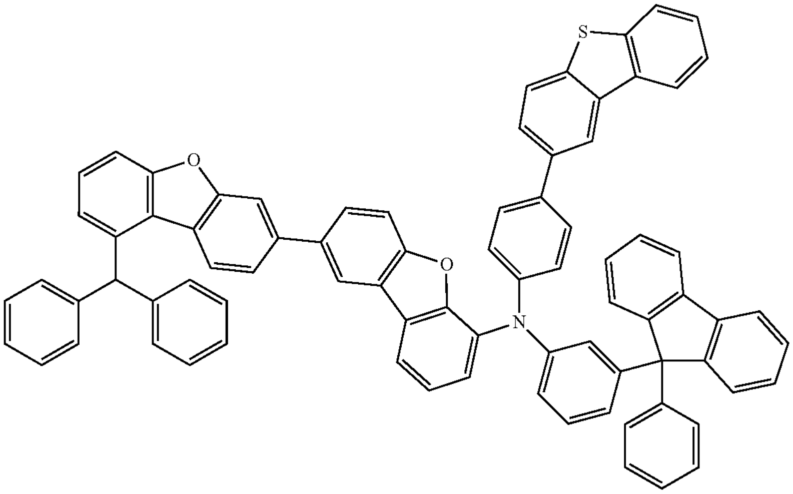
P-10
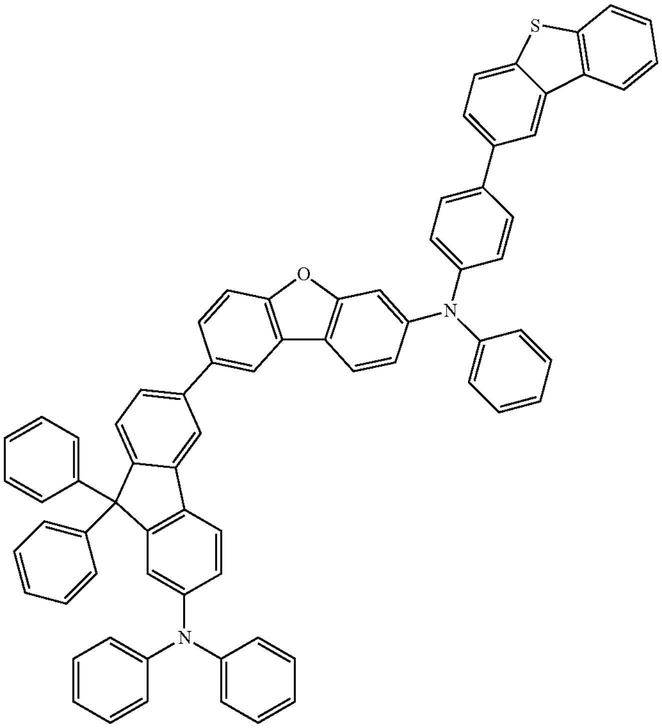

-continued
P-11
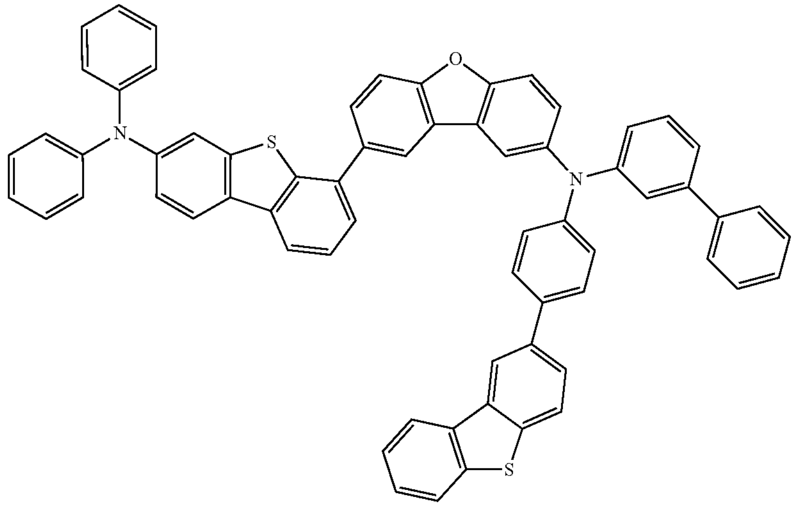
P-12
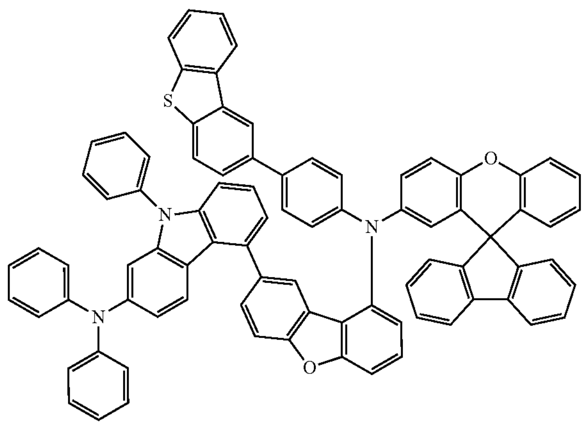
P-13
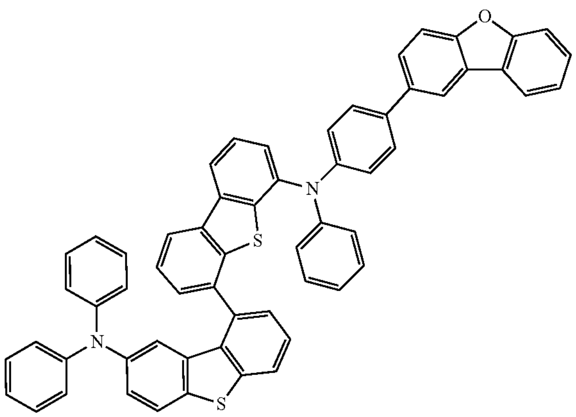
P-14
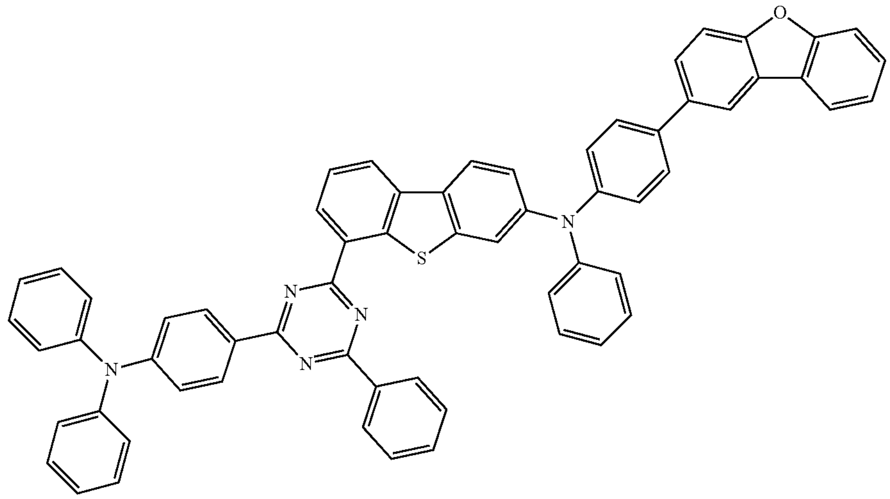

-continued
P-15
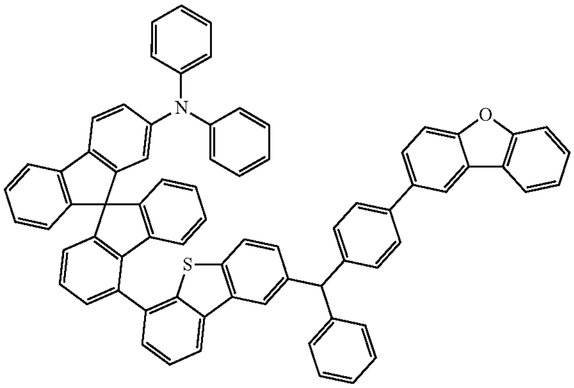
P-16
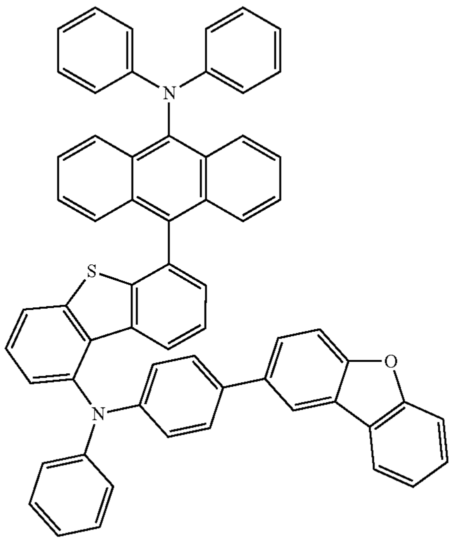
P-17
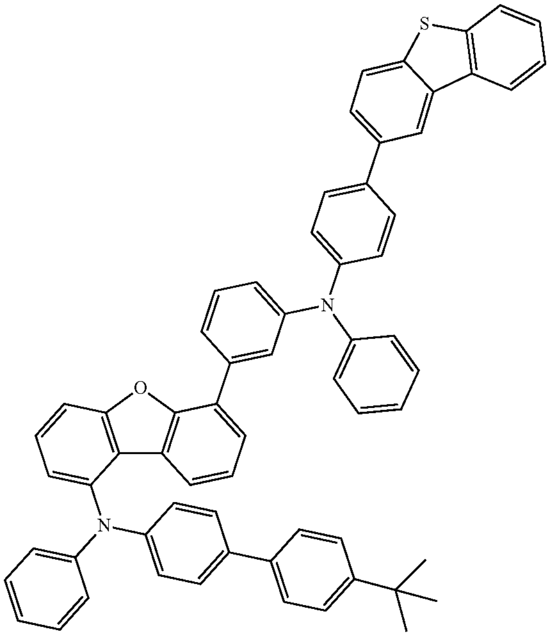
P-18
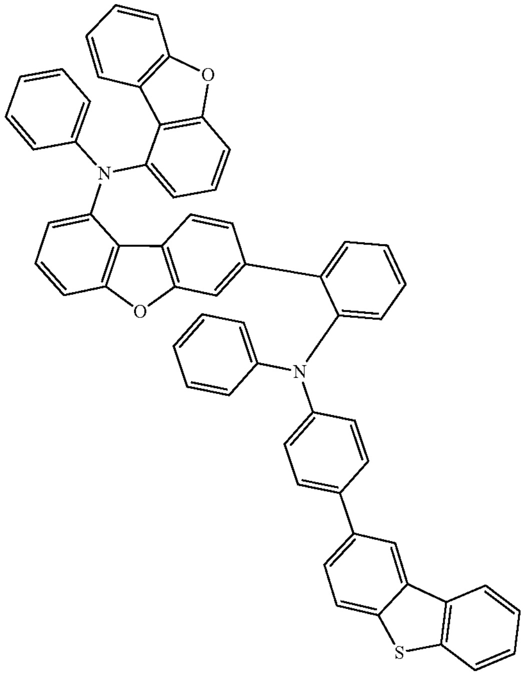
P-19
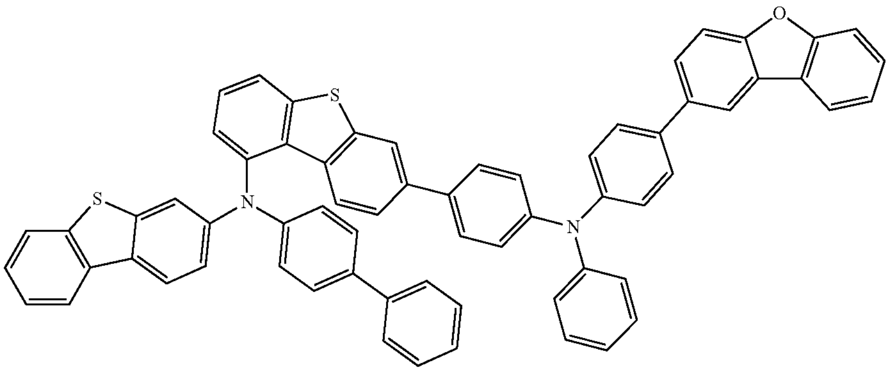

-continued
P-20
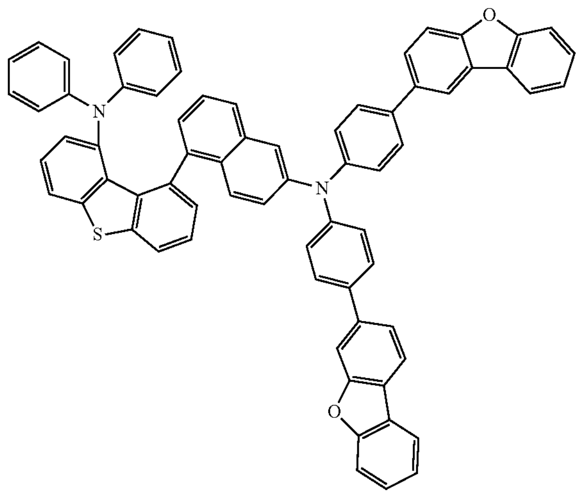
P-21
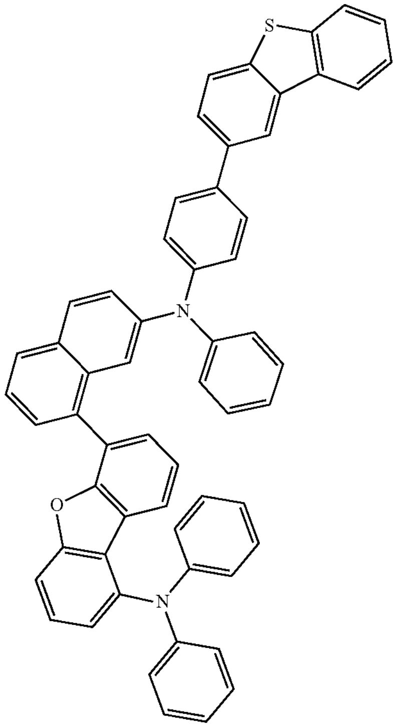
P-22
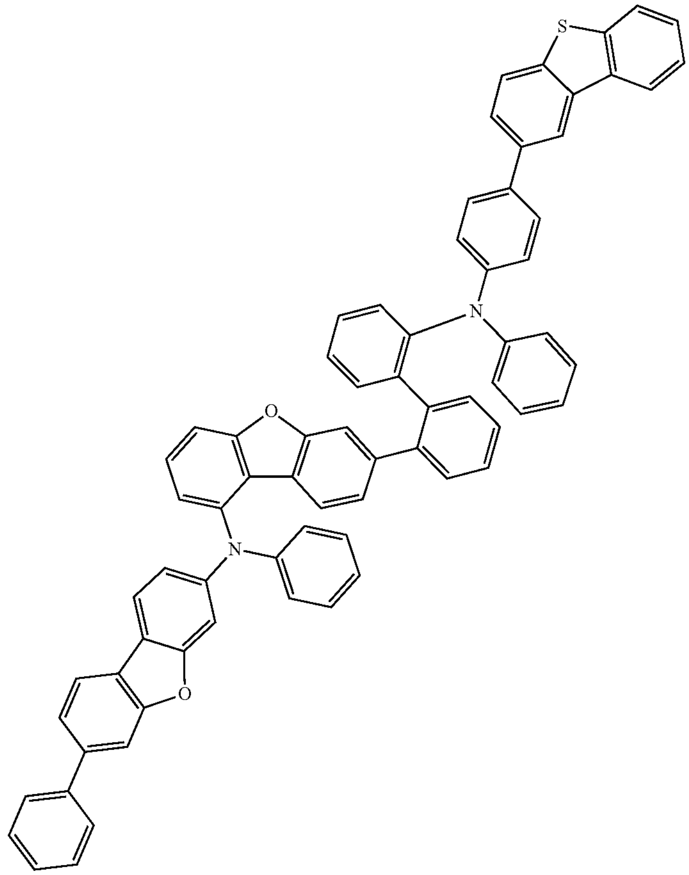

-continued
P-23
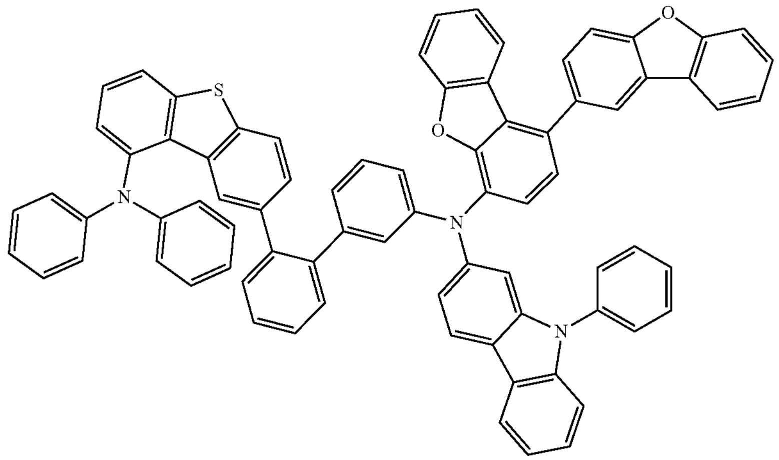
P-24
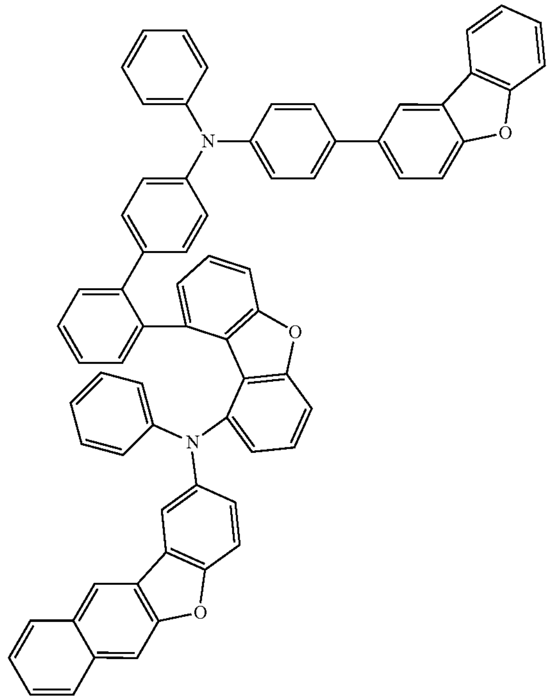
P-25
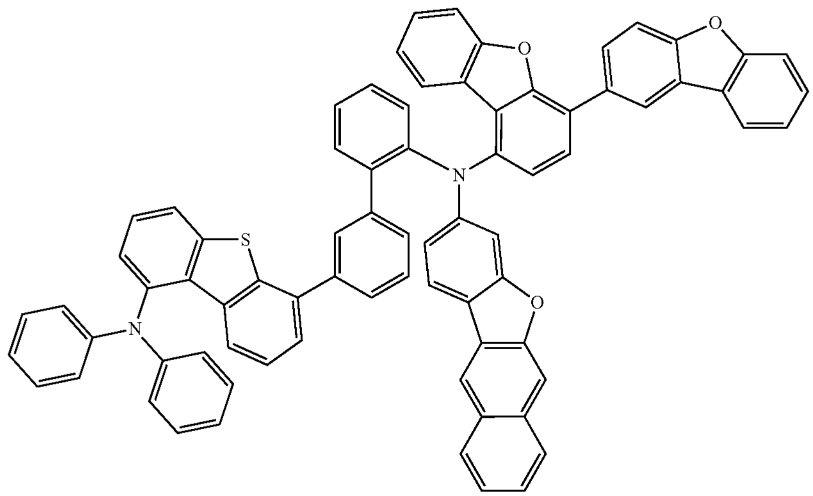

-continued
P-26
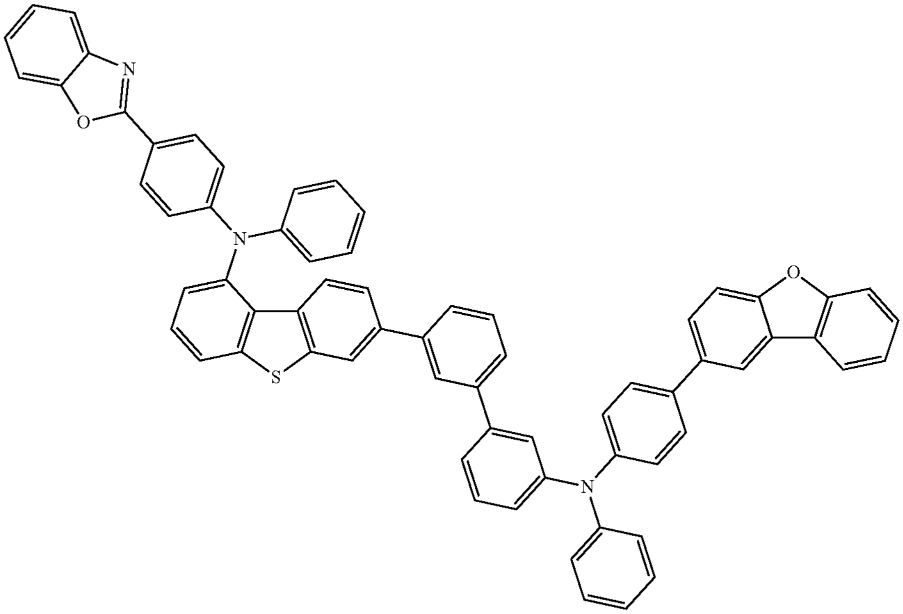
P-27
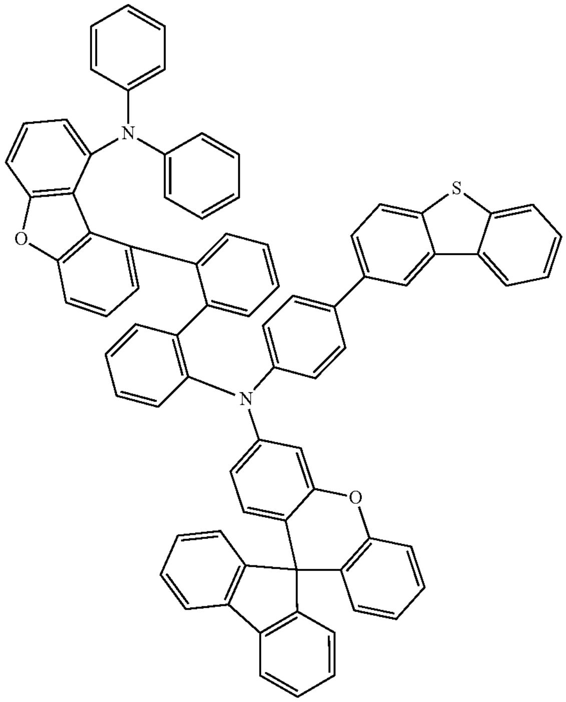
P-28
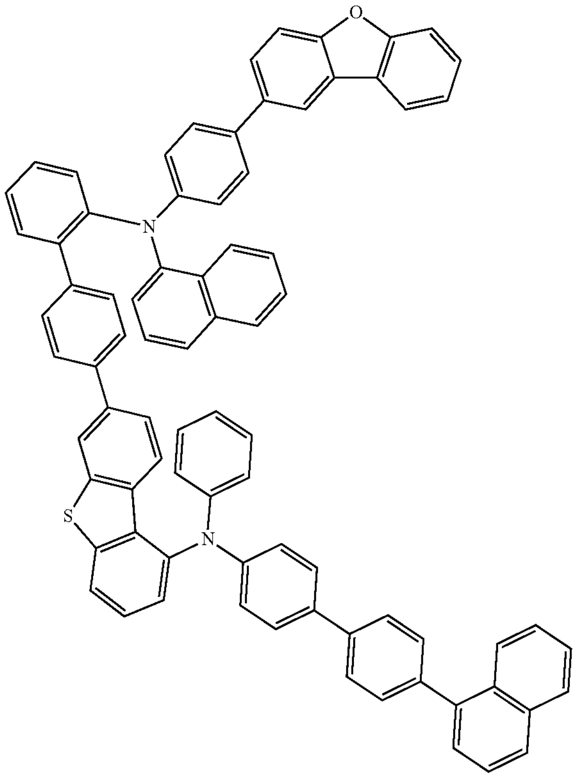

-continued
P-29
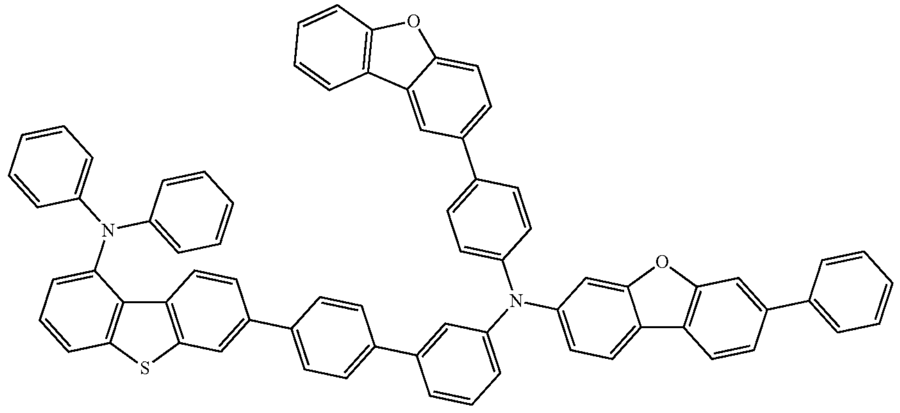
P-30
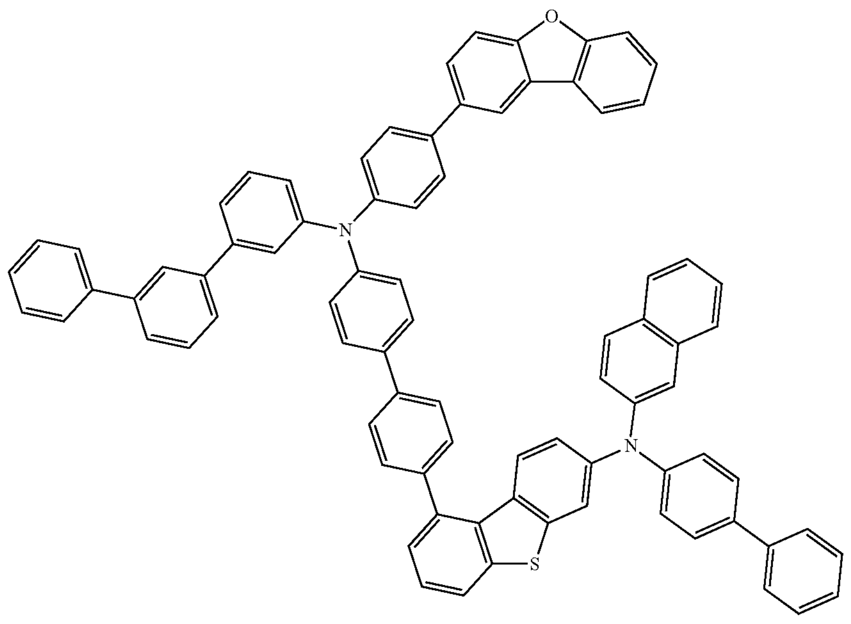
P-31
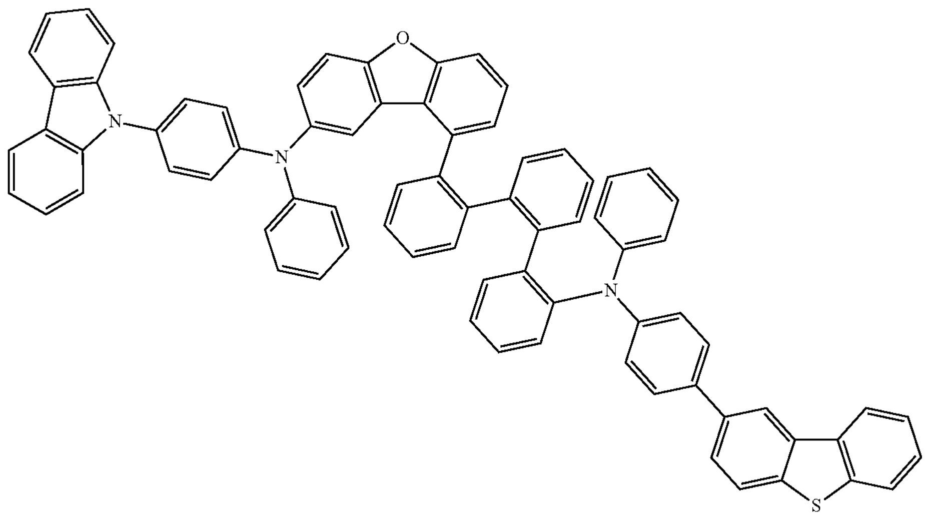

-continued
P-32
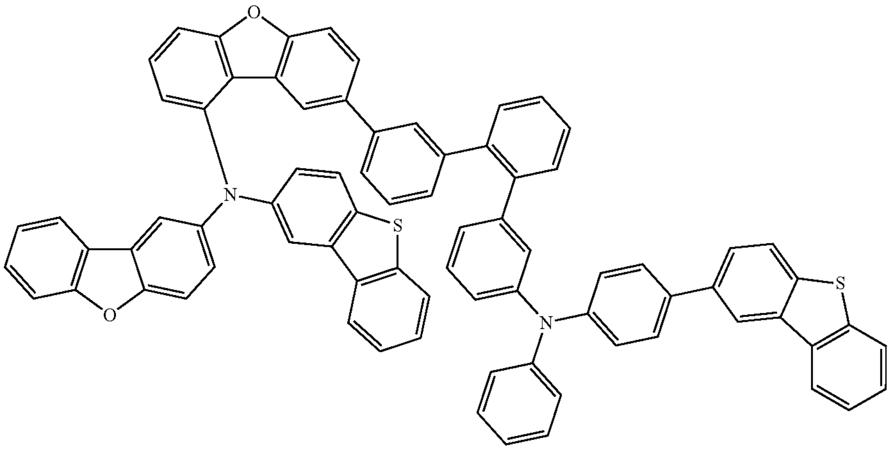
P-33
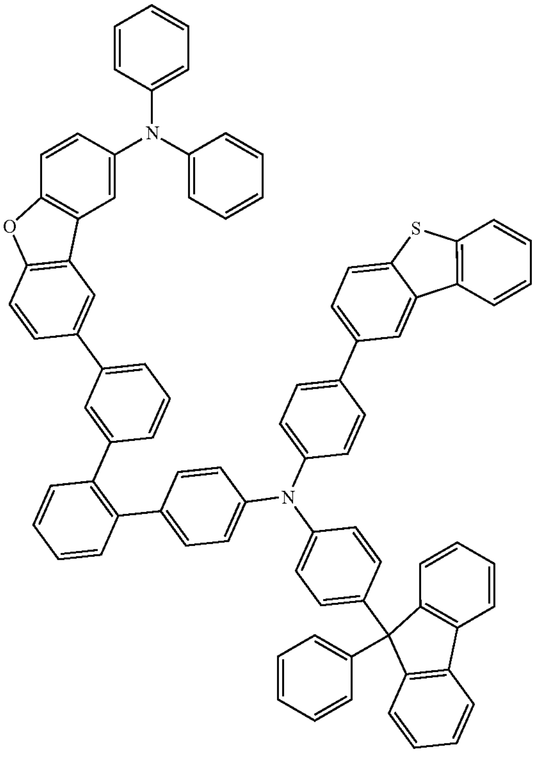
P-34
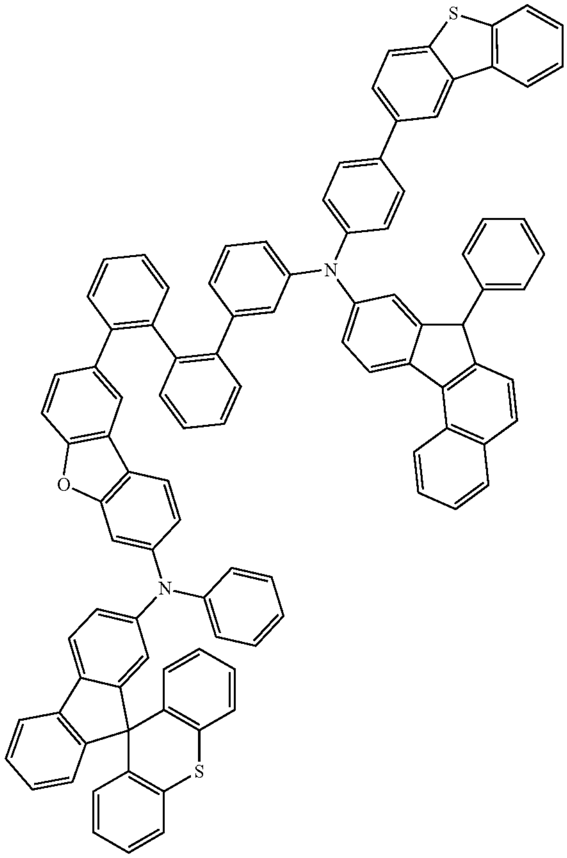

-continued
P-35
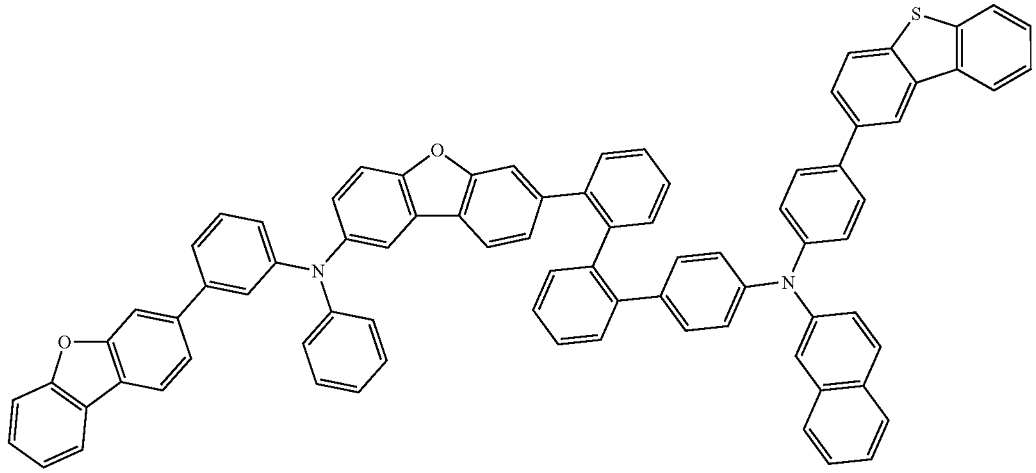
P-36
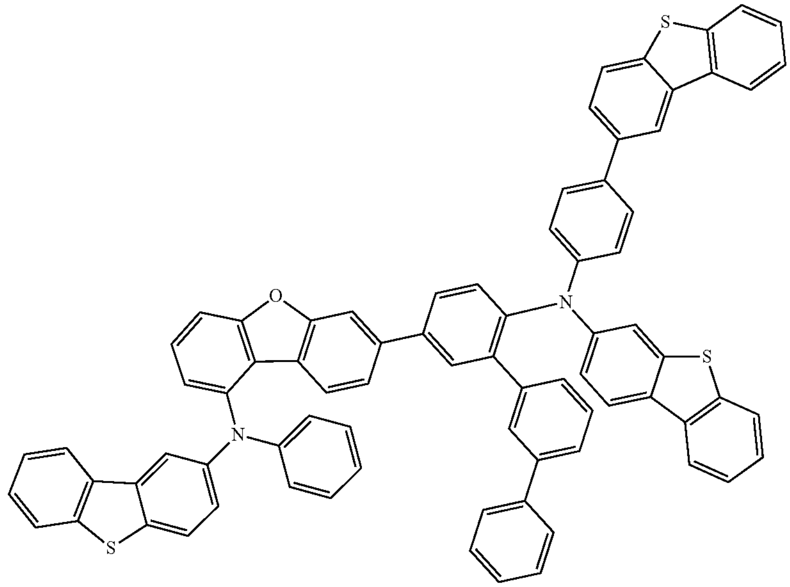
P-37
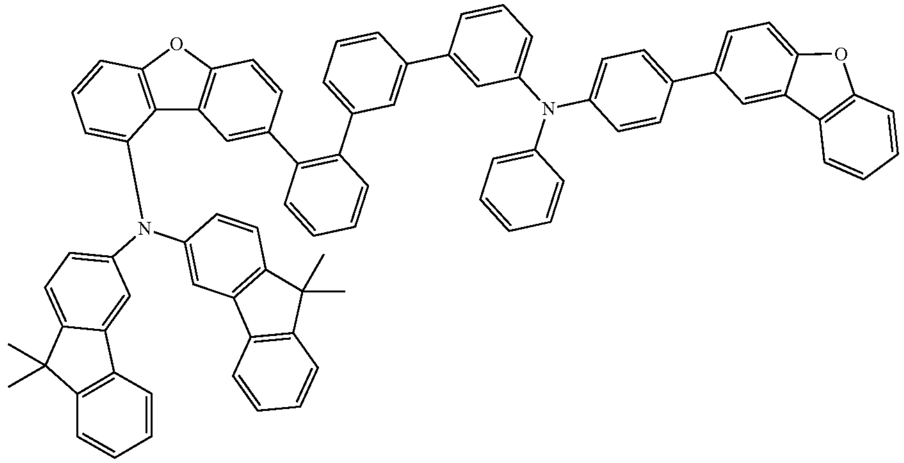

-continued
P-38
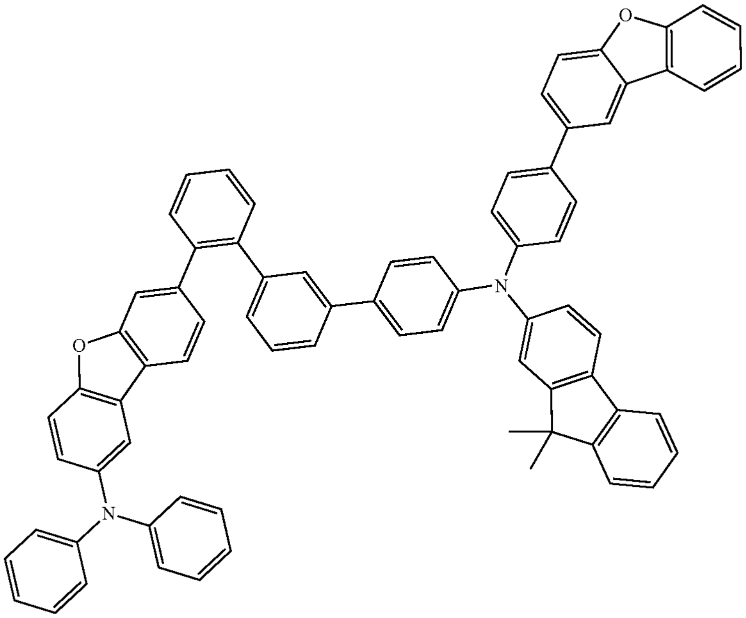
P-39
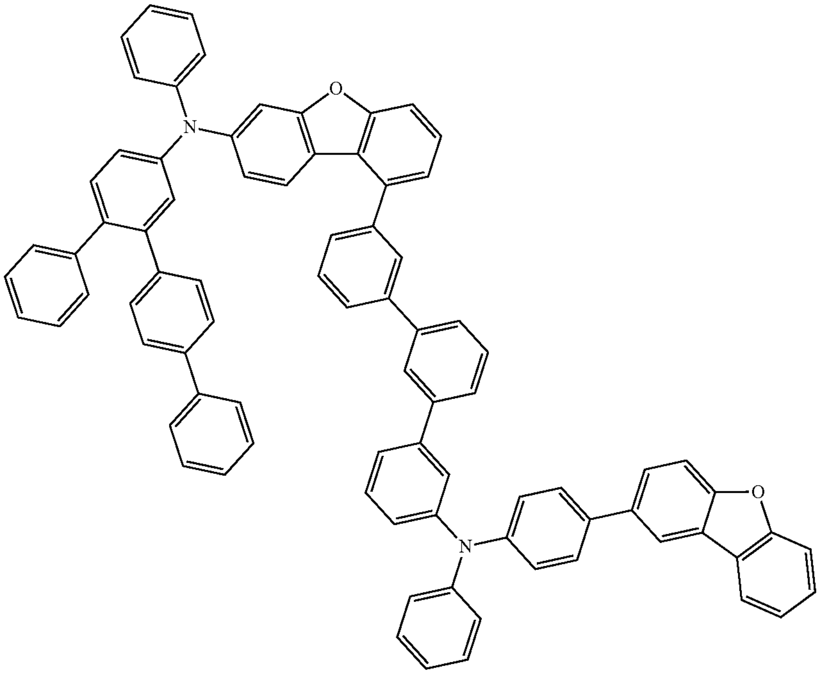

-continued
P-40
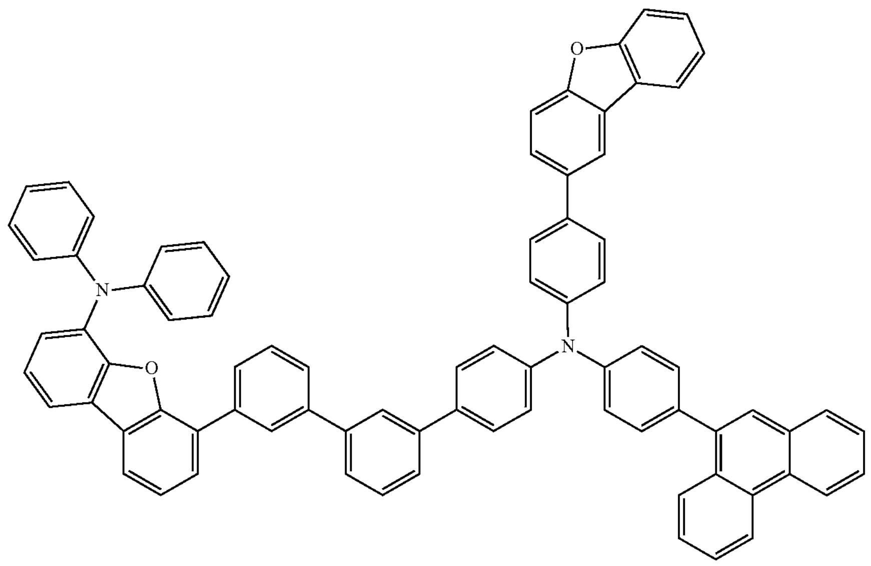
P-41
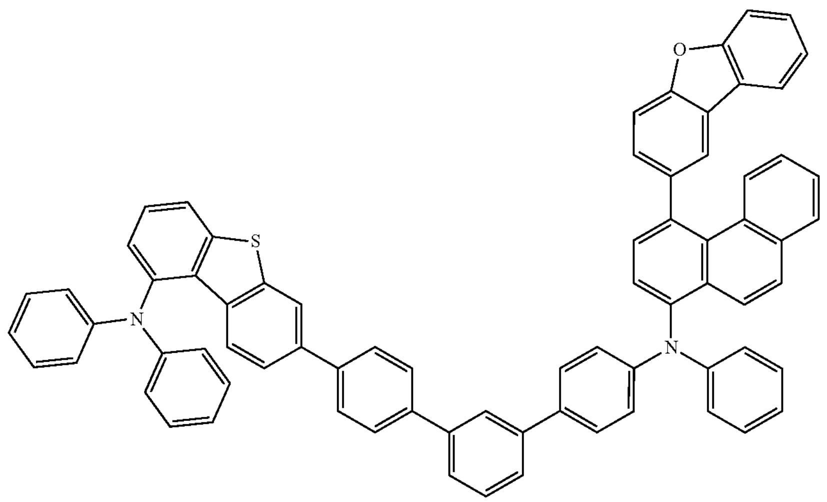

-continued
P-42
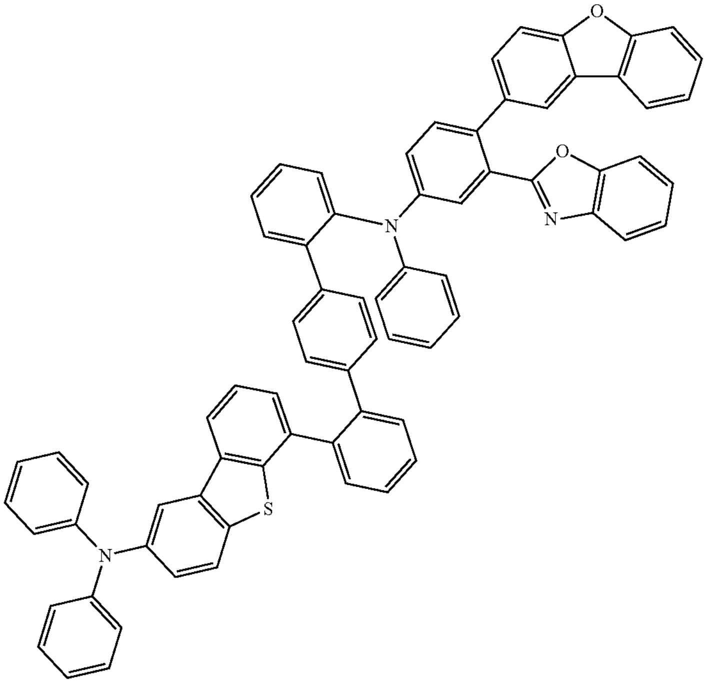
P-43
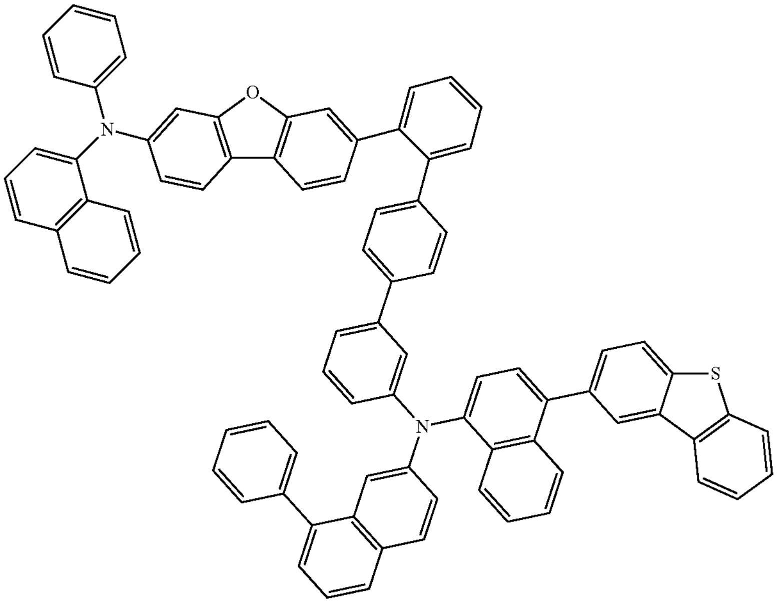

-continued
P-44
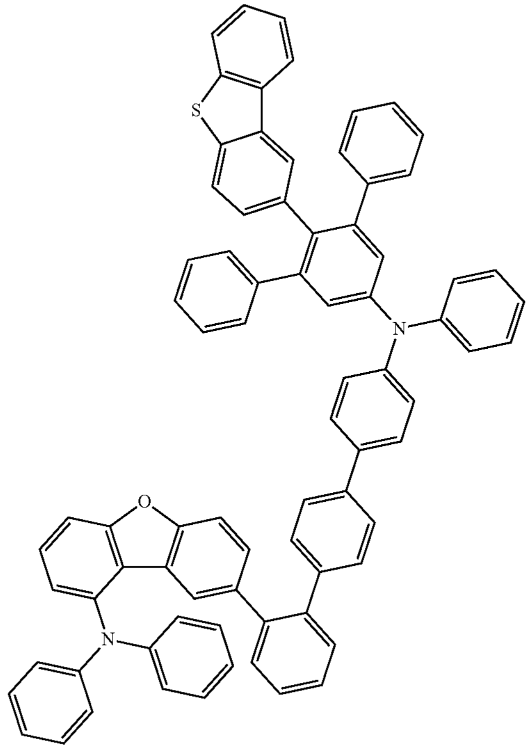
P-45
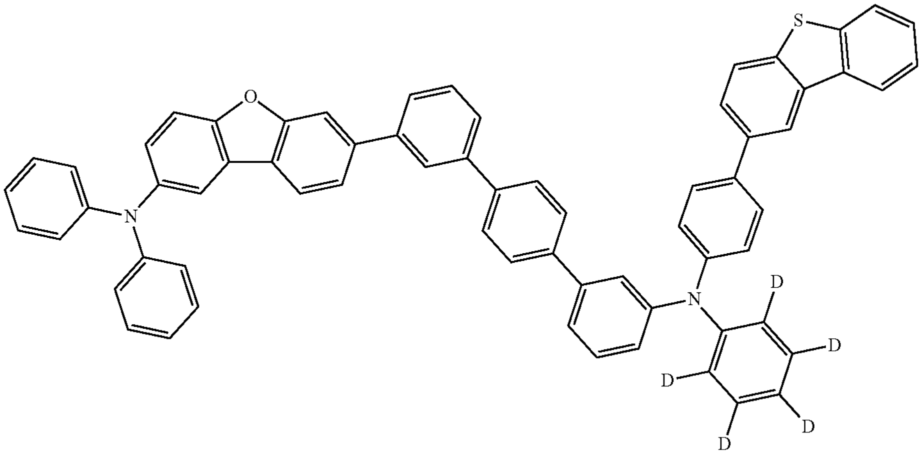

-continued
P-46
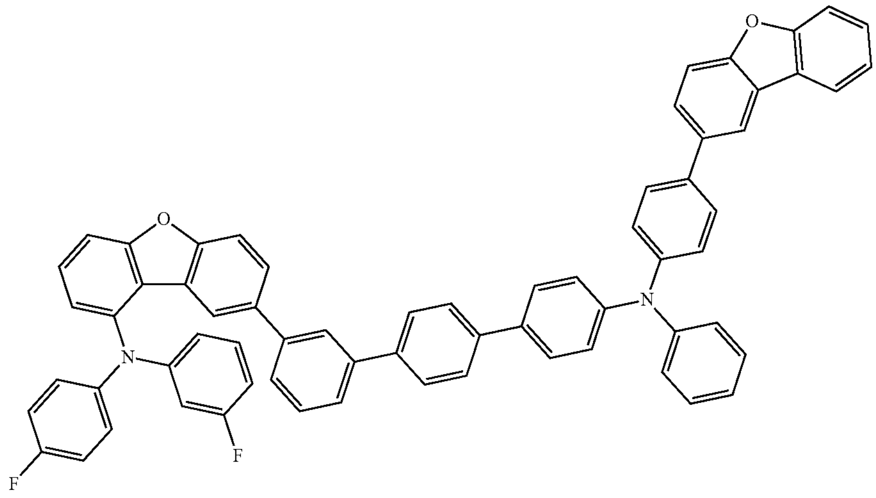
P-47
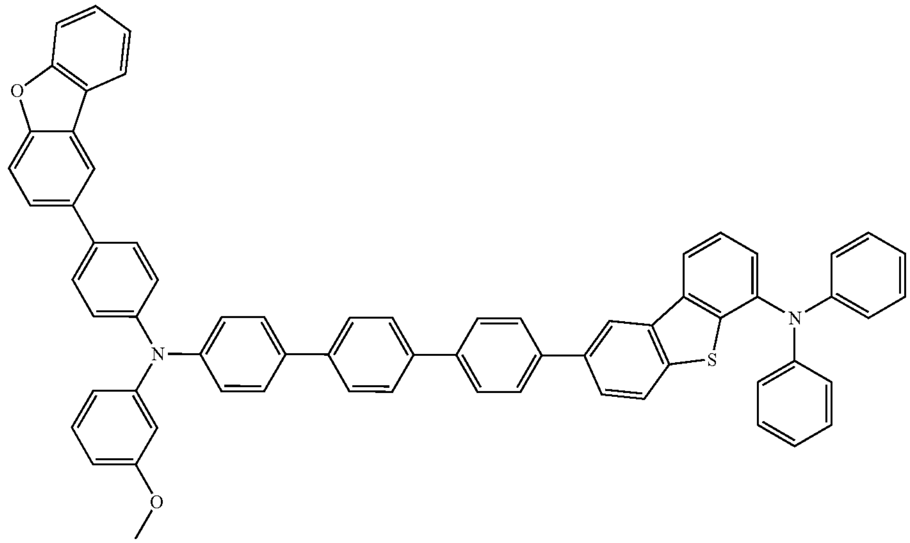
P-48
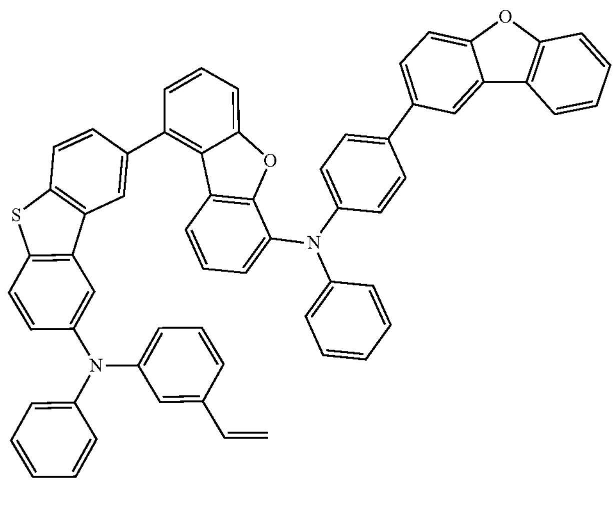

-continued
P-49
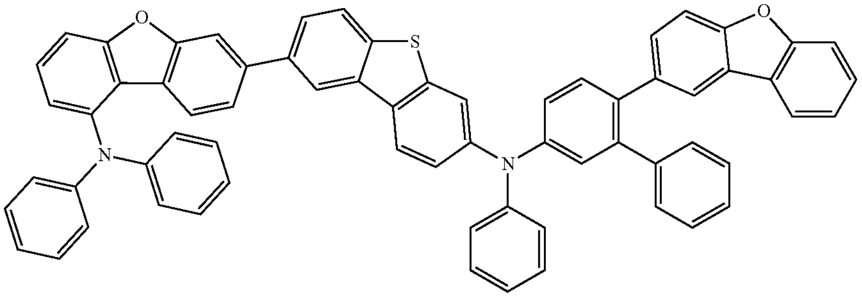
P-50
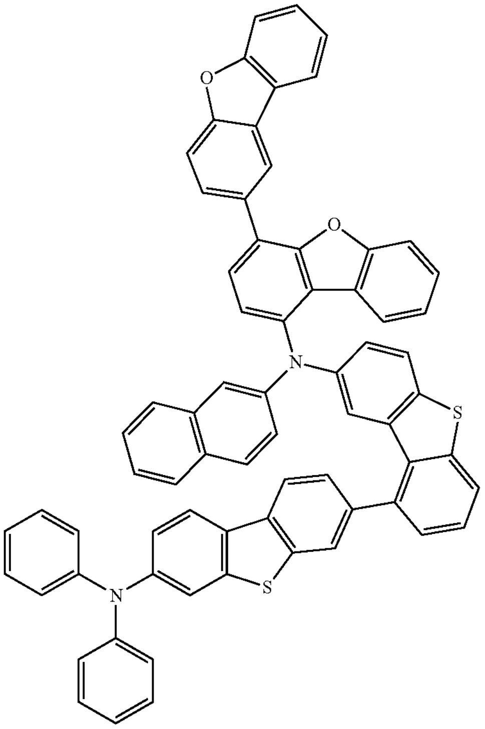
P-51
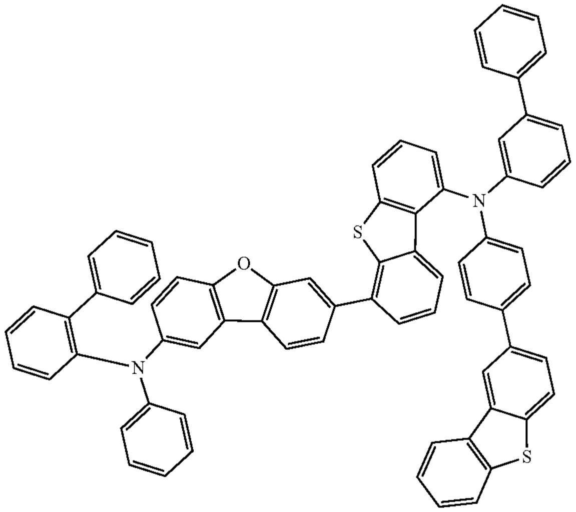
P-52
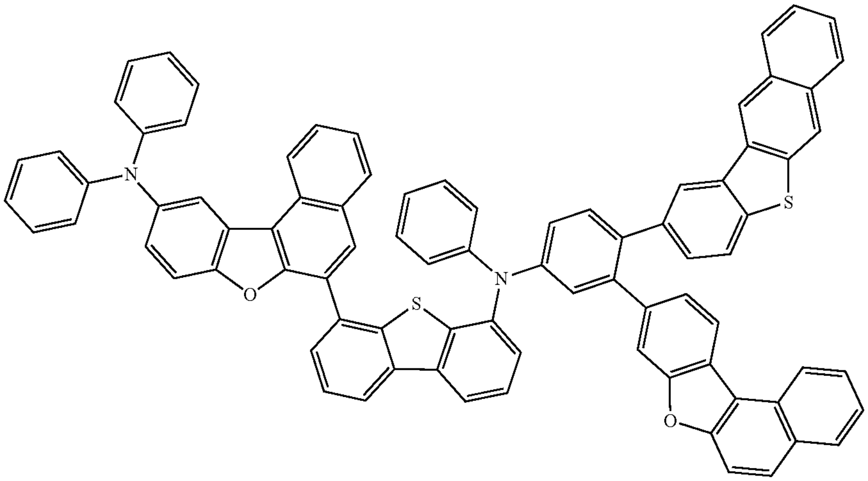

-continued
P-53
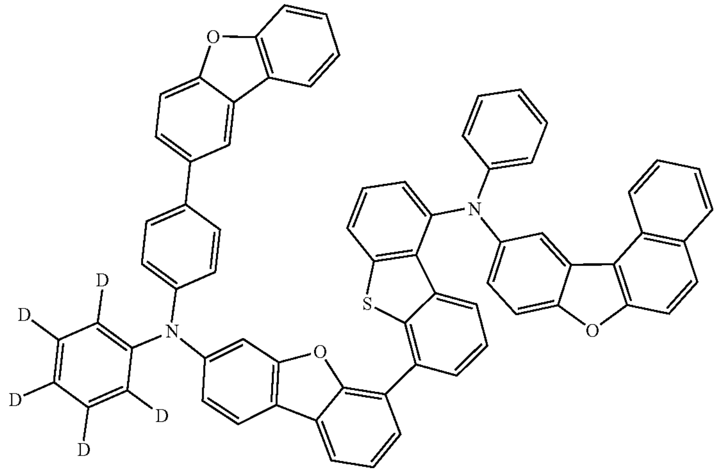
P-54
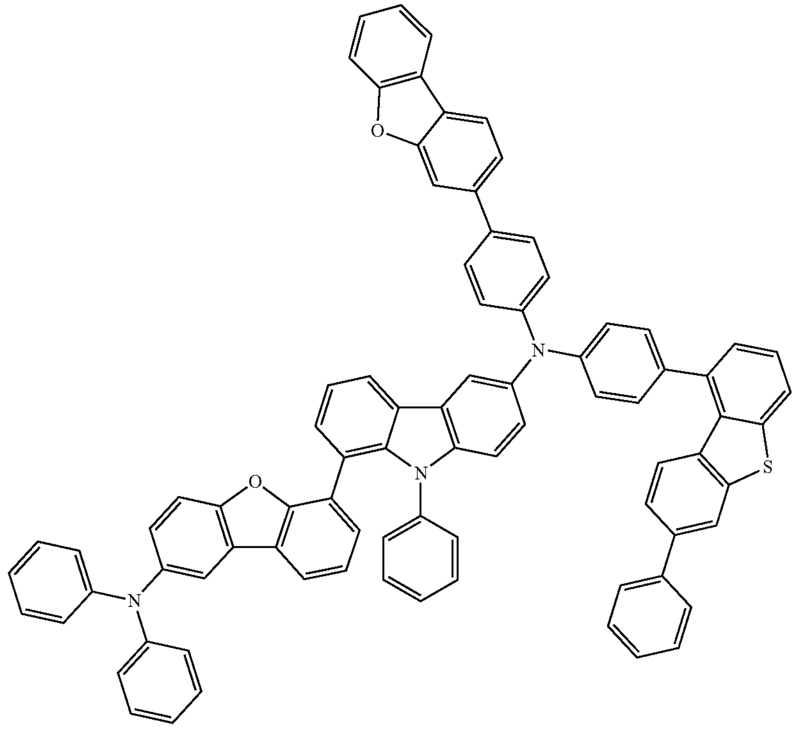

-continued
P-55
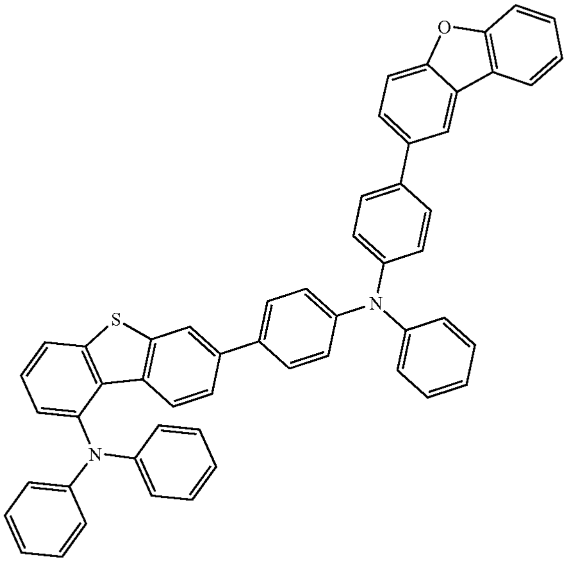
P-56
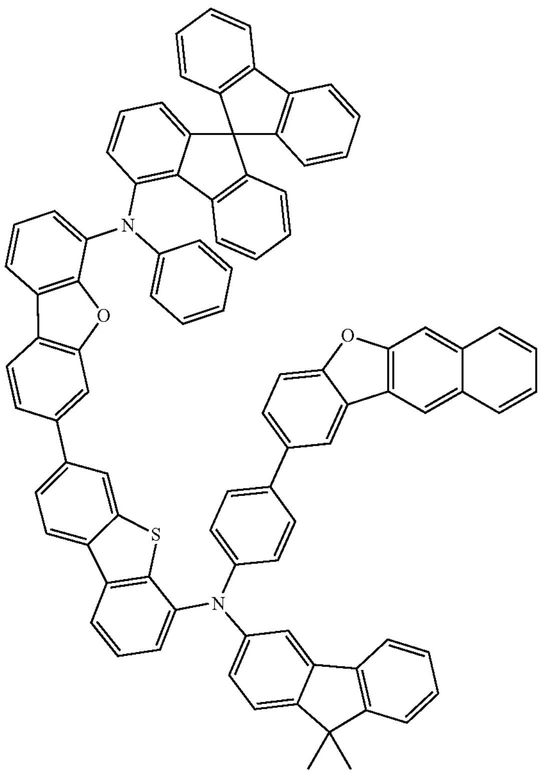
P-57
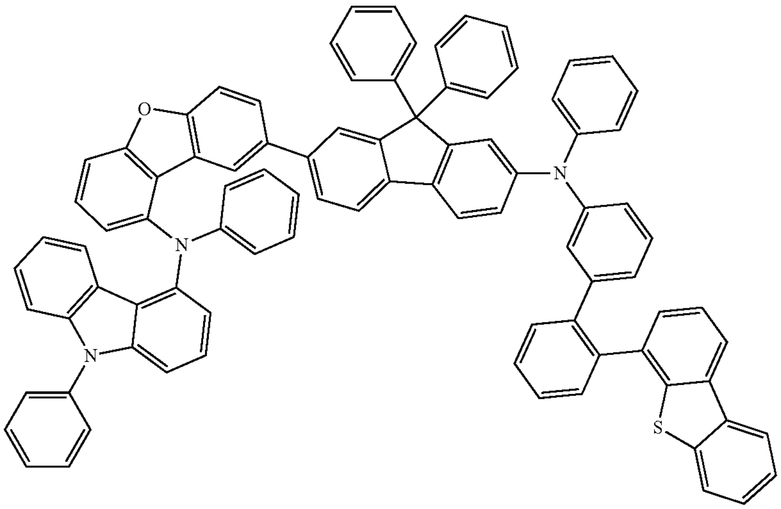

-continued
P-58
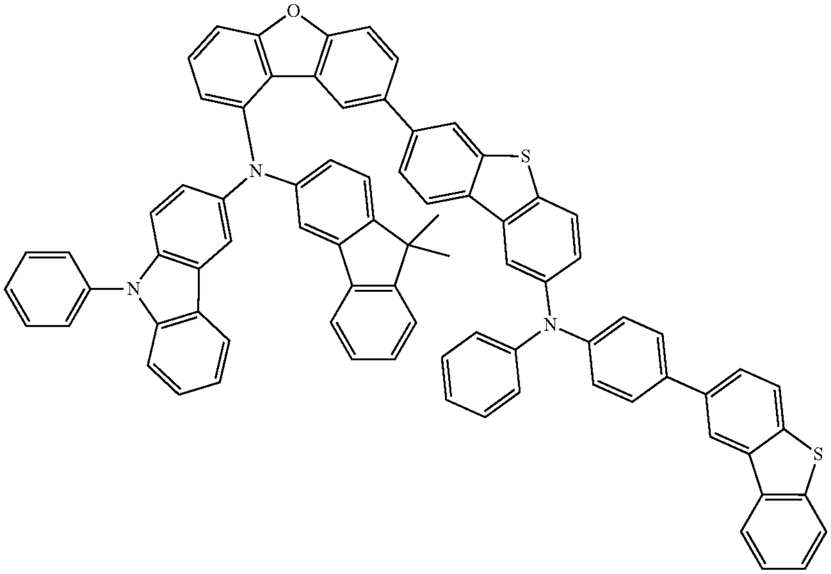
P-59
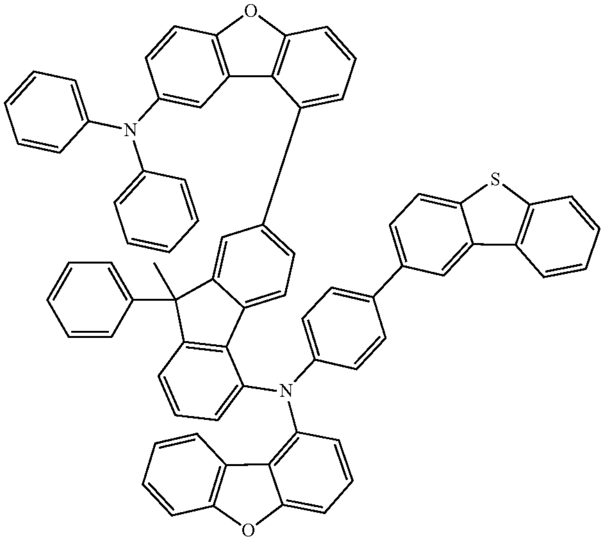
P-60
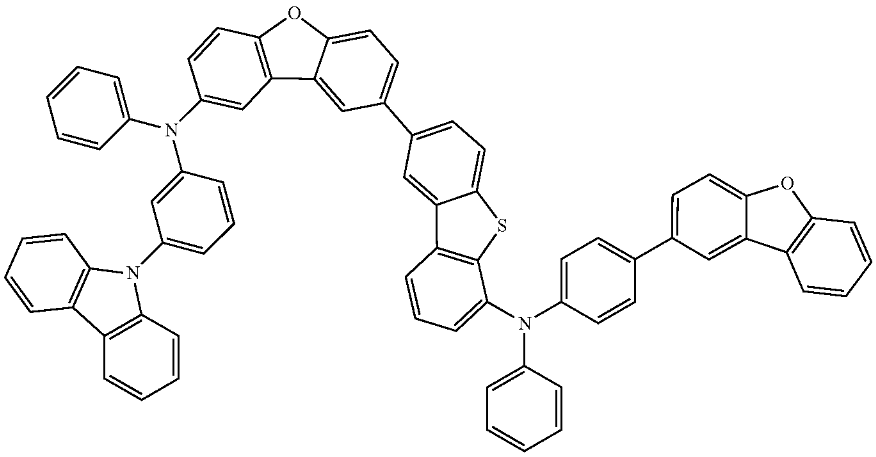

-continued
P-61
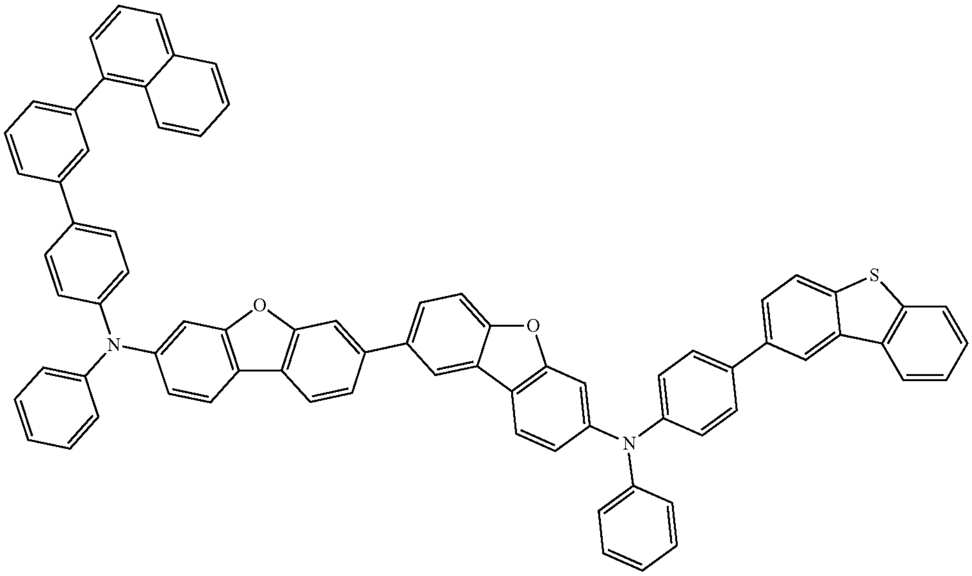
P-62
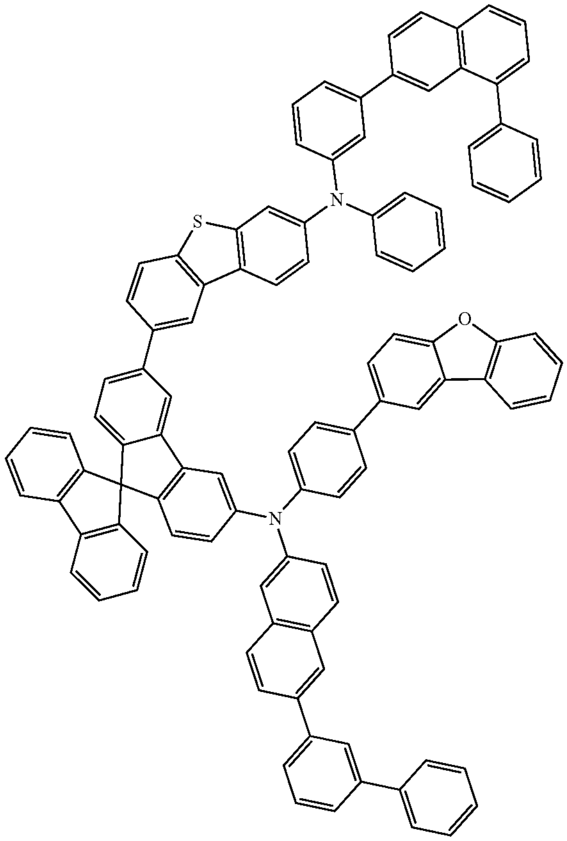
P-63
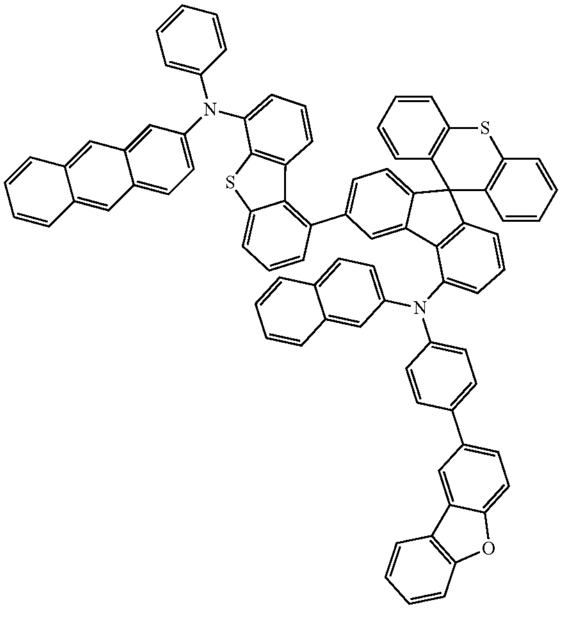

-continued
P-64
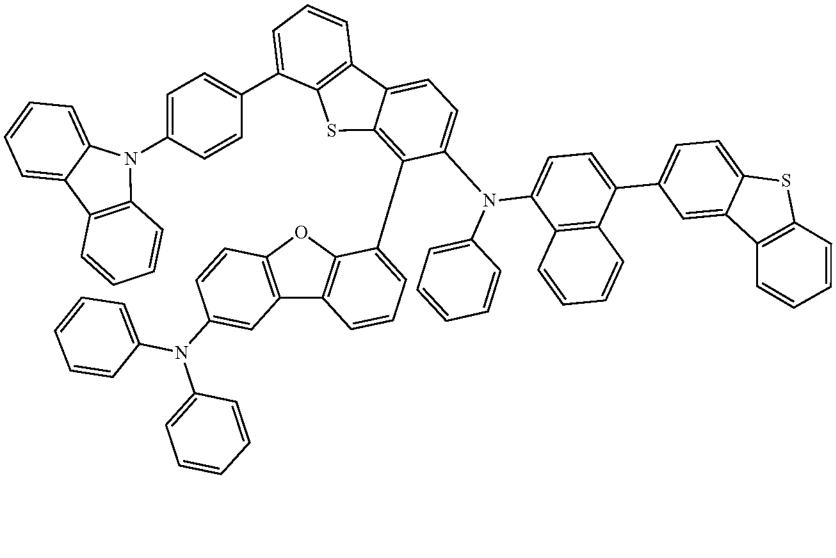
P-65
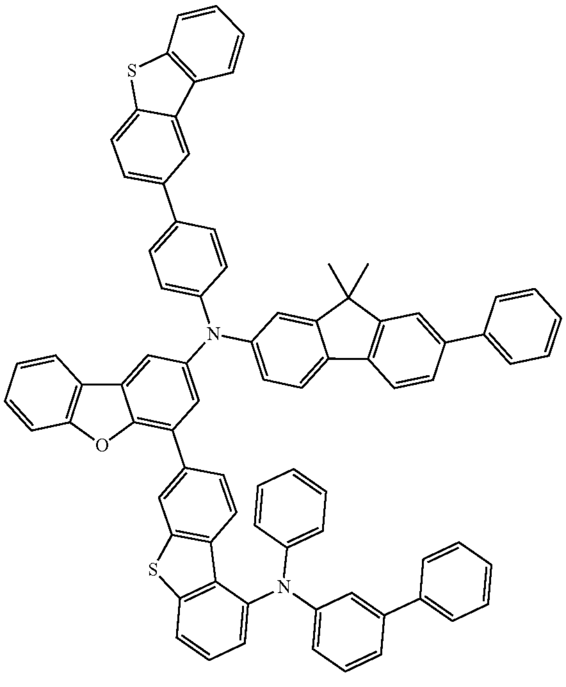
P-66
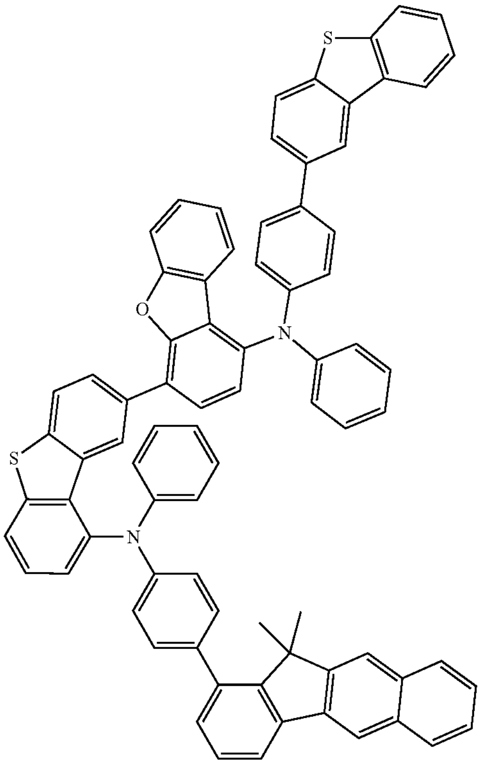

-continued
P-67
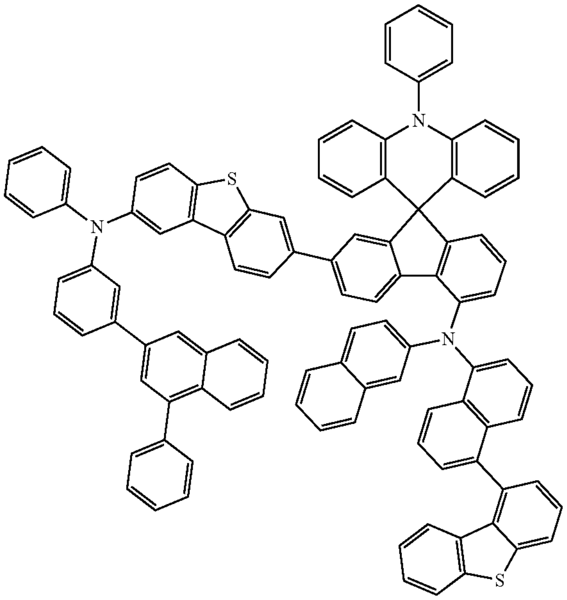
P-68
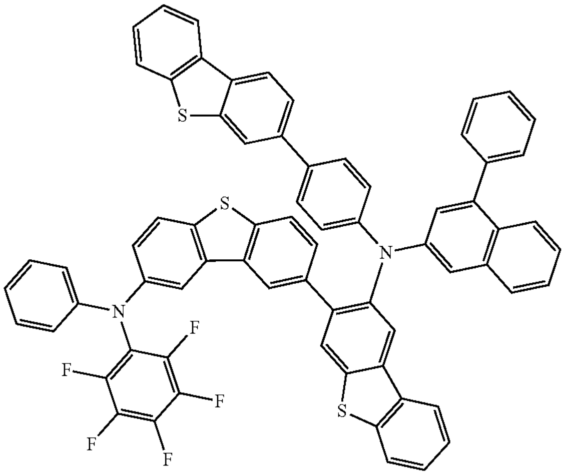
P-69
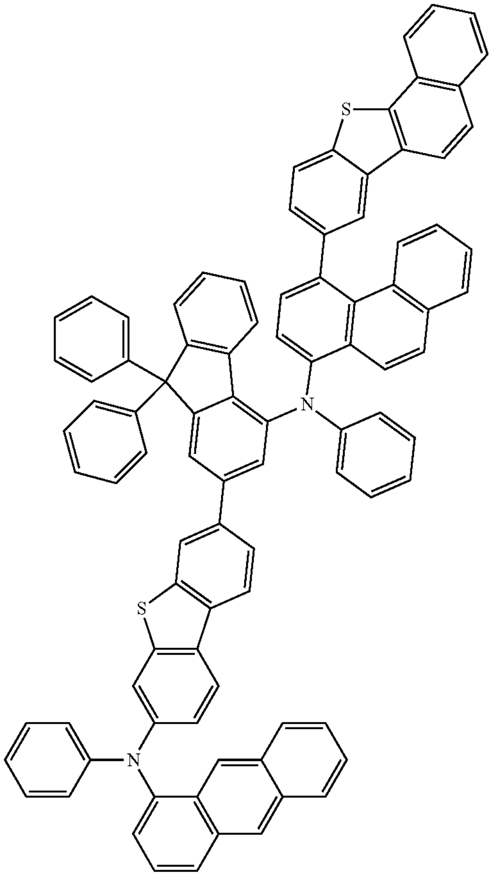
P-70
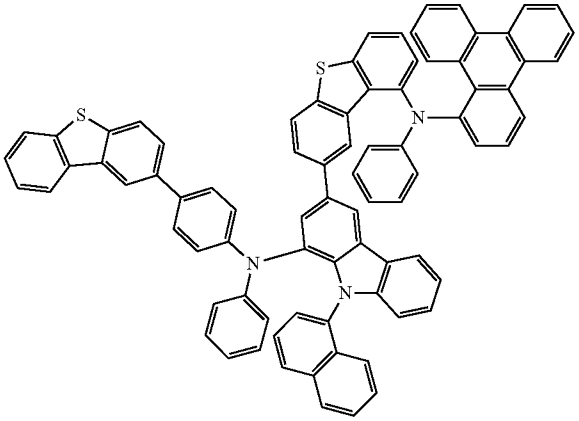

-continued
P-71
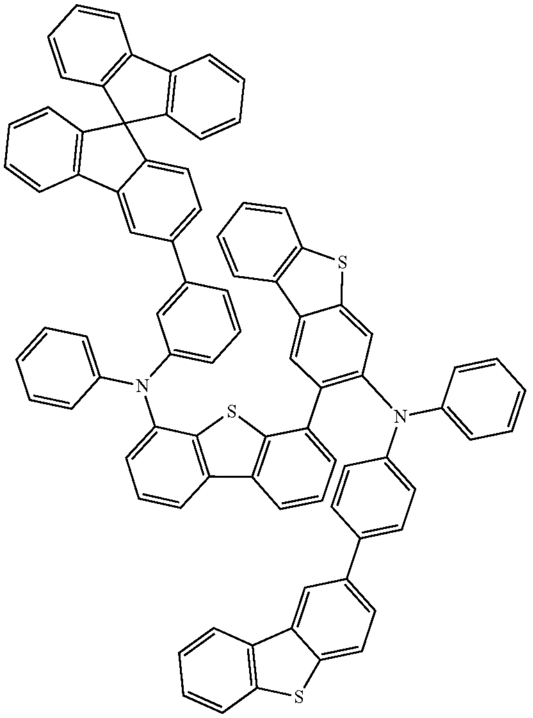
P-72
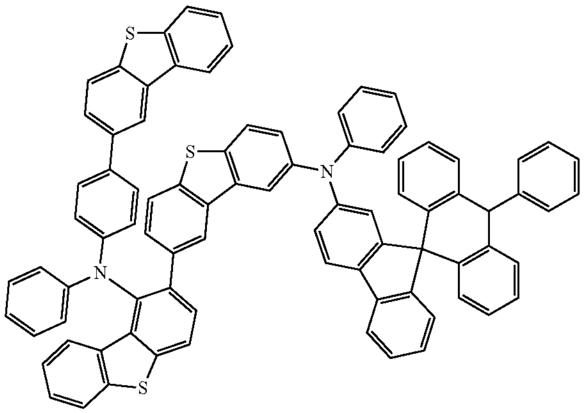
P-73
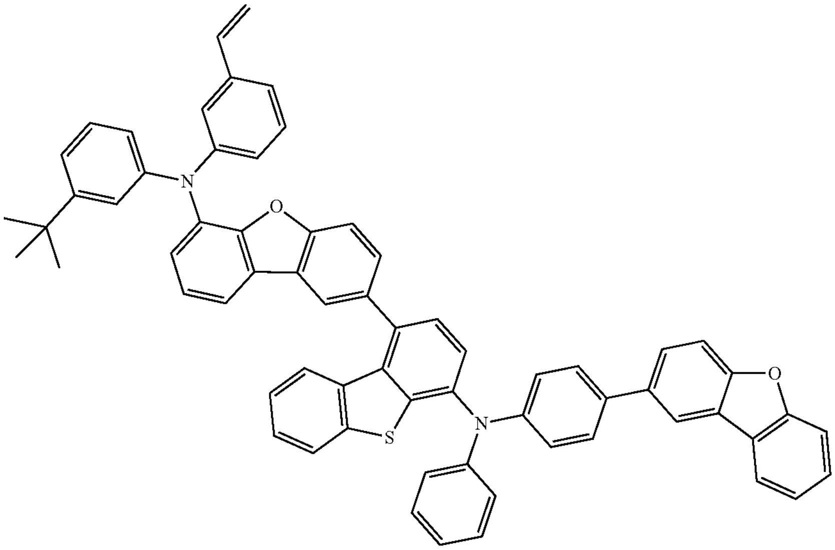

-continued
P-74
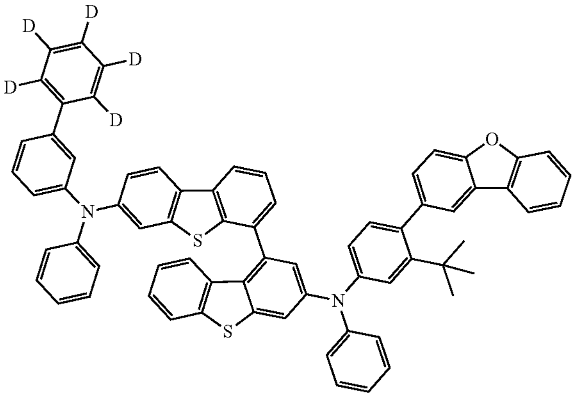
P-75
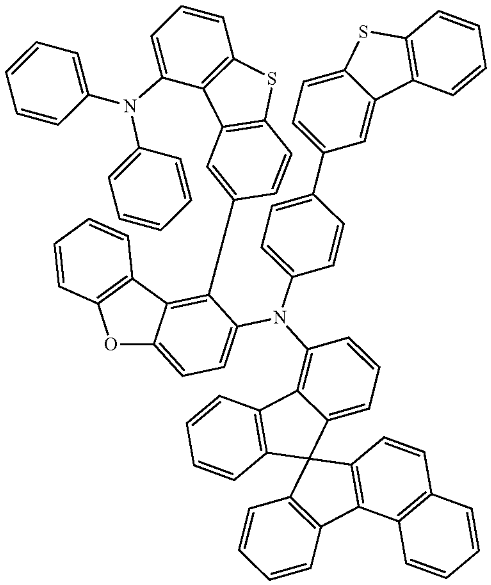
P-76
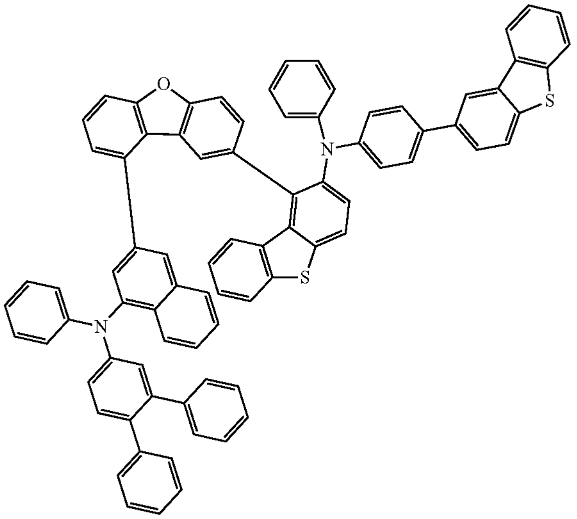
P-77
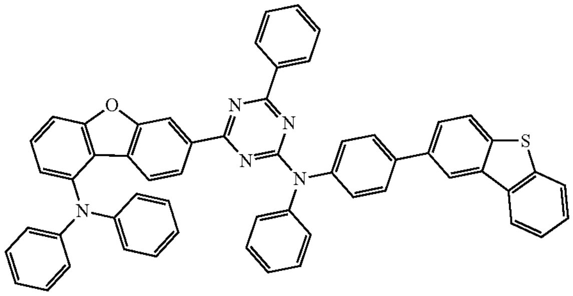

-continued
P-78
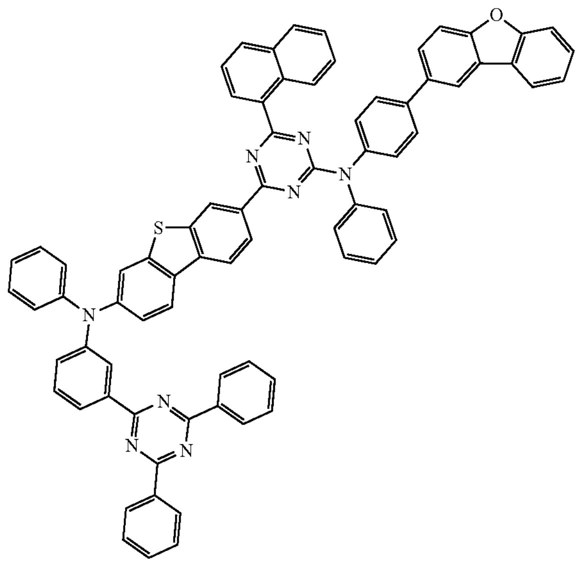
P-79
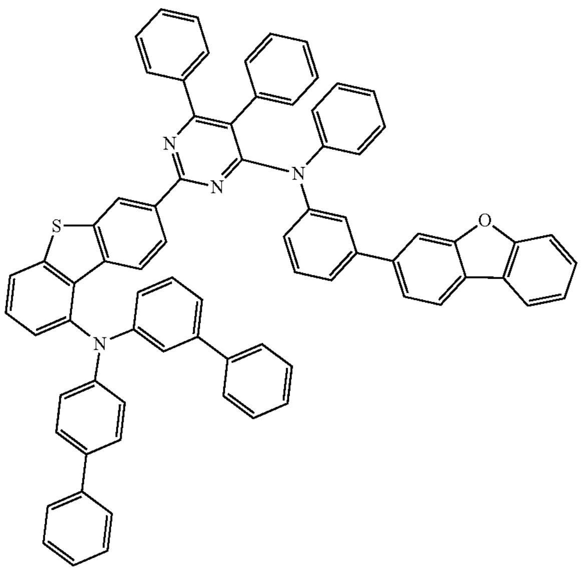
P-80
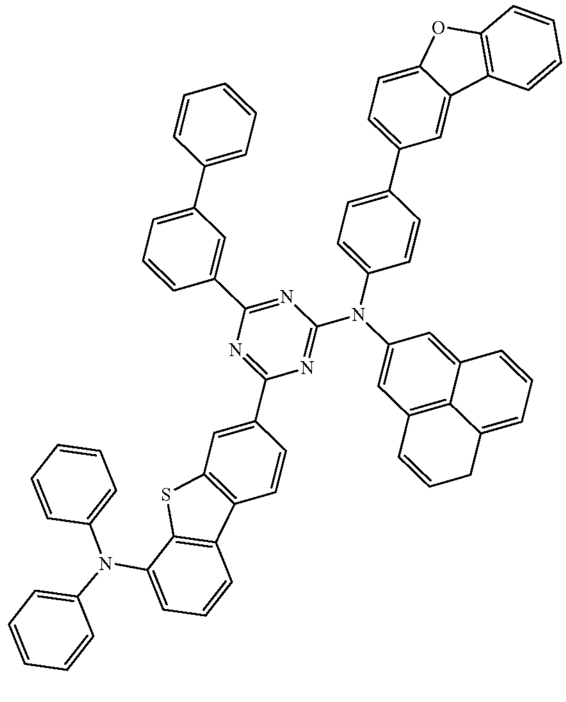
P-81
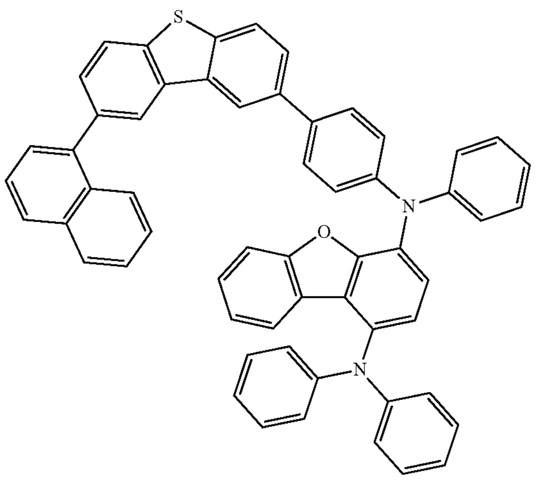

-continued
P-82
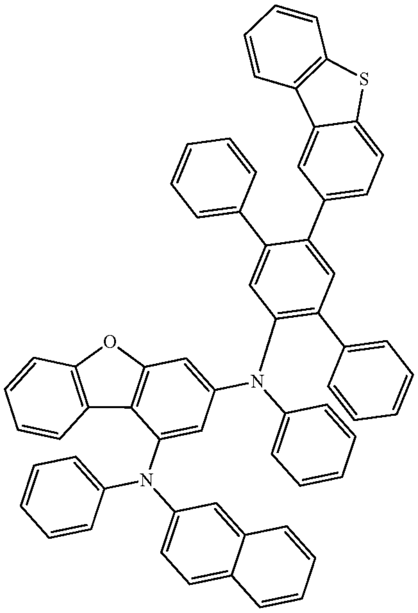
P-83
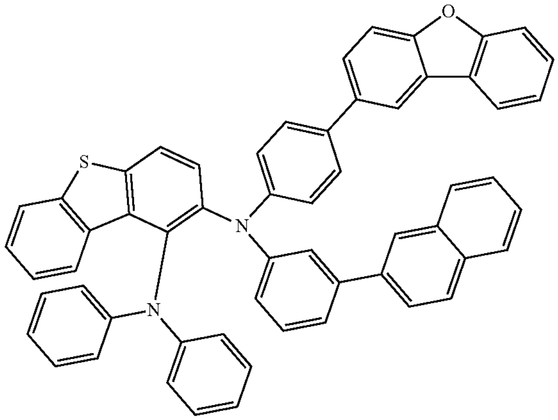
P-84
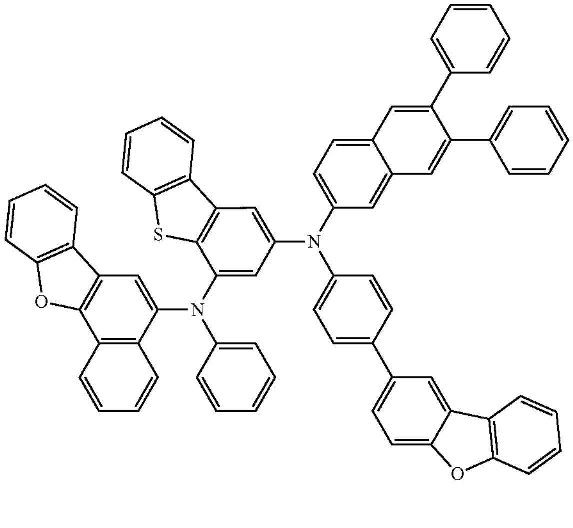
P-85
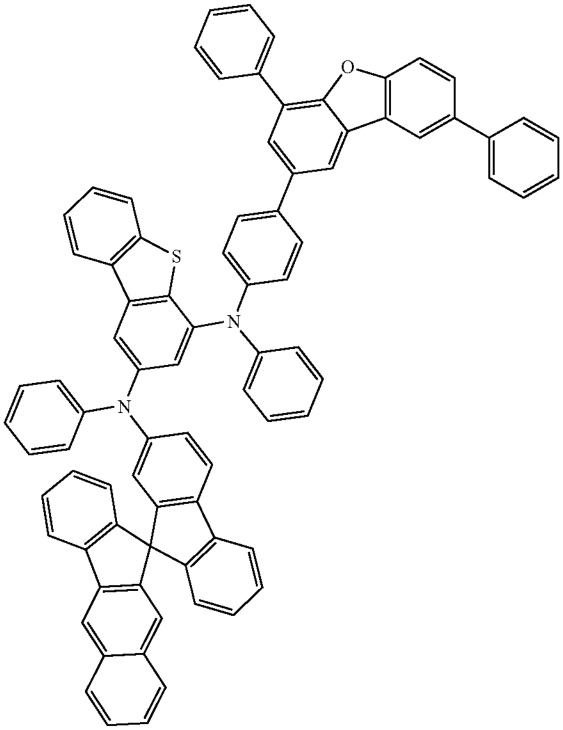

-continued
P-86
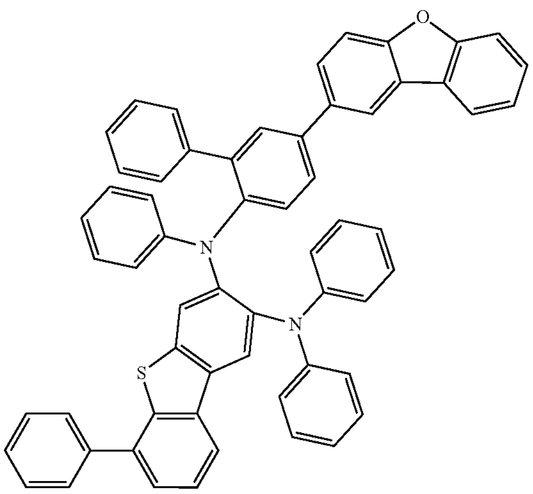
P-87
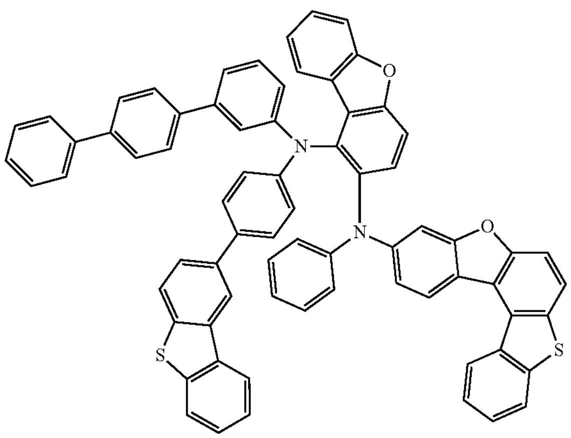
P-88
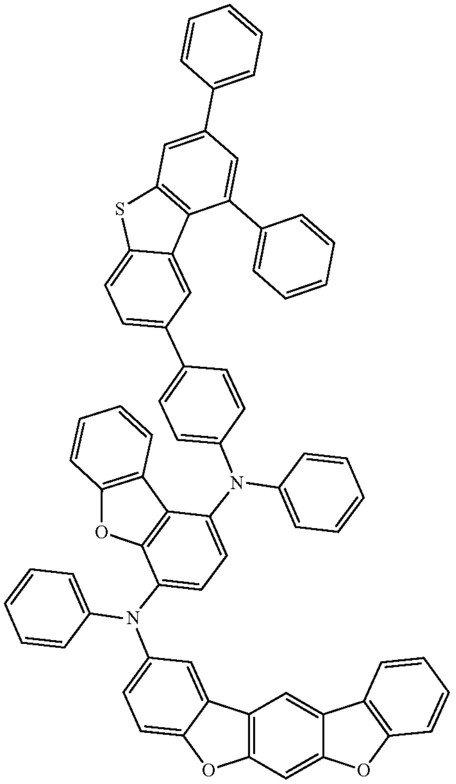
P-89
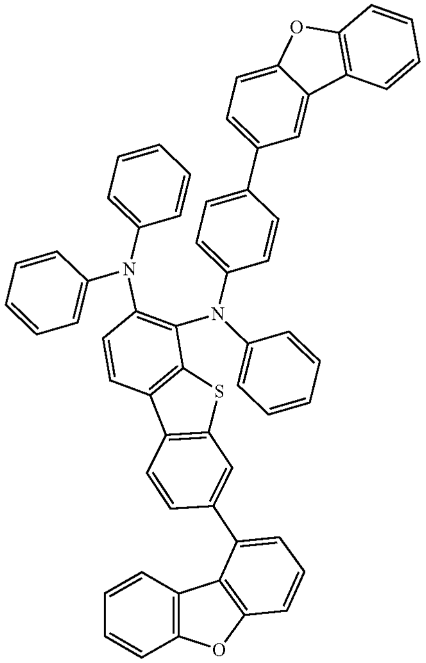

-continued
P-90
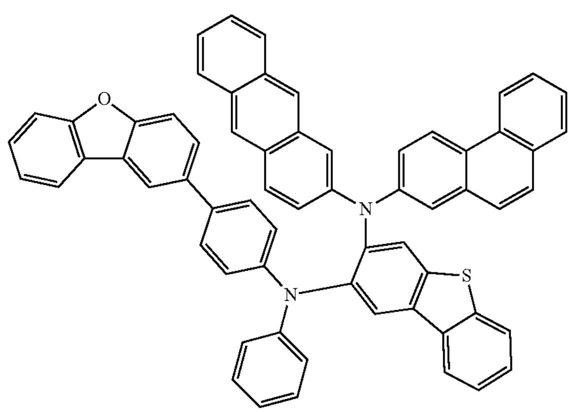
P-91
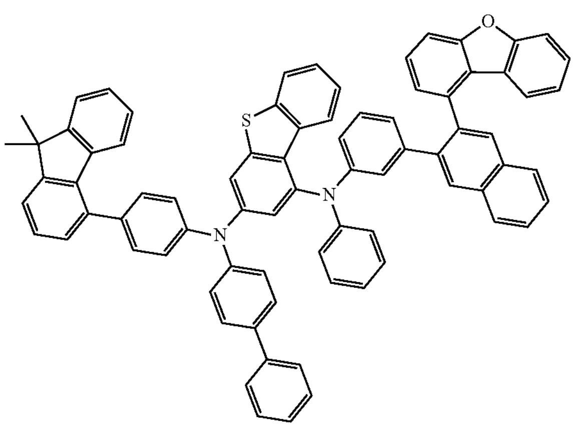
P-92
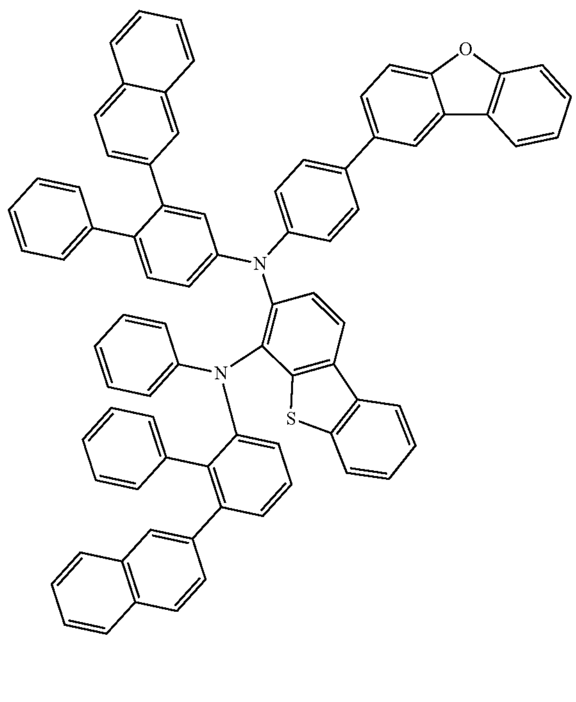
P-93
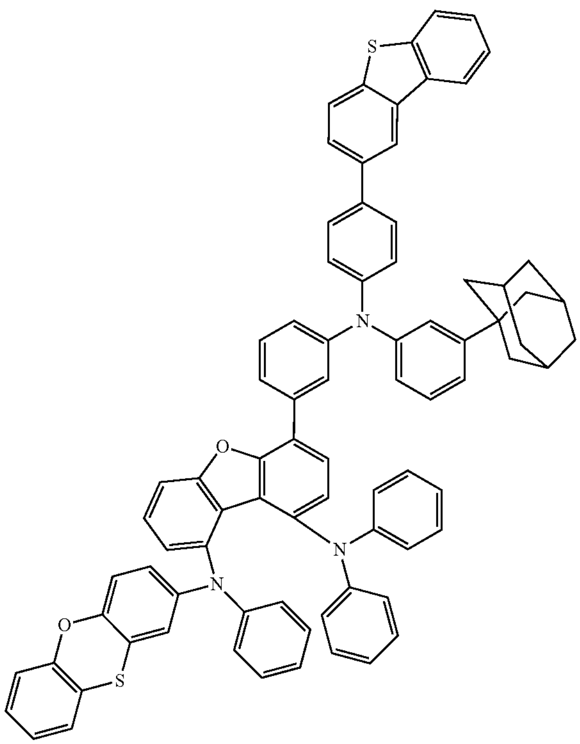

-continued
P-94
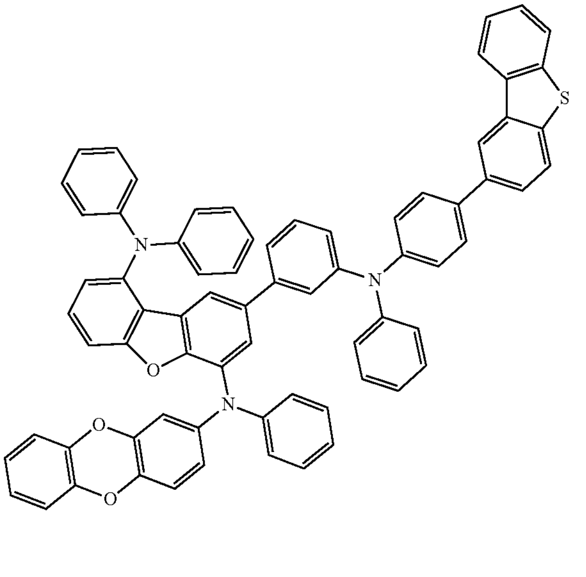
P-95
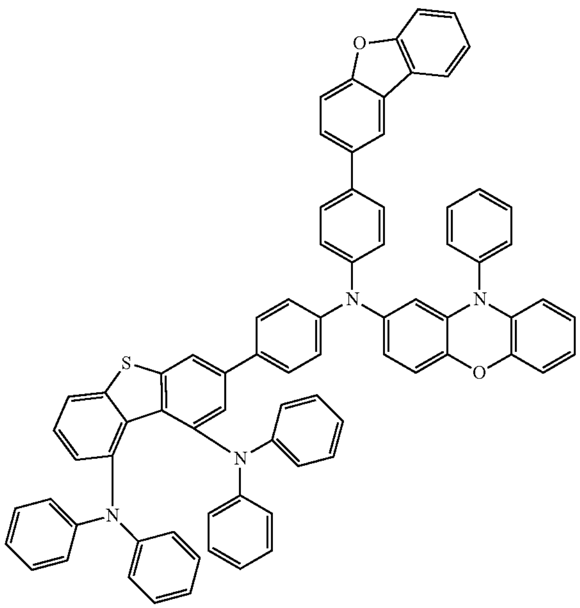
P-96
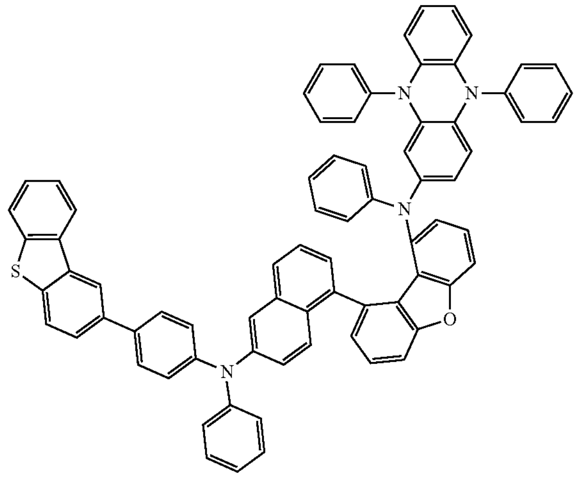
P-97
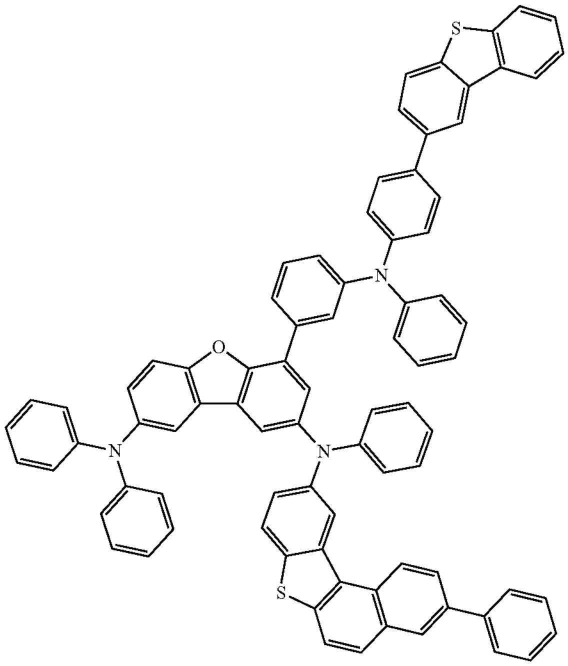

-continued
P-98
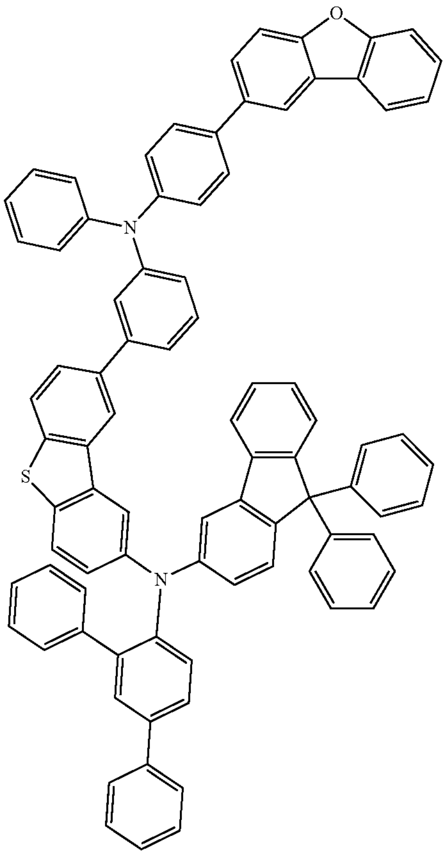
P-99
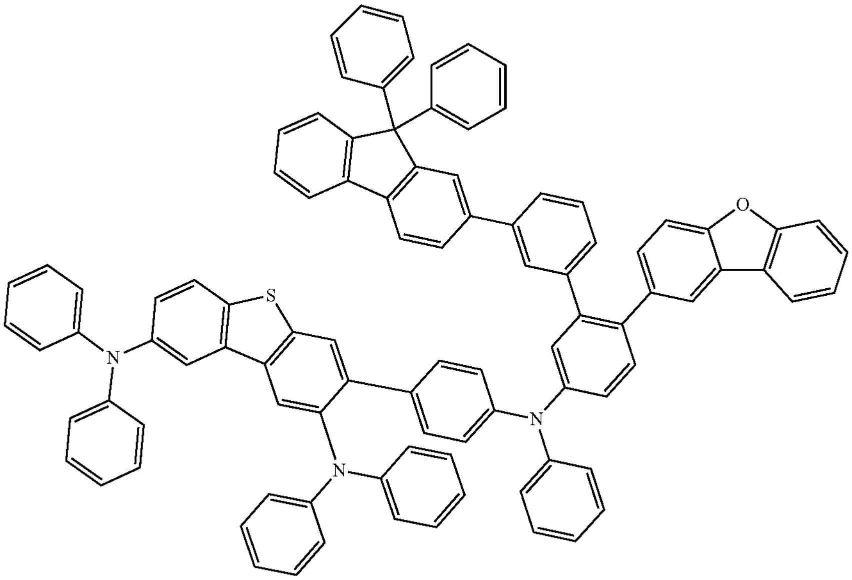

-continued
P-100
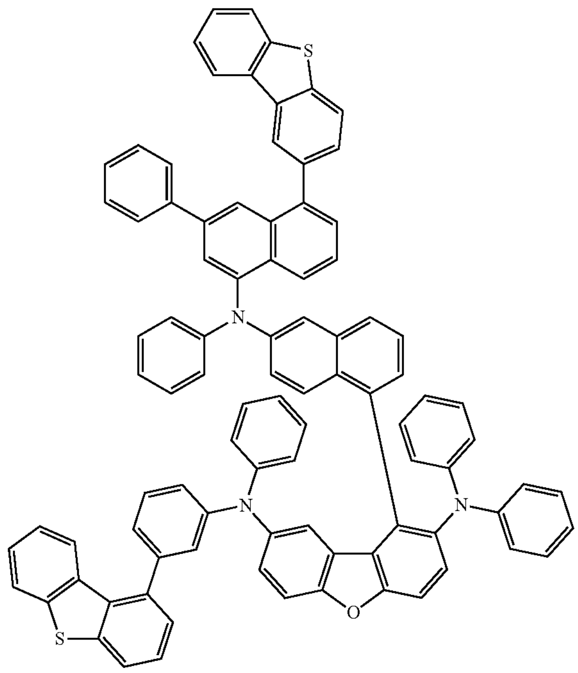
P-101
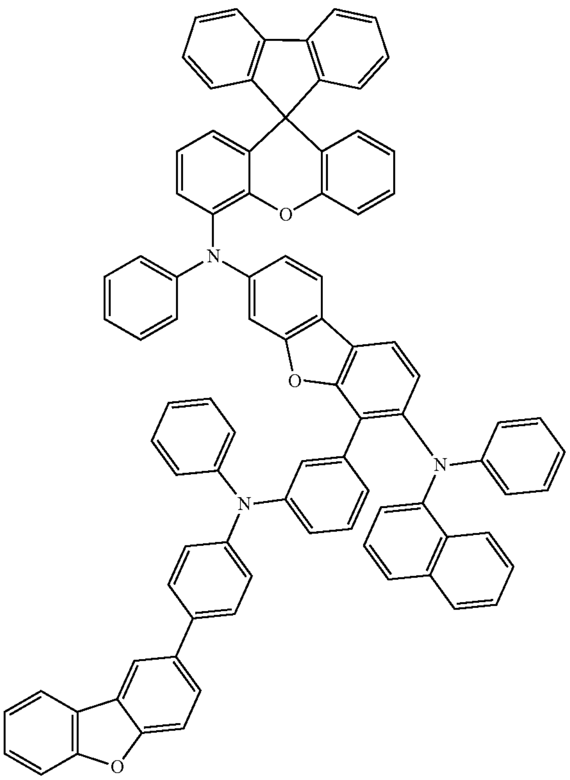
P-102
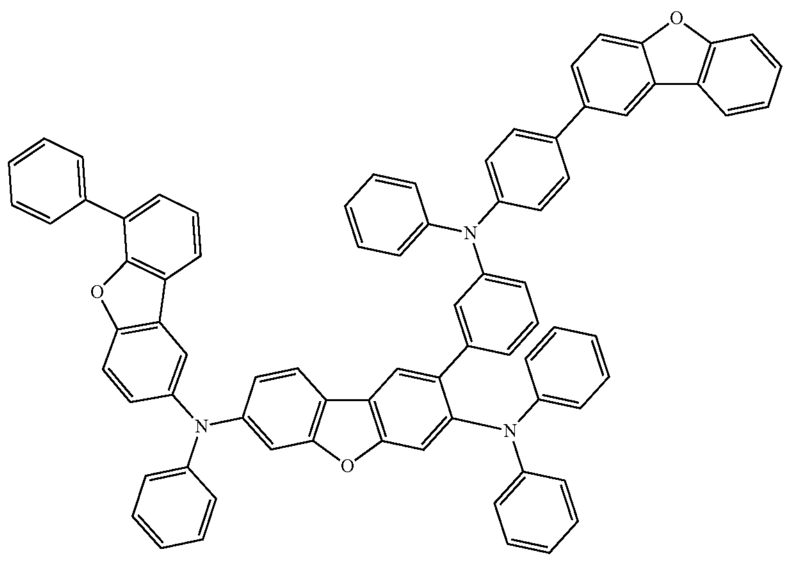

-continued
P-103
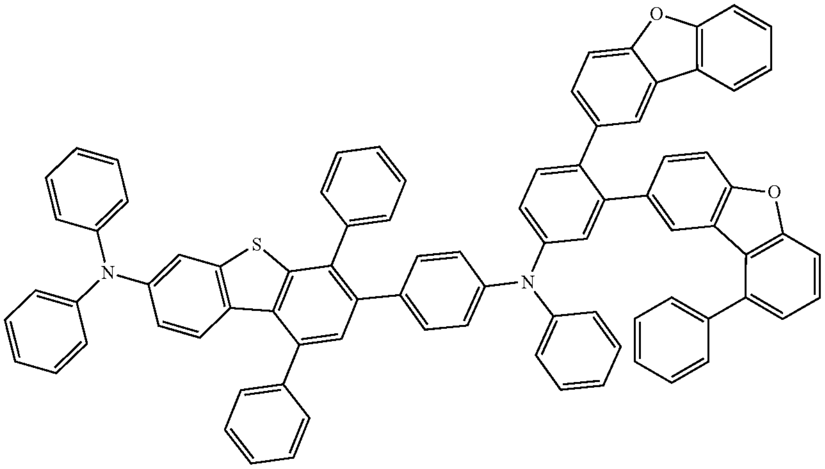
P-104
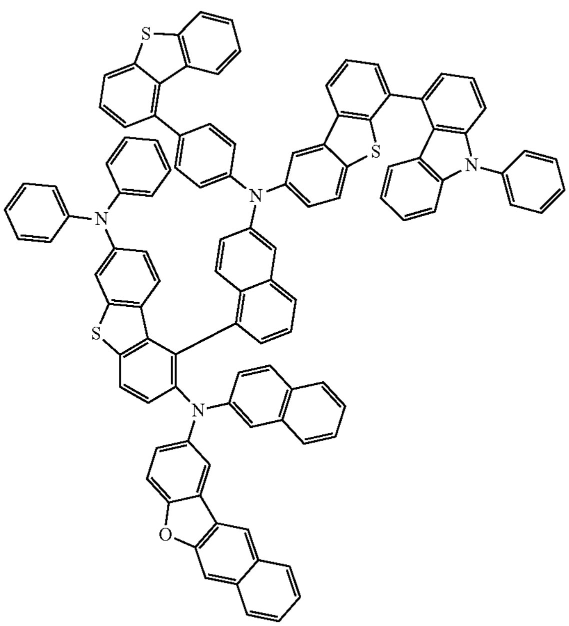
P-105
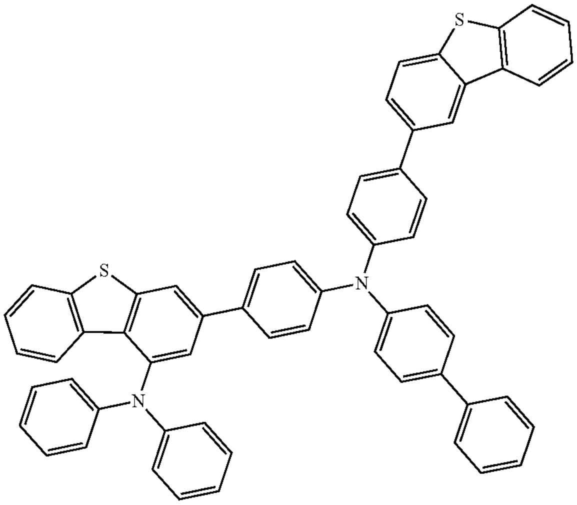

-continued
P-106
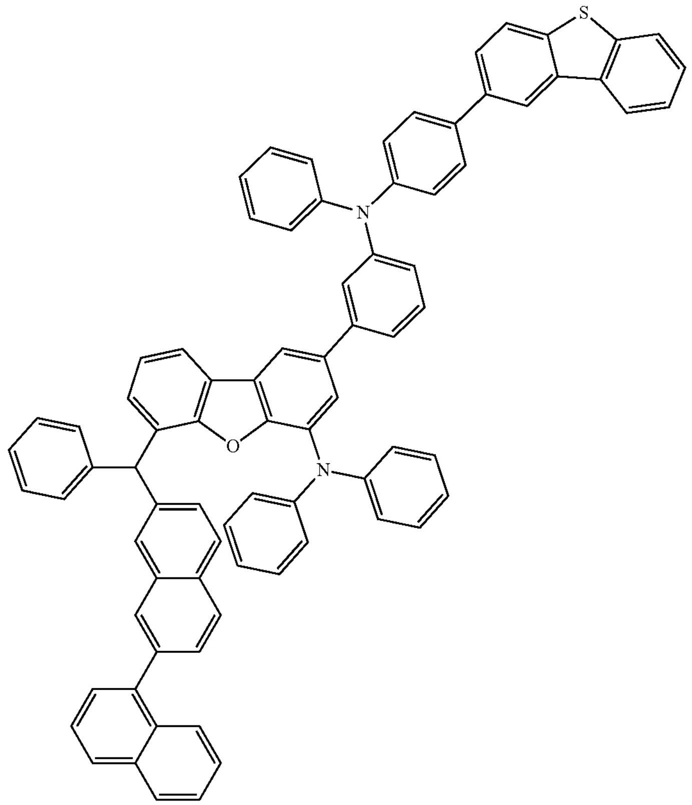
P-107
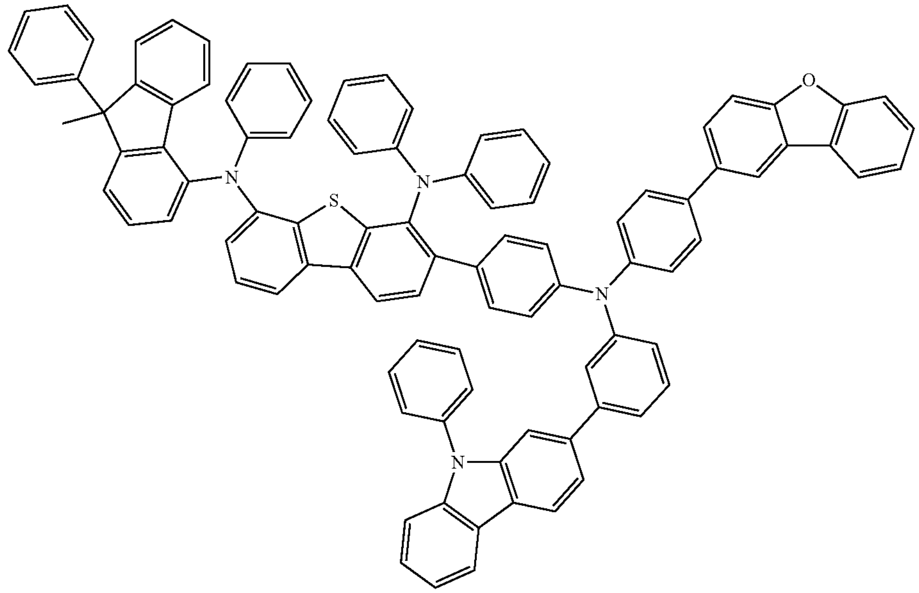

-continued
P-108
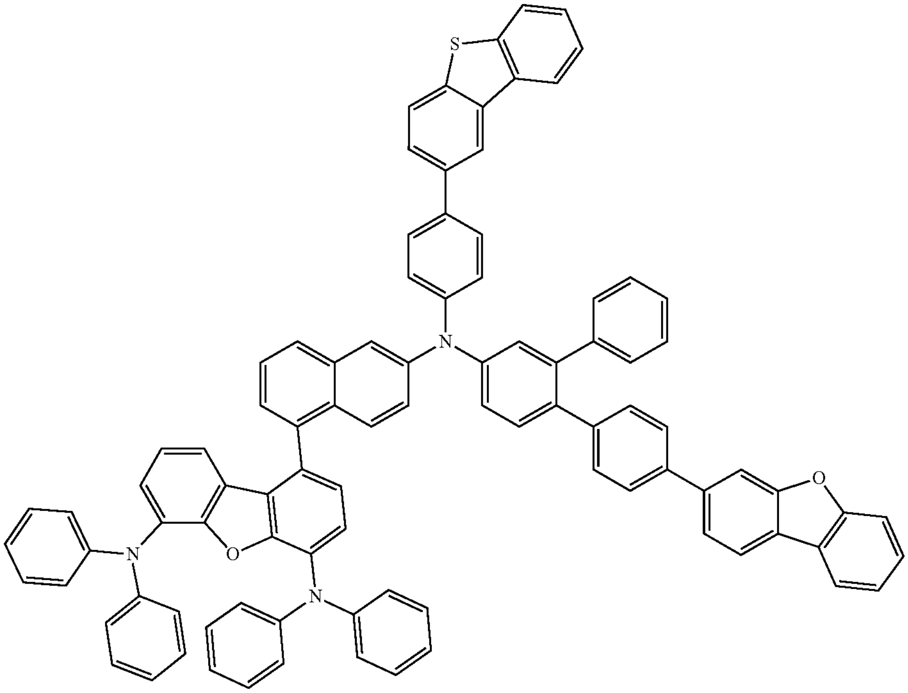
P-109
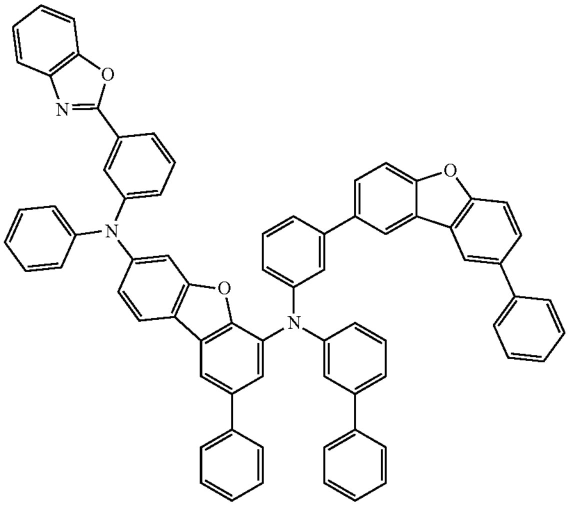
P-110
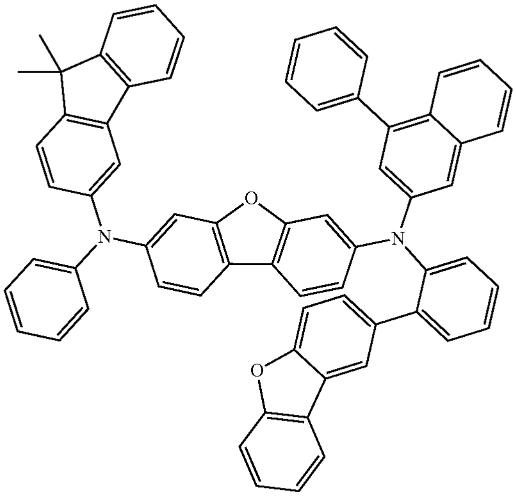

-continued
P-111
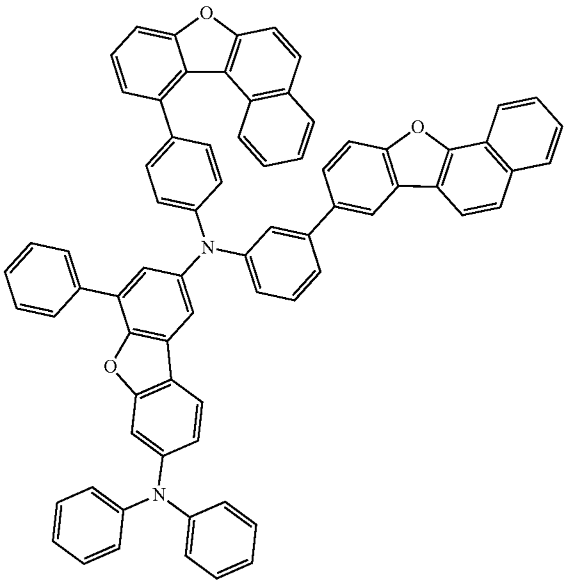
P-112
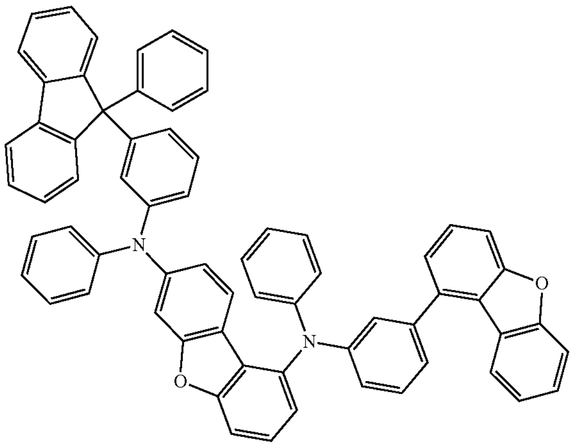
P-113
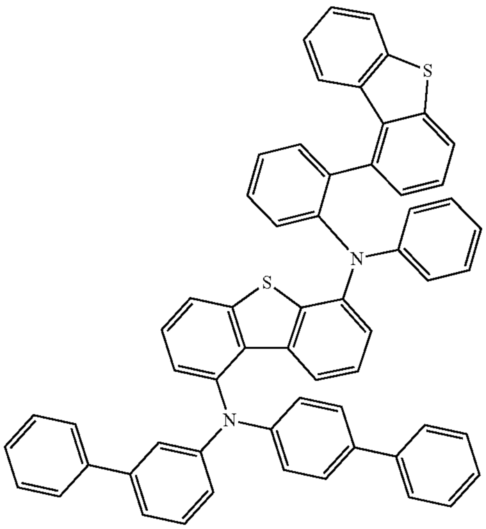
P-114
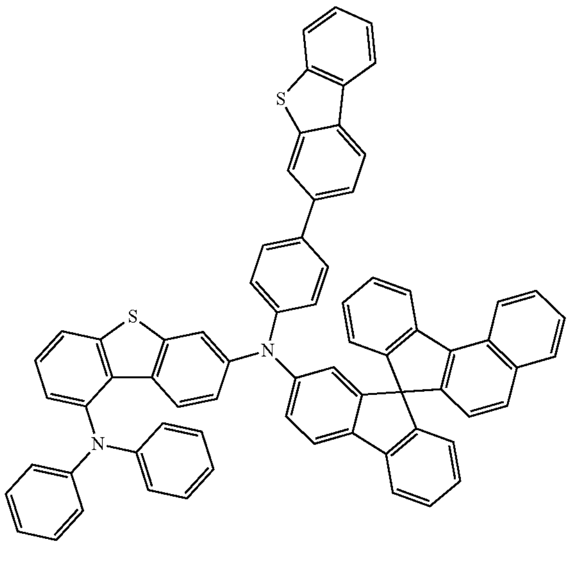

-continued
P-115
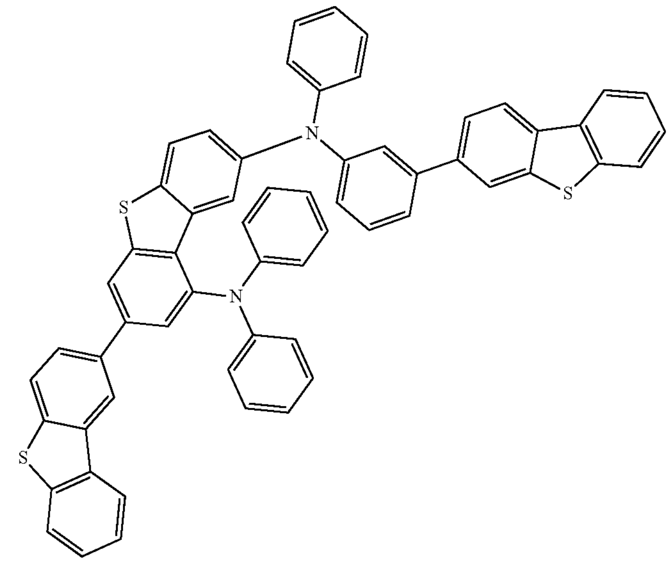
P-116
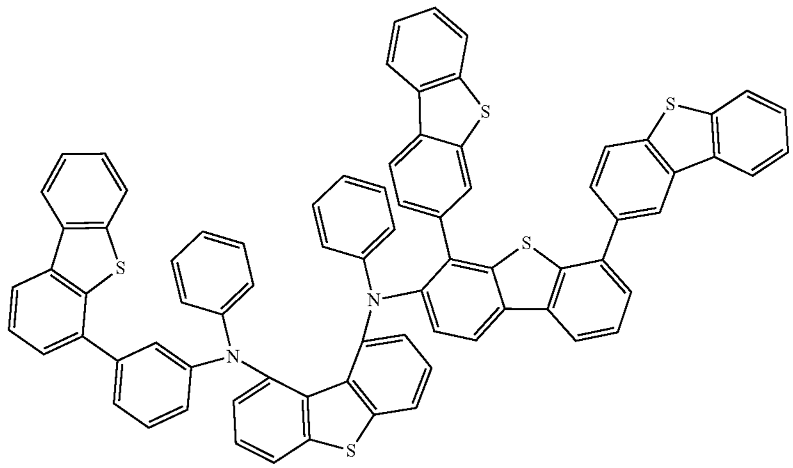
P-117
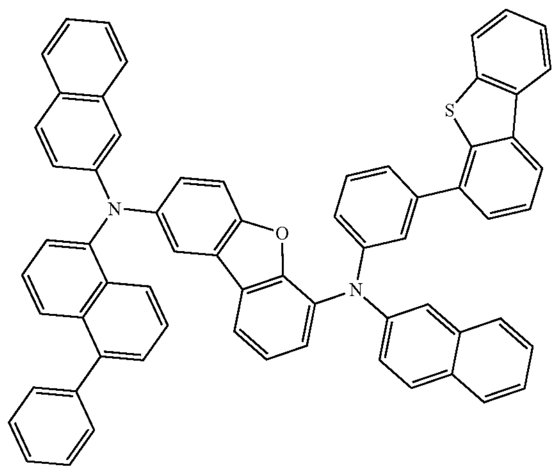
P-118
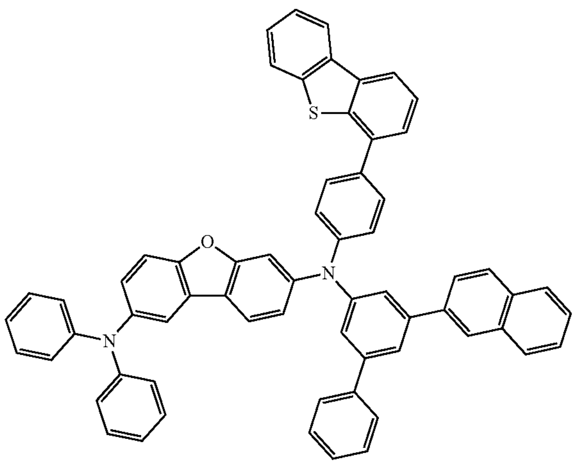

-continued
P-119
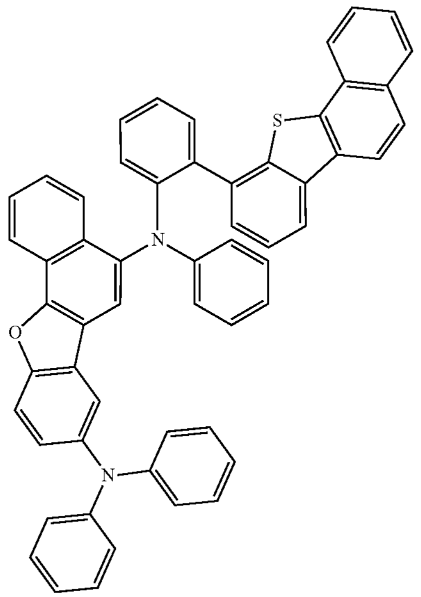
P-120
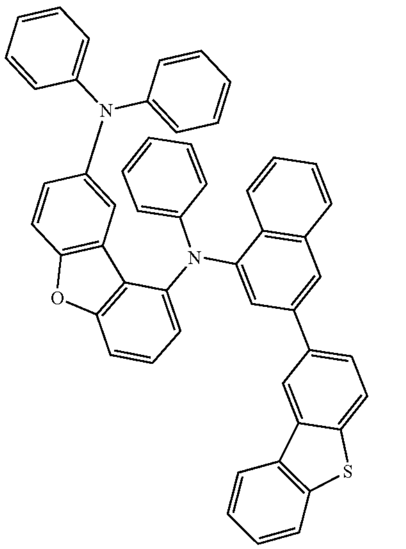
P-121
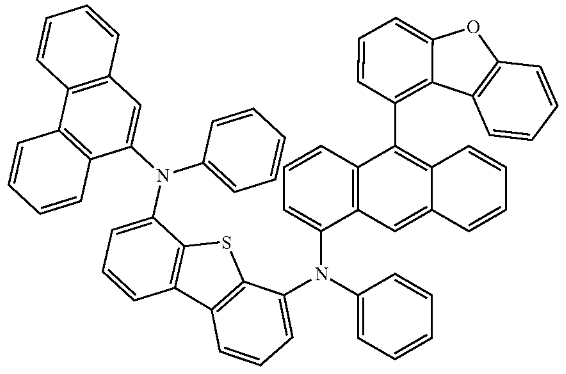
P-122
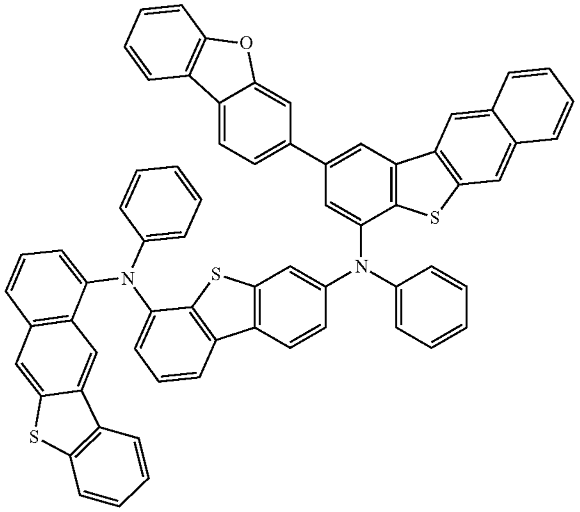

-continued
P-123
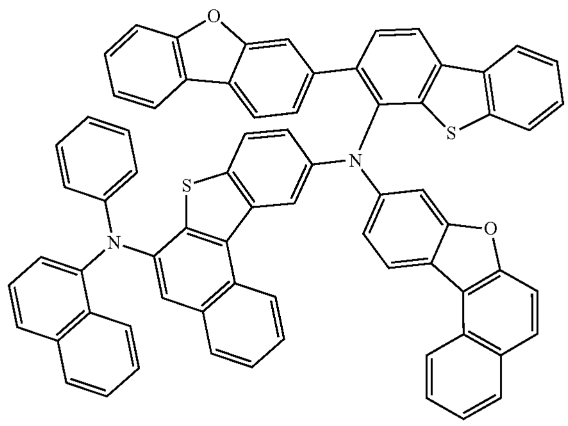
P-124
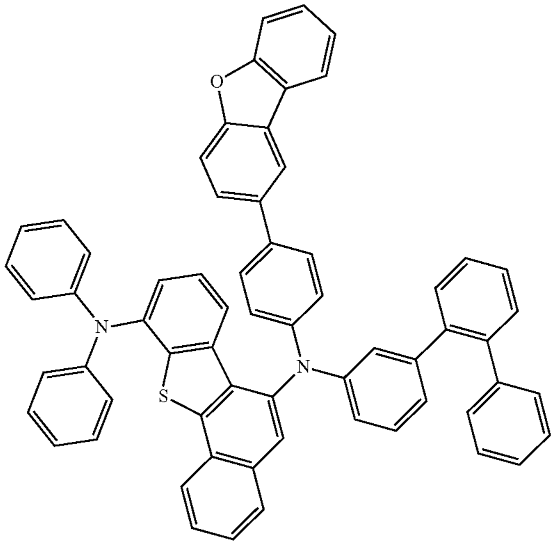
P-125
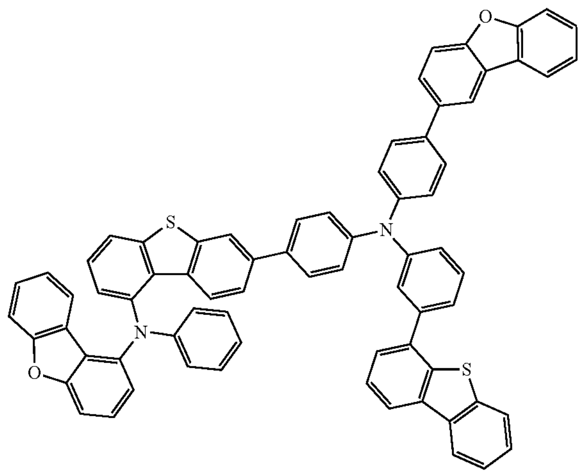
P-126
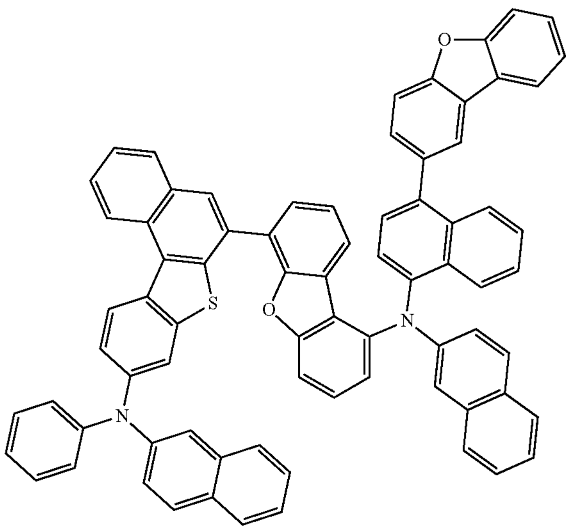

-continued
P-127
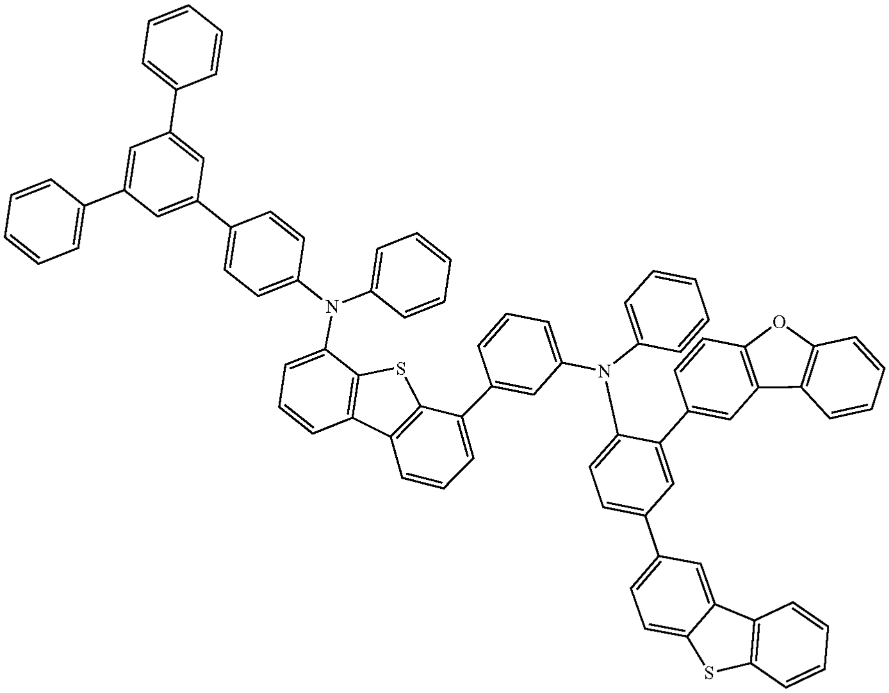
P-128
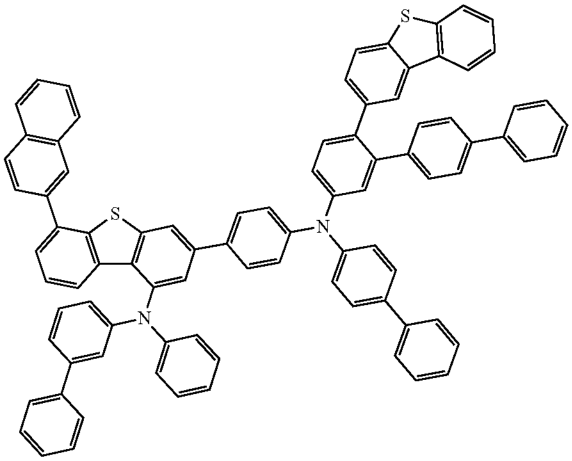
P-129
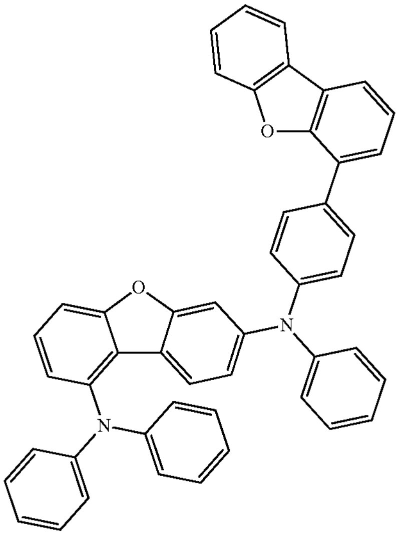

-continued
P-130
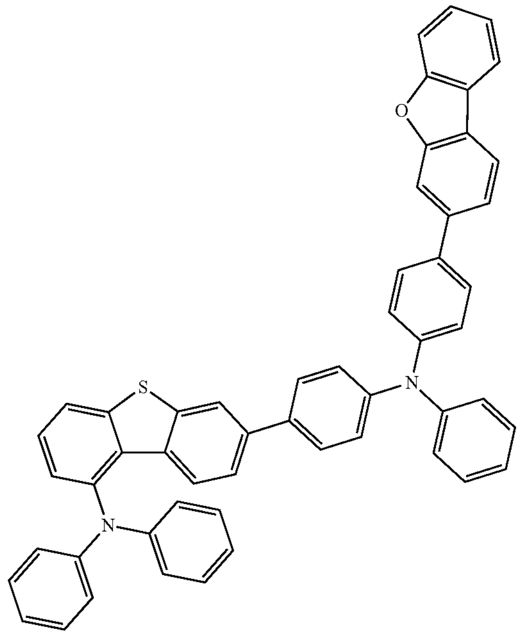
P-131
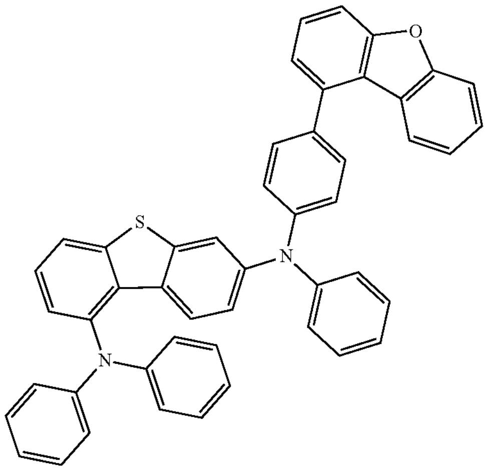
P-132
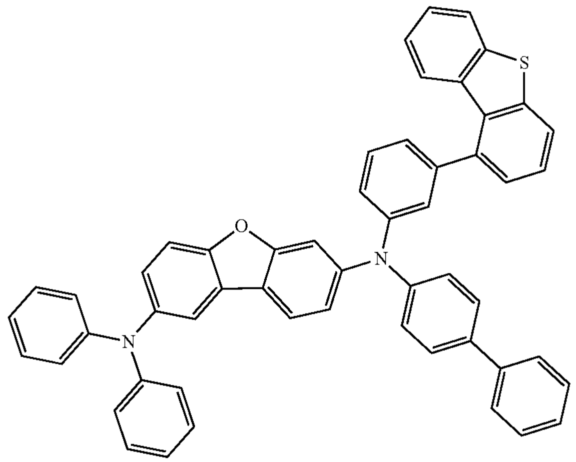
P-133
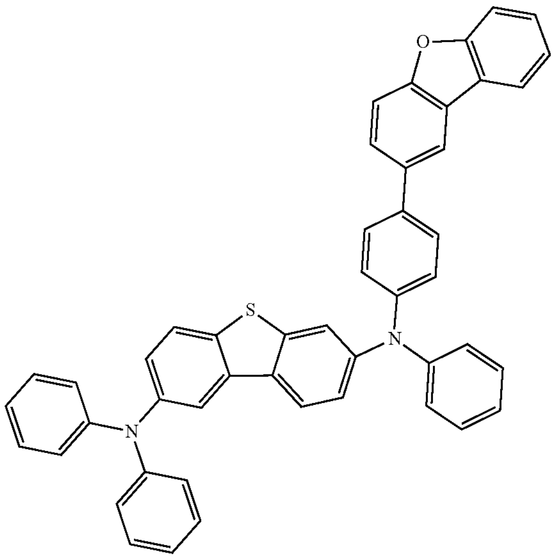
P-134
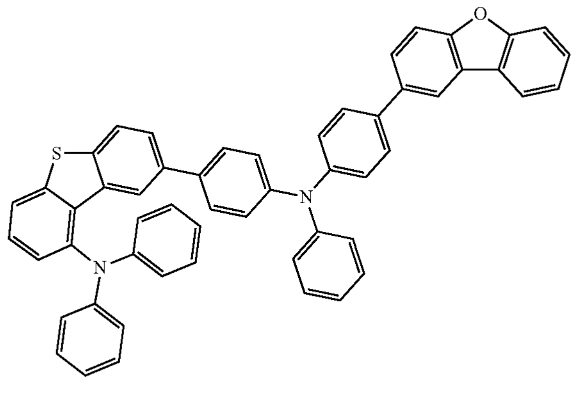
P-135
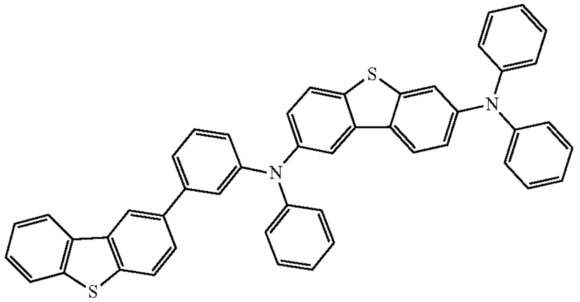

-continued
P-136
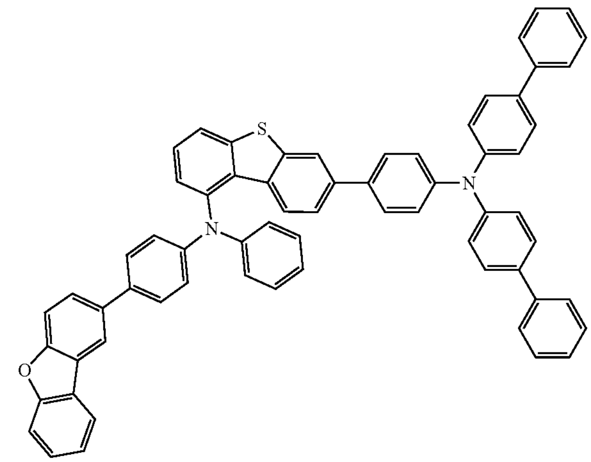
P-137
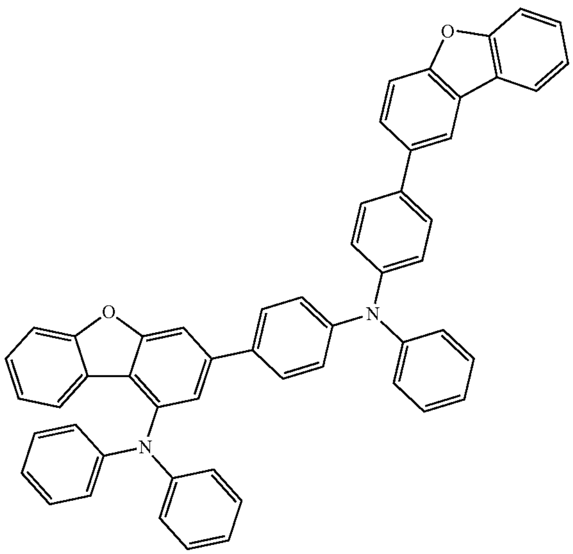
P-138
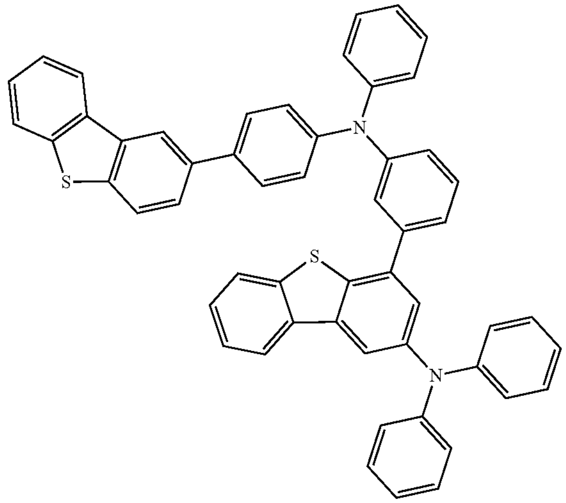
P-139
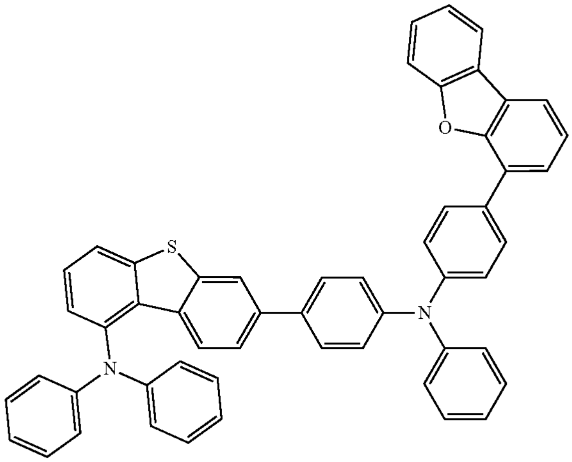
P-140
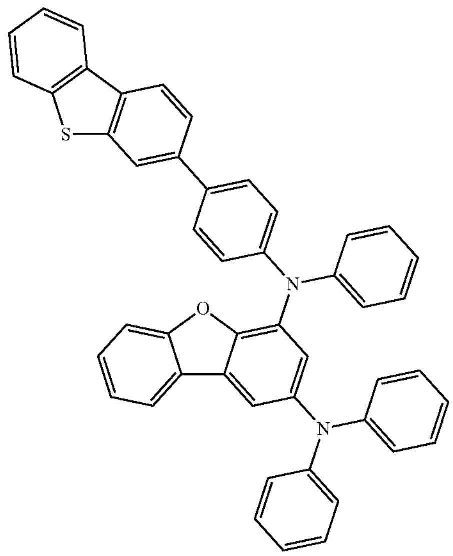
P-141
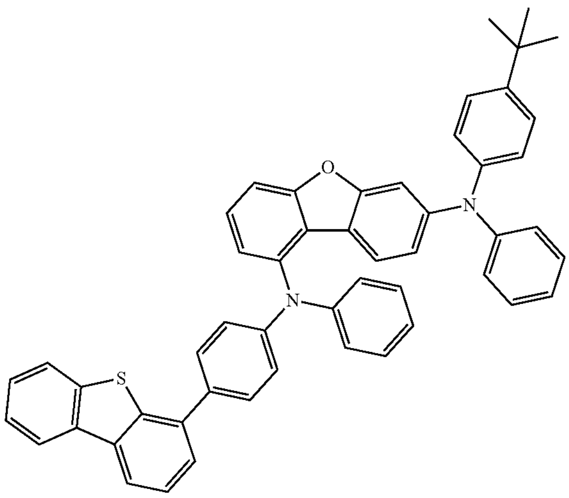

-continued
P-142
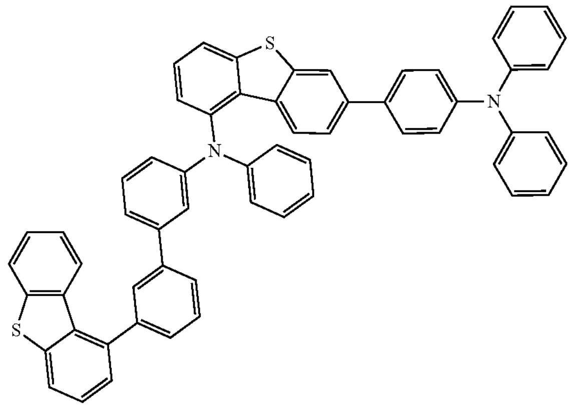
P-143
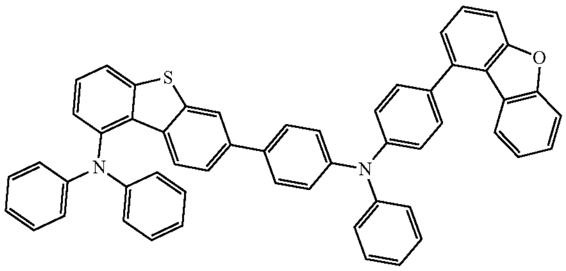
P-144
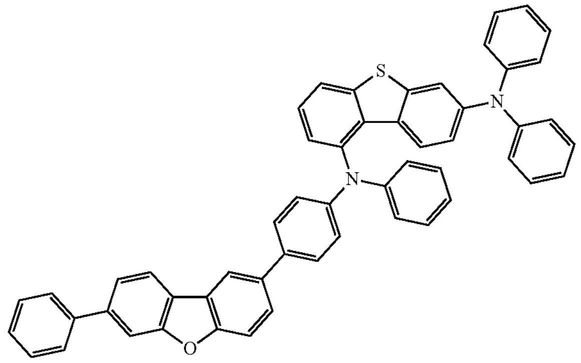
P-145
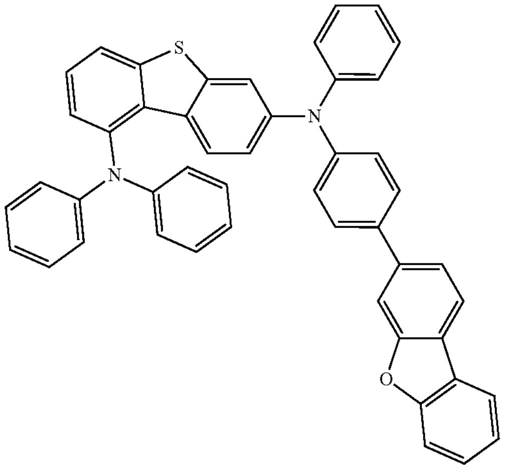
P-146
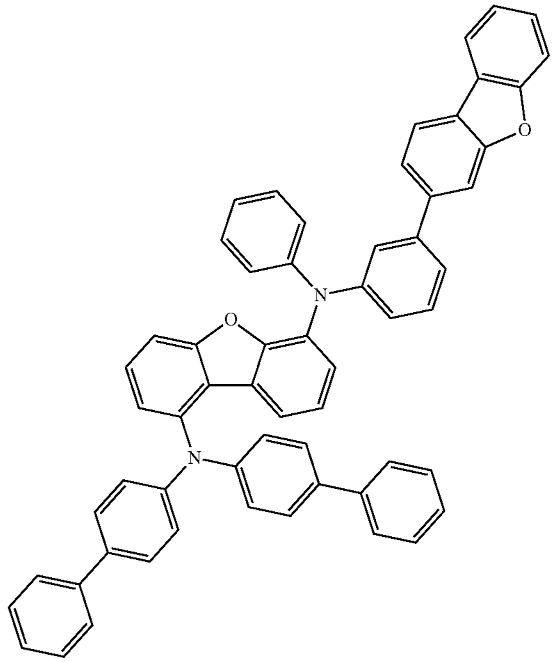
P-147
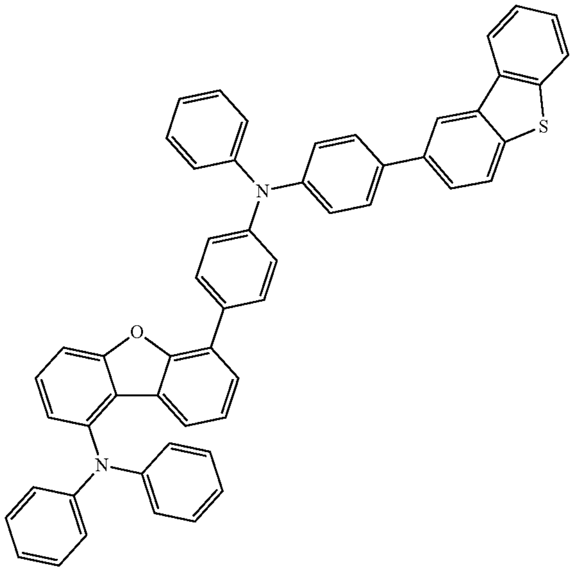

-continued

P-148

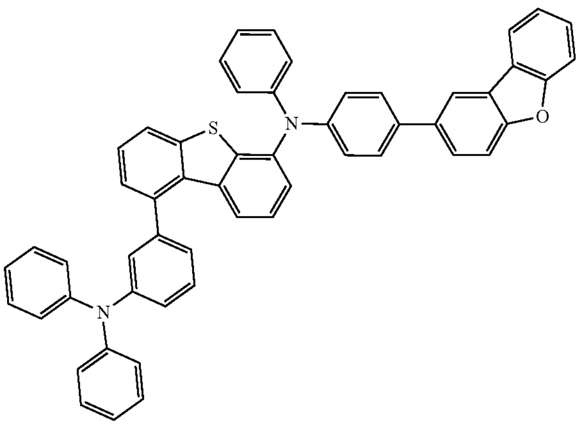

P-149

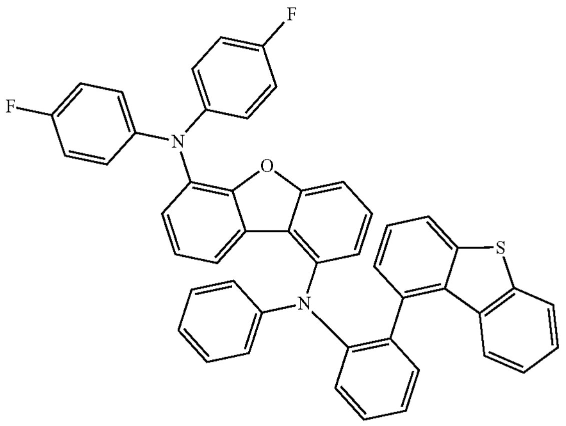

P-150

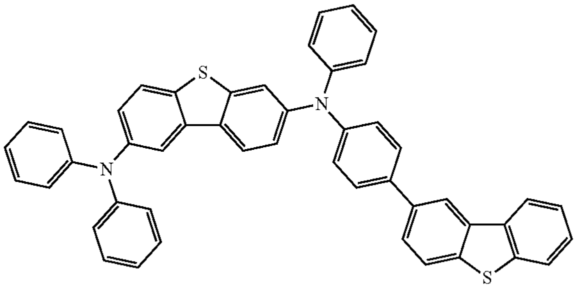

P-151

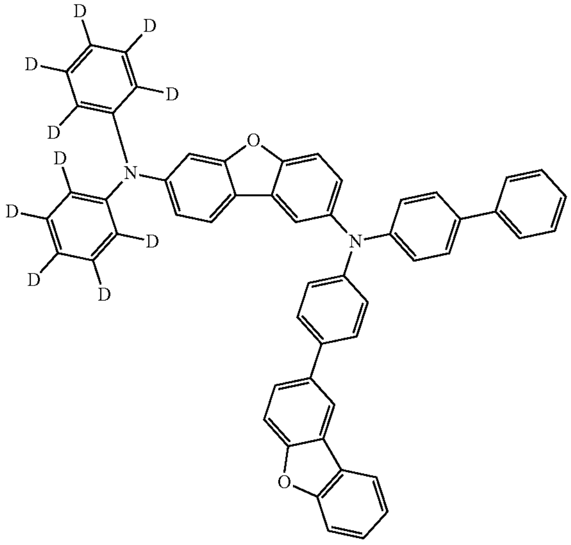

P-152

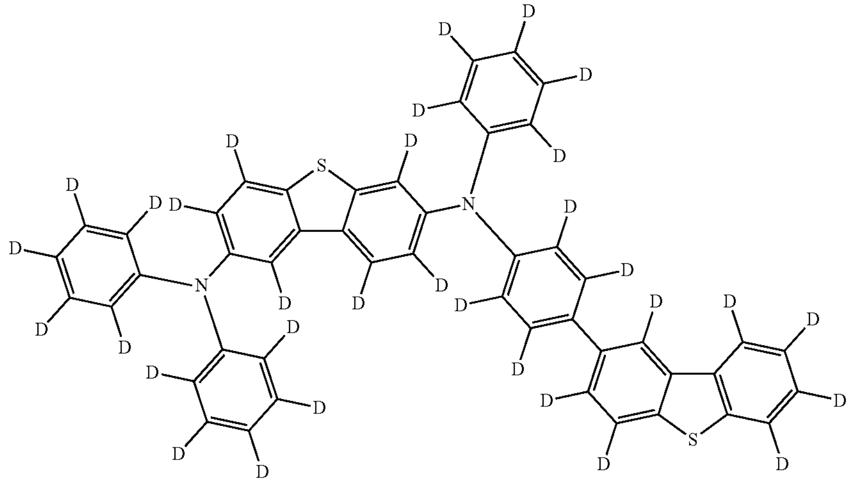

Referring to FIG. 1, the organic electronic element (100) according to the present invention includes a first electrode (110), a second electrode (170), and an organic material layer including a single compound or 2 or more compounds represented by Formula 1 between the first electrode (110) and the second electrode (170). In this case, the first electrode (110) may be an anode, and the second electrode (170) may be a cathode. In the case of an inverted type, the first electrode may be a cathode and the second electrode may be an anode.

Figure 2:
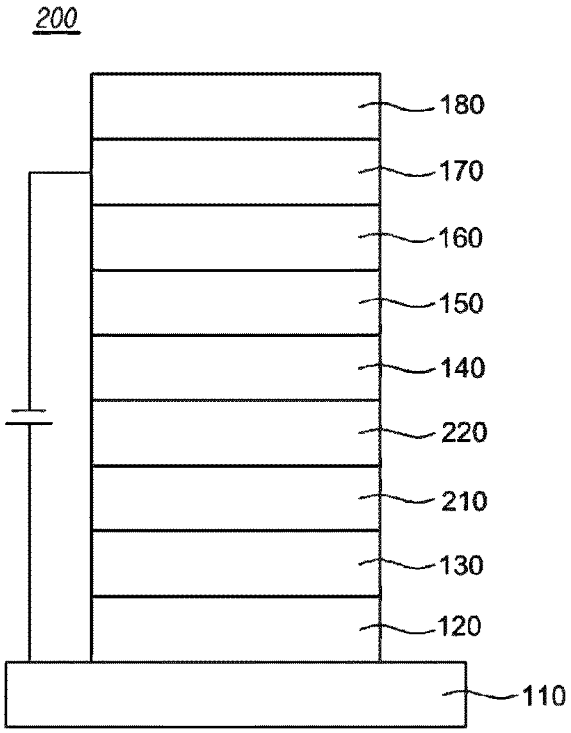

The organic material layer may sequentially include a hole injection layer (120), a hole transport layer (130), an emitting layer (140), an electron transport layer (150), and an electron injection layer (160) on the first electrode (110). In this case, the remaining layers except for the emitting layer (140) may not be formed. It may further include a hole blocking layer, an electron blocking layer, an emitting-auxiliary layer (220), a buffer layer (210), etc. and the electron transport layer (150) and the like may serve as a hole blocking layer. (See FIG. 2)

Also, the organic electronic element according to an embodiment of the present invention may further include a protective layer or a light efficiency enhancing layer (180). The light efficiency enhancing layer may be formed on one of both surfaces of the first electrode not in contact with the organic material layer or on one of both surfaces of the second electrode not in contact with the organic material layer. The compound according to an embodiment of the present invention applied to the organic material layer may be used as a host or dopant of the hole injection layer (120), the hole transport layer (130), the emitting-auxiliary layer (220), electron transport auxiliary layer, the electron transport layer (150), and an electron injection layer (160), the emitting layer (140) or as a material for the light efficiency enhancing layer. Preferably, for example, the compound according to Formula 1 of the present invention may be used as a material of the emitting-auxiliary layer or the emitting layer.

Figure 3:
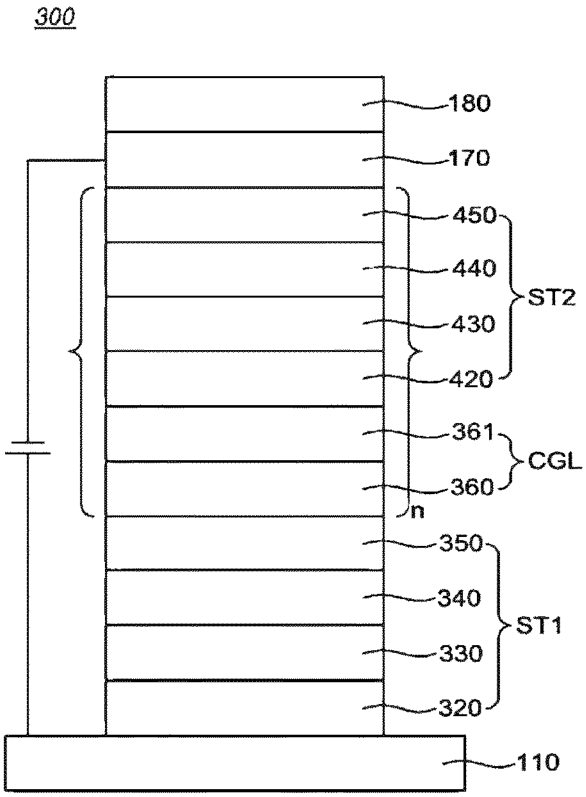
Figure 4:
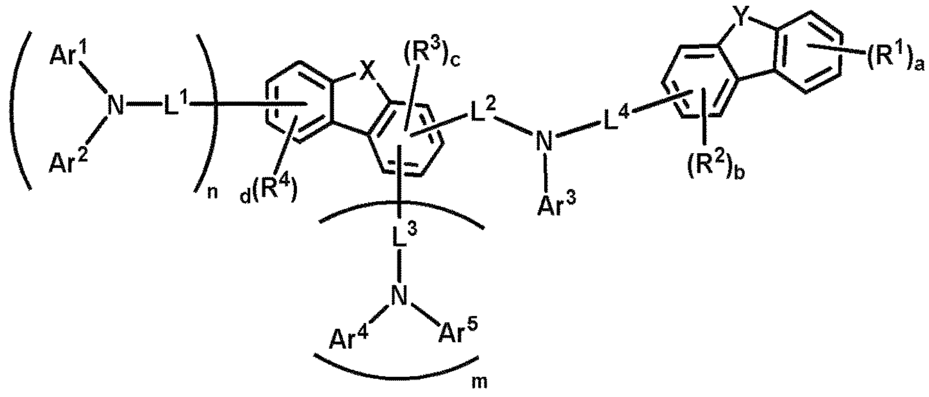
FIG. 4 shows a Formula according to an aspect of the present invention.

The organic material layer may include 2 or more stacks including a hole transport layer, an emitting layer and an electron transport layer sequentially formed on the anode, further include a charge generation layer formed between the 2 or more stacks (see FIG. 3).

Otherwise, even with the same core, the band gap, electrical characteristics, interface characteristics, etc. may vary depending on which position the substituent is bonded to, therefore the choice of core and the combination of sub-substituents bound thereto are also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electroluminescent device according to an embodiment of the present invention may be manufactured using a PVD (physical vapor deposition) method. For example, depositing a metal or a metal oxide having conductivity or an alloy thereof on a substrate to form an anode, and after forming an organic material layer including the hole injection layer (120), the hole transport layer (130), the emitting layer (140), the electron transport layer (150) and the electron injection layer (160) thereon, it can be prepared by depositing a material that can be used as a cathode thereon.

Also, in the present invention, the organic material layer is formed by any one of a spin coating process, a nozzle printing process, an inkjet printing process, a slot coating process, a dip coating process, and a roll-to-roll process, and the organic material layer provides an organic electronic element comprising the compound as an electron transport material.

As another specific example, the same or different compounds of the compound represented by Formula 1 are mixed and used in the organic material layer.

Also, the present invention provides an emitting-auxiliary layer composition comprising the compound represented by Formula 1, and provides an organic electronic element including the emitting-auxiliary layer.

Also, the present invention provides a hole transport layer composition comprising the compound represented by Formula 1, and provides an organic electronic element including the hole transport layer.

Also, the present invention provides a light efficiency enhancing layer composition comprising the compound represented by Formula 1, and provides an organic electric device including the light efficiency enhancing layer.

Also, the present invention provides an electronic device comprising a display device including the organic electronic element; and a control unit for driving the display device;

In another aspect, the organic electronic element is at least one of an organic electroluminescent device, an organic solar cell, an organic photoreceptor, an organic transistor, and a device for monochromatic or white lighting. At this time, the electronic device may be a current or future wired/wireless communication terminal, and covers all kinds of electronic devices including mobile communication terminals such as mobile phones, a personal digital assistant (PDA), an electronic dictionary, a point-to-multipoint (PMP), a remote controller, a navigation unit, a game player, various kinds of TVs, and various kinds of computers.

Hereinafter, a synthesis example of the compound represented by Formula 1 of the present invention and a manufacturing example of an organic electronic element of the present invention will be described in detail with reference to Examples, but the present invention is not limited to the following Examples.

Synthesis Example 1

The compound represented by Formula 1 according to the present invention (Final product) may be prepared by reacting as shown in Scheme 1 below, but is not limited thereto. $Hal^1$ to $Hal^3$ are I, Br or Cl.

<Reaction Scheme 1>

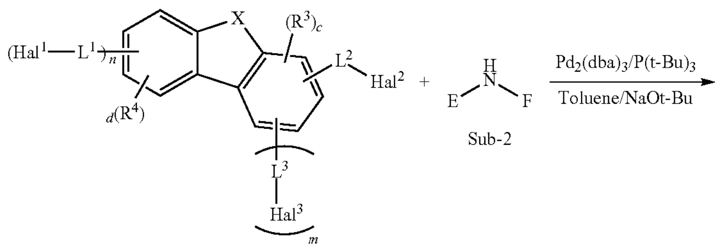

Sub-1

Sub-2

-continued
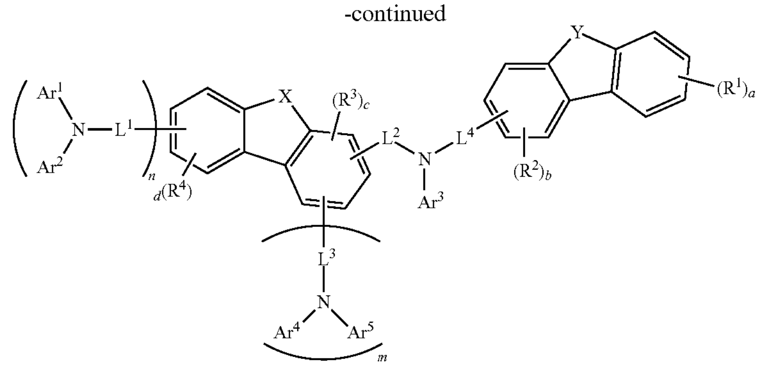
Final Product
E = $Ar^1$, $Ar^5$,
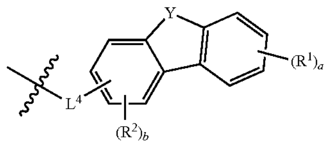
F = $Ar^2$, $Ar^3$, $Ar^4$
I. Synthesis of Sub-1
Sub-1 of Scheme 1 is synthesized by the reaction routes of Schemes 2 and 3 below, but is not limited thereto. $Hal^1$ to $Hal^5$ are I, Br or Cl.
<Reaction Scheme 2> If X is S
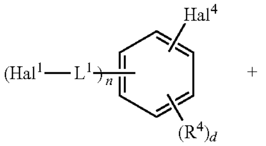
Sub-1-a
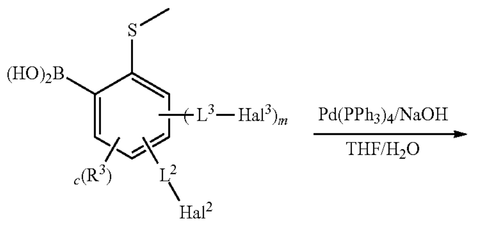
Sub-1-b
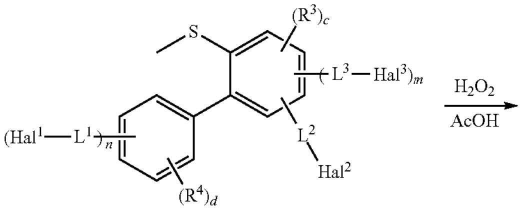
Sub-1-c
-continued
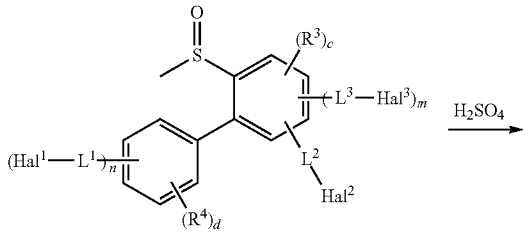
Sub-1-d
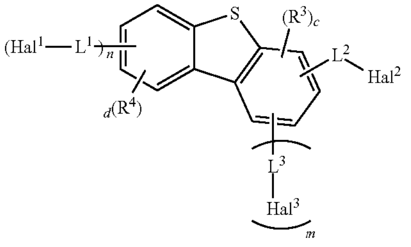
Sub-1
<Reaction Scheme 3> If X is O
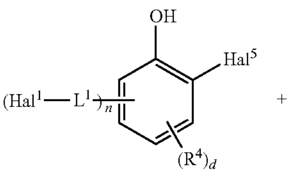
Sub-1-e -continued

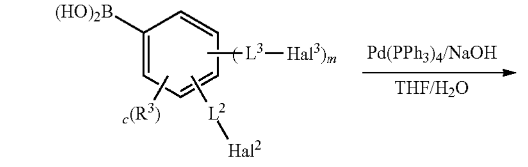

Sub-1-f

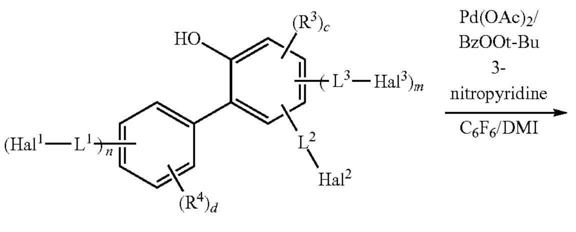

Sub-1-g

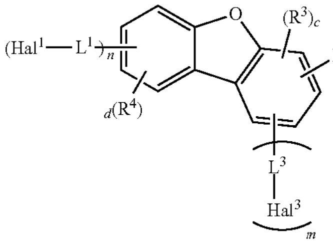

Sub-1

1. Synthesis of Sub-1-1

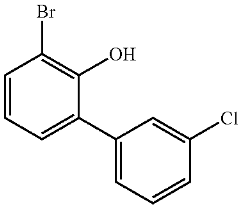

+

Sub-1-e-1

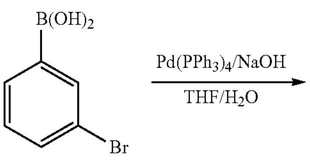

Sub-1-f-1

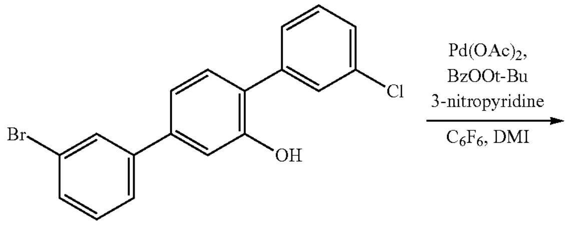

Sub-1-g-1

-continued

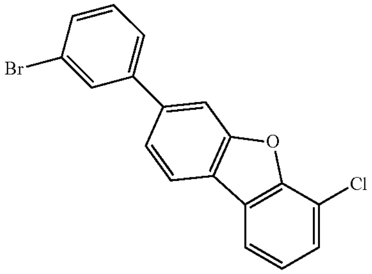

Sub-1-1

(1) Synthesis of Sub-1-g-1

After dissolving Sub-1-e-1 (30.0 g, 60.5 mmol) in THF (302 mL) in a round-bottom flask, Sub-1-f-1 (12.1 g, 60.5 mmol), $Pd(PPh_3)_4$ (4.2 g, 3.6 mmol), NaOH (7.3 g, 181.4 mmol), $H_2O$ (151 mL) were added and stirred at 80° C. After the reaction was completed, the mixture was extracted with $CH_2Cl_2$ and water, the organic layer was dried over $MgSO_4$, concentrated, and the resulting compound was recrystallized by silicagel column to obtain 15.0 g of a product. (Yield: 69%)

(2) Synthesis of Sub-1-1

The obtained Sub-1-g-1 (15.0 g, 41.7 mmol) was placed in a round-bottom flask with $Pd(OAc)_2$ (0.5 g, 2.1 mmol) and 3-nitropyridine (0.3 g, 2.1 mmol), after dissolving in $C_6F_6$ (62 mL) and DMI (42 mL), tert-butylperoxybenzoate (16.2 g, 83.4 mmol) was added and the mixture was stirred at 90° C. After the reaction was completed, the mixture was extracted with $CH_2Cl_2$ and water, the organic layer was dried over $MgSO_4$, concentrated, and the resulting compound was recrystallized by silicagel column to obtain 9.4 g of a product. (Yield: 63%)

2. Synthesis of Sub-1-2

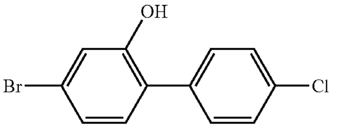

+

Sub-1-e-2

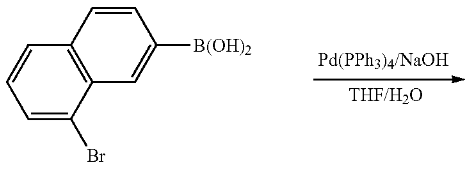

Sub-1-f-2

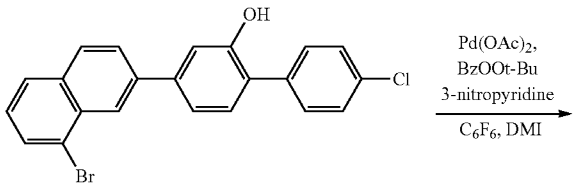

Sub-1-g-2

-continued

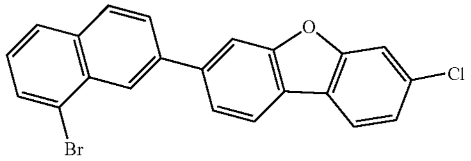

Sub-1-2

(1) Synthesis of Sub-1-g-2

After placing Sub-1-e-2 (30.0 g, 105.8 mmol), THF (529 mL), Sub-1-f-2 (26.5 g, 105.8 mmol), $Pd(PPh_3)_4$ (7.3 g, 6.4 mmol), NaOH (12.7 g, 317.4 mmol), $H_2O$ (265 mL) in a round-bottom flask, 29.0 g of the product was obtained in the same manner as in Sub-1-g-1 at 80° C. (Yield: 67%)

(2) Synthesis of Sub-1-2

The obtained Sub-1-g-2 (29.0 g, 70.9 mmol) was dissolved in a round bottom flask, after $Pd(OAc)_2$ (0.8 g, 3.5 mmol), 3-nitropyridine (0.4 g, 3.5 mmol), $C_6F_6$ (106 mL), DMI (71 mL), tert-butyl peroxybenzoate (27.5 g, 141.8 mmol) were added, 17.9 g of the product was obtained by performing an experiment at 90° C. in the same manner as in Sub-1-1. (Yield: 62%)

3. Synthesis of Sub-1-55

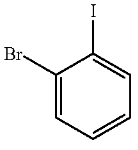

+

Sub-1-a-55

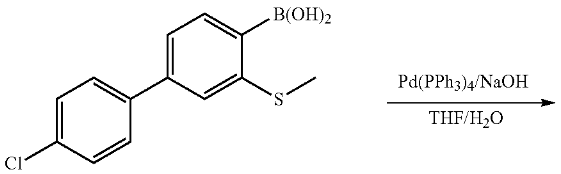

Sub-1-b-55

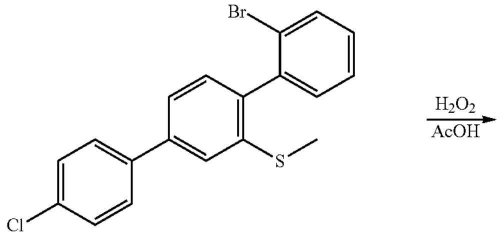

Sub-1-c-55

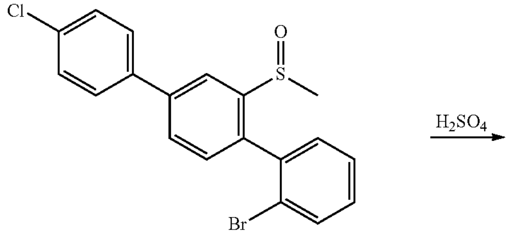

Sub-1-d-55

-continued

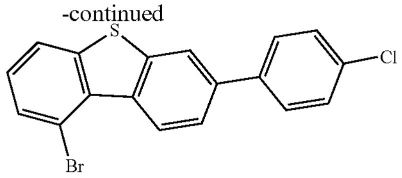

Sub-1-55

(1) Synthesis of Sub-1-c-55

After dissolving Sub-1-a-55 (30.0 g, 106.0 mmol) in THF (530 mL) in a round-bottom flask, Sub-1-b-55 (29.5 g, 106.0 mmol), $Pd(PPh_3)_4$ (7.4 g, 6.4 mmol), NaOH (12.7 g, 318.1 mmol), $H_2O$ (265 mL) were added and stirred at 80° C. After the reaction was completed, the mixture was extracted with $CH_2Cl_2$ and water, the organic layer was dried over $MgSO_4$, concentrated, and the resulting compound was recrystallized by silicagel column to obtain 33.1 g of a product. (Yield: 80%)

(2) Synthesis of Sub-1-d-55

Sub-1-c-55 (33.1 g, 84.8 mmol), $H_2O_2$ (8.5 mL), and acetic acid (339 mL) were placed in a round bottom flask and stirred at room temperature. When the reaction was completed, acetic acid was removed and water was added to obtain a solid, and the solid was dissolved in $CH_2Cl_2$ and concentrated on silicagel column to obtain 30.6 g of the product. (Yield: 89%)

(3) Synthesis of Sub-1-55

Sub-1-d-55 (30.6 g, 405.73 mmol) was dissolved in an excess of $H_2SO_4$ (91.9 mL) in a round bottom flask, followed by stirring at room temperature for 6 hours. When the reaction was completed, the reaction was neutralized using an aqueous NaOH solution, extracted with $CH_2Cl_2$, the organic layer was dried over $MgSO_4$, concentrated, and the resulting compound was recrystallized by silicagel column to obtain 24.3 g of a product. (Yield: 86%)

4. Synthesis of Sub-1-83

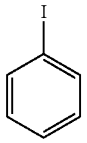

Sub-1-a-83

+

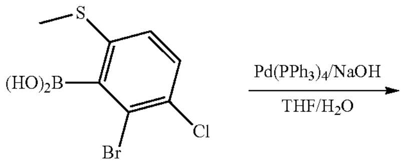

Sub-1-b-83

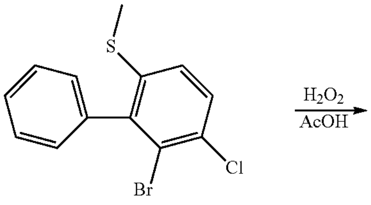

Sub-1-c-83

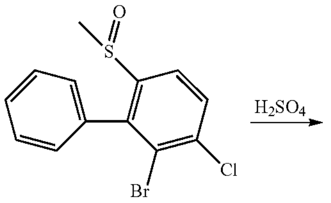

Sub-1-d-83

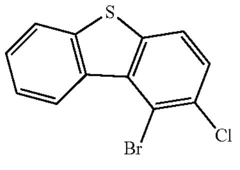

Sub-1-83

(1) Synthesis Sub-1-c-83

After placing Sub-1-a-83 (30.0 g, 147.1 mmol), THF (735 mL), Sub-1-b-83 (41.4 g, 147.1 mmol), $Pd(PPh_3)_4$ (10.2 g, 8.8 mmol), NaOH (17.7 g, 441.2 mmol), $H_2O$ (368 mL) in a round-bottom flask, the experiment was performed in the same manner as in Sub-1-g-1 at 80° C. to obtain 33.2 g of the product. (Yield: 72%)

(2) Synthesis Sub-1-d-83

Sub-1-c-83 (33.2 g, 105.9 mmol), $H_2O_2$ (10.6 mL), acetic acid (424 mL) were placed in a round-bottom flask and tested in the same manner as in Sub-1-d-55 at room temperature to obtain 31.4 g of the product. (Yield: 90%)

(3) Synthesis Sub-1-83

Sub-1-d-83 (31.4 g, 95.3 mmol) and $H_2SO_4$ (94.2 mL) were added and dissolved, followed by the same experiment as in Sub-1-55 to obtain 25.0 g of the product. (Yield: 88%)

5. Synthesis of Sub-1-97

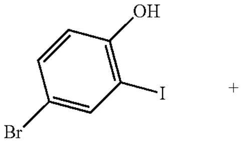

Sub-1-e-97

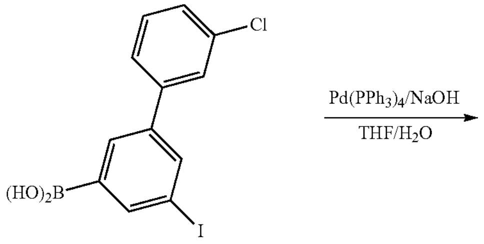

Sub-1-f-97

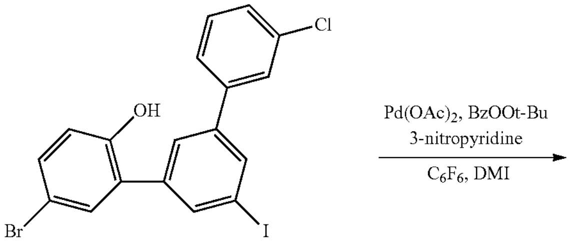

Sub-1-g-97

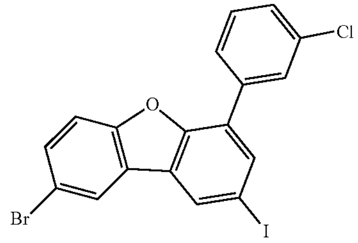

Sub-1-97

(1) Synthesis of Sub-1-g-97

After placing Sub-1-e-97 (30.0 g, 100.4 mmol), THF (502 mL), Sub-1-f-97 (36.0 g, 100.4 mmol), $Pd(PPh_3)_4$ (7.0 g, 6.0 mmol), NaOH (12.0 g, 301.1 mmol), $H_2O$ (251 mL) in a round flask, the experiment was performed in the same manner as in Sub-1-g-1 above at 80° C. to obtain 34.1 g of the product. (Yield: 70%)

(2) Synthesis of Sub-1-97

After dissolving Sub-1-g-97 (34.1 g, 70.3 mmol) in a round-bottomed flask, $Pd(OAc)_2$ (0.8 g, 3.5 mmol), 3-nitropyridine (0.4 g, 3.5 mmol), $C_6F_6$ (105 mL), DMI (70 mL), tert-butylperoxybenzoate (27.3 g, 140.5 mmol) were added, and the experiment was performed in the same manner as in Sub-1-1 above at 90° C. 21.1 g of the product was obtained. (Yield: 63%)

6. Synthesis of Sub-1-114

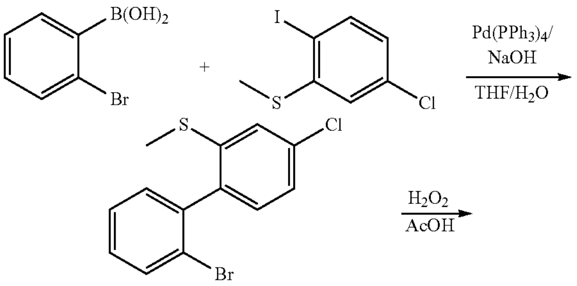

Sub-1-c-114

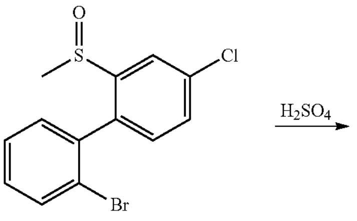

Sub-1-d-114

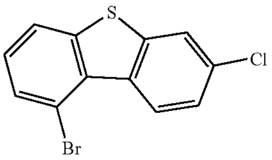

Sub-1-114

(1) Synthesis of Sub-1-c-114

After placing Sub-1-a-114 (30.0 g, 149 mmol), THF (750 ml), Sub-1-b-114 (42.5 g, 149 mmol), $Pd(PPh_3)_4$ (10.4 g, 8.96 mmol), NaOH (17.9 g, 448 mmol) and $H_2O$ (375 mL) in a round-bottom flask, the experiment was performed in the same manner as in Sub-1-g-1 at 80° C. to obtain 39.4 g of the product. (Yield: 84%)

(2) Synthesis of Sub-1-d-114

Sub-1-c-114 (39.4 g, 126 mmol), $H_2O_2$ (35.9 mL), and acetic acid (500 mL) were placed in a round-bottom flask, and at room temperature, 38.1 g of the product was obtained by performing an experiment in the same manner as for Sub-1-d-55. (Yield: 92%)

(3) Synthesis of Sub-1-d-114

Sub-1-d-114 (38.1 g, 115 mmol) and $H_2SO_4$ (114 mL) were added and dissolved, followed by the same procedure as in Sub-1-55 to obtain 30.2 g of the product. (Yield: 88%)

7. Synthesis Example of Sub-1-127

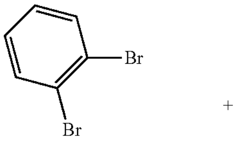

Sub-1-e-127

-continued

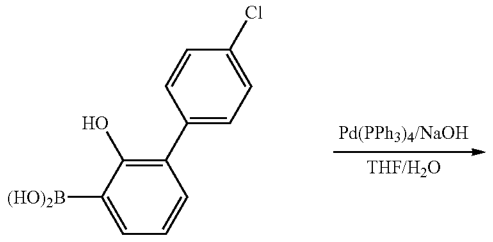

Sub-1-f-127

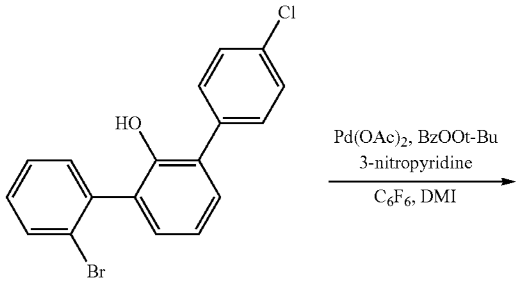

Sub-1-g-127

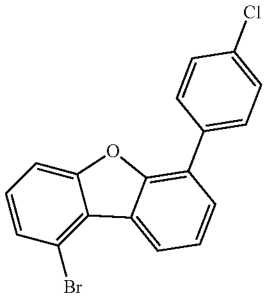

Sub-1-127

(1) Synthesis of Sub-1-g-127

After placing Sub-1-e-127 (30.0 g, 127 mmol), THF (640 mL), Sub-1-f-127 (31.6 g, 127 mmol), $Pd(PPh_3)_4$ (8.82 g, 7.63 mmol), NaOH (15.3 g, 382 mmol), $H_2O$ (320 mL) in a round-bottom flask, the experiment was performed in the same manner as in Sub-1-g-1 at 80° C. to obtain 35.7 g of the product. (Yield: 78%)

(2) Synthesis of Sub-1-127

After dissolving Sub-1-g-127 (35.7 g, 99.2 mmol) in a round-bottom flask, $Pd(OAc)_2$ (1.11 g, 4.96 mmol), 3-nitropyridine (0.62 g, 4.96 mmol), $C_6F_6$ (148 mL), DMI (99 mL), tert-butylperoxybenzoate (38.5 g, 198 mmol) were added and tested in the same manner as in Sub-1-1 at 90° C. to obtain 14.9 g of the product. (Yield: 42%)

8. Synthesis Example of Sub-1-131

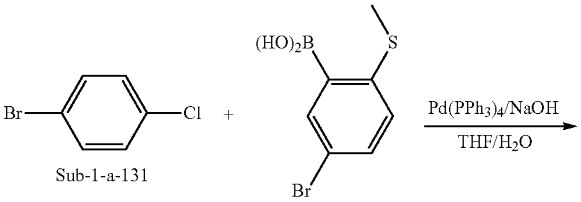

Sub-1-a-131

Sub-1-b-131

-continued

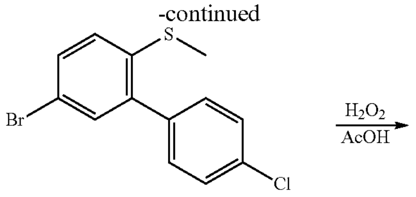

Sub-1-c-131

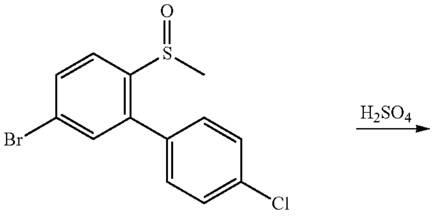

Sub-1-d-131

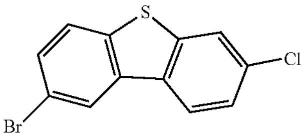

Sub-1-131

(1) Synthesis of Sub-1-c-131

After putting Sub-1-a-131 (30.0 g, 157 mmol), THF (780 mL), Sub-1-b-131 (38.7 g, 157 mmol), $Pd(PPh_3)_4$ (10.9 g, 9.40 mmol), NaOH (18.8 g, 470 mmol), $H_2O$ (390 mL) in a round-bottom flask, the experiment was performed at 80° C. in the same manner as in Sub-1-g-1 to obtain 40.3 g of the product. (Yield: 82%)

(2) Synthesis of Sub-1-d-131

Sub-1-c-131 (40.3 g, 129 mmol), $H_2O_2$ (36.7 mL) and acetic acid (515 mL) were placed in a round-bottom flask and tested in the same manner as in Sub-1-d-55 at room temperature to produce the product 38.5 g were obtained. (Yield: 91%)

(3) Synthesis of Sub-1-131

Sub-1-d-131 (38.5 g, 117 mmol) and $H_2SO_4$ (116 mL) were added and dissolved, followed by the same experiment as in Sub-1-55 to obtain 32.4 g of the product. (Yield: 93%)

9. Synthesis of Sub-1-132

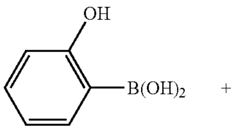

Sub-1-e-132

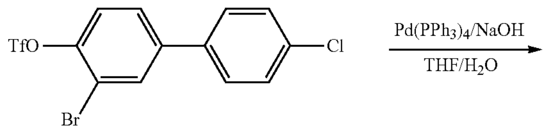

Sub-1-f-132

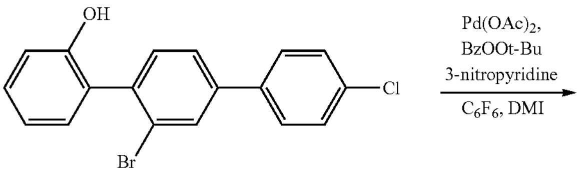

Sub-1-g-132

-continued

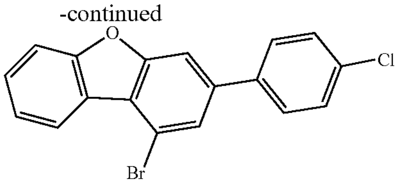

Sub-1-132

(1) Synthesis of Sub-1-g-132

After placing Sub-1-f-132 (30.0 g, 72.2 mmol), THF (360 mL), Sub-1-e-132 (10.0 g, 72.2 mmol), $Pd(PPh_3)_4$ (5.0 g, 4.33 mmol), NaOH (8.7 g, 217 mmol), $H_2O$ (180 mL) in a round-bottom flask, 18.7 g of the product were obtained by performing an experiment in the same manner as in Sub-1-g-1 at 80° C. (Yield: 72%)

(2) Synthesis of Sub-1-132

After dissolving Sub-1-g-132 (18.7 g, 52.0 mmol) in a round-bottom flask, $Pd(OAc)_2$ (0.58 g, 2.60 mmol), 3-nitro-pyridine (0.32 g, 2.60 mmol), $C_6F_6$ (78 mL), DMI (52 mL), tert-butylperoxybenzoate (20.2 g, 104 mmol) were added and tested in the same manner as in Sub-1-1 at 90° C. to obtain 12.6 g of the product. (Yield: 68%)

10. Synthesis Example of Sub-1-133

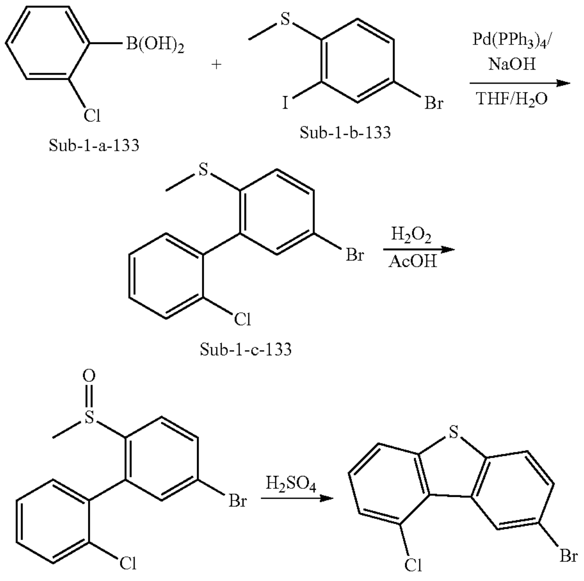

Sub-1-a-133
Sub-1-b-133
Sub-1-c-133
Sub-1-d-133
Sub-1-133

(1) Synthesis of Sub-1-c-133

After placing Sub-1-a-133 (30.0 g, 192 mmol), THF (960 mL), Sub-1-b-133 (63.1 g, 192 mmol), $Pd(PPh_3)_4$ (13.3 g, 11.5 mmol), NaOH (23.0 g, 576 mmol), $H_2O$ (480 mL) in a round-bottom flask, 48.1 g of the product was obtained by performing an experiment in the same manner as in Sub-1-g-1 at 80° C. (Yield: 80%)

(2) Synthesis of Sub-1-d-133

Sub-1-c-133 (48.1 g, 154 mmol), $H_2O_2$ (43.9 mL), and acetic acid (614 mL) were placed in a round-bottom flask, at room temperature, 44.5 g of the product was obtained in the same manner as in Sub-1-d-55. (Yield: 88%)

(3) Synthesis of Sub-1-133

Sub-1-d-133 (44.5 g, 135 mmol) and $H_2SO_4$ (134 mL) were added and dissolved, followed by the same experiment as in Sub-1-55 to obtain 36.6 g of the product. (Yield: 91%)

The compound belonging to Sub-1 may be the following compounds, but is not limited thereto, and Table 1 below shows Field Desorption-Mass Spectrometry (FD-MS) values of the compounds belonging to Sub-1.

Sub-1-1

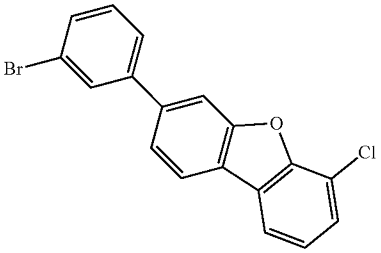

Sub-1-2

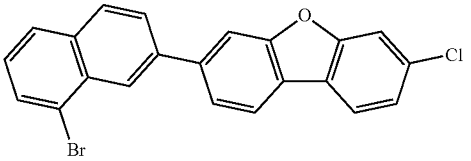

Sub-1-3

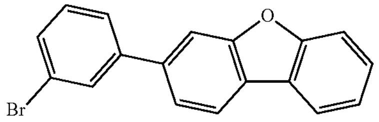

Sub-1-4

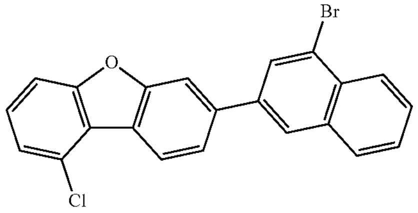

Sub-1-5

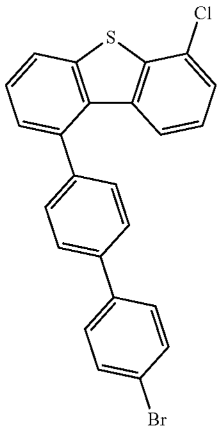

-continued
Sub-1-6
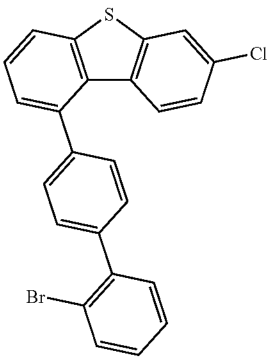
Sub-1-7
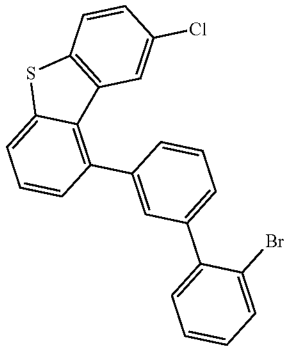
Sub-1-8
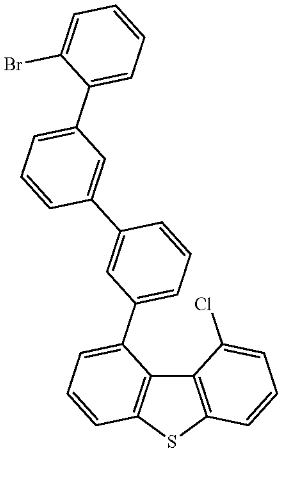
Sub-1-9
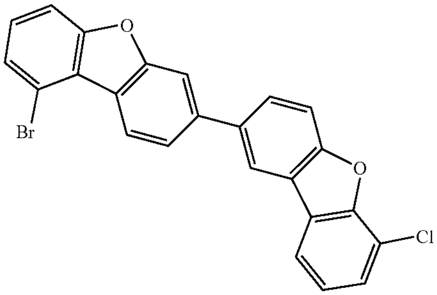
-continued
Sub-1-10
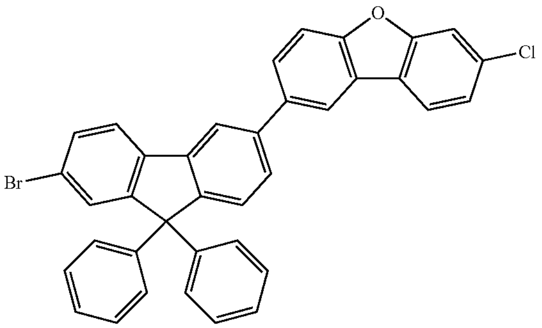
Sub-1-11
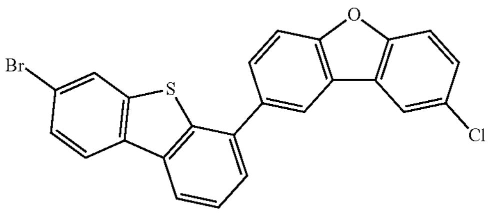
Sub-1-12
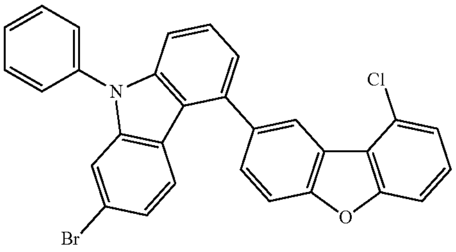
Sub-1-13
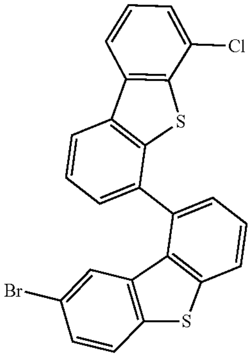
Sub-1-14
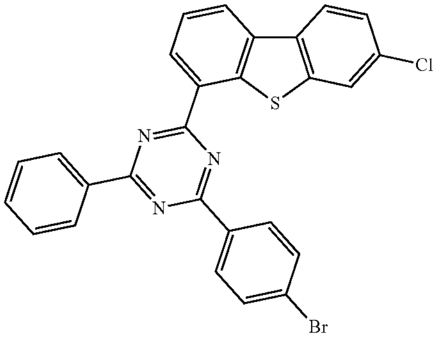

-continued
Sub-1-15
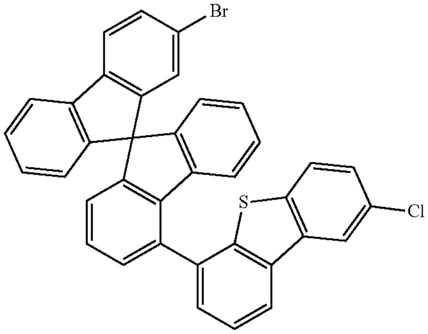
Sub-1-16
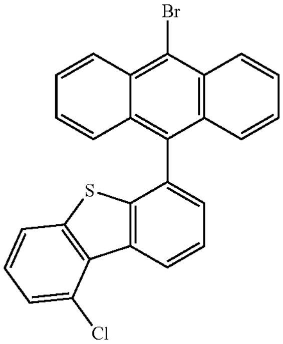
Sub-1-17
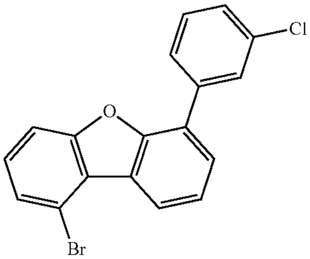
Sub-1-18
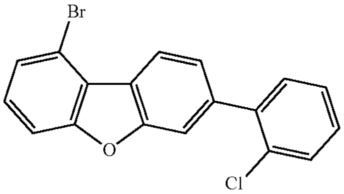
Sub-1-19
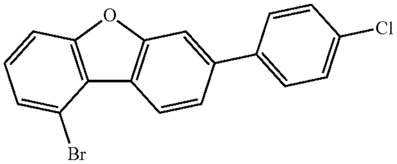
Sub-1-20
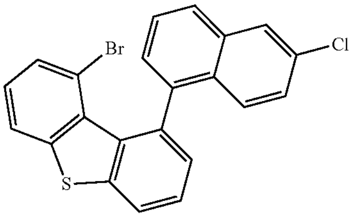
-continued
Sub-1-21
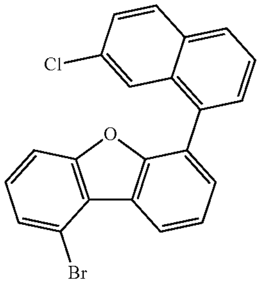
Sub-1-22
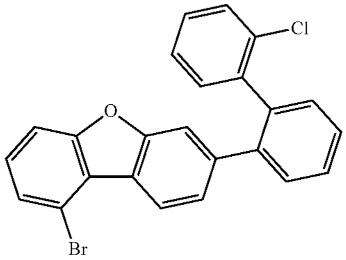
Sub-1-23
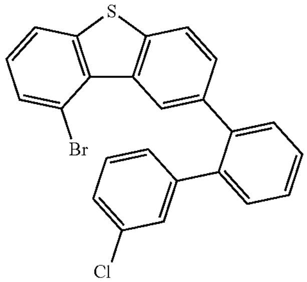
Sub-1-24
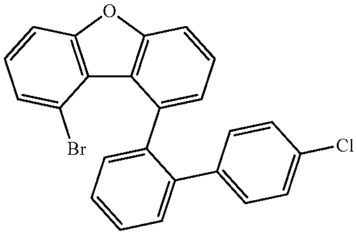
Sub-1-25
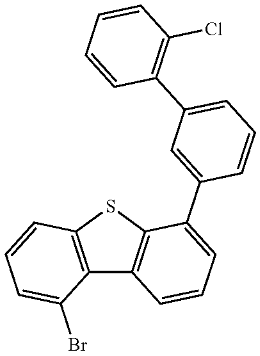
Sub-1-26
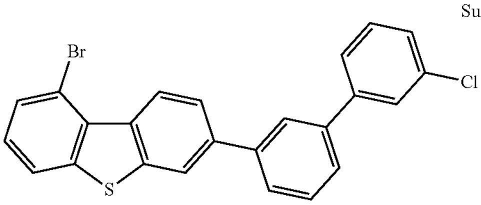

-continued
Sub-1-27
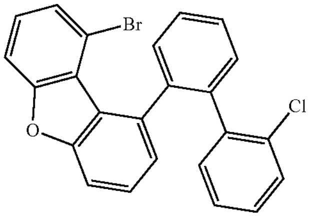
Sub-1-28
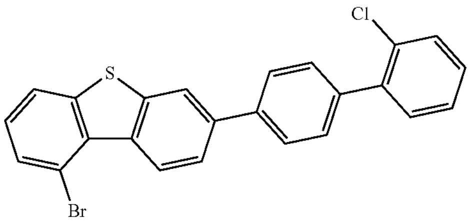
Sub-1-29
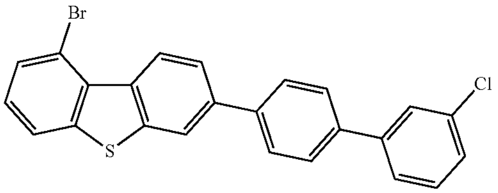
Sub-1-30
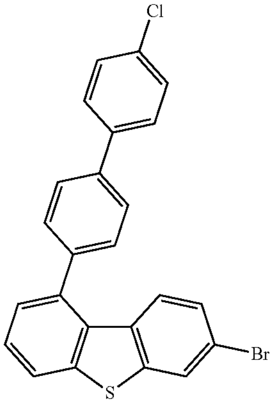
Sub-1-31
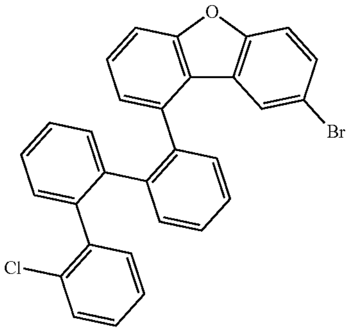
-continued
Sub-1-32
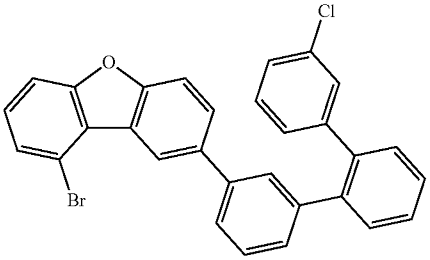
Sub-1-33
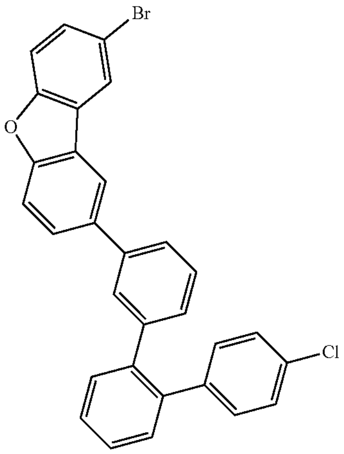
Sub-1-34
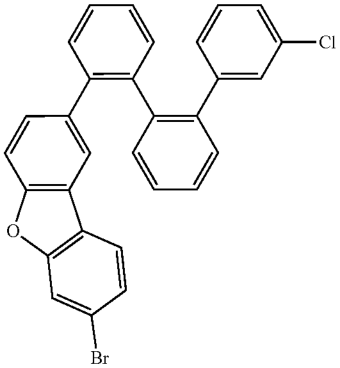
Sub-1-35
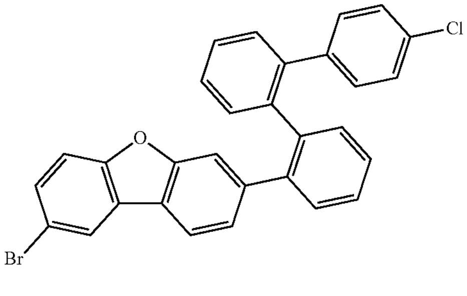

-continued
Sub-1-36
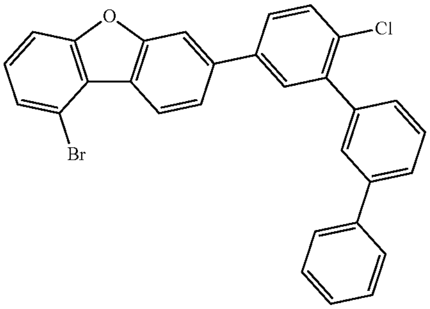
Sub-1-37
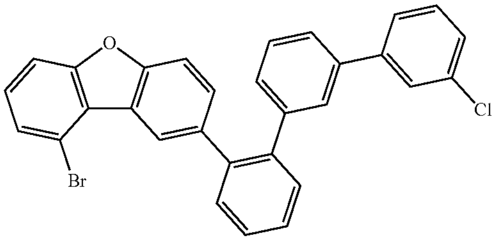
Sub-1-38
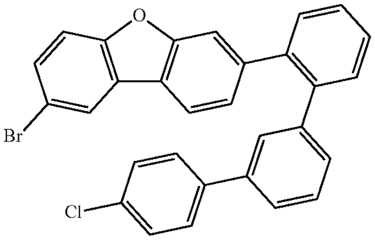
Sub-1-39
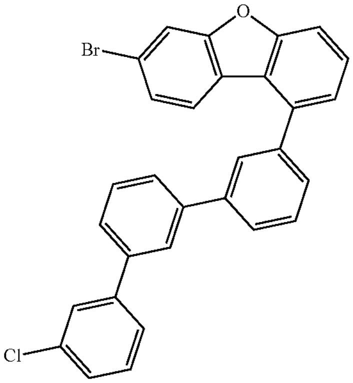
Sub-1-40
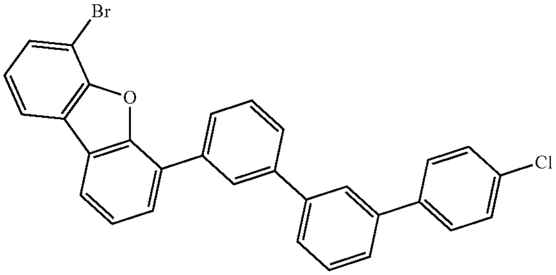
-continued
Sub-1-41
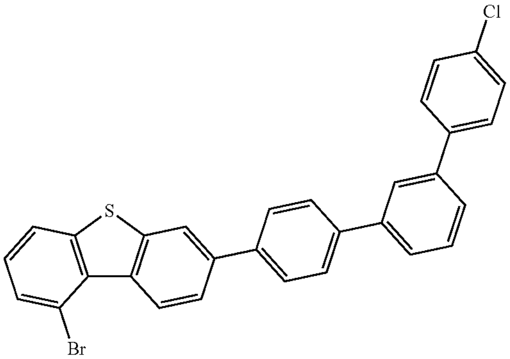
Sub-1-42
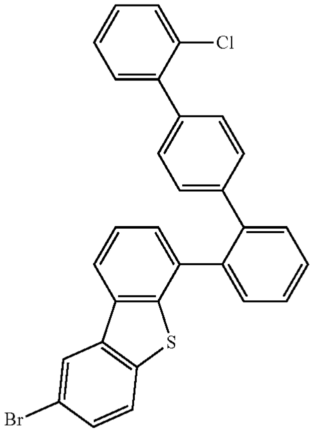
Sub-1-43
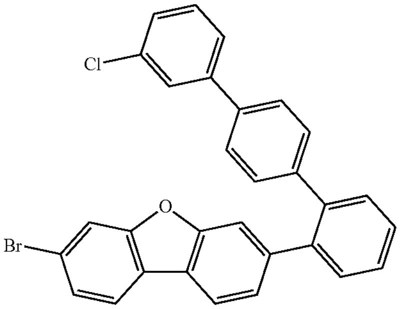
Sub-1-44
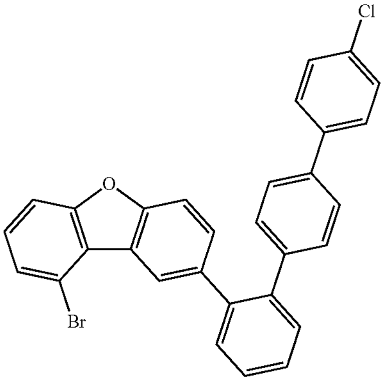

-continued
Sub-1-45
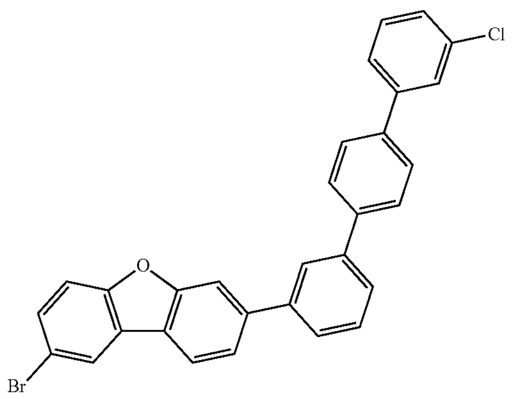
Sub-1-46
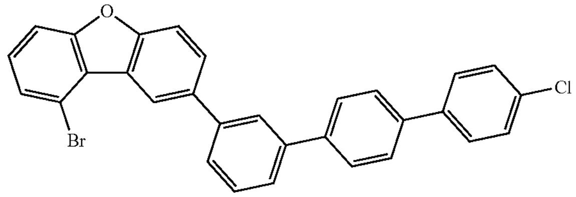
Sub-1-47
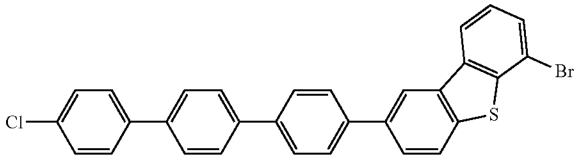
Sub-1-48
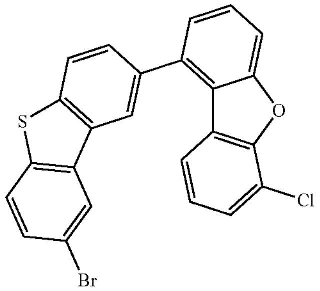
Sub-1-49
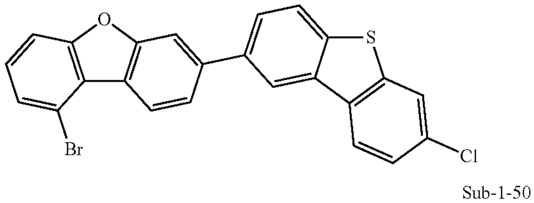
Sub-1-50
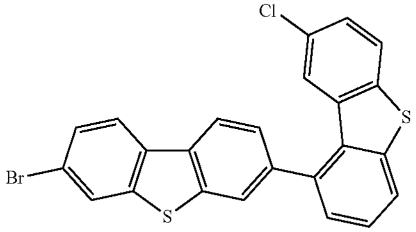
-continued
Sub-1-51
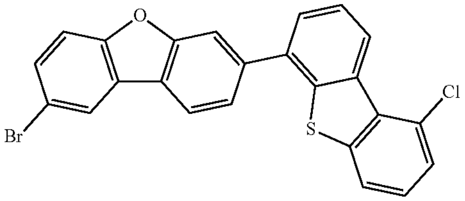
Sub-1-52
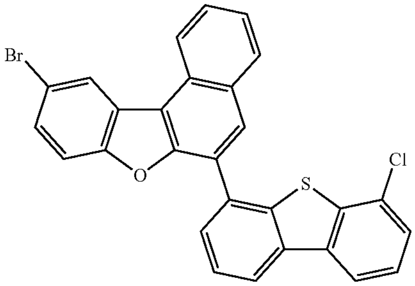
Sub-1-53
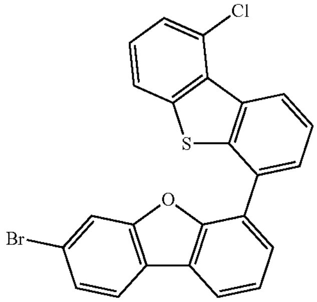
Sub-1-54
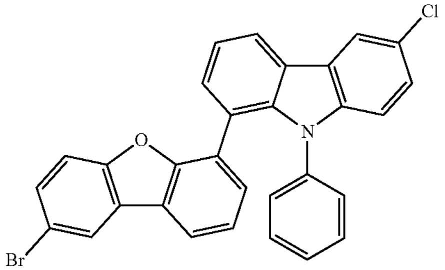
Sub-1-55
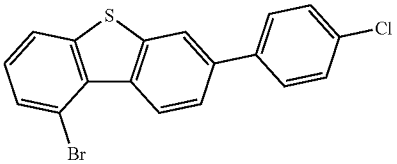
Sub-1-56
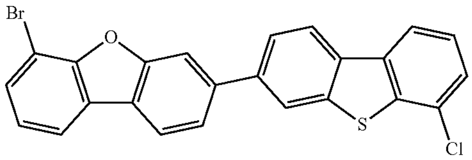

-continued
Sub-1-57
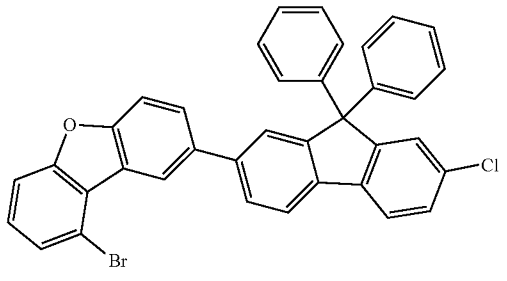
Sub-1-58
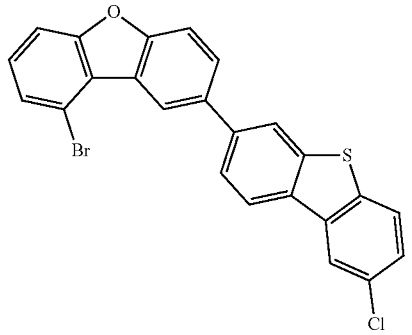
Sub-1-59
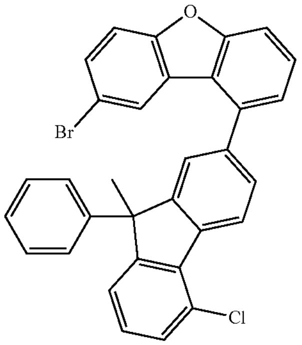
Sub-1-60
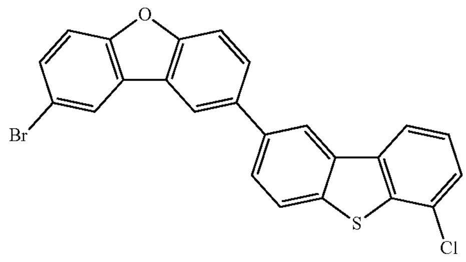
Sub-1-61
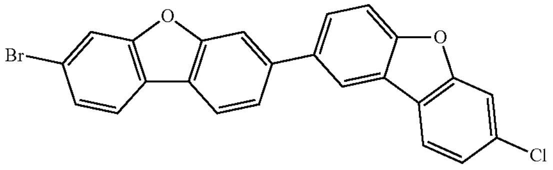
-continued
Sub-1-62
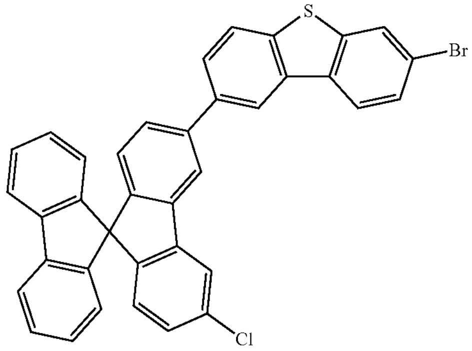
Sub-1-63
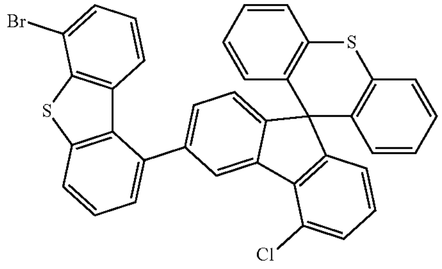
Sub-1-64
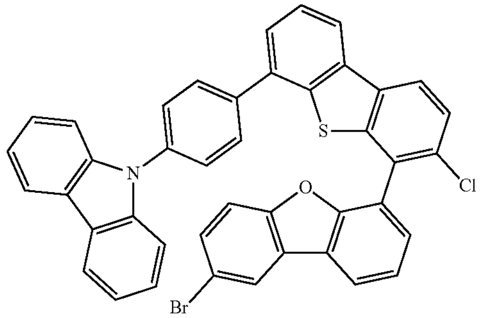
Sub-1-65
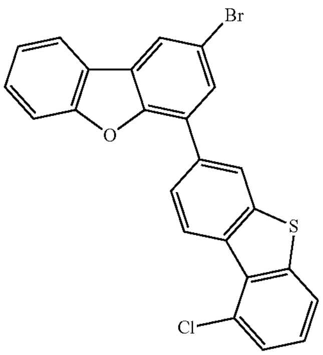

-continued
Sub-1-66
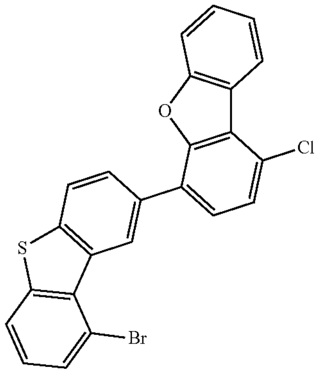
Sub-1-67
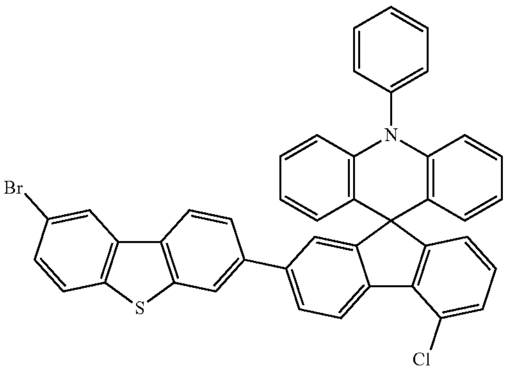
Sub-1-68
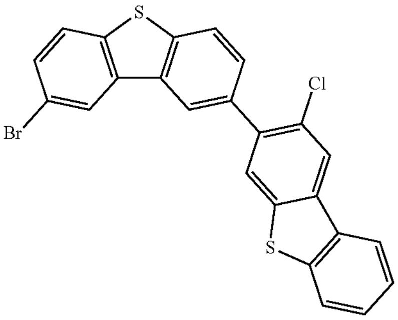
Sub-1-69
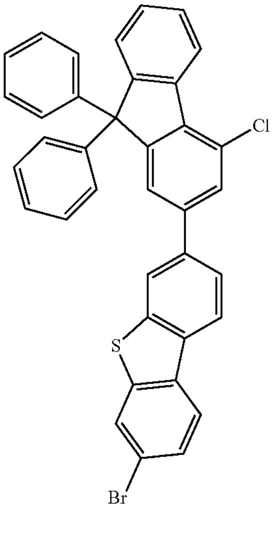
-continued
Sub-1-70
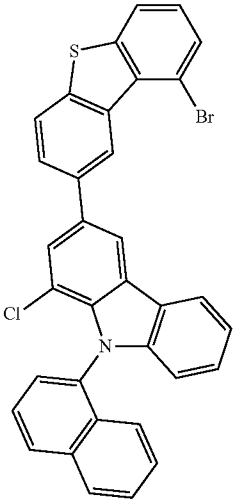
Sub-1-71
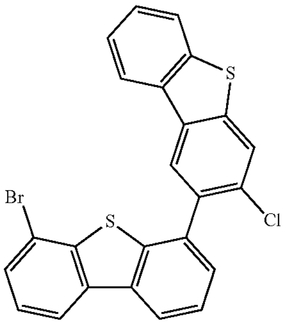
Sub-1-72
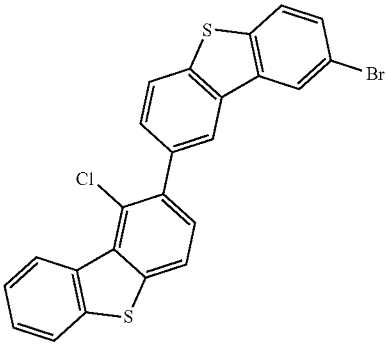
Sub-1-73
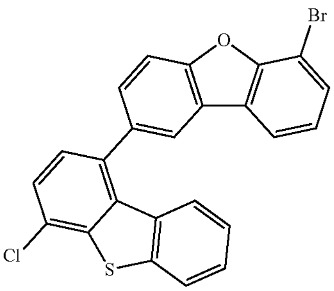

-continued
Sub-1-74
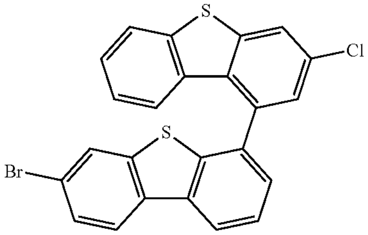
Sub-1-75
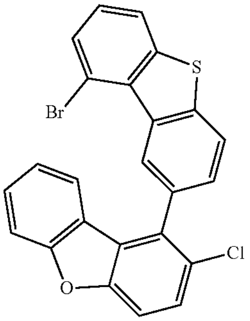
Sub-1-76
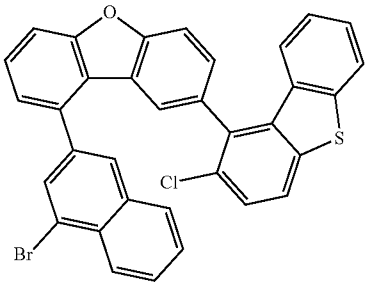
Sub-1-77
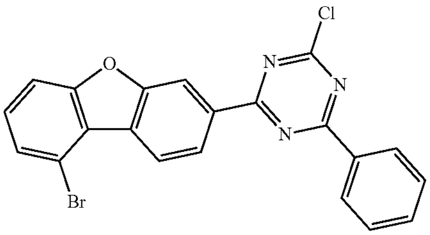
Sub-1-78
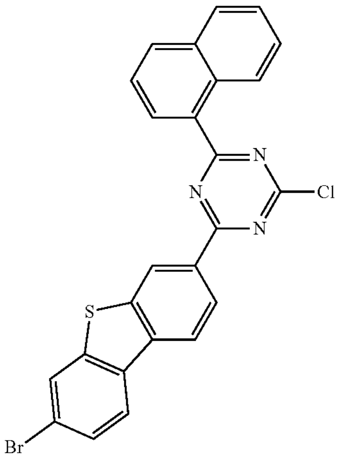
-continued
Sub-1-79
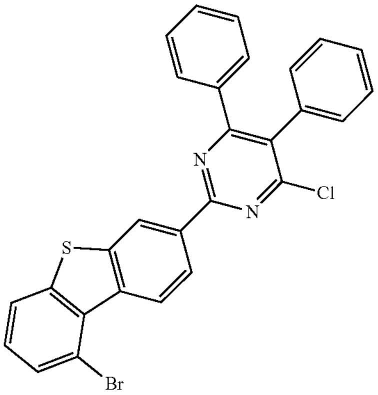
Sub-1-80
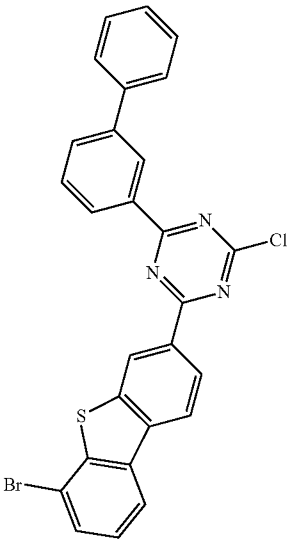
Sub-1-81
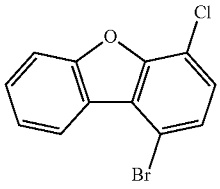
Sub-1-82
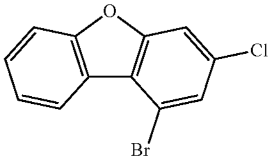
Sub-1-83
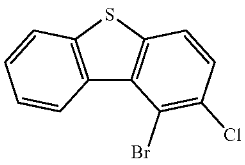

-continued
Sub-1-84
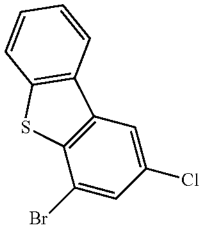
Sub-1-85
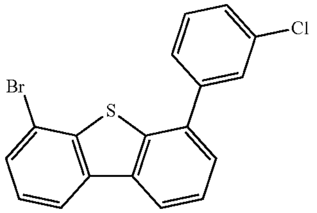
Sub-1-86
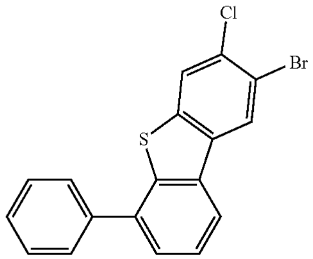
Sub-1-87
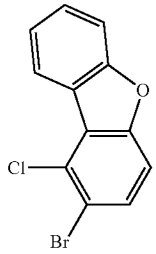
Sub-1-88
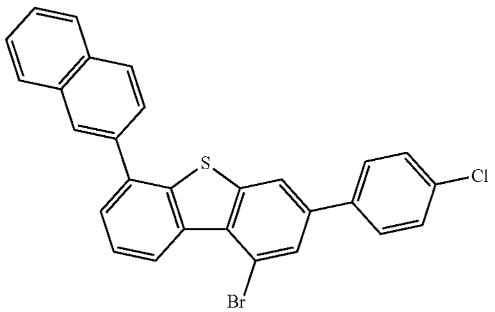
Sub-1-89
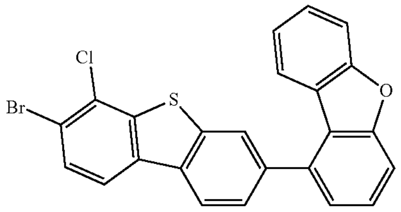
-continued
Sub-1-90
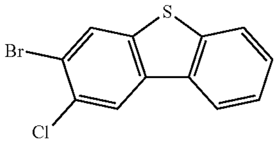
Sub-1-91
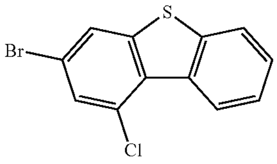
Sub-1-92
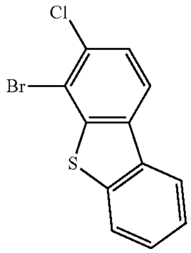
Sub-1-93
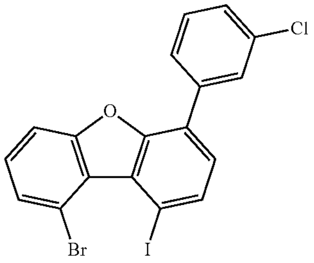
Sub-1-94
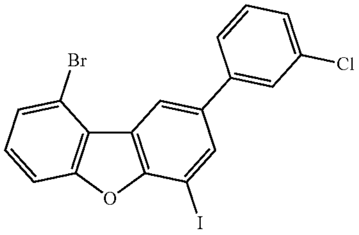
Sub-1-95
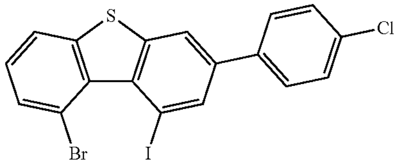
Sub-1-96
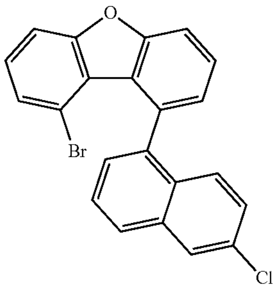

-continued
Sub-1-97
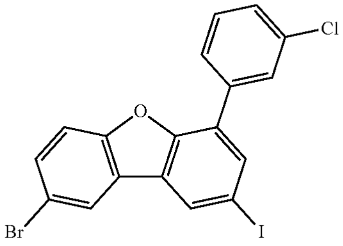
Sub-1-98
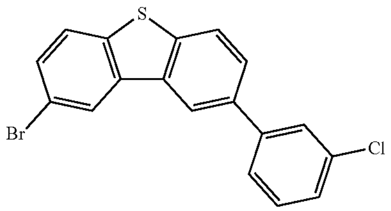
Sub-1-99
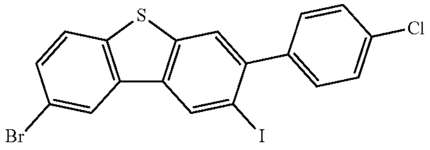
Sub-1-100
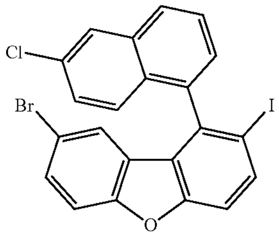
Sub-1-101
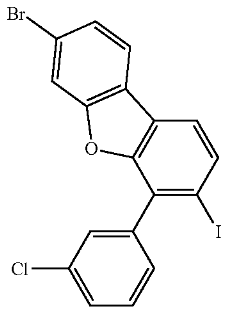
Sub-1-102
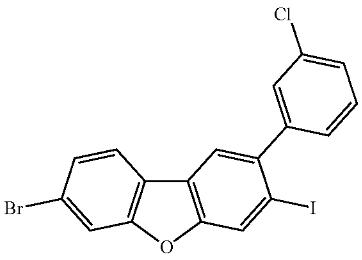
-continued
Sub-1-103
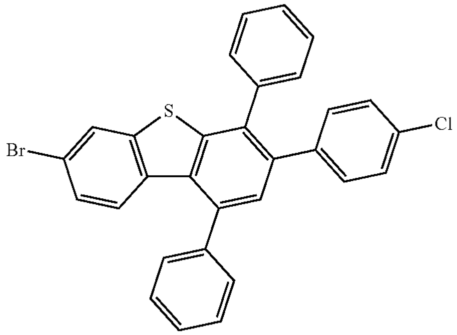
Sub-1-104
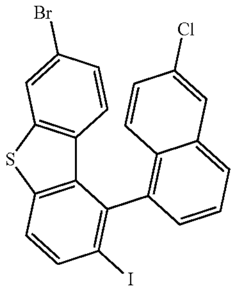
Sub-1-105
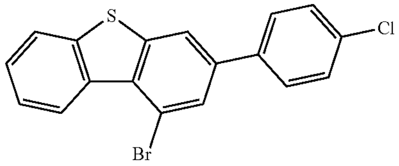
Sub-1-106
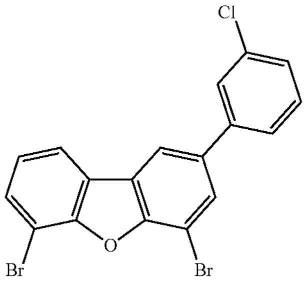
Sub-1-107
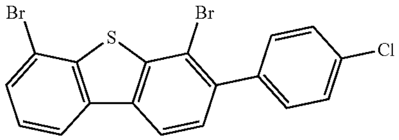
Sub-1-108
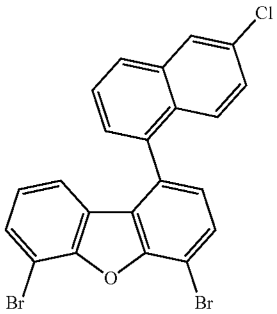

-continued
Sub-1-109
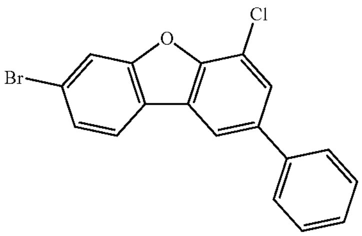
Sub-1-110
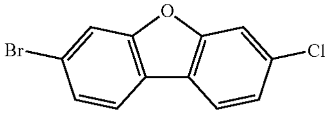
Sub-1-111
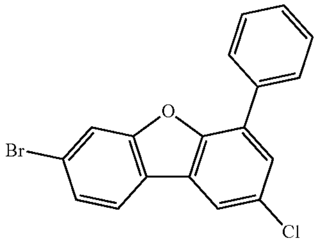
Sub-1-112
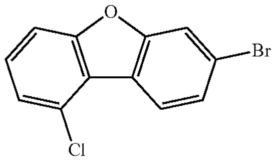
Sub-1-113
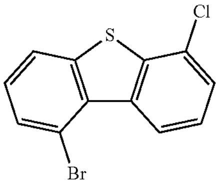
Sub-1-114
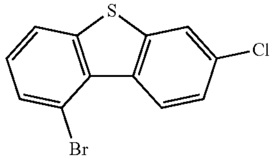
Sub-1-115
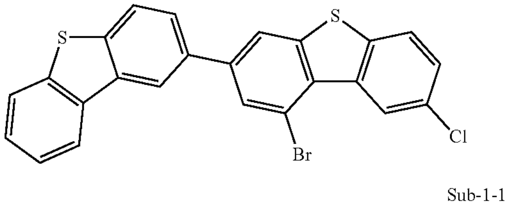
Sub-1-116
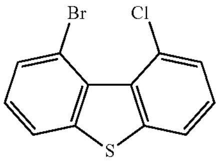
-continued
Sub-1-117
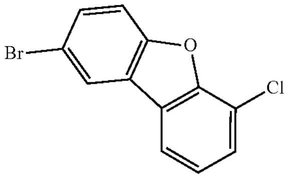
Sub-1-118
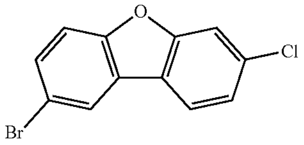
Sub-1-119
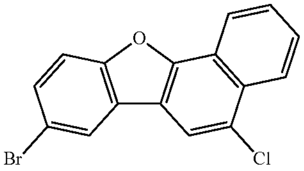
Sub-1-120
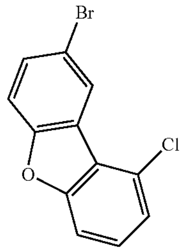
Sub-1-121
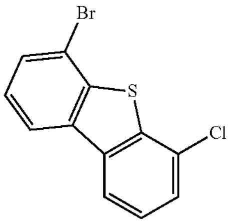
Sub-1-122
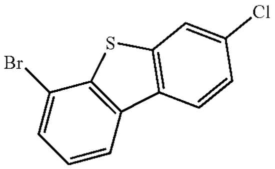
Sub-1-123
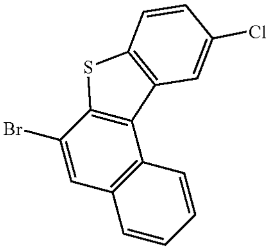

-continued
Sub-1-124
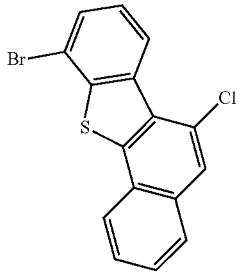
Sub-1-125
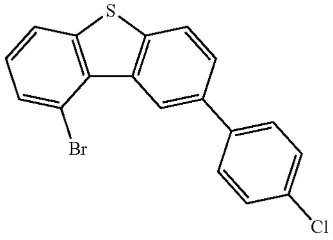
Sub-1-126
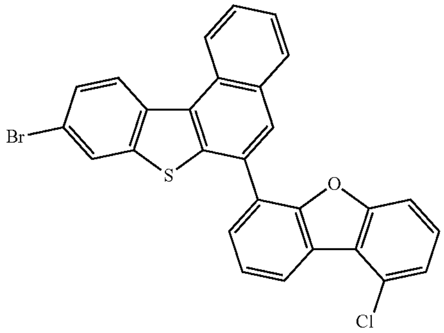
Sub-1-127
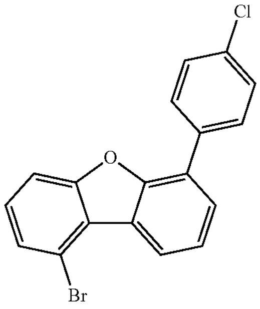
Sub-1-128
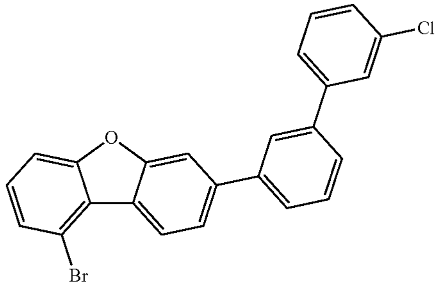
-continued
Sub-1-129
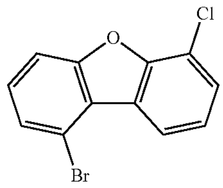
Sub-1-130
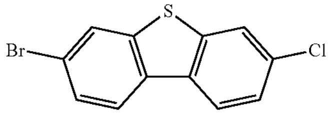
Sub-1-131
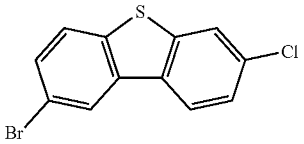
Sub-1-132
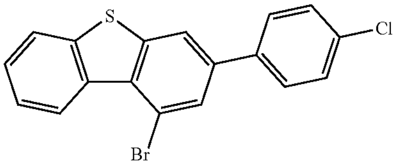
Sub-1-133
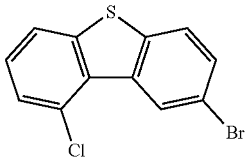
Sub-1-134
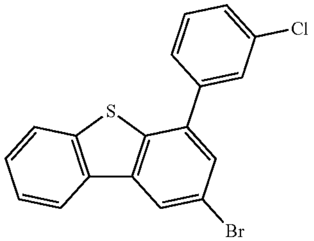
Sub-1-135
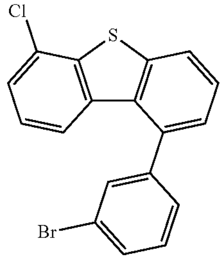

TABLE 1

| compound | FD-MS | compound | FD-MS |
|---|---|---|---|
| Sub-1-1 | m/z = 355.96($C_{18}H_{10}BrClO$ = 357.63) | Sub-1-2 | m/z = 405.98($C_{22}H_{12}BrClO$ = 407.69) |
| Sub-1-3 | m/z = 355.96($C_{18}H_{10}BrClO$ = 357.63) | Sub-1-4 | m/z = 355.96($C_{18}H_{10}BrClO$ = 357.63) |
| Sub-1-5 | m/z = 447.97($C_{24}H_{14}BrClS$ = 449.79) | Sub-1-6 | m/z = 447.97($C_{24}H_{14}BrClS$ = 449.79) |
| Sub-1-7 | m/z = 447.97($C_{24}H_{14}BrClS$ = 449.79) | Sub-1-8 | m/z = 524.00($C_{30}H_{18}BrClS$ = 525.89) |
| Sub-1-6 | m/z = 445.97($C_{24}H_{12}BrClO_2$ = 447.71) | Sub-1-10 | m/z = 596.05($C_{37}H_{22}BrClO$ = 597.94) |
| Sub-1-11 | m/z = 461.95($C_{24}H_{12}BrClOS$ = 463.77) | Sub-1-12 | m/z = 521.02($C_{30}H_{17}BrClNO$ = 522.83) |
| Sub-1-13 | m/z = 477.93($C_{24}H_{12}BrClS_2$ = 479.83) | Sub-1-14 | m/z = 526.99($C_{27}H_{15}BrClN_3S$ = 528.85) |
| Sub-1-15 | m/z = 610.02($C_{37}H_{20}BrClS$ = 611.98) | Sub-1-16 | m/z = 471.97($C_{26}H_{14}BrClS$ = 473.81) |
| Sub-1-17 | m/z = 355.96($C_{18}H_{10}BrClO$ = 357.63) | Sub-1-18 | m/z = 355.96($C_{18}H_{10}BrClO$ = 357.63) |
| Sub-1-19 | m/z = 355.96($C_{18}H_{10}BrClO$ = 357.63) | Sub-1-20 | m/z = 421.95($C_{22}H_{12}BrClS$ = 423.75) |
| Sub-1-21 | m/z = 405.98($C_{22}H_{12}BrClO$ = 407.69) | Sub-1-22 | m/z = 431.99($C_{24}H_{14}BrClO$ = 433.73) |
| Sub-1-23 | m/z = 447.97($C_{24}H_{14}BrClS$ = 449.79) | Sub-1-24 | m/z = 431.99($C_{24}H_{14}BrClO$ = 433.73) |
| Sub-1-25 | m/z = 447.97($C_{24}H_{14}BrClS$ = 449.79) | Sub-1-26 | m/z = 447.97($C_{24}H_{14}BrClS$ = 449.79) |
| Sub-1-27 | m/z = 431.99($C_{24}H_{14}BrClO$ = 433.73) | Sub-1-28 | m/z = 447.97($C_{24}H_{14}BrClS$ = 449.79) |
| Sub-1-29 | m/z = 447.97($C_{24}H_{14}BrClS$ = 449.79) | Sub-1-30 | m/z = 447.97($C_{24}H_{14}BrClS$ = 449.79) |
| Sub-1-31 | m/z = 508.02($C_{30}H_{18}BrClO$ = 509.83) | Sub-1-32 | m/z = 508.02($C_{30}H_{18}BrClO$ = 509.83) |
| Sub-1-33 | m/z = 508.02($C_{30}H_{18}BrClO$ = 509.83) | Sub-1-34 | m/z = 508.02($C_{30}H_{18}BrClO$ = 509.83) |
| Sub-1-35 | m/z = 508.02($C_{30}H_{18}BrClO$ = 509.83) | Sub-1-36 | m/z = 508.02($C_{30}H_{18}BrClO$ = 509.83) |
| Sub-1-37 | m/z = 508.02($C_{30}H_{18}BrClO$ = 509.83) | Sub-1-38 | m/z = 508.02($C_{30}H_{18}BrClO$ = 509.83) |
| Sub-1-39 | m/z = 508.02($C_{30}H_{18}BrClO$ = 509.83) | Sub-1-40 | m/z = 508.02($C_{30}H_{18}BrClO$ = 509.83) |
| Sub-1-41 | m/z = 524.00($C_{30}H_{18}BrClS$ = 525.89) | Sub-1-42 | m/z = 524.00($C_{30}H_{18}BrClS$ = 525.89) |
| Sub-1-43 | m/z = 508.02($C_{30}H_{18}BrClO$ = 509.83) | Sub-1-44 | m/z = 508.02($C_{30}H_{18}BrClO$ = 509.83) |
| Sub-1-45 | m/z = 508.02($C_{30}H_{18}BrClO$ = 509.83) | Sub-1-46 | m/z = 508.02($C_{30}H_{18}BrClO$ = 509.83) |
| Sub-1-47 | m/z = 524.00($C_{30}H_{18}BrClS$ = 525.89) | Sub-1-48 | m/z = 461.95($C_{24}H_{12}BrClOS$ = 463.77) |
| Sub-1-49 | m/z = 461.95($C_{24}H_{12}BrClOS$ = 463.77) | Sub-1-50 | m/z = 477.93($C_{24}H_{12}BrClS_2$ = 479.83) |
| Sub-1-51 | m/z = 461.95($C_{24}H_{12}BrClOS$ = 463.77) | Sub-1-52 | m/z = 511.96($C_{28}H_{14}BrClOS$ = 513.83) |
| Sub-1-53 | m/z = 461.95($C_{24}H_{12}BrClOS$ = 463.77) | Sub-1-54 | m/z = 521.02($C_{30}H_{17}BrClNO$ = 522.83) |
| Sub-1-55 | m/z = 371.94($C_{18}H_{10}BrClS$ = 373.69) | Sub-1-56 | m/z = 461.95($C_{24}H_{12}BrClOS$ = 463.77) |
| Sub-1-57 | m/z = 596.05($C_{37}H_{22}BrClO$ = 597.94) | Sub-1-58 | m/z = 461.95($C_{24}H_{12}BrClOS$ = 463.77) |
| Sub-1-59 | m/z = 534.04($C_{32}H_{20}BrClO$ = 535.87) | Sub-1-60 | m/z = 461.95($C_{24}H_{12}BrClOS$ = 463.77) |
| Sub-1-61 | m/z = 445.97($C_{24}H_{12}BrClO_2$ = 447.71) | Sub-1-62 | m/z = 610.02($C_{37}H_{20}BrClS$ = 611.98) |
| Sub-1-63 | m/z = 641.99($C_{37}H_{20}BrClS_2$ = 644.04) | Sub-1-64 | m/z = 703.04($C_{42}H_{23}BrClNOS$ = 705.07) |
| Sub-1-65 | m/z = 461.95($C_{24}H_{12}BrClOS$ = 463.77) | Sub-1-66 | m/z = 461 .95($C_{24}H_{12}BrClOS$ = 463.77) |
| Sub-1-67 | m/z = 701.06($C_{43}H_{25}BrClNS$ = 703.09) | Sub-1-68 | m/z = 477.93($C_{24}H_{12}BrClS_2$ = 479.83) |
| Sub-1-69 | m/z = 612.03($C_{37}H_{22}BrClS$ = 614.00) | Sub-1-70 | m/z = 587.01($C_{34}H_{19}BrClNS$ = 588.95) |
| Sub-1-71 | m/z = 477.93($C_{24}H_{12}BrClS_2$ = 479.83) | Sub-1-72 | m/z = 477.93($C_{24}H_{12}BrClS_2$ = 479.83) |
| Sub-1-73 | m/z = 461.95($C_{24}H_{12}BrClOS$ = 463.77) | Sub-1-74 | m/z = 477.93($C_{24}H_{12}BrClS_2$ = 479.83) |
| Sub-1-75 | m/z = 461.95($C_{24}H_{12}BrClOS$ = 463.77) | Sub-1-76 | m/z = 588.00($C_{34}H_{18}BrClOS$ = 589.93) |
| Sub-1-77 | m/z = 434.98($C_{21}H_{11}BrClN_3O$ = 436.69) | Sub-1-78 | m/z = 500.97($C_{25}H_{13}BrClN_3S$ = 502.81) |
| Sub-1-79 | m/z = 525.99($C_{28}H_{16}BrClN_2S$ = 527.86) | Sub-1-80 | m/z = 526.99($C_{27}H_{15}BrClN_3S$ = 528.85) |
| Sub-1-81 | m/z = 279.93($C_{12}H_6BrClO$ = 281.53) | Sub-1-82 | m/z = 279.93($C_{12}H_6BrClO$ = 281.53) |
| Sub-1-83 | m/z = 295.91($C_{12}H_6BrClS$ = 297.59) | Sub-1-84 | m/z = 295.91($C_{12}H_6BrClS$ = 297.59) |
| Sub-1-85 | m/z = 371.94($C_{18}H_{10}BrClS$ = 373.69) | Sub-1-86 | m/z = 371.94($C_{18}H_{10}BrClS$ = 373.69) |
| Sub-1-87 | m/z = 279.93($C_{12}H_6BrClO$ = 281.53) | Sub-1-88 | m/z = 497.98($C_{28}H_{16}BrClS$ = 499.85) |
| Sub-1-89 | m/z = 461.95($C_{24}H_{12}BrClOS$ = 463.77) | Sub-1-90 | m/z = 295.91($C_{12}H_6BrClS$ = 297.59) |
| Sub-1-91 | m/z = 295.91($C_{12}H_6BrClS$ = 297.59) | Sub-1-92 | m/z = 295.91($C_{12}H_6BrClS$ = 297.59) |
| Sub-1-93 | m/z = 481.86($C_{18}H_9BrClIO$ = 483.53) | Sub-1-94 | m/z = 481.86($C_{18}H_9BrClIO$ = 483.53) |
| Sub-1-95 | m/z = 497.83($C_{18}H_9BrClIS$ = 499.59) | Sub-1-96 | m/z = 405.98($C_{22}H_{12}BrClO$ = 407.69) |
| Sub-1-97 | m/z = 481.86($C_{18}H_9BrClIO$ = 483.53) | Sub-1-98 | m/z = 371.94($C_{18}H_{10}BrClS$ = 373.69) |
| Sub-1-99 | m/z = 497.83($C_{18}H_9BrClIS$ = 499.59) | Sub-1-100 | m/z = 531.87($C_{22}H_{11}BrClIO$ = 533.59) |
| Sub-1-101 | m/z = 481.86($C_{18}H_9BrClIO$ = 483.53) | Sub-1-102 | m/z = 481.86($C_{18}H_9BrClIO$ = 483.53) |
| Sub-1-103 | m/z = 524.00($C_{30}H_{18}BrClS$ = 525.89) | Sub-1-104 | m/z = 547.85($C_{22}H_{11}BrClIS$ = 549.65) |
| Sub-1-105 | m/z = 371.94($C_{18}H_{10}BrClS$ = 373.69) | Sub-1-106 | m/z = 433.87($C_{18}H_9Br_2ClO$ = 436.53) |
| Sub-1-107 | m/z = 449.85($C_{18}H_9Br_2ClS$ = 452.59) | Sub-1-108 | m/z = 483.89($C_{22}H_{11}Br_2ClO$ = 486.59) |
| Sub-1-109 | m/z = 355.96($C_{18}H_{10}BrClO$ = 357.63) | Sub-1-110 | m/z = 279.93($C_{12}H_6BrClO$ = 281.53) |
| Sub-1-111 | m/z = 355.96($C_{18}H_{10}BrClO$ = 357.63) | Sub-1-112 | m/z = 279.93($C_{12}H_6BrClO$ = 281.53) |
| Sub-1-113 | m/z = 295.91($C_{12}H_6BrClS$ = 297.59) | Sub-1-114 | m/z = 295.91($C_{12}H_6BrClS$ = 297.59) |
| Sub-1-115 | m/z = 477.93($C_{24}H_{12}BrClS_2$ = 479.83) | Sub-1-116 | m/z = 295.91($C_{12}H_6BrClS$ = 297.59) |
| Sub-1-117 | m/z = 279.93($C_{12}H_6BrClO$ = 281.53) | Sub-1-118 | m/z = 279.93($C_{12}H_6BrClO$ = 281.53) |
| Sub-1-119 | m/z = 329.94($C_{16}H_8BrClO$ = 331.59) | Sub-1-120 | m/z = 279.93($C_{12}H_6BrClO$ = 281.53) |
| Sub-1-121 | m/z = 295.91($C_{12}H_6BrClS$ = 297.59) | Sub-1-122 | m/z = 295 .91($C_{12}H_6BrClS$ = 297.59) |
| Sub-1-123 | m/z = 345.92($C_{16}H_8BrClS$ = 347.65) | Sub-1-124 | m/z = 345.92($C_{16}H_8BrClS$ = 347.65) |
| Sub-1-125 | m/z = 371.94($C_{18}H_{10}BrClS$ = 373.69) | Sub-1-126 | m/z = 511.96($C_{28}H_{14}BrClOS$ = 513.83) |
| Sub-1-127 | m/z = 355.96($C_{18}H_{10}BrClO$ = 357.63) | Sub-1-128 | m/z = 431.99($C_{24}H_{14}BrClO$ = 433.73) |
| Sub-1-129 | m/z = 279.93($C_{12}H_6BrClO$ = 281.53) | Sub-1-130 | m/z = 295.91($C_{12}H_6BrClS$ = 297.59) |
| Sub-1-131 | m/z = 295.91($C_{12}H_6BrClS$ = 297.59) | Sub-1-132 | m/z = 355.96($C_{18}H_{10}BrClO$ = 357.63) |
| Sub-1-133 | m/z = 295.91($C_{12}H_6BrClS$ = 297.59) | Sub-1-134 | m/z = 371.94($C_{18}H_{10}BrClS$ = 373.69) |
| Sub-1-135 | m/z = 371.94($C_{18}H_{10}BrClS$ = 373.69) | | |

II. Synthesis of Sub-2

Sub-2 of Scheme 1 is synthesized by the reaction route of Scheme 4 below, but is not limited thereto. $Hal^6$ is I, Br or Cl.

<Reaction Scheme 4>

<Reaction Scheme 4>

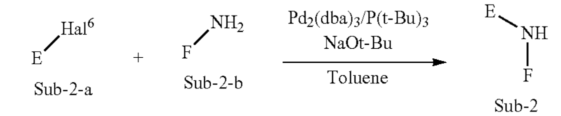

Sub-2-a Sub-2-b Sub-2

In Reaction Scheme 4, E and F are as defined in Scheme 1.

1. Synthesis Example of Sub-2-2

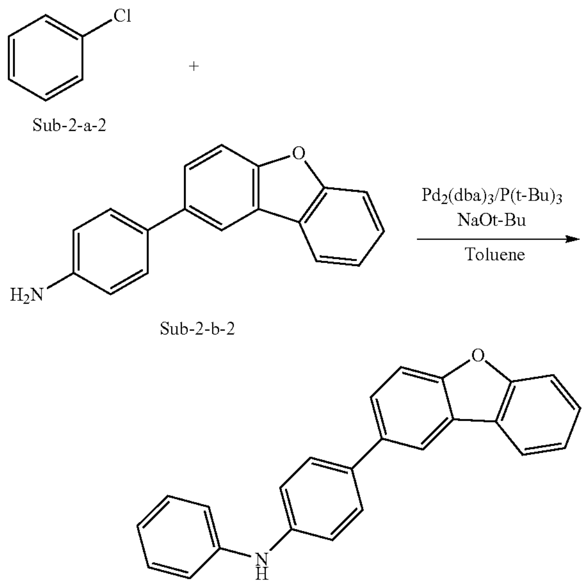

Sub-2-a-2 Sub-2-b-2 Sub-2-2

After placing Sub-2-a-2 (20.0 g, 177.7 mmol), Sub-2-b-2 (44.5 g, 177.7 mmol), $Pd_2(dba)_3$ 4.9 g, 5.3 mmol), $P(t-Bu)_3$ (2.2 g, 10.7 mmol), NaOt-Bu (34.2 g, 355.4 mmol), toluene (888 mL) to a round-bottom flask, proceed with the reaction at 80° C. When the reaction is complete, the mixture is extracted with $CH_2Cl_2$ and water, and the organic layer is dried over $MgSO_4$ and concentrated. Then, the resulting organic material was recrystallized by silicagel column to obtain 45.3 g of a product. (yield 76%)

2. Synthesis Example of Sub-2-3

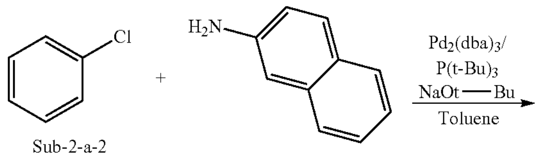

Sub-2-a-2 Sub-2-b-3

-continued

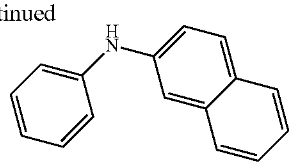

Sub-2-3

Sub-2-a-2 (20.0 g, 177.7 mmol), Sub-2-b-3 (70.9 g, 177.7 mmol), $Pd_2(dba)_3$ (4.9 g, 5.3 mmol), $P(t-Bu)_3$ (2.2 g, 10.7 mmol), NaOt-Bu (34.2 g, 355.4 mmol), toluene (888 mL) were tested in a round-bottom flask in the same manner as in Sub-2-2 to obtain 30.0 g of the product. (Yield: 77%)

3. Synthesis Example of Sub-2-94

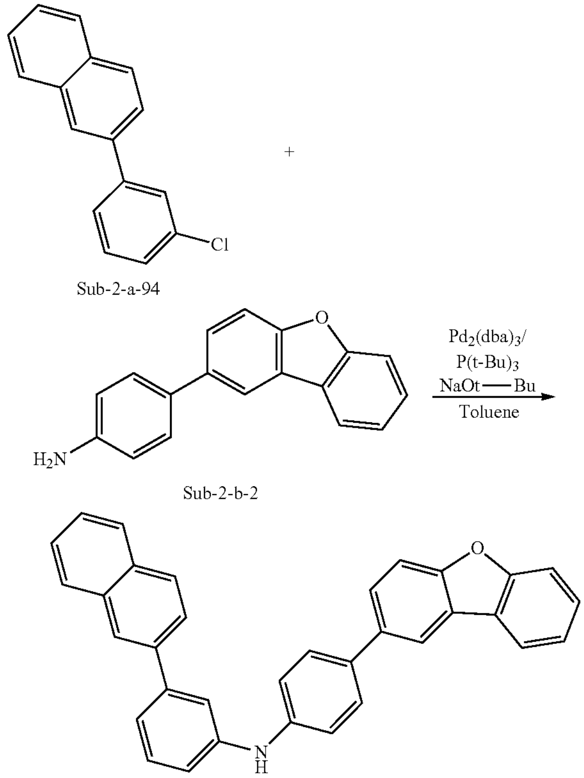

Sub-2-a-94 Sub-2-b-2 Sub-2-94

Sub-2-a-94 (20.0 g, 83.8 mmol), Sub-2-b-2 (21.0 g, 83.8 mmol), $Pd_2(dba)_3$ (2.3 g, 2.5 mmol), $P(t-Bu)_3$ (1.0 g, 5.0 mmol), NaOt-Bu (16.1 g, 167.6 mmol), toluene (419 mL) were tested in a round-bottom flask in the same manner as in Sub-2-2 to obtain 30.2 g of the product. (Yield: 78%)

4. Synthesis Example of Sub-2-96

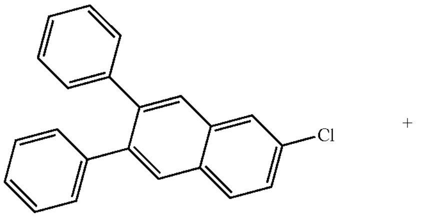

Sub-2-a-96

-continued

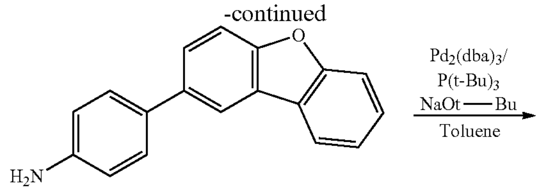

Sub-2-b-2

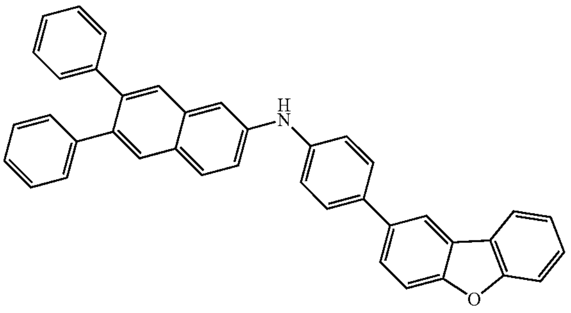

Sub-2-96

Sub-2-a-96 (20.0 g, 63.5 mmol), Sub-2-b-2 (15.9 g, 63.5 mmol), $Pd_2(dba)_3$ (1.8 g, 1.9 mmol), $P(t\text{-}Bu)_3$ (0.8 g, 3.8 mmol), NaOt-Bu (12.2 g, 127.1 mmol), toluene (318 mL) were tested in a round-bottom flask in the same manner as in Sub-2-2 to obtain 26.3 g of the product. (Yield: 77%)

5. Synthesis Example of Sub-2-114

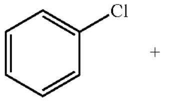

Sub-2-a-2

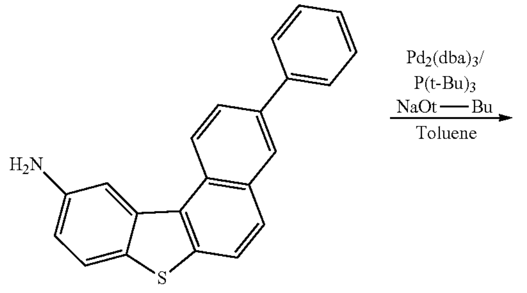

Sub-2-b-114

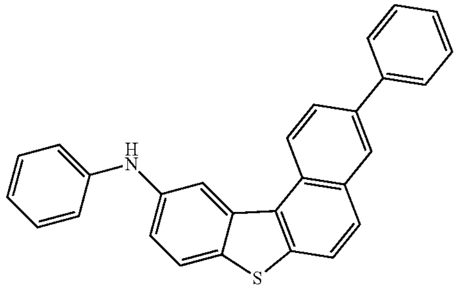

Sub-2-114

Sub-2-a-2 (20.0 g, 177.7 mmol), Sub-2-b-114 (5.4 g, 60.3 mmol), $Pd_2(dba)_3$ (4.9 g, 5.3 mmol), $P(t\text{-}Bu)_3$ (2.2 g, 10.7 mmol), NaOt-Bu (34.2 g, 355.4 mmol), toluene (888 mL) were tested in a round-bottom flask in the same manner as in Sub-2-2 to obtain 56.4 g of the product. (Yield: 79%)

6. Synthesis Example of Sub-2-156

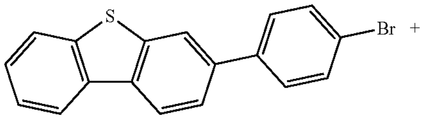

Sub-2-a-156

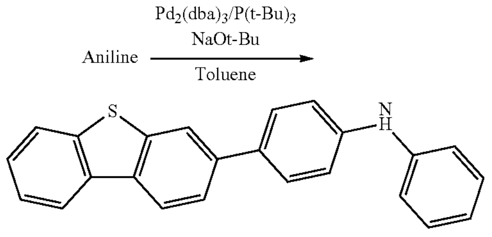

Sub-2-156

Sub-2-a-156 (30.0 g, 88.4 mmol), Aniline (8.2 g, 88.4 mmol), $Pd_2(dba)_3$ (2.43 g, 2.65 mmol), $P(t\text{-}Bu)_3$ (1.07 g, 5.31 mmol), NaOt-Bu (17.0 g, 177 mmol), toluene (440 mL) were tested in a round-bottom flask in the same manner as in Sub-2-2 to obtain 22.4 g of the product. (Yield: 72%)

7. Synthesis Example of Sub-2-159

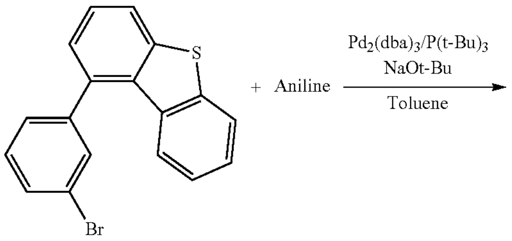

Sub-2-a-159

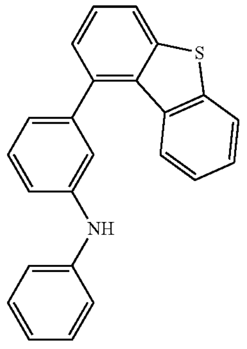

Sub-2-159

Sub-2-a-159 (30.0 g, 88.4 mmol), Aniline (8.2 g, 88.4 mmol), $Pd_2(dba)_3$ (2.43 g, 2.65 mmol), $P(t\text{-}Bu)_3$ (1.07 g, 5.31 mmol), NaOt-Bu (17.0 g, 177 mmol), toluene (440 mL) were tested in a round-bottom flask in the same manner as in Sub-2-2 to obtain 21.4 g of the product. (Yield: 69%)

8. Synthesis Example of Sub-2-162

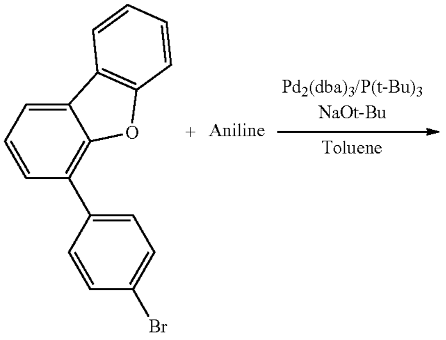

Sub-2-a-162

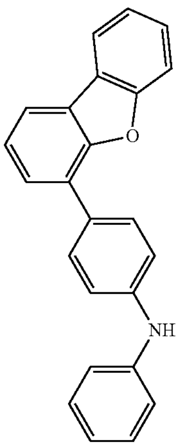

Sub-2-162

Sub-2-a-162 (30.0 g, 92.8 mmol), Aniline (8.6 g, 92.8 mmol), $Pd_2(dba)_3$ (2.55 g, 2.78 mmol), $P(t-Bu)_3$ (1.13 g, 5.57 mmol), NaOt-Bu (17.8 g, 186 mmol), toluene (465 mL) were tested in a round-bottom flask in the same manner as in Sub-2-2 to obtain 23.4 g of the product. (Yield: 75%)

The compound belonging to Sub-2 may be the following compounds, but is not limited thereto, and Table 2 below shows FD-MS (Field Desorption-Mass Spectrometry) values of the compounds belonging to Sub-2.

Sub-2-1

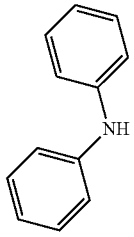

Sub-2-2

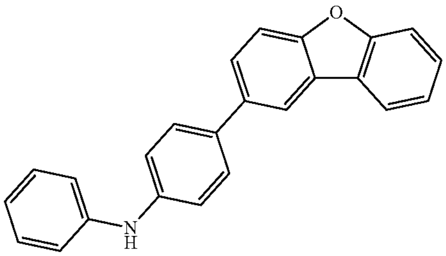

-continued

Sub-2-3

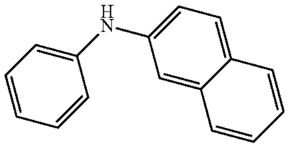

Sub-2-4

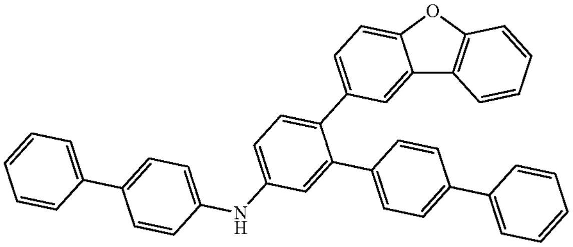

Sub-2-5

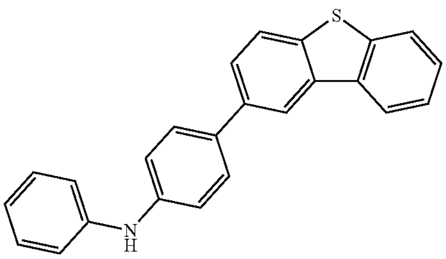

Sub-2-6

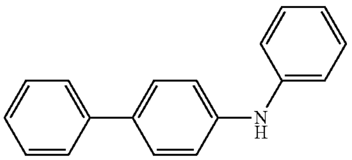

Sub-2-7

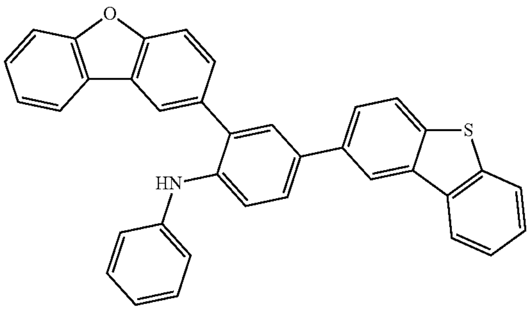

Sub-2-8

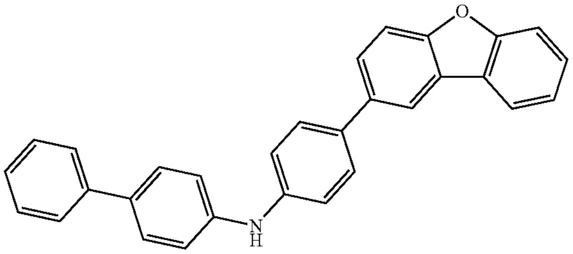

-continued
Sub-2-9
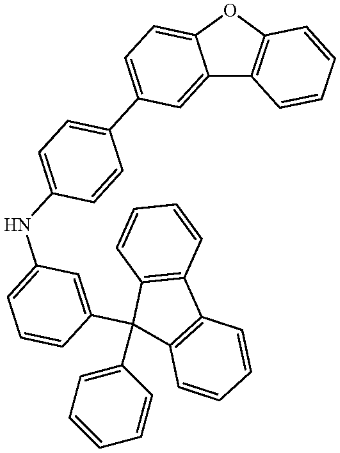
Sub-2-10
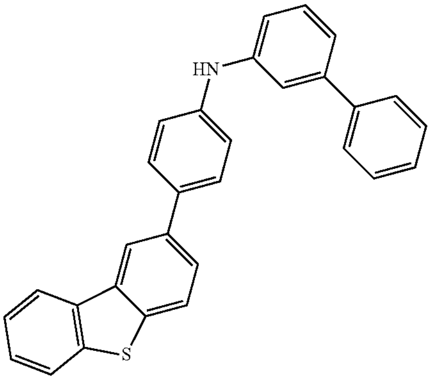
Sub-2-11
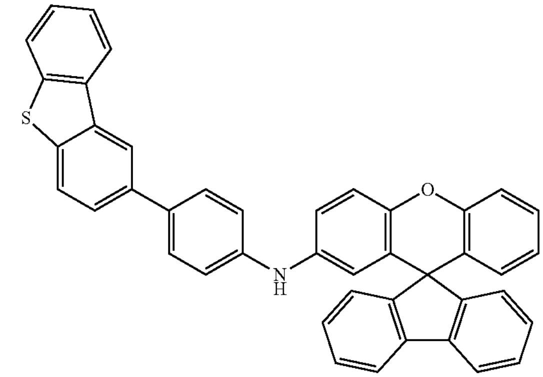
Sub-2-12
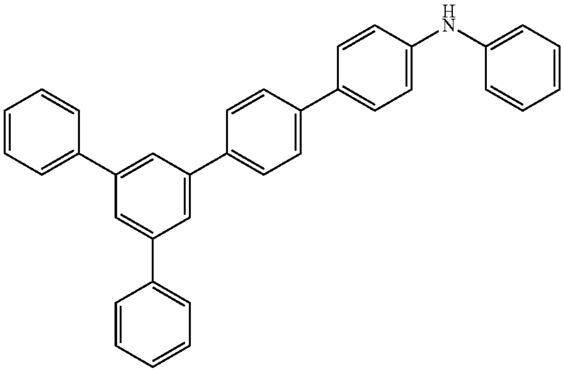
-continued
Sub-2-13
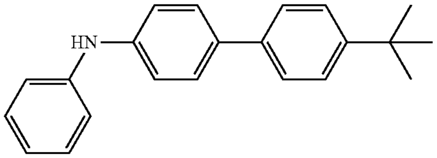
Sub-2-14
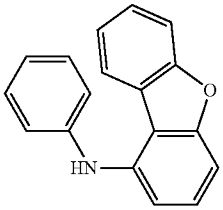
Sub-2-15
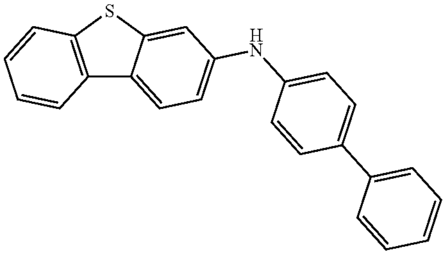
Sub-2-16
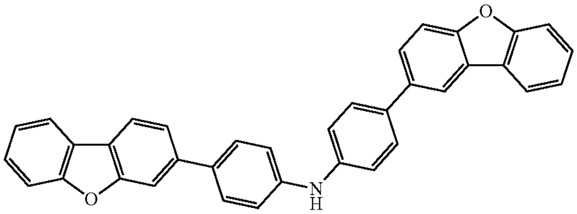
Sub-2-17
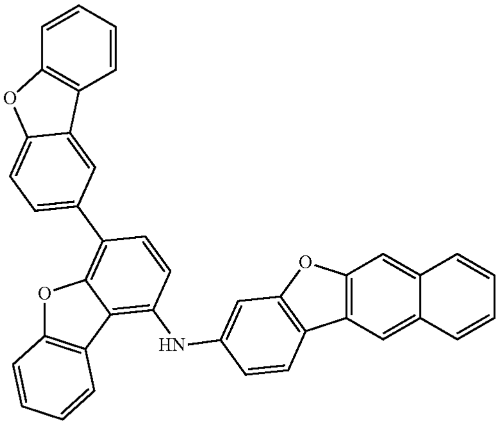

-continued
Sub-2-18
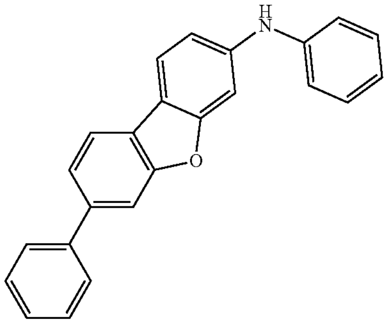
Sub-2-19
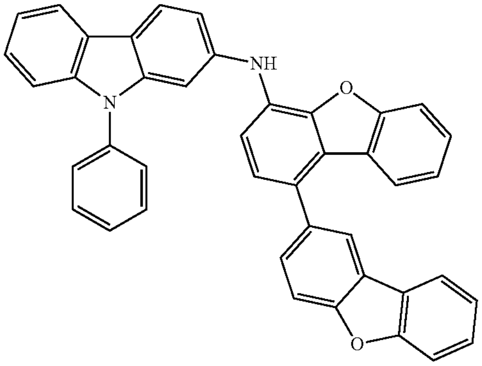
Sub-2-20
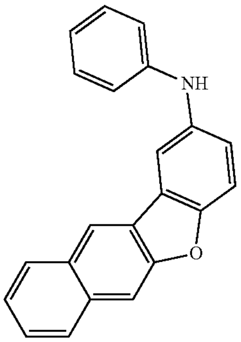
Sub-2-21
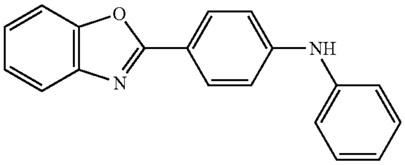
Sub-2-22
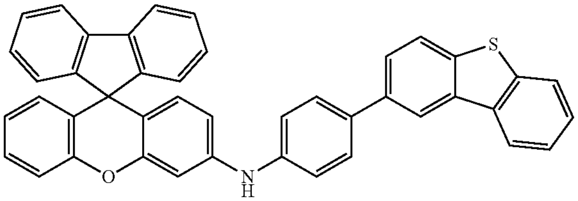
-continued
Sub-2-23
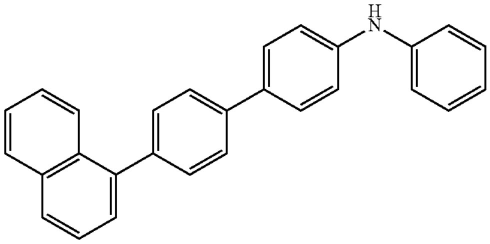
Sub-2-24
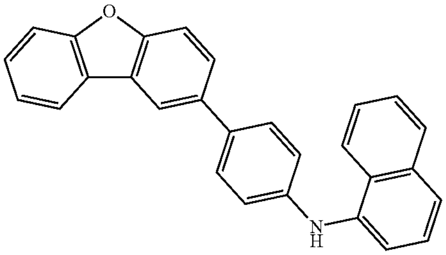
Sub-2-25
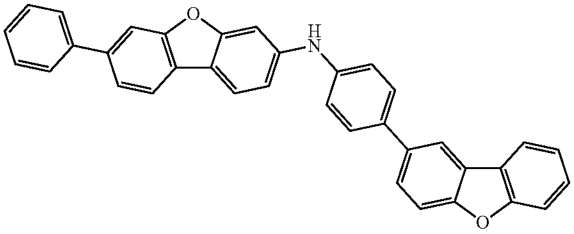
Sub-2-26
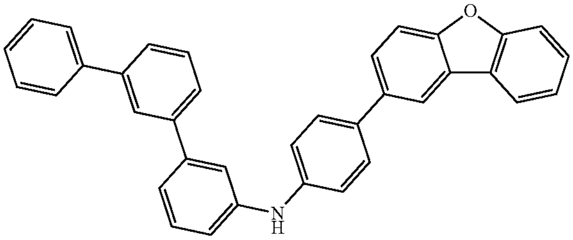
Sub-2-27
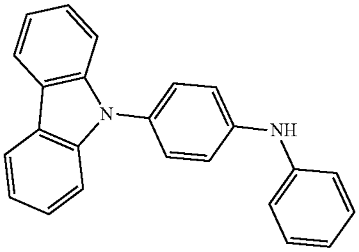

-continued
Sub-2-28
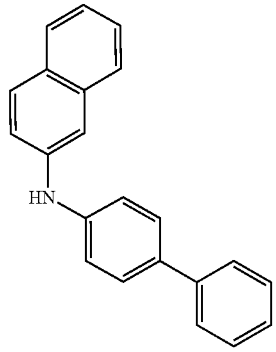
Sub-2-29
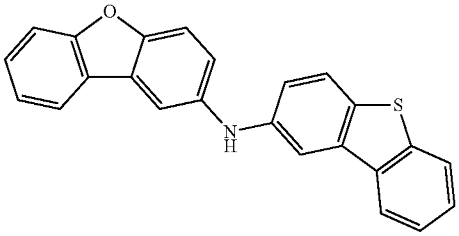
Sub-2-30
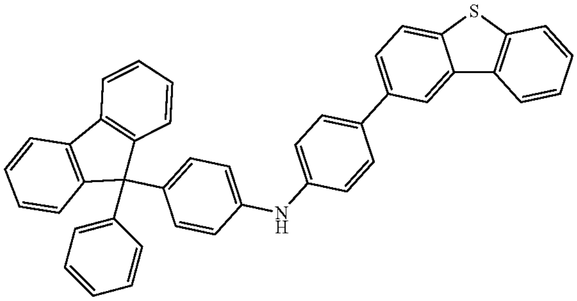
Sub-2-31
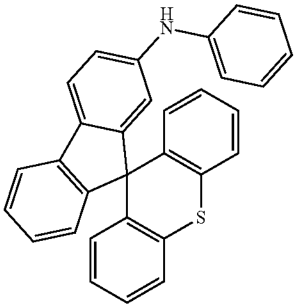
Sub-2-32
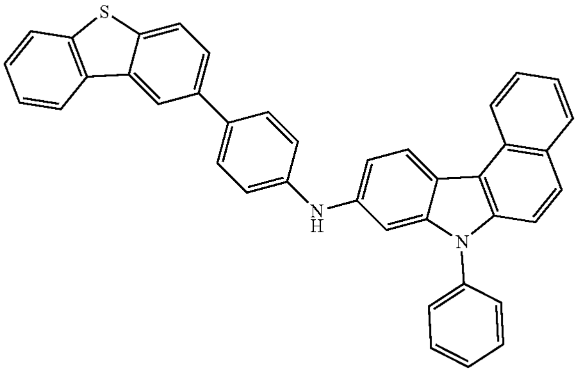
-continued
Sub-2-33
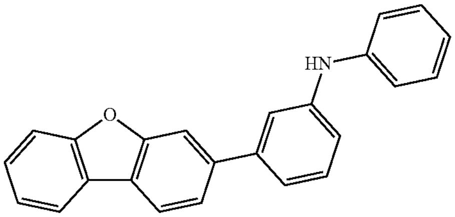
Sub-2-34
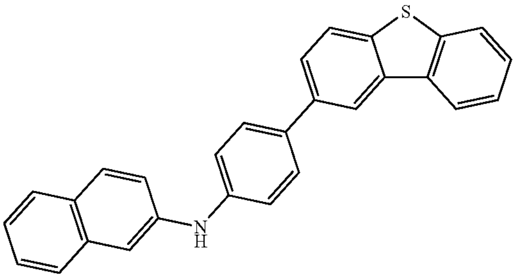
Sub-2-35
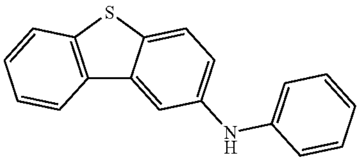
Sub-2-36
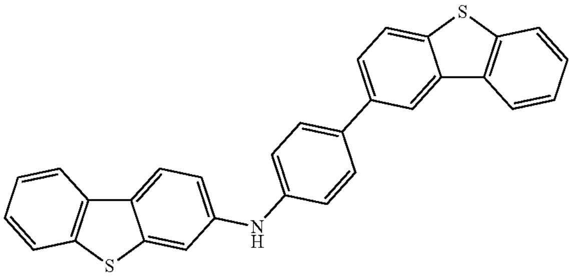
Sub-2-37
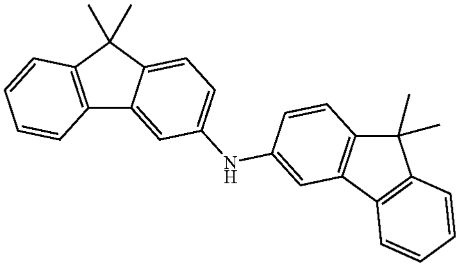
Sub-2-38
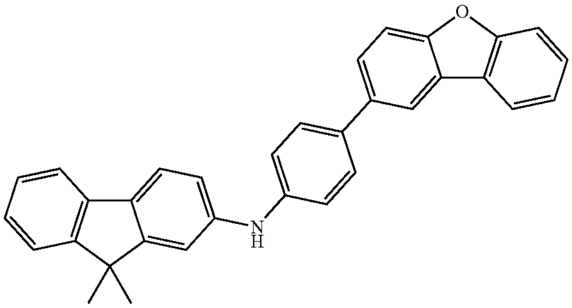

-continued
Sub-2-39
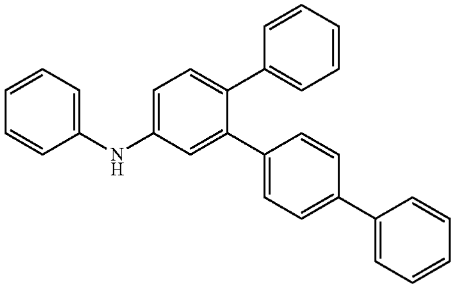
Sub-2-40
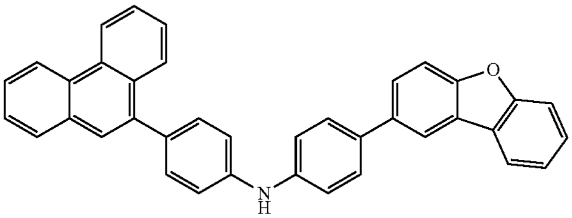
Sub-2-41
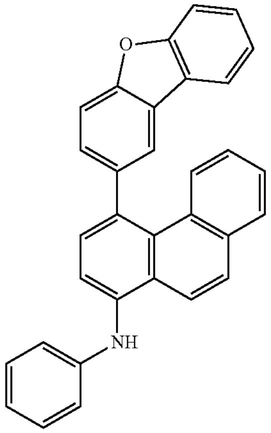
Sub-2-42
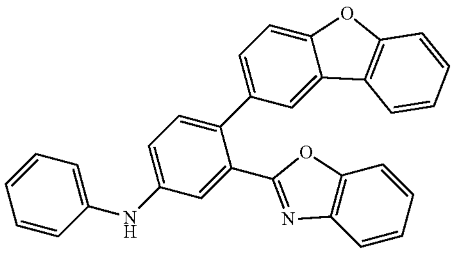
Sub-2-43
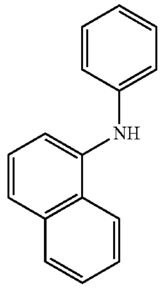
-continued
Sub-2-44
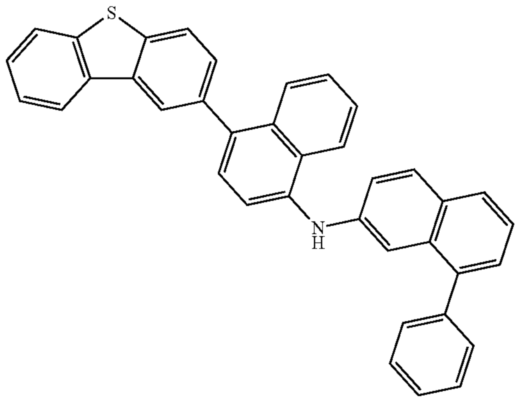
Sub-2-45
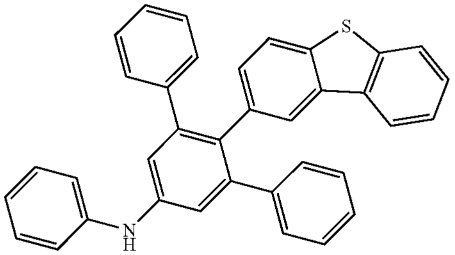
Sub-2-46
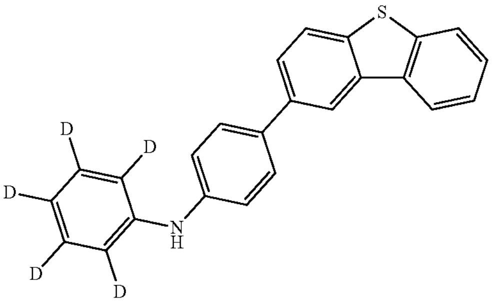
Sub-2-47
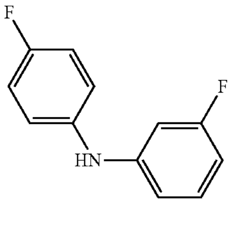
Sub-2-48
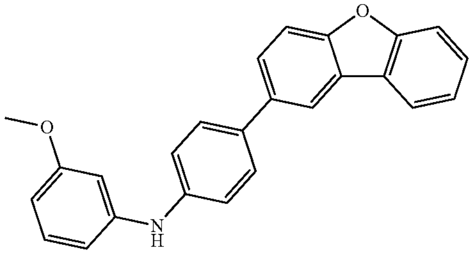

-continued
Sub-2-49
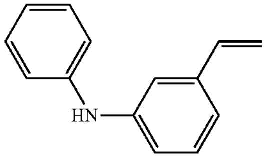
Sub-2-50
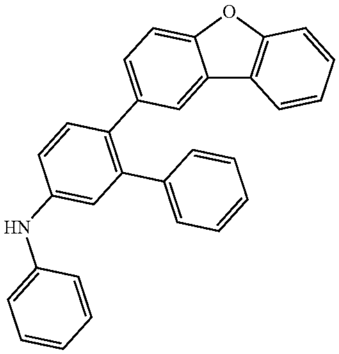
Sub-2-51
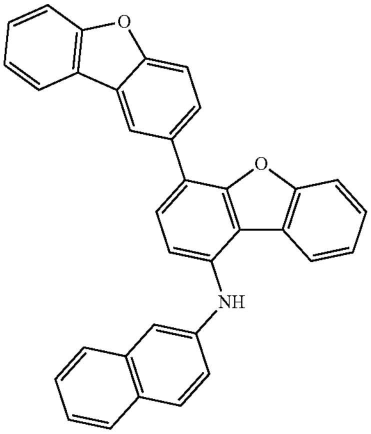
Sub-2-52
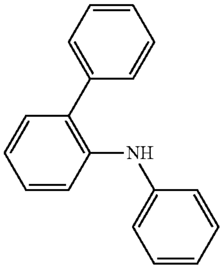
Sub-2-53
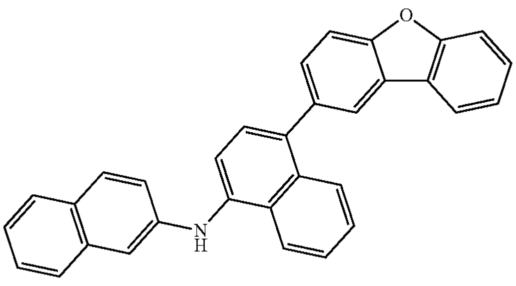
-continued
Sub-2-54
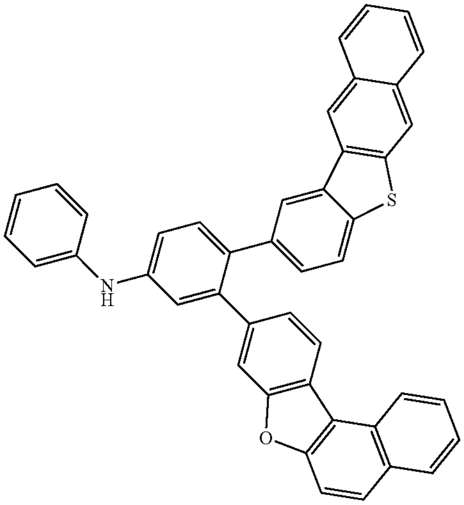
Sub-2-55
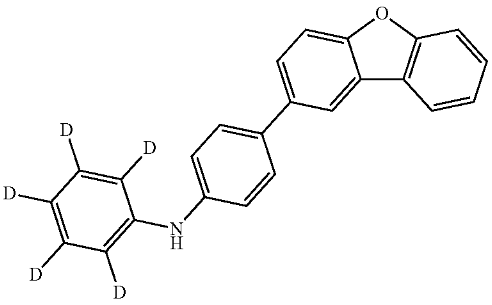
Sub-2-56
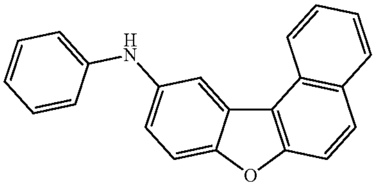
Sub-2-57
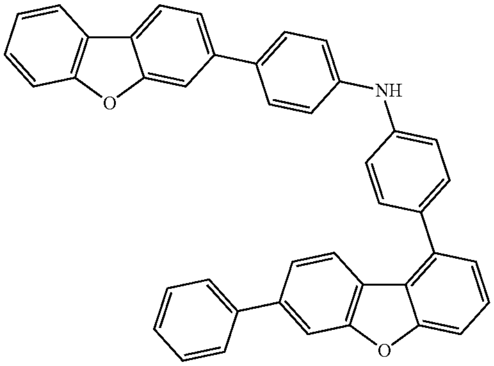

Sub-2-58
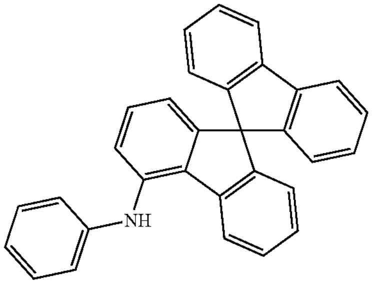
Sub-2-59
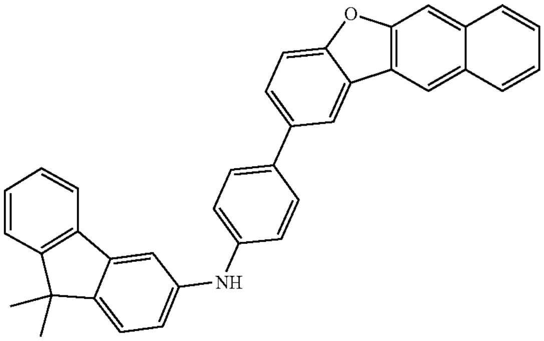
Sub-2-60
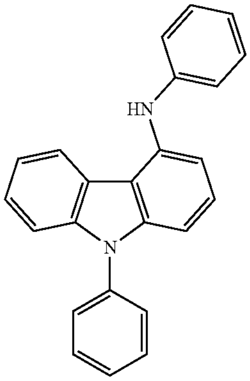
Sub-2-61
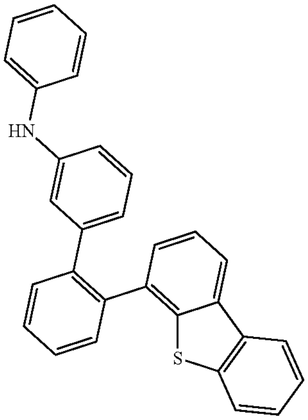
Sub-2-62
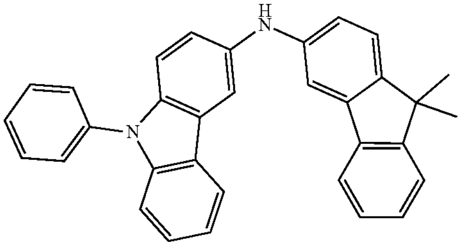
Sub-2-63
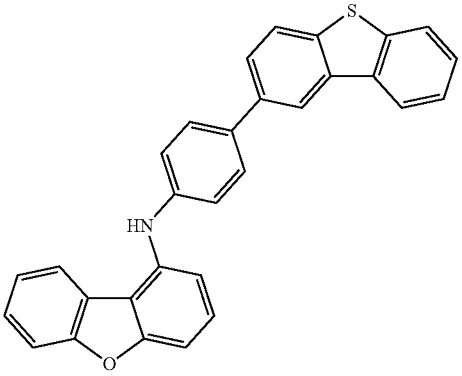
Sub-2-64
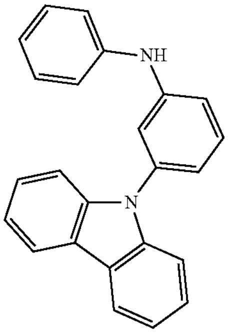
Sub-2-65
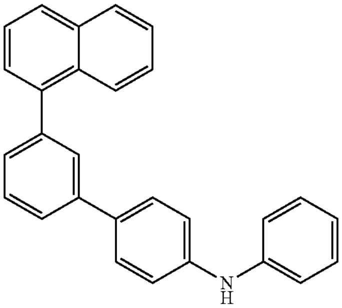
Sub-2-66
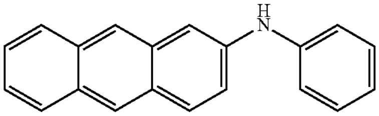
Sub-2-67
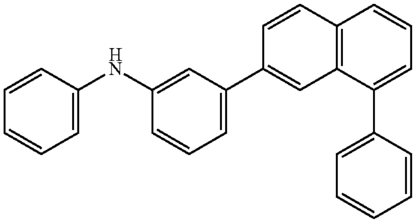

-continued
Sub-2-68
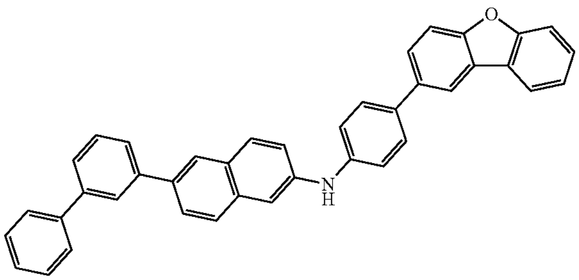
Sub-2-69
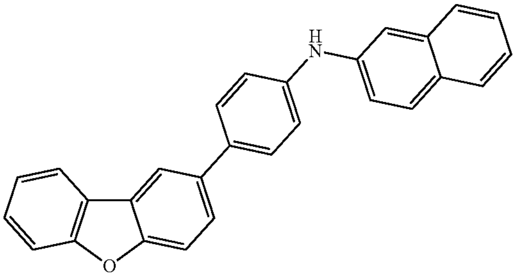
Sub-2-70
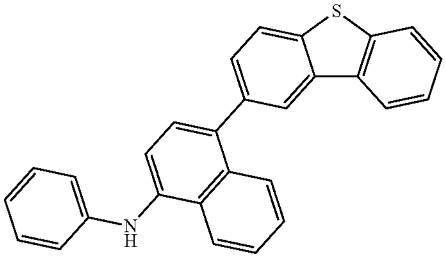
Sub-2-71
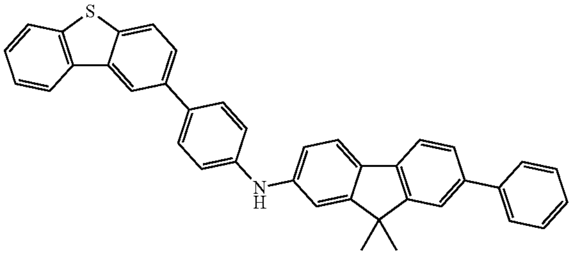
Sub-2-72
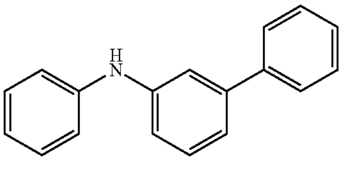
Sub-2-73
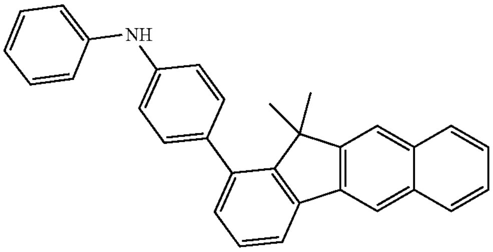
-continued
Sub-2-74
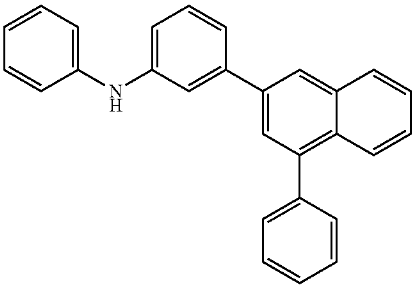
Sub-2-75
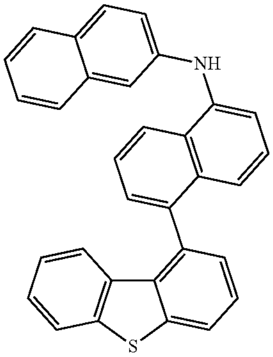
Sub-2-76
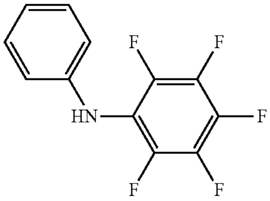
Sub-2-77
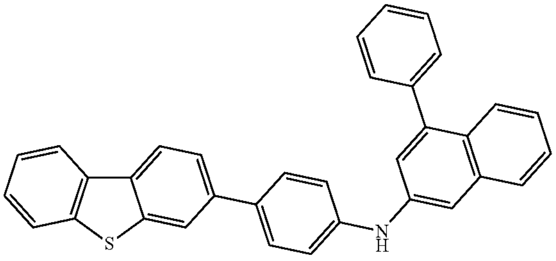
Sub-2-78
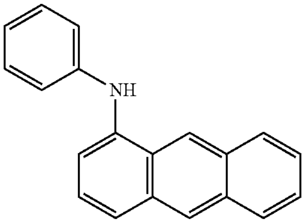

-continued
Sub-2-79
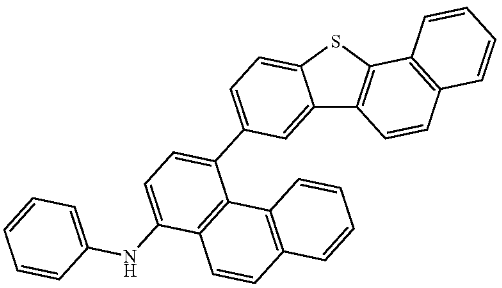
Sub-2-80
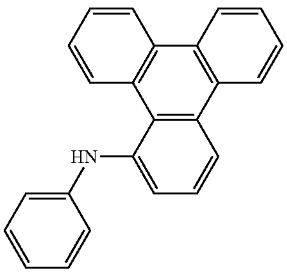
Sub-2-81
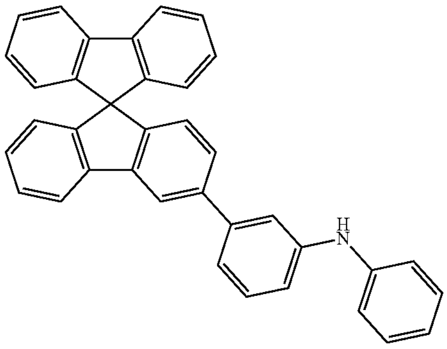
Sub-2-82
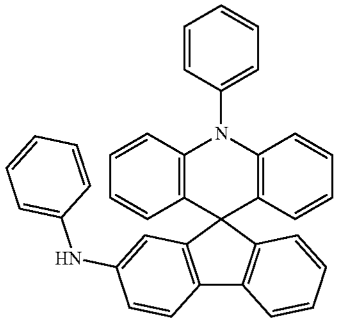
Sub-2-83
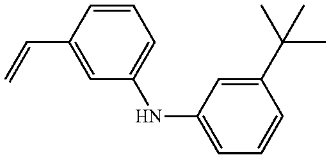
Sub-2-84
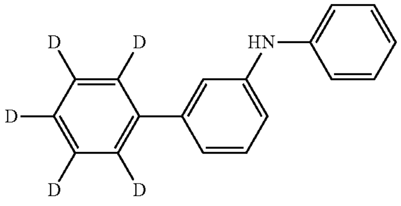
-continued
Sub-2-85
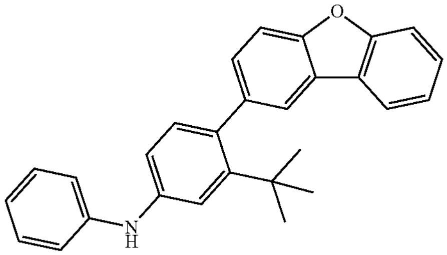
Sub-2-86
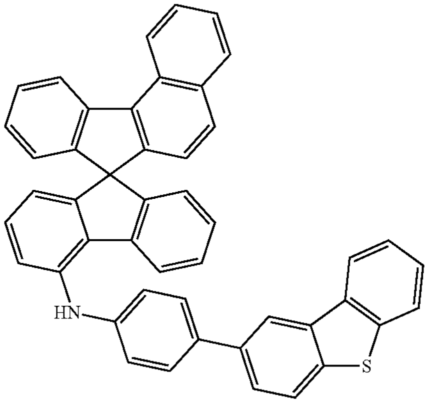
Sub-2-87
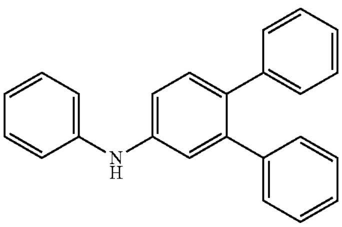
Sub-2-88
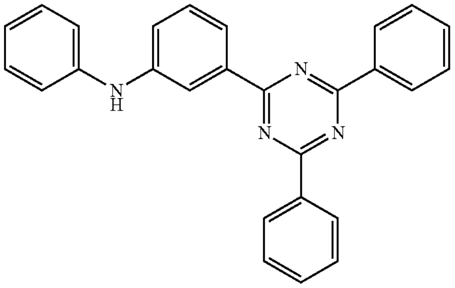
Sub-2-89
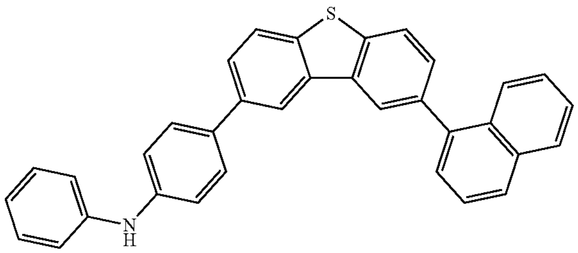

-continued
Sub-2-90
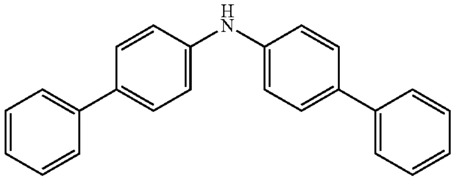
Sub-2-91
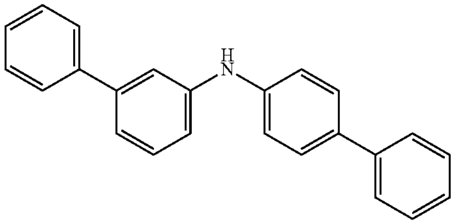
Sub-2-92
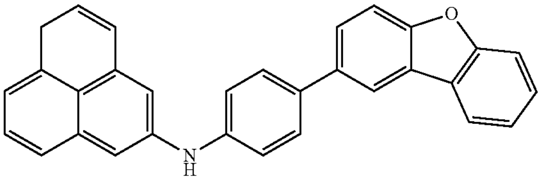
Sub-2-93
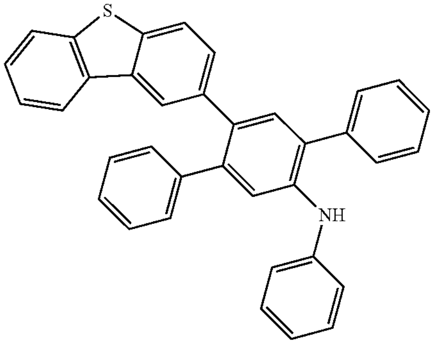
Sub-2-94
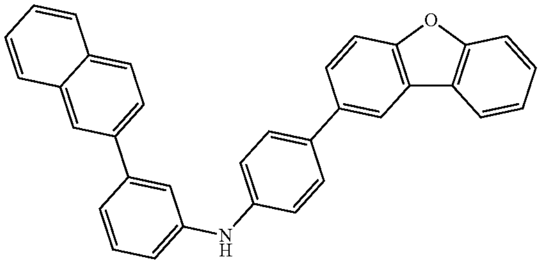
Sub-2-95
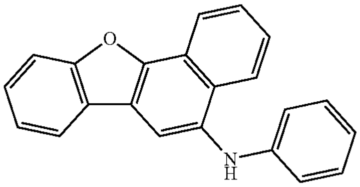
-continued
Sub-2-96
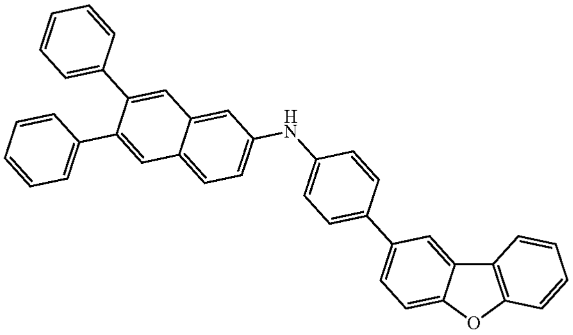
Sub-2-97
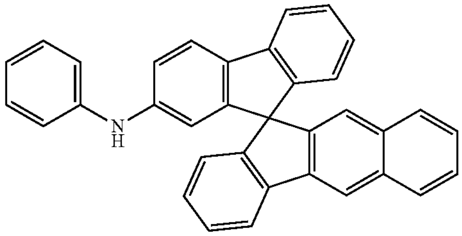
Sub-2-98
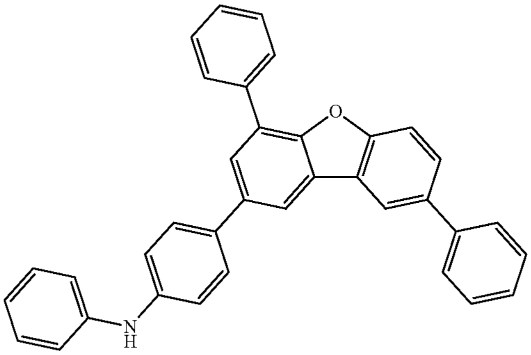
Sub-2-99
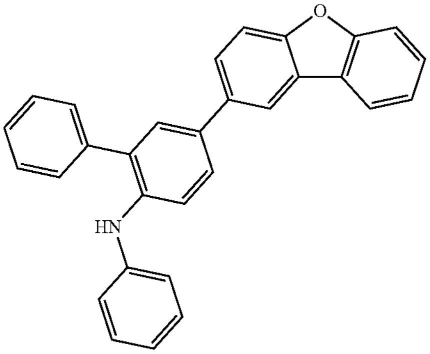

-continued
Sub-2-100
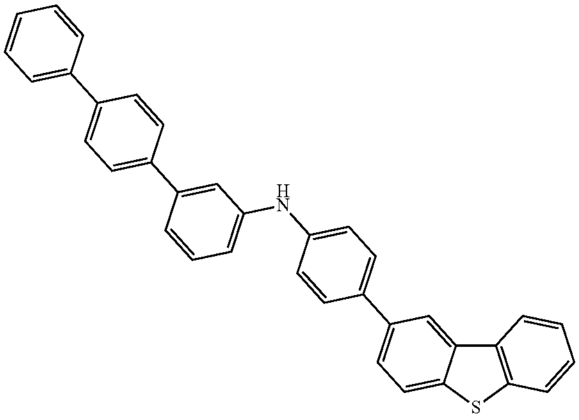
Sub-2-101
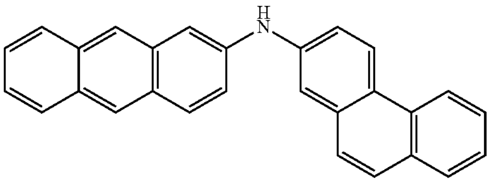
Sub-2-102
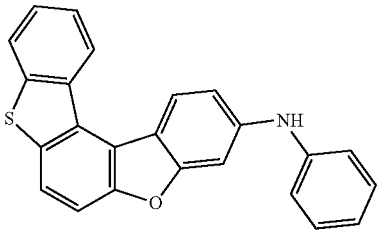
Sub-2-103
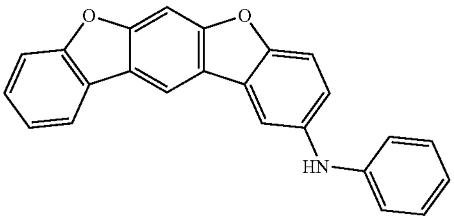
Sub-2-104
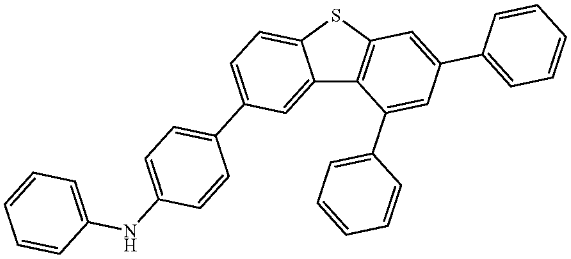
-continued
Sub-2-105
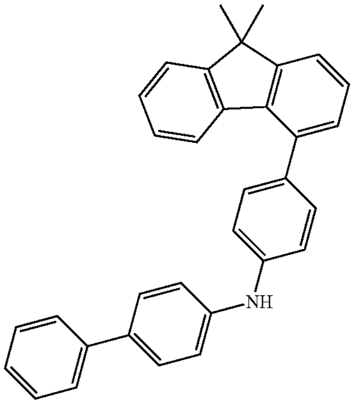
Sub-2-106
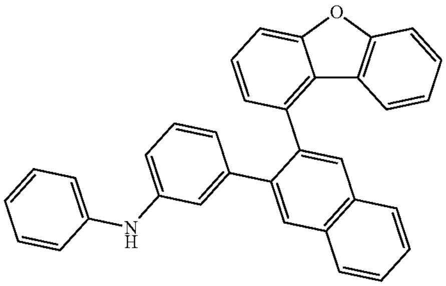
Sub-2-107
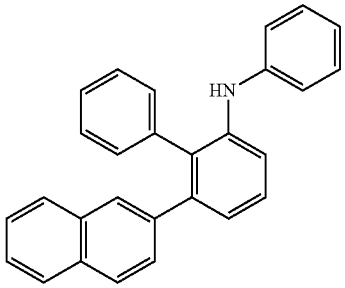
Sub-2-108
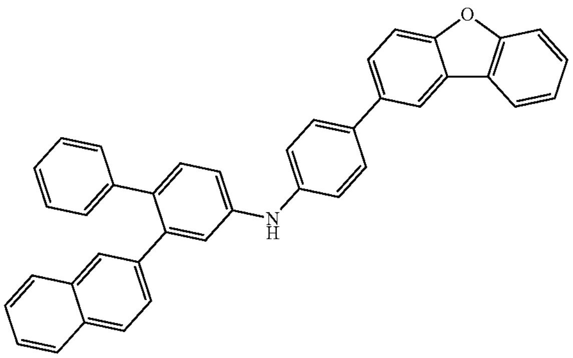

-continued
Sub-2-109
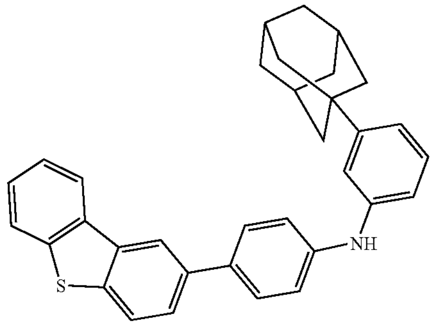
Sub-2-110
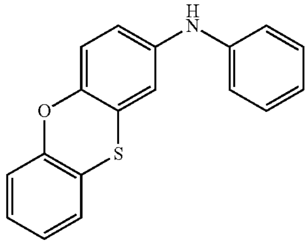
Sub-2-111
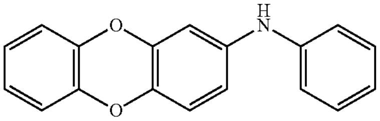
Sub-2-112
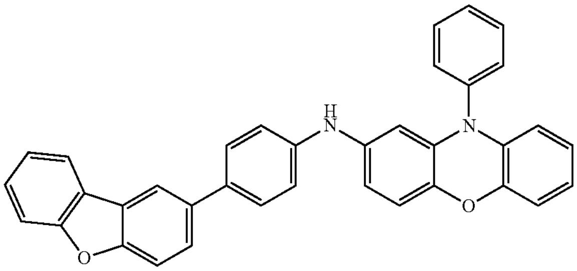
Sub-2-113
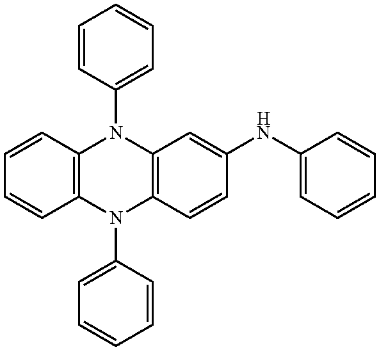
-continued
Sub-2-114
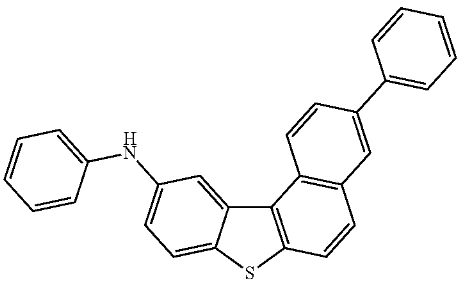
Sub-2-115
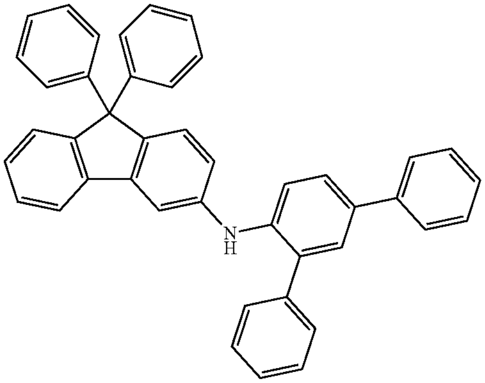
Sub-2-116
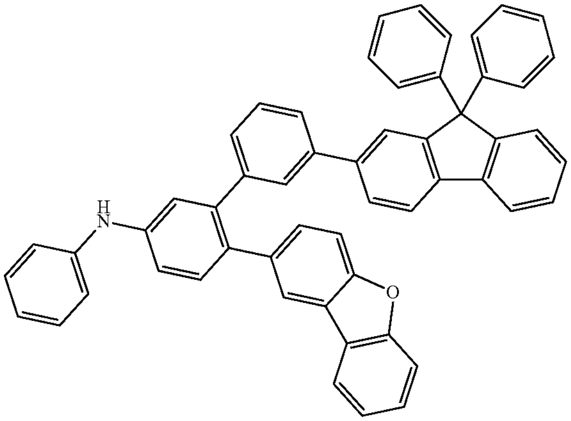
Sub-2-117
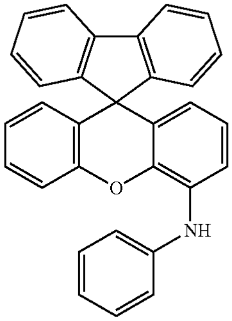

-continued
Sub-2-118
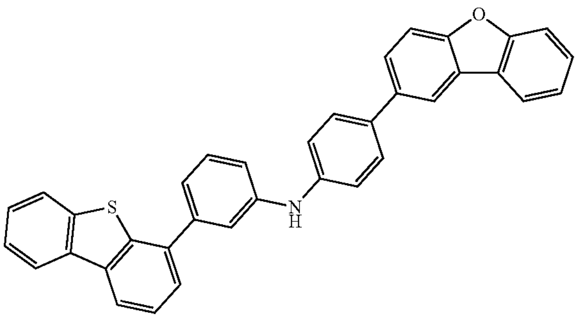
Sub-2-119
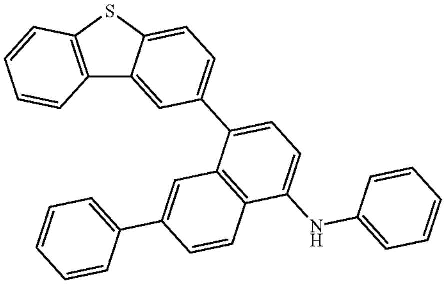
Sub-2-120
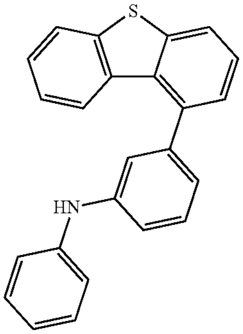
Sub-2-121
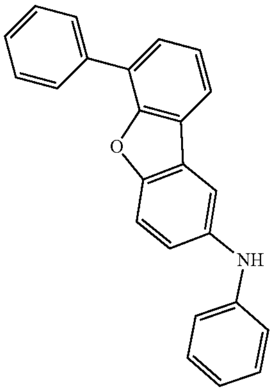
-continued
Sub-2-122
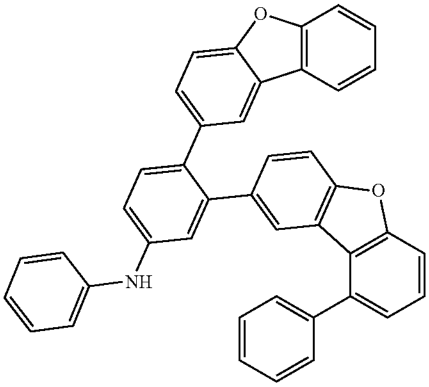
Sub-2-123
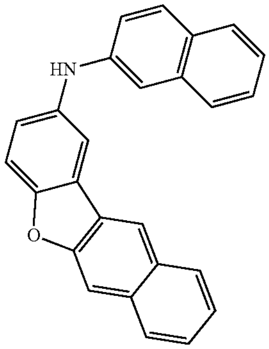
Sub-2-124
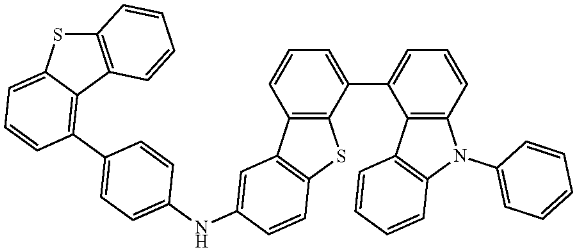
Sub-2-125
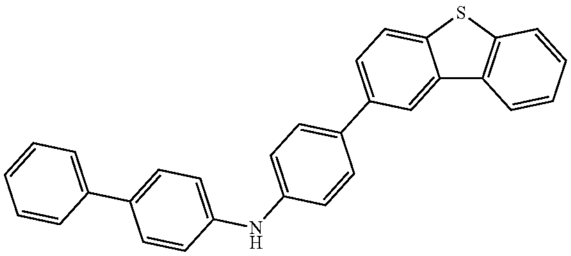
Sub-2-126
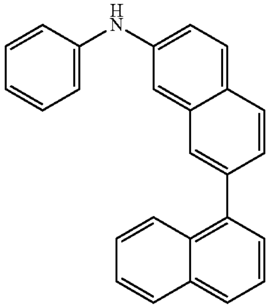

-continued
Sub-2-127
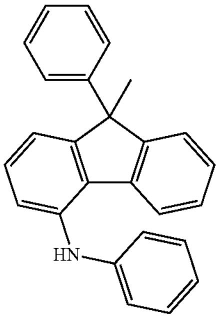
Sub-2-128
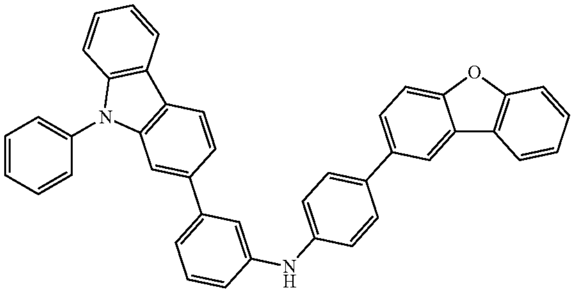
Sub-2-129
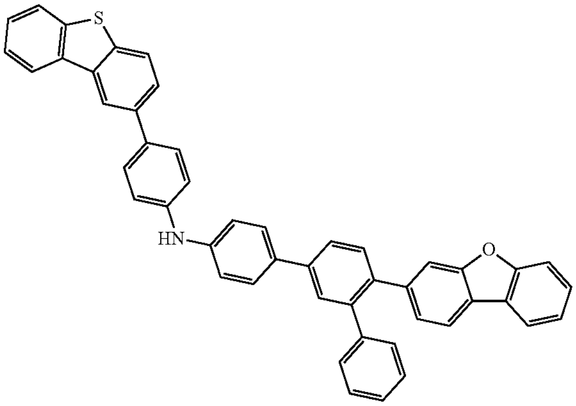
Sub-2-130
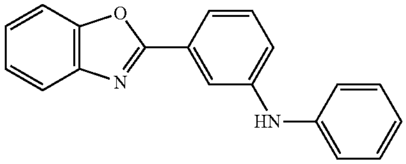
Sub-2-131
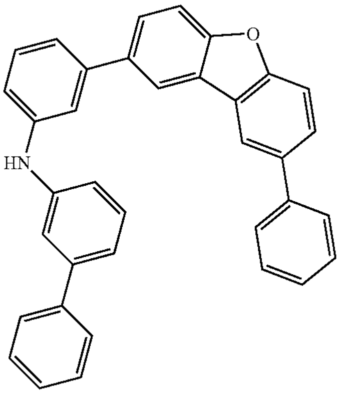
-continued
Sub-2-132
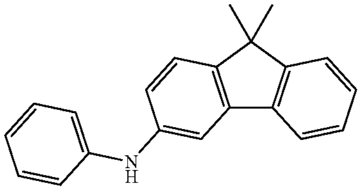
Sub-2-133
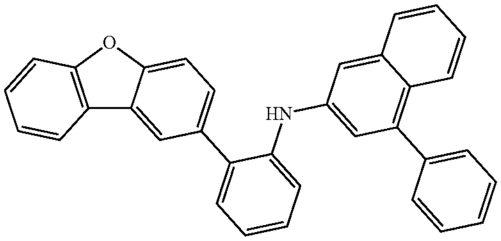
Sub-2-134
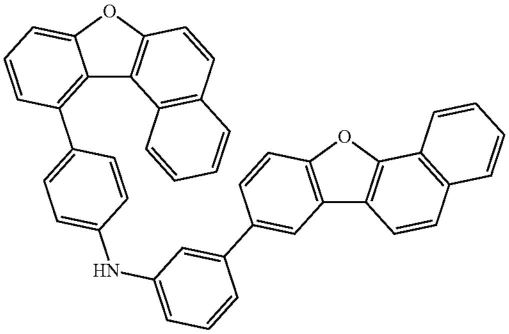
Sub-2-135
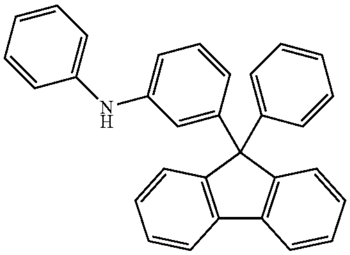
Sub-2-136
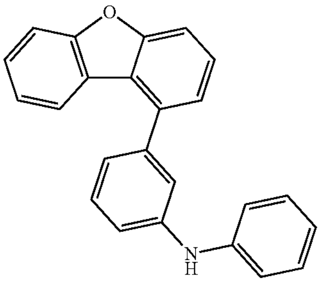

-continued
Sub-2-137
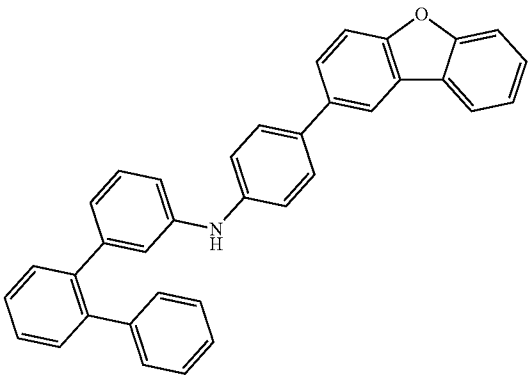
Sub-2-138
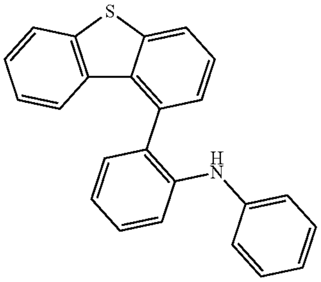
Sub-2-139
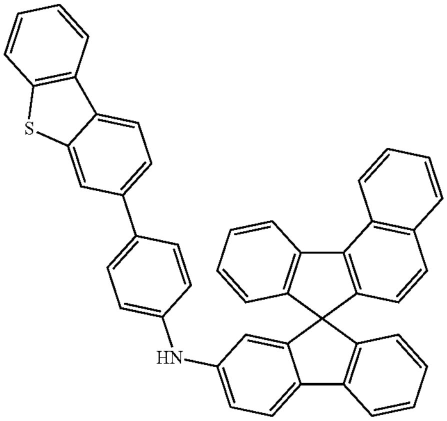
Sub-2-140
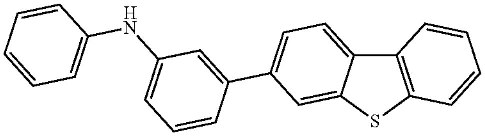
Sub-2-141
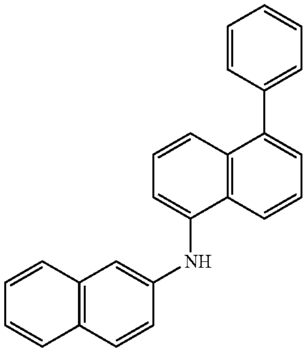
-continued
Sub-2-142
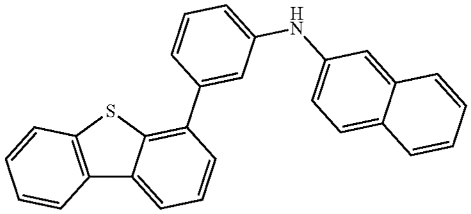
Sub-2-143
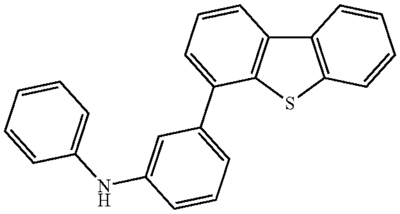
Sub-2-144
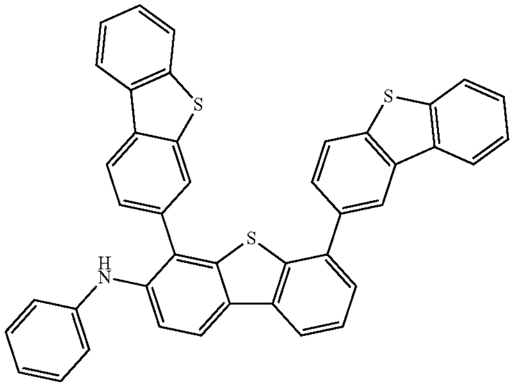
Sub-2-145
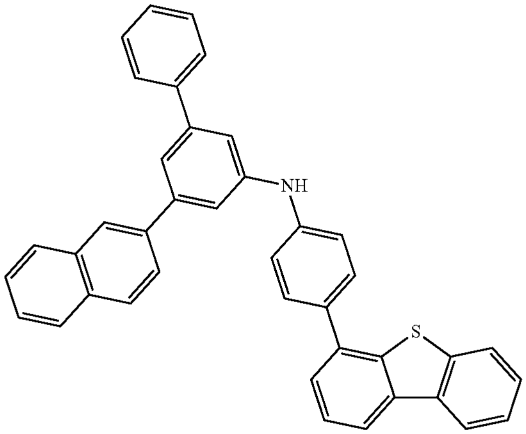

-continued
Sub-2-146
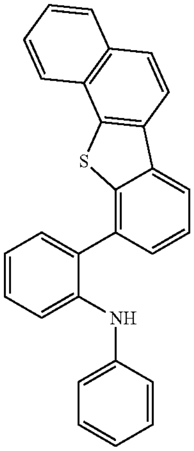
Sub-2-147
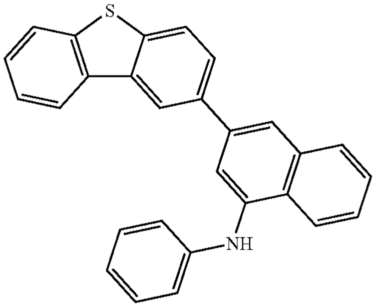
Sub-2-148
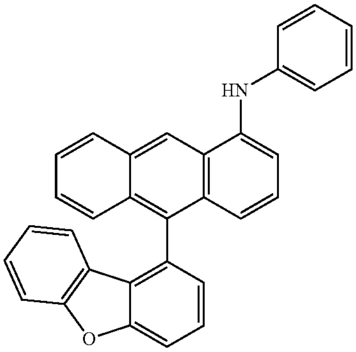
Sub-2-149
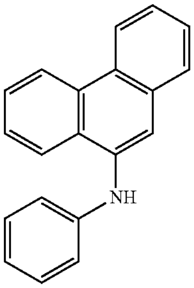
Sub-2-150
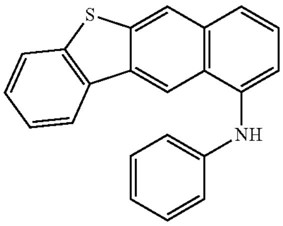
-continued
Sub-2-151
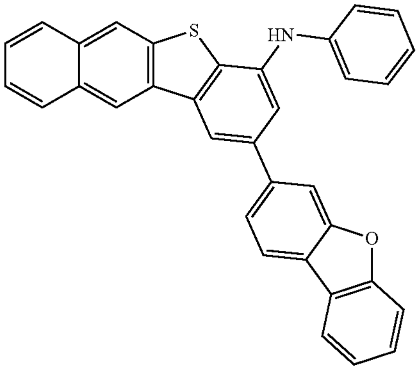
Sub-2-152
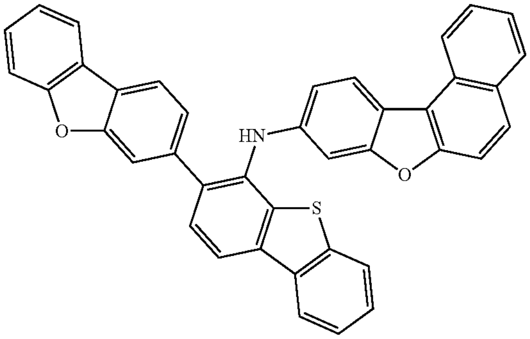
Sub-2-153
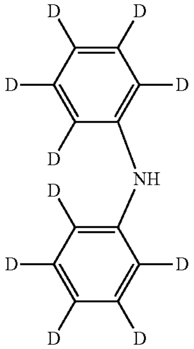
Sub-2-154
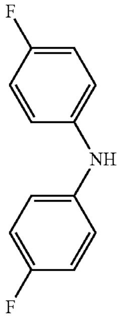

-continued
Sub-2-155
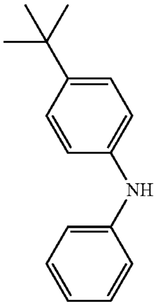
Sub-2-156
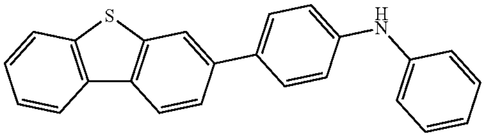
Sub-2-157
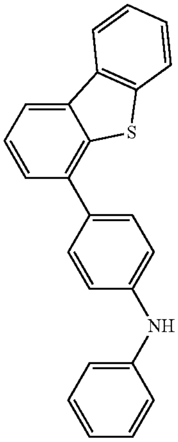
Sub-2-158
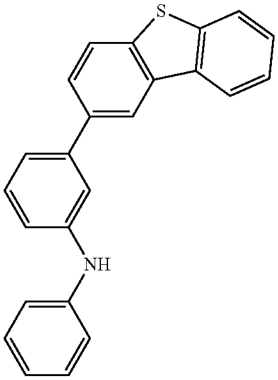
-continued
Sub-2-159
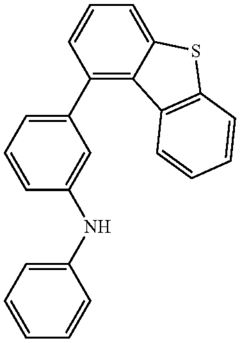
Sub-2-160
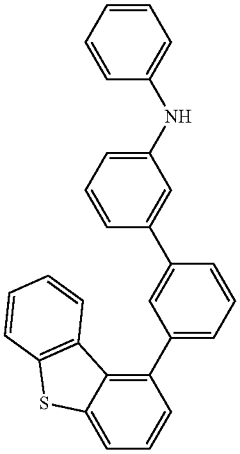
Sub-2-161
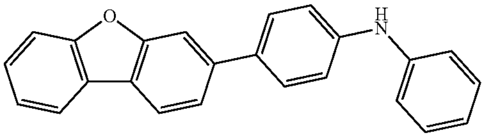

-continued

Sub-2-162

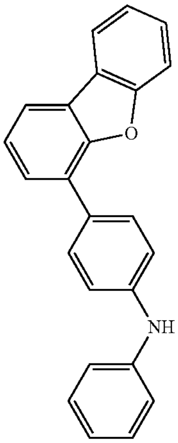

Sub-2-163

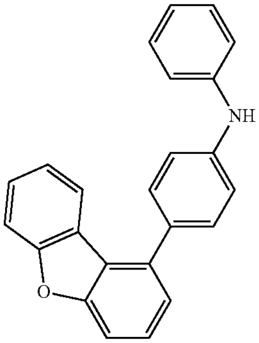

-continued

Sub-2-164

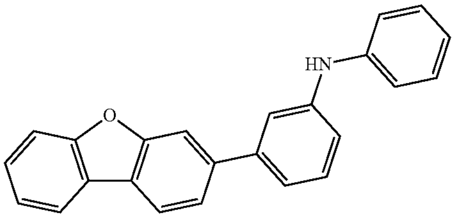

Sub-2-165

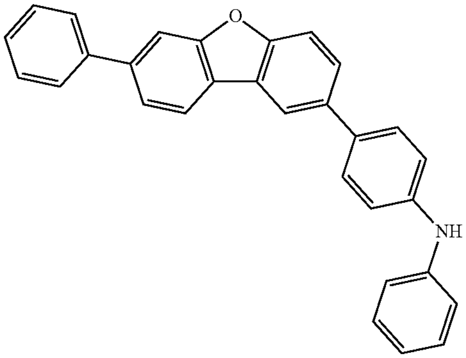

TABLE 2

| compound | FD-MS | compound | FD-MS |
|---|---|---|---|
| Sub-2-1 | m/z = 169.09($C_{12}H_{11}N$ = 169.23) | Sub-2-2 | m/z = 335.13($C_{24}H_{17}NO$ = 335.41) |
| Sub-2-3 | m/z = 219.10($C_{16}H_{13}N$ = 219.29) | Sub-2-4 | m/z = 579.20($C_{42}H_{29}NS$ = 579.76) |
| Sub-2-5 | m/z = 351.11($C_{24}H_{17}NS$ = 351.47) | Sub-2-6 | m/z = 245.12($C_{18}H_{15}N$ = 245.33) |
| Sub-2-7 | m/z = 517.15($C_{36}H_{23}NOS$ = 517.65) | Sub-2-8 | m/z = 411.16($C_{30}H_{21}NO$ = 411.5) |
| Sub-2-9 | m/z = 591.20($C_{43}H_{29}NS$ = 591.77) | Sub-2-10 | m/z = 427.14($C_{30}H_{21}NS$ = 427.57) |
| Sub-2-11 | m/z = 605.18($C_{43}H_{27}NOS$ = 605.76) | Sub-2-12 | m/z = 397.18($C_{30}H_{23}N$ = 397.52) |
| Sub-2-13 | m/z = 301.18($C_{22}H_{23}N$ = 301.43) | Sub-2-14 | m/z = 259.10($C_{18}H_{13}NO$ = 259.31) |
| Sub-2-15 | m/z = 351.11($C_{24}H_{17}NS$ = 351.47) | Sub-2-16 | m/z = 501.17($C_{36}H_{23}NO_2$ = 501.59) |
| Sub-2-17 | m/z = 565.17($C_{40}H_{23}NO_3$ = 565.63) | Sub-2-18 | m/z = 335.13($C_{24}H_{17}NO$ = 335.41) |
| Sub-2-19 | m/z = 590.20($C_{42}H_{26}N_2O_2$ = 590.68) | Sub-2-20 | m/z = 309.12($C_{22}H_{15}NO$ = 309.37) |
| Sub-2-21 | m/z = 286.11($C_{19}H_{14}N_2O$ = 286.33) | Sub-2-22 | m/z = 605.18($C_{43}H_{27}NOS$ = 605.76) |
| Sub-2-23 | m/z = 371.17($C_{28}H_{21}N$ = 371.48) | Sub-2-24 | m/z = 385.15($C_{28}H_{19}NO$ = 385.47) |
| Sub-2-25 | m/z = 501.17($C_{36}H_{23}NO_2$ = 501.59) | Sub-2-26 | m/z = 487.19($C_{36}H_{25}NO$ = 487.60) |
| Sub-2-27 | m/z = 334.15($C_{24}H_{18}N_2$ = 334.42) | Sub-2-28 | m/z = 295.14($C_{22}H_{17}N$ = 295.39) |
| Sub-2-29 | m/z = 365.09($C_{24}H_{15}NOS$ = 365.45) | Sub-2-30 | m/z = 591.20($C_{43}H_{29}NS$ = 591.77) |
| Sub-2-31 | m/z = 439.14($C_{31}H_{21}NS$ = 439.58) | Sub-2-32 | m/z = 566.18($C_{40}H_{26}N_2S$ = 566.72) |
| Sub-2-33 | m/z = 335.13($C_{24}H_{17}NO$ = 335.41) | Sub-2-34 | m/z = 401.12($C_{28}H_{19}NS$ = 401.53) |
| Sub-2-35 | m/z = 275.08($C_{18}H_{13}NS$ = 275.37) | Sub-2-36 | m/z = 457.10($C_{30}H_{19}NS_2$ = 457.61) |
| Sub-2-37 | m/z = 401.21($C_{30}H_{27}N$ = 401.55) | Sub-2-38 | m/z = 451.19($C_{33}H_{25}NO$ = 451.57) |
| Sub-2-39 | m/z = 397.18($C_{30}H_{23}N$ = 397.52) | Sub-2-40 | m/z = 511.19($C_{38}H_{25}NO$ = 511.62) |
| Sub-2-41 | m/z = 435.16($C_{32}H_{21}NO$ = 435.53) | Sub-2-42 | m/z = 452.15($C_{31}H_{20}N_2O_2$ = 452.51) |
| Sub-2-43 | m/z = 219.10($C_{16}H_{13}N$ = 219.29) | Sub-2-44 | m/z = 527.17($C_{38}H_{25}NS$ = 527.69) |
| Sub-2-45 | m/z = 503.17($C_{36}H_{25}NS$ = 503.66) | Sub-2-46 | m/z = 356.14($C_{24}H_{12}D_5NS$ = 356.5) |
| Sub-2-47 | m/z = 205.07($C_{12}H_9F_2N$ = 205.21) | Sub-2-48 | m/z = 365.14($C_{25}H_{19}NO_2$ = 365.43) |
| Sub-2-49 | m/z = 195.10($C_{14}H_{13}N$ = 195.27) | Sub-2-50 | m/z = 411.16($C_{30}H_{21}NO$ = 411.50) |
| Sub-2-51 | m/z = 475.16($C_{34}H_{21}NO_2$ = 475.55) | Sub-2-52 | m/z = 245.12($C_{18}H_{15}N$ = 245.33) |
| Sub-2-53 | m/z = 435.16($C_{32}H_{21}NO$ = 435.53) | Sub-2-54 | m/z = 617.18($C_{44}H_{27}NOS$ = 617.77) |
| Sub-2-55 | m/z = 340.16($C_{24}H_{12}D_5NO$ = 340.44) | Sub-2-56 | m/z = 309.12($C_{22}H_{15}NO$ = 309.37) |
| Sub-2-57 | m/z = 577.20($C_{42}H_{27}NO_2$ = 577.68) | Sub-2-58 | m/z = 407.17($C_{31}H_{21}N$ = 407.52) |
| Sub-2-59 | m/z = 501.21($C_{37}H_{27}NO$ = 501.63) | Sub-2-60 | m/z = 334.15($C_{24}H_{18}N_2$ = 334.42) |
| Sub-2-61 | m/z = 427.14($C_{30}H_{21}NS$ = 427.57) | Sub-2-62 | m/z = 450.21($C_{33}H_{26}N_2$ = 450.59) |
| Sub-2-63 | m/z = 441.12($C_{30}H_{19}NOS$ = 441.55) | Sub-2-64 | m/z = 334.15($C_{24}H_{18}N_2$ = 334.42) |
| Sub-2-65 | m/z = 371.17($C_{28}H_{21}N$ = 371.48) | Sub-2-66 | m/z = 269.12($C_{20}H_{15}N$ = 269.35) |
| Sub-2-67 | m/z = 371.17($C_{28}H_{21}N$ = 371.48) | Sub-2-68 | m/z = 537.21($C_{40}H_{27}NO$ = 537.66) |
| Sub-2-69 | m/z = 385.15($C_{28}H_{19}NO$ = 385.47) | Sub-2-70 | m/z = 401.12($C_{28}H_{19}NS$ = 401.53) |
| Sub-2-71 | m/z = 543.20($C_{39}H_{29}NS$ = 543.73) | Sub-2-72 | m/z = 245.12($C_{18}H_{15}N$ = 245.33) |

TABLE 2-continued

| compound | FD-MS | compound | FD-MS |
|---|---|---|---|
| Sub-2-73 | m/z = 411.20($C_{31}H_{25}N$ = 411.55) | Sub-2-74 | m/z = 371.17($C_{28}H_{21}N$ = 371.48) |
| Sub-2-75 | m/z = 451.14($C_{32}H_{21}NS$ = 451.59) | Sub-2-76 | m/z = 259.04($C_{12}H_6F_5N$ = 259.18) |
| Sub-2-77 | m/z = 477.16($C_{34}H_{23}NS$ = 477.63) | Sub-2-78 | m/z = 269.12($C_{20}H_{15}N$ = 269.35) |
| Sub-2-79 | m/z = 501.16($C_{36}H_{23}NS$ = 501.65) | Sub-2-80 | m/z = 319.14($C_{24}H_{17}N$ = 319.41) |
| Sub-2-81 | m/z = 483.20($C_{37}H_{25}N$ = 483.61) | Sub-2-82 | m/z = 498.21($C_{37}H_{26}N_2$ = 498.63) |
| Sub-2-83 | m/z = 251.17($C_{18}H_{21}N$ = 251.37) | Sub-2-84 | m/z = 250.15($C_{18}H_{10}D_5N$ = 250.36) |
| Sub-2-85 | m/z = 391.19($C_{28}H_{25}NO$ = 391.51) | Sub-2-86 | m/z = 639.20($C_{47}H_{29}NS$ = 639.82) |
| Sub-2-87 | m/z = 321.15($C_{24}H_{19}N$ = 321.42) | Sub-2-88 | m/z = 400.17($C_{27}H_{20}N_4$ = 400.49) |
| Sub-2-89 | m/z = 477.16($C_{34}H_{23}NS$ = 477.63) | Sub-2-90 | m/z = 321.15($C_{24}H_{19}N$ = 321.42) |
| Sub-2-91 | m/z = 321.15($C_{24}H_{19}N$ = 321.42) | Sub-2-92 | m/z = 423.16($C_{31}H_{21}NO$ = 423.52) |
| Sub-2-93 | m/z = 503.17($C_{36}H_{25}NS$ = 503.66) | Sub-2-94 | m/z = 461.18($C_{34}H_{23}NO$ = 461.56) |
| Sub-2-95 | m/z = 309.12($C_{22}H_{15}NO$ = 309.37) | Sub-2-96 | m/z = 537.21($C_{40}H_{27}NO$ = 537.66) |
| Sub-2-97 | m/z = 457.18($C_{35}H_{23}N$ = 457.58) | Sub-2-98 | m/z = 487.19($C_{36}H_{25}NO$ = 487.60) |
| Sub-2-99 | m/z = 411.16($C_{30}H_{21}NO$ = 411.5) | Sub-2-100 | m/z = 503.17($C_{36}H_{25}NS$ = 503.66) |
| Sub-2-101 | m/z = 369.15($C_{28}H_{19}N$ = 369.47) | Sub-2-102 | m/z = 365.09($C_{24}H_{15}NOS$ = 365.45) |
| Sub-2-103 | m/z = 349.11($C_{24}H_{15}NO_2$ = 349.39) | Sub-2-104 | m/z = 503.17($C_{36}H_{25}NS$ = 503.66) |
| Sub-2-105 | m/z = 437.21($C_{33}H_{27}N$ = 437.59) | Sub-2-106 | m/z = 461.18($C_{34}H_{23}NO$ = 461.56) |
| Sub-2-107 | m/z = 371.17($C_{26}H_{21}N$ = 371.48) | Sub-2-108 | m/z = 537.21($C_{40}H_{27}NO$ = 537.66) |
| Sub-2-109 | m/z = 485.22($C_{34}H_{31}NS$ = 485.69) | Sub-2-110 | m/z = 291.07($C_{18}H_{13}NOS$ = 291.37) |
| Sub-2-111 | m/z = 275.09($C_{18}H_{13}NO_2$ = 275.31) | Sub-2-112 | m/z = 516.18($C_{36}H_{24}N_2O_2$ = 516.60) |
| Sub-2-113 | m/z = 425.19($C_{30}H_{23}N_3$ = 425.54) | Sub-2-114 | m/z = 401.12($C_{28}H_{19}NS$ = 401.53) |
| Sub-2-115 | m/z = 561.25($C_{43}H_{31}N$ = 561.73) | Sub-2-116 | m/z = 727.29($C_{55}H_{37}NO$ = 727.91) |
| Sub-2-117 | m/z = 423.16($C_{31}H_{21}NO$ = 423.52) | Sub-2-118 | m/z = 517.15($C_{36}H_{23}NOS$ = 517.65) |
| Sub-2-119 | m/z = 477.16($C_{34}H_{23}NS$ = 477.63) | Sub-2-120 | m/z = 351.11($C_{24}H_{17}NS$ = 351.47) |
| Sub-2-121 | m/z = 335.13($C_{24}H_{17}NO$ = 335.41) | Sub-2-122 | m/z = 577.20($C_{42}H_{27}NO_2$ = 577.68) |
| Sub-2-123 | m/z = 359.13($C_{26}H_{17}NO$ = 359.43) | Sub-2-124 | m/z = 698.19($C_{48}H_{30}N_2S_2$ = 698.90) |
| Sub-2-125 | m/z = 427.14($C_{30}H_{21}NS$ = 427.57) | Sub-2-126 | m/z = 345.15($C_{26}H_{19}N$ = 345.45) |
| Sub-2-127 | m/z = 347.17($C_{26}H_{21}N$ = 347.46) | Sub-2-128 | m/z = 576.22($C_{42}H_{26}N_2O$ = 576.70) |
| Sub-2-129 | m/z = 669.21($C_{46}H_{31}NOS$ = 669.84) | Sub-2-130 | m/z = 286.11($C_{19}H_{14}N_2O$ = 286.33) |
| Sub-2-131 | m/z = 487.19($C_{36}H_{25}NO$ = 487.60) | Sub-2-132 | m/z = 285.15($C_{21}H_{19}N$ = 285.39) |
| Sub-2-133 | m/z = 461.18($C_{34}H_{23}NO$ = 461.56) | Sub-2-134 | m/z = 601.20($C_{44}H_{27}NO_2$ = 601.71) |
| Sub-2-135 | m/z = 409.18($C_{31}H_{23}N$ = 409.53) | Sub-2-136 | m/z = 335.13($C_{24}H_{17}NO$ = 335.41) |
| Sub-2-137 | m/z = 487.19($C_{36}H_{25}NO$ = 487.60) | Sub-2-138 | m/z = 351.11($C_{24}H_{17}NS$ = 351.47) |
| Sub-2-139 | m/z = 639.20($C_{47}H_{29}NS$ = 639.82) | Sub-2-140 | m/z = 351.11($C_{24}H_{17}NS$ = 351.47) |
| Sub-2-141 | m/z = 345.15($C_{26}H_{19}N$ = 345.45) | Sub-2-142 | m/z = 401.12($C_{26}H_{19}NS$ = 401.53) |
| Sub-2-143 | m/z = 351.11($C_{24}H_{17}NS$ = 351.47) | Sub-2-144 | m/z = 639.11($C_{42}H_{25}NS_3$ = 639.85) |
| Sub-2-145 | m/z = 553.19($C_{40}H_{27}NS$ = 553.72) | Sub-2-146 | m/z = 401.12($C_{28}H_{19}NS$ = 401.53) |
| Sub-2-147 | m/z = 401.12($C_{28}H_{19}NS$ = 401.53) | Sub-2-145 | m/z = 435.16($C_{32}H_{21}NO$ = 435.53) |
| Sub-2-149 | m/z = 269.12($C_{20}H_{15}N$ = 269.35) | Sub-2-150 | m/z = 325.09($C_{22}H_{15}NS$ = 325.43) |
| Sub-2-151 | m/z = 491.13($C_{34}H_{21}NOS$ = 491.61) | Sub-2-152 | m/z = 581.14($C_{40}H_{23}NO_2S$ = 581.69) |
| Sub-2-153 | m/z = 179.15($C_{12}HD_{10}N$ = 179.29) | Sub-2-154 | m/z = 205.07($C_{12}H_9F_2N$ = 205.21) |
| Sub-2-155 | m/z = 225.15($C_{16}H_{19}N$ = 225.34) | Sub-2-156 | m/z = 351.11($C_{24}H_{17}NS$ = 351.47) |
| Sub-2-157 | m/z = 351.11($C_{24}H_{17}NS$ = 351.47) | Sub-2-158 | m/z = 351.11($C_{24}H_{17}NS$ = 351.47) |
| Sub-2-159 | m/z = 351.11($C_{24}H_{17}NS$ = 351.47) | Sub-2-160 | m/z = 427.14($C_{30}H_{21}NS$ = 427.57) |
| Sub-2-161 | m/z = 335.13($C_{24}H_{17}NO$ = 335.41) | Sub-2-162 | m/z = 335.13($C_{24}H_{17}NO$ = 335.41) |
| Sub-2-163 | m/z = 335.13($C_{24}H_{17}NO$ = 335.41) | Sub-2-164 | m/z = 335.13($C_{24}H_{17}NO$ = 335.41) |
| Sub-2-165 | m/z = 411.16($C_{30}H_{21}NO$ = 411.50) | | |

III. Synthesis of Final Product

1. Synthesis Example of P-1

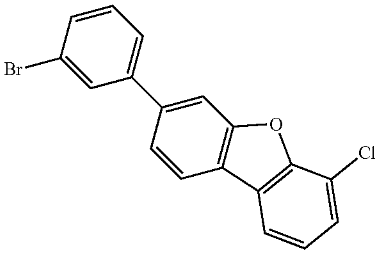

Sub-1-1

+

-continued

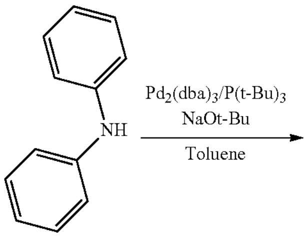

Sub-2-1

-continued

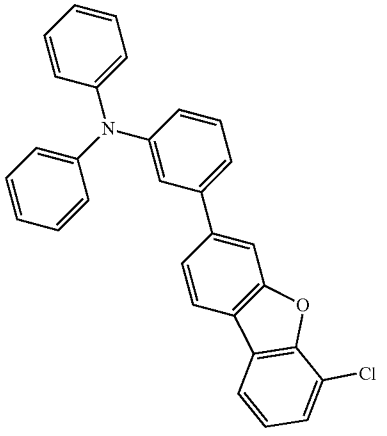

inter-1-1

+

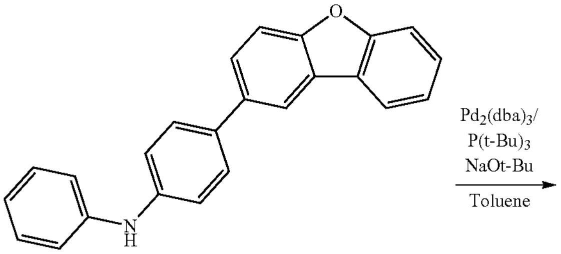

sub-2-2

-continued

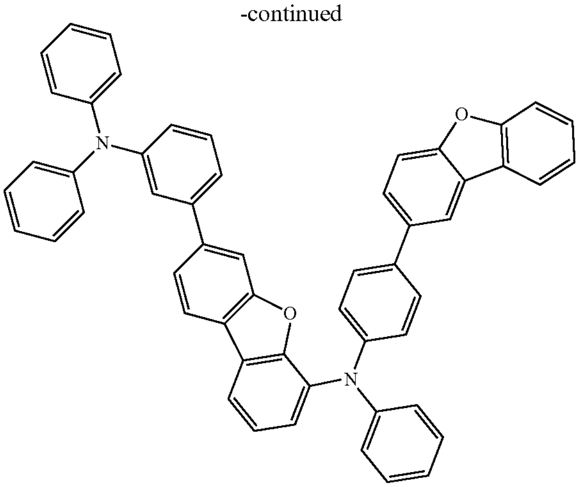

P-1

(1) Synthesis of Inter-1-1

After placing Sub-1-1 (20.0 g, 55.9 mmol), Sub-2-1 (9.1 g, 55.9 mmol), $Pd_2(dba)_3$ (1.5 g, 1.7 mmol), $P(t\text{-}Bu)_3$ (0.7 g, 3.4 mmol), NaOt-Bu (10.7 g, 111.8 mmol), toluene (280 mL) to a round-bottom flask, proceed with the reaction at 80° C. When the reaction is complete, the mixture is extracted with $CH_2Cl_2$ and water, and the organic layer is dried over $MgSO_4$ and concentrated. Then, the resulting organic material was recrystallized by silicagel column to obtain 17.5 g of a product. (yield 70%)

(2) Synthesis of P-1

After placing Inter-1-1 (10.0 g, 22.4 mmol), Sub-2-2 (7.3 g, 22.4 mmol), $Pd_2(dba)_3$ (0.6 g, 0.7 mmol), $P(t\text{-}Bu)_3$ (0.3 g, 1.4 mmol), NaOt-Bu (4.3 g, 44.8 mmol), toluene (112 mL) into a round-bottom flask, 10.3 g of the product was obtained by performing an experiment at 80° C. in the same manner as Inter-1-1. (Yield: 71%)

2. Synthesis Example of P-2

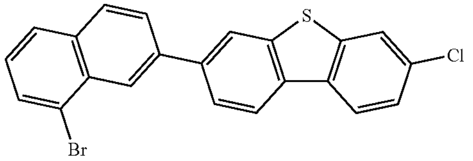

Sub-1-2

+

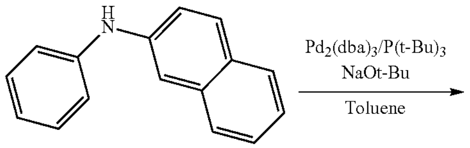

Sub-2-3

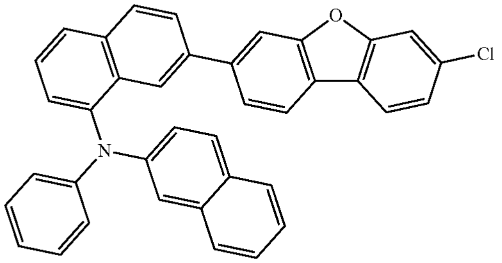

inter-1-2

+

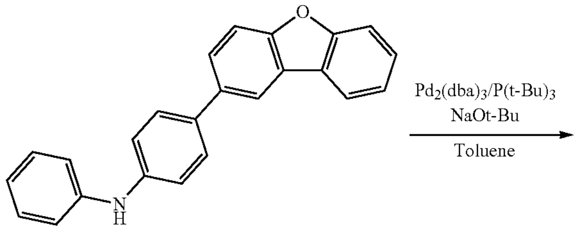

sub-2-2

-continued

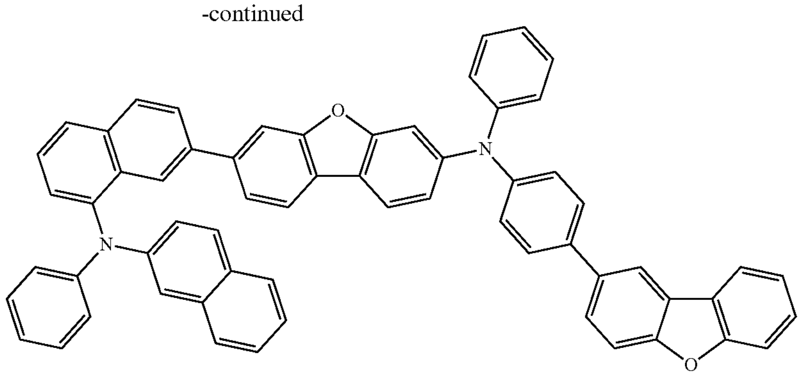

P-2

(1) Synthesis of Inter-1-2

After placing Sub-1-2 (20.0 g, 49.1 mmol), Sub-2-3 (10.4 g, 49.1 mmol), $Pd_2(dba)_3$ (1.4 g, 1.5 mmol), $P(t-Bu)_3$ (0.6 g, 2.9 mmol), NaOt-Bu (9.4 g, 98.1 mmol), and toluene (245 mL) in a round-bottom flask, 18.2 g of the product was obtained by performing an experiment in the same manner as Inter-1-1 above at 80° C. (Yield: 68%)

(2) Synthesis of P-2

After placing Inter-1-2 (10.0 g, 18.3 mmol), Sub-2-2 (5.9 g, 18.3 mmol), $Pd_2(dba)_3$ (0.5 g, 0.6 mmol), $P(t-Bu)_3$ (0.2 g, 1.1 mmol), NaOt-Bu (3.5 g, 36.6 mmol), toluene (92 mL) in a round-bottom flask, 10.5 g of the product was obtained by performing an experiment in the same manner as Inter-1-1 above at 80° C. (Yield: 68%)

3. Synthesis Example of P-49

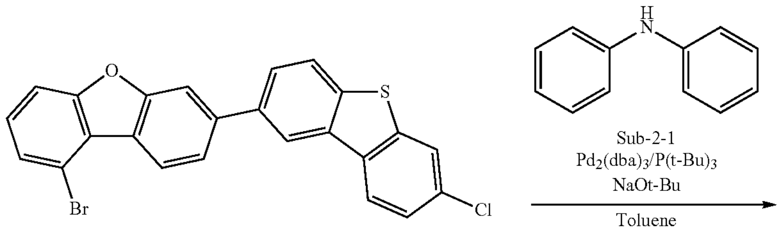

Sub-1-49

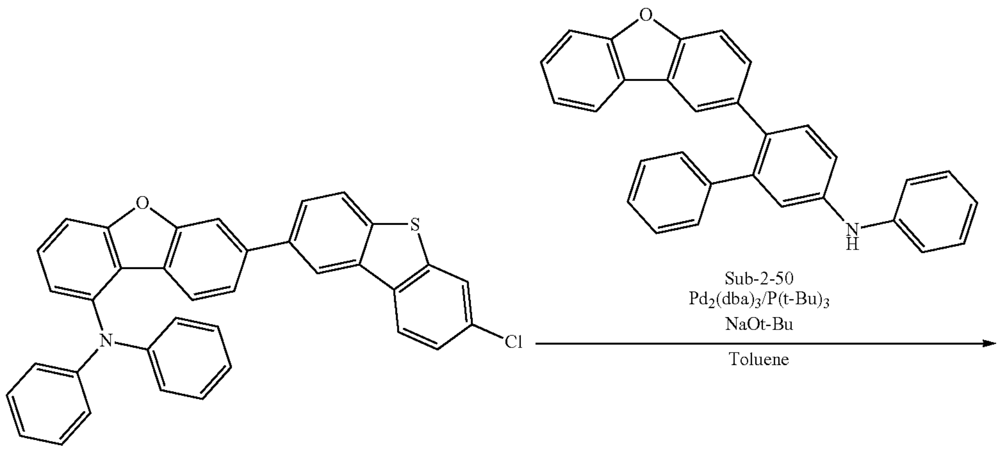

Inter-1-49

-continued

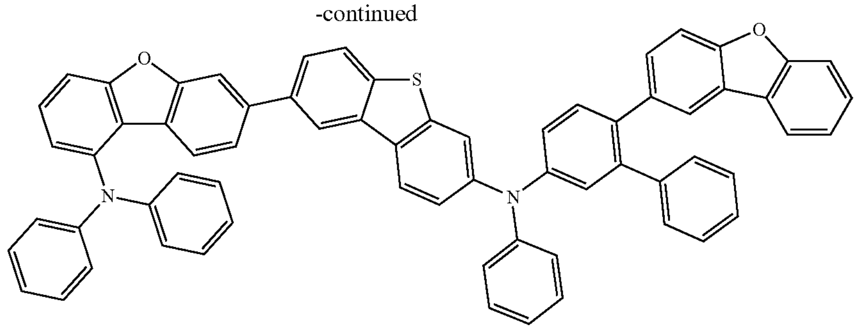

P-49

(1) Synthesis of Inter-1-49

After placing Sub-1-49 (10.0 g, 21.6 mmol), Sub-2-1 (3.6 g, 21.6 mmol), $Pd_2(dba)_3$ (0.59 g, 0.65 mmol), $P(t\text{-}Bu)_3$ (0.26 g, 1.29 mmol), NaOt-Bu (4.1 g, 43.1 mmol), toluene (108 mL) in a round-bottom flask, 8.5 g of the product was obtained by performing an experiment in the same manner as Inter-1-1 above at 80° C. (Yield: 71%)

(2) Synthesis of P-49

After placing Inter-1-49 (8.5 g, 15.3 mmol), Sub-2-50 (6.3 g, 15.3 mmol), $Pd_2(dba)_3$ (0.42 g, 0.46 mmol), $P(t\text{-}Bu)_3$ (0.19 g, 0.92 mmol), NaOt-Bu (2.9 g, 30.6 mmol), toluene (77 mL) in a round-bottom flask, 10.2 g of the product was obtained by performing an experiment in the same manner as Inter-1-1 above at 80° C. (Yield: 72%)

4. Synthesis Example of P-55

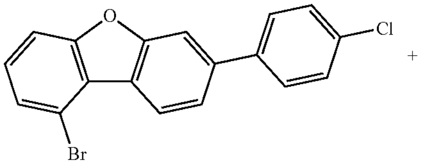

Sub-1-55

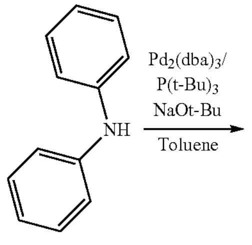

Sub-2-1

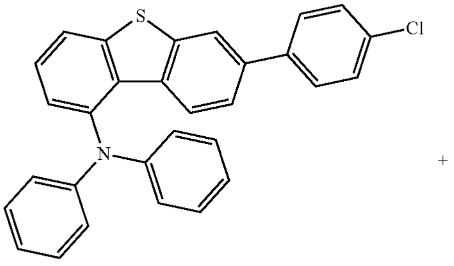

inter-1-55

-continued

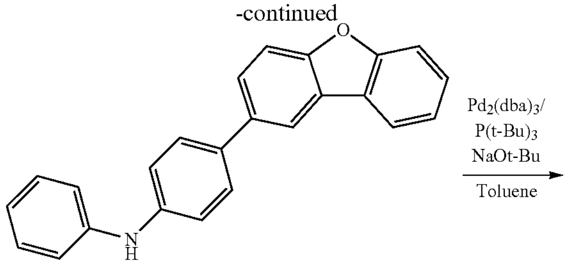

sub-2-2

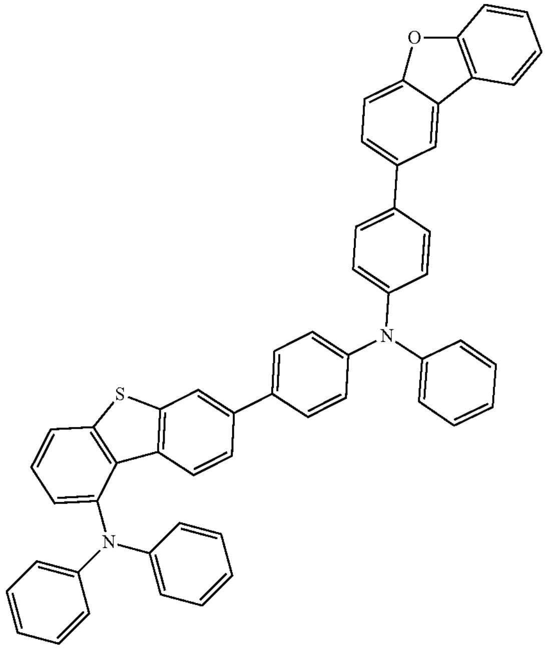

P-55

(1) Synthesis of Inter-1-55

After placing Sub-1-55 (20.0 g, 53.5 mmol), Sub-2-1 (8.8 g, 53.5 mmol), $Pd_2(dba)_3$ (1.5 g, 1.6 mmol), $P(t\text{-}Bu)_3$ (0.7 g, 3.2 mmol), NaOt-Bu (10.3 g, 107.0 mmol), toluene (268 mL) in a round-bottom flask, 17.6 g of the product was obtained by performing an experiment in the same manner as Inter-1-1 above at 80° C. (Yield: 71%)

(2) Synthesis of P-55

After placing Inter-1-55 (10.0 g, 21.6 mmol), Sub-2-2 (7.0 g, 21.6 mmol), $Pd_2(dba)_3$ (0.6 g, 0.7 mmol), $P(t\text{-}Bu)_3$ (0.3 g, 1.3 mmol), NaOt-Bu (4.2 g, 43.3 mmol), toluene (108 mL) in a round-bottom flask, 11.9 g of the product was obtained by performing an experiment in the same manner as Inter-1-1 above at 80° C. (Yield: 72%)

5. Synthesis Example of P-83

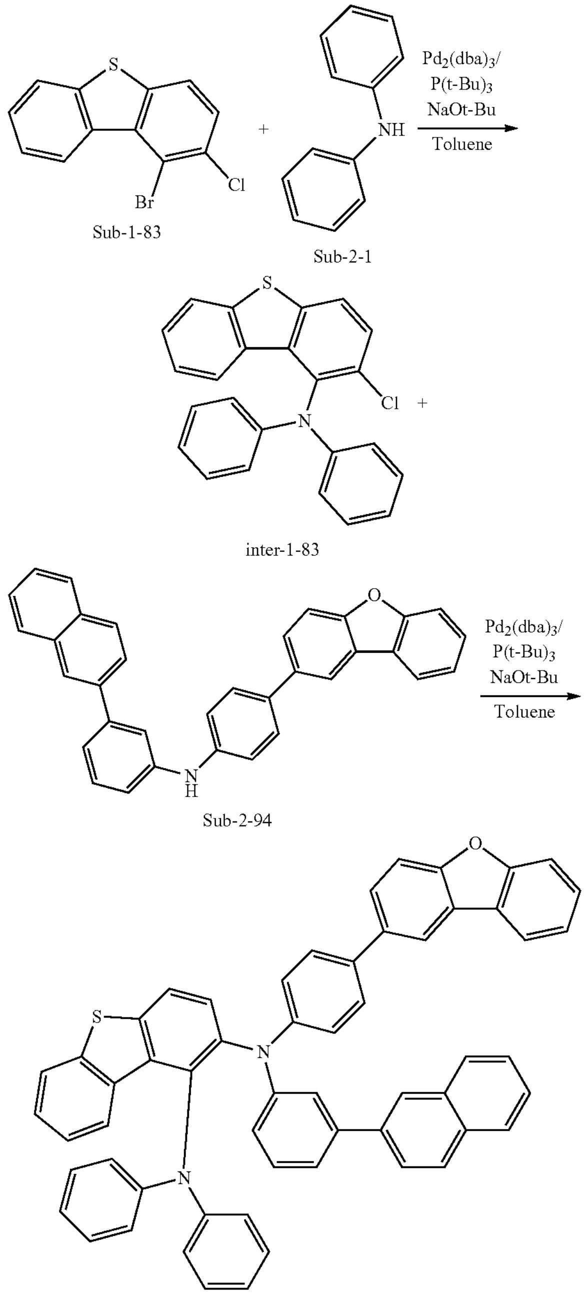

Sub-1-83
Sub-2-1
inter-1-83
Sub-2-94
P-83

(1) Synthesis of Inter-1-83

After placing Sub-1-83 (20.0 g, 67.2 mmol), Sub-2-1 (11.6 g, 25.9 mmol), $Pd_2(dba)_3$ (1.9 g, 2.0 mmol), $P(t\text{-}Bu)_3$ (0.8 g, 4.0 mmol), NaOt-Bu (12.9 g, 134.4 mmol), toluene (336 mL) in a round-bottom flask, 17.4 g of the product was obtained by performing an experiment in the same manner as Inter-1-1 above at 80° C. (Yield: 67%)

(2) Synthesis of P-83

After placing Inter-1-83 (10.0 g, 25.9 mmol), Sub-2-94 (11.6 g, 25.9 mmol), $Pd_2(dba)_3$ (0.7 g, 0.8 mmol), $P(t\text{-}Bu)_3$ (0.3 g, 1.6 mmol), NaOt-Bu (5.0 g, 51.8 mmol), toluene (130 mL) in a round-bottom flask, 14.5 g of the product was obtained by performing an experiment in the same manner as Inter-1-1 above at 80° C. (Yield: 69%)

6. Synthesis Example of P-97

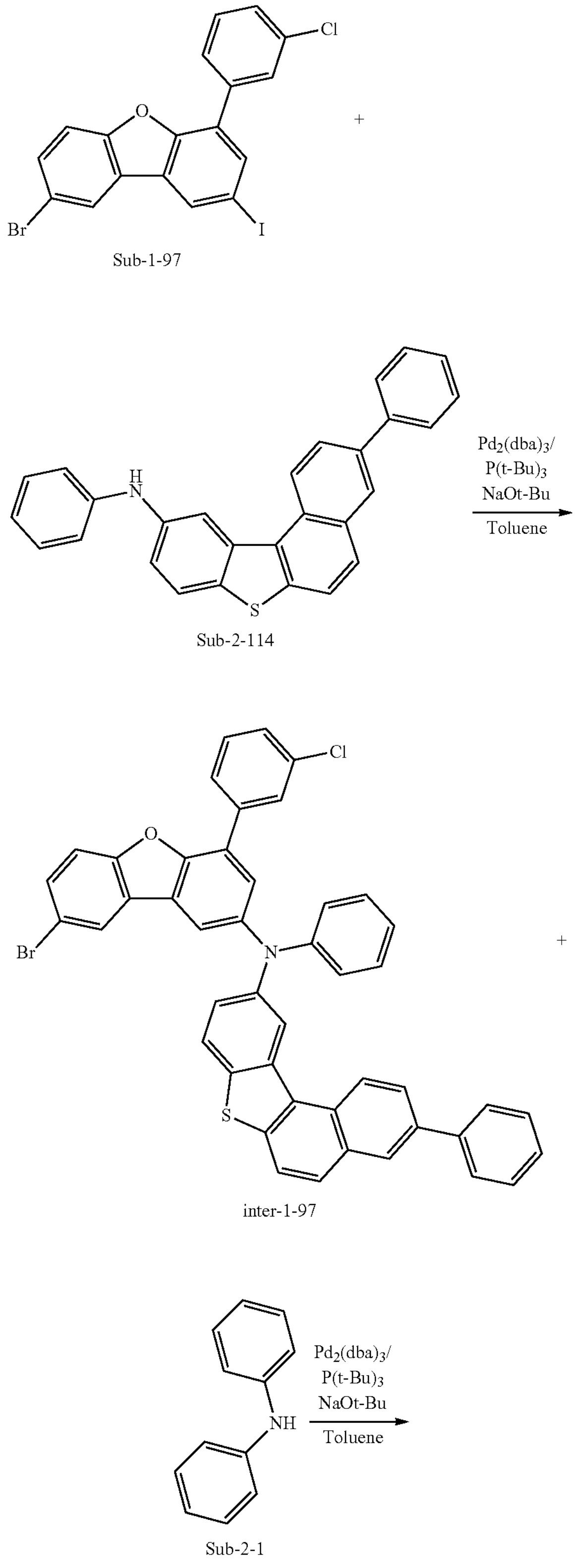

Sub-1-97
Sub-2-114
inter-1-97
Sub-2-1

-continued

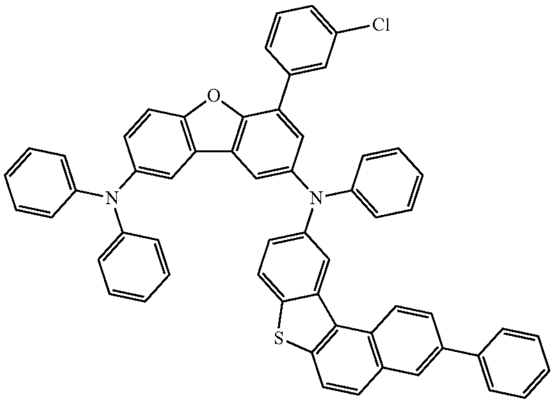

inter-2-97

+

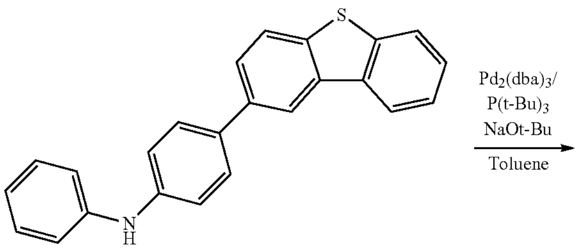

Sub-2-5

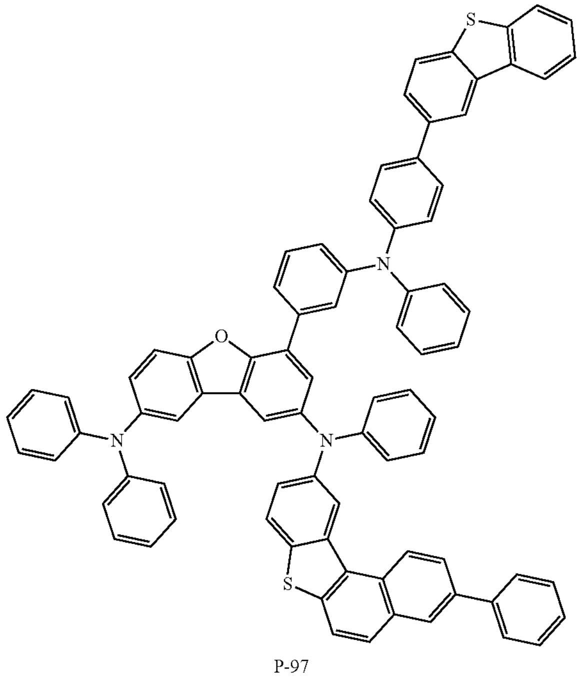

P-97

(1) Synthesis of Inter-1-97

After placing Sub-1-97 (20.0 g, 41.4 mmol), Sub-2-114 (16.0 g, 41.4 mmol), $Pd_2(dba)_3$ (1.1 g, 1.2 mmol), $P(t\text{-}Bu)_3$ (0.5 g, 2.5 mmol), NaOt-Bu (8.0 g, 82.7 mmol), toluene (207 mL) in a round-bottom flask, 22.5 g of the product was obtained by performing an experiment in the same manner as Inter-1-1 above at 80° C. (Yield: 72%)

(2) Synthesis of P-2-97

After placing Inter-1-97 (15.0 g, 19.8 mmol), Sub-2-1 (3.2 g, 19.8 mmol), $Pd_2(dba)_3$ (0.5 g, 0.6 mmol), $P(t\text{-}Bu)_3$ (0.2 g, 1.2 mmol), NaOt-Bu (3.8 g, 39.6 mmol), toluene (99 mL) in a round-bottom flask, 12.6 g of the product was obtained by performing an experiment in the same manner as Inter-1-1 above at 80° C. (Yield: 75%)

(3) Synthesis of P-97

After placing Inter-2-97 (10.0 g, 11.8 mmol), Sub-2-5 (4.0 g, 11.8 mmol), $Pd_2(dba)_3$ (0.3 g, 0.4 mmol), $P(t\text{-}Bu)_3$ (0.1 g, 0.7 mmol), NaOt-Bu (2.3 g, 23.7 mmol), toluene (59 mL) in a round-bottom flask, 9.7 g of the product was obtained by performing an experiment in the same manner as Inter-1-1 above at 80° C. (Yield: 71%)

7. Synthesis Example of P-129

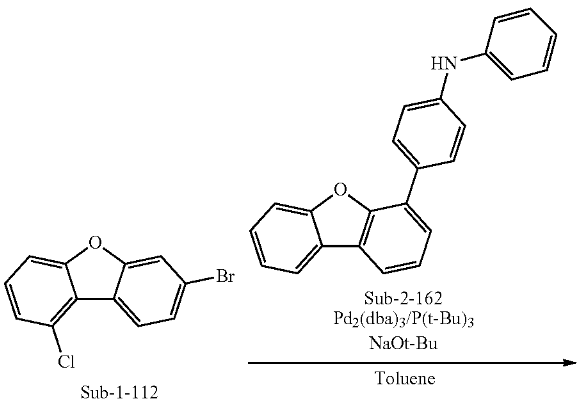

Sub-1-112

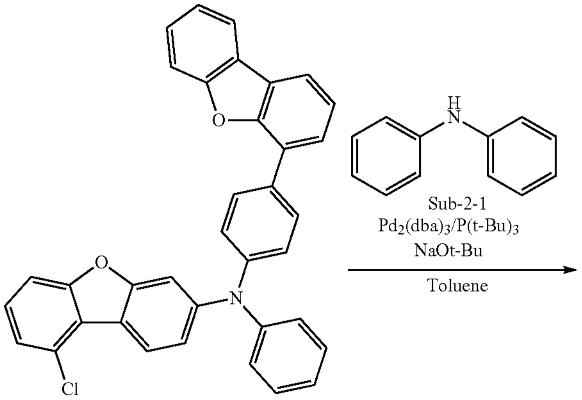

Inter-1-129

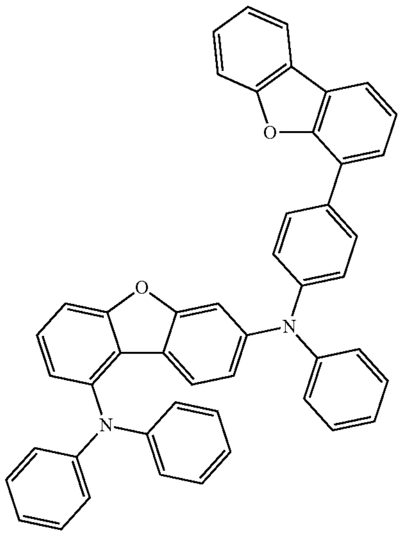

P-129

(1) Synthesis of Inter-1-129

After placing Sub-1-112 (10.0 g, 35.5 mmol), Sub-2-162 (11.9 g, 35.5 mmol), $Pd_2(dba)_3$ (0.98 g, 1.07 mmol), P(t-$Bu)_3$ (0.43 g, 2.13 mmol), NaOt-Bu (6.8 g, 71.0 mmol), toluene (178 mL) in a round-bottom flask, 14.1 g of the product was obtained by performing an experiment in the same manner as Inter-1-1 above at 80° C. (Yield: 74%)

(2) Synthesis of P-129

After placing Inter-1-129 (14.1 g, 26.3 mmol), Sub-2-1 (4.4 g, 26.3 mmol), $Pd_2(dba)_3$ (0.72 g, 0.79 mmol), $P(t-Bu)_3$ (0.32 g, 1.58 mmol), NaOt-Bu (5.1 g, 52.6 mmol), toluene (131 mL) in a round-bottom flask, 12.3 g of the product was obtained by performing an experiment in the same manner as Inter-1-1 above at 80° C. (Yield: 70%)

8. Synthesis Example of P-133

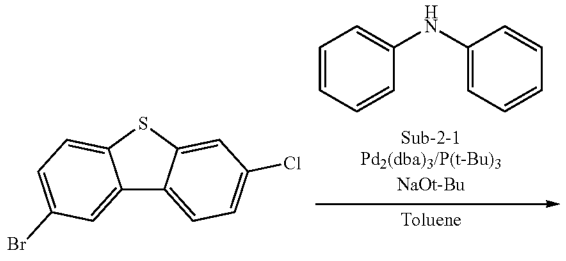

Sub-1-131

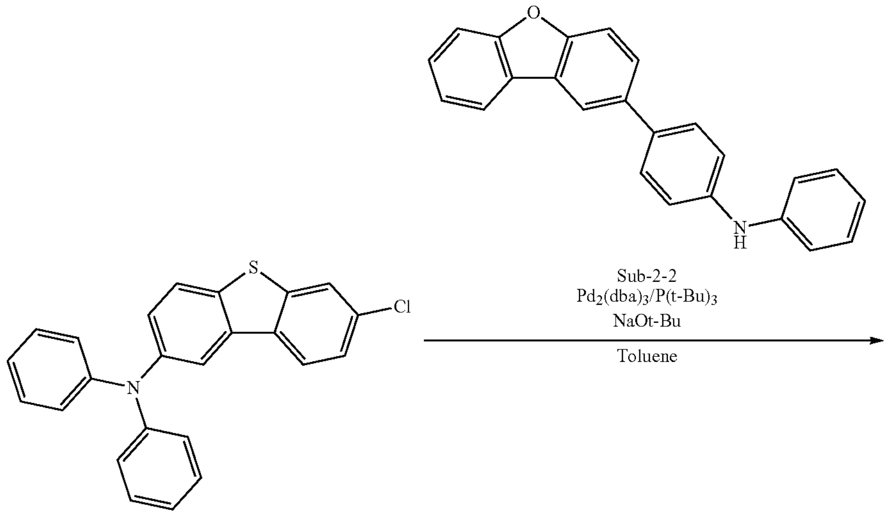

Inter-1-133

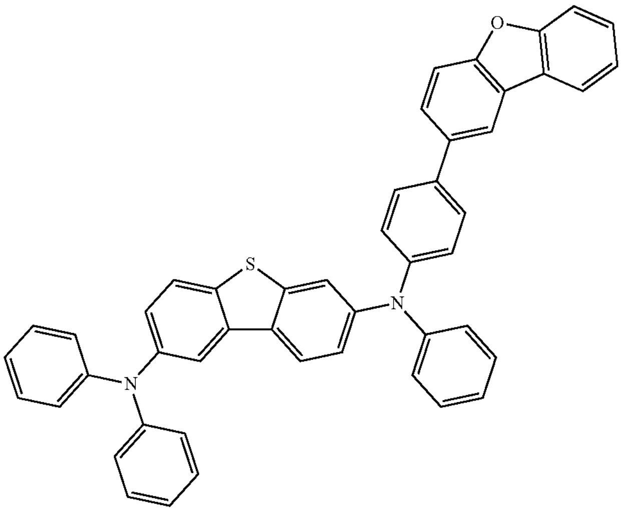

P-133

(1) Synthesis of Inter-1-133

After placing Sub-1-131 (40.0 g, 134 mmol), Sub-2-1 (22.7 g, 134 mmol), $Pd_2(dba)_3$ (3.69 g, 4.03 mmol), $P(t-Bu)_3$ (1.63 g, 8.06 mmol), NaOt-Bu (25.8 g, 269 mmol), toluene (672 mL) in a round-bottom flask, 40.5 g of the product was obtained by performing an experiment in the same manner as Inter-1-1 above at 80° C. (Yield: 78%)

(2) Synthesis of P-133

After placing Inter-1-133 (15.0 g, 38.9 mmol), Sub-2-2 (13.0 g, 38.9 mmol), $Pd_2(dba)_3$ (1.07 g, 1.17 mmol), $P(t-Bu)_3$ (0.47 g, 2.33 mmol), NaOt-Bu (7.5 g, 77.7 mmol), toluene (194 mL) in a round-bottom flask, 19.4 g of the product was obtained by performing an experiment in the same manner as Inter-1-1 above at 80° C. (Yield: 73%)

9. Synthesis Example of P-134

(1) Synthesis of Inter-1-134

After placing Sub-1-125 (10.0 g, 26.8 mmol), Sub-2-1 (4.5 g, 26.8 mmol), $Pd_2(dba)_3$ (0.74 g, 0.80 mmol), $P(t-Bu)_3$ (0.32 g, 1.61 mmol), NaOt-Bu (5.1 g, 53.5 mmol), toluene (134 mL) in a round-bottom flask, 8.4 g of the product was obtained by performing an experiment in the same manner as Inter-1-1 above at 80° C. (Yield: 68%)

(2) Synthesis of P-134

After placing Inter-1-134 (8.4 g, 18.2 mmol), Sub-2-2 (6.1 g, 18.2 mmol), $Pd_2(dba)_3$ (0.50 g, 0.55 mmol), $P(t-Bu)_3$ (0.22 g, 1.09 mmol), NaOt-Bu (3.5 g, 36.4 mmol), toluene (91 mL) in a round-bottom flask, 9.3 g of the product was obtained by performing an experiment in the same manner as Inter-1-1 above at 80° C. (Yield: 67%)

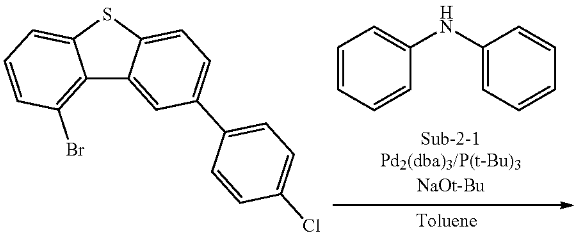

Sub-1-125

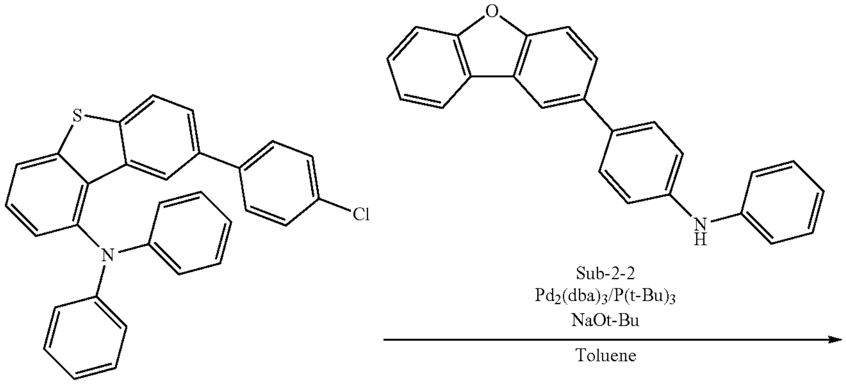

Inter-1-134

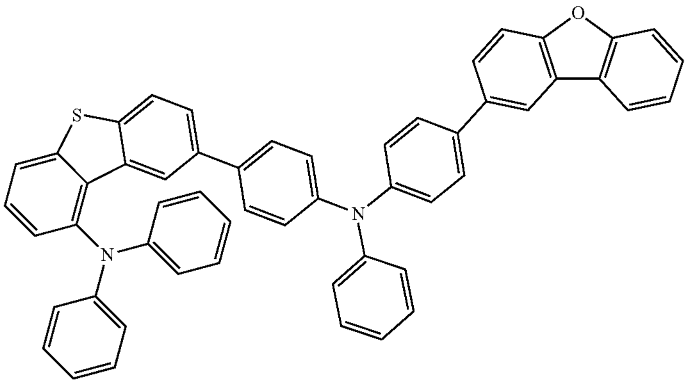

P-134

10. Synthesis Example of P-150
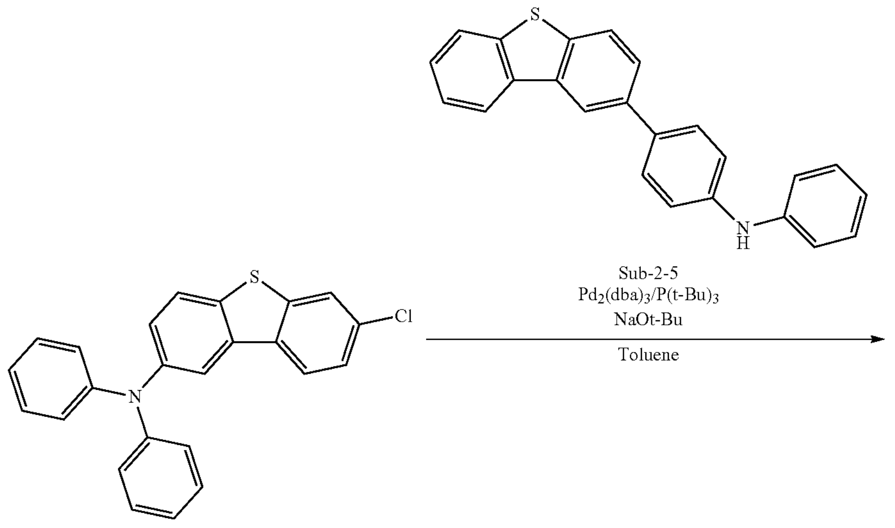
Inter-1-133
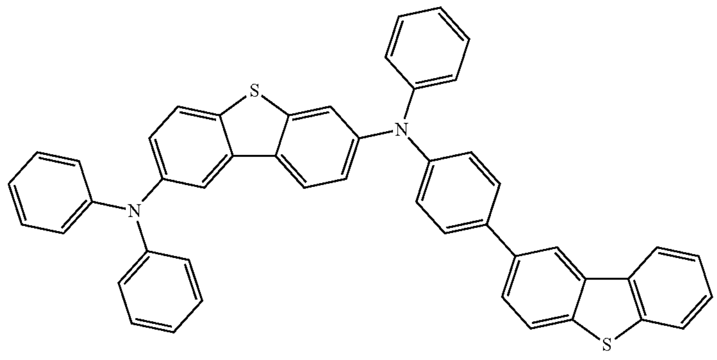
P-150
After placing Inter-1-133 (25.0 g, 64.8 mmol), Sub-2-5 (22.8 g, 64.8 mmol), $Pd_2(dba)_3$ (1.78 g, 1.94 mmol), P(t-Bu)$_3$ (0.79 g, 3.89 mmol), NaOt-Bu (12.5 g, 130 mmol), toluene (324 mL) in a round-bottom flask, 33.1 g of the product was obtained by performing an experiment in the same manner as Inter-1-1 above at 80° C. (Yield: 73%)
11. Synthesis Example of P-152
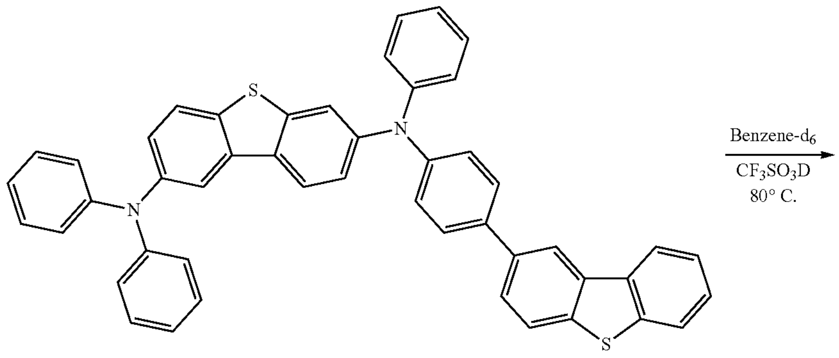
P-150

-continued

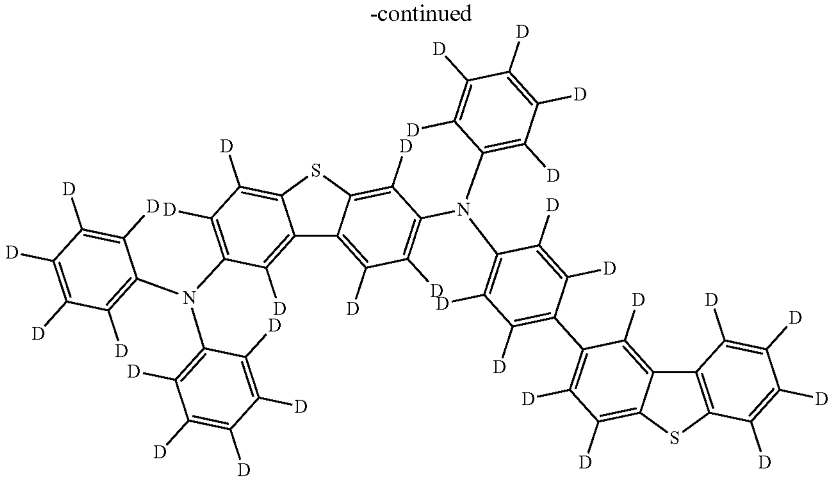

P-152

The obtained P-150 (15.0 g, 21.4 mmol) was dissolved in perdeuterated benzene ($C_6D_6$) (161.8 g, 1926 mmol) and $CF_3SO_3D$ (16.1 g, 107 mmol) was added, and then reacted at 80° C. for 3 hours and formed a deuterated material. Periodically take a sample and measure the degree of deuterium by LC-MS. After the deuterium exchange reaction is completed at a desired substitution rate, cool to room temperature, quenching by adding $Na_2CO_3$ in $D_2O$, and concentrate the organic solvent. Recrystallization using toluene and acetone solvent gave 14.1 g (yield: 90%) of deuterated compound P-152. The final mass was determined by LC-MS to confirm that it was 85.2% deuterated.

Meanwhile, the FD-MS values of the compounds P-1 to P-152 of the present invention prepared according to the above synthesis examples are shown in Table 3 below.

TABLE 3

| compound | FD-MS | compound | FD-MS |
|---|---|---|---|
| P-1 | m/z = 744.28($C_{54}H_{36}N_2O_2$ = 744.89) | P-2 | m/z = 844.31($C_{62}H_{40}N_2O_2$ = 845.01) |
| P-3 | m/z = 820.31($C_{60}H_{40}N_2O_2$ = 820.99) | P-4 | m/z = 870.32($C_{64}H_{42}N_2O_2$ = 871.05) |
| P-5 | m/z = 852.26($C_{60}H_{40}N_2S_2$ = 853.11) | P-6 | m/z = 852.26($C_{60}H_{40}N_2S_2$ = 853.11) |
| P-7 | m/z = 852.26($C_{60}H_{40}N_2S_2$ = 853.11) | P-8 | m/z = 928.29($C_{66}H_{44}N_2S_2$ = 929.21) |
| P-9 | m/z = 1090.36($C_{79}H_{50}N_2O_2S$ = 1091.34) | P-10 | m/z = 1000.35($C_{73}H_{48}N_2OS$ = 1001.26) |
| P-11 | m/z = 942.27($C_{66}H_{42}N_2OS_2$ = 943.20) | P-12 | m/z = 1179.39($C_{85}H_{53}N_3O_2S$ = 1180.44) |
| P-13 | m/z = 866.24($C_{60}H_{38}N_2OS_2$ = 867.10) | P-14 | m/z = 915.30($C_{63}H_{41}N_5OS$ = 916.12) |
| P-15 | m/z = 998.33($C_{73}H_{46}N_2OS$ = 999.24) | P-16 | m/z = 860.29($C_{62}H_{40}N_2OS$ = 861.08) |
| P-17 | m/z = 892.35($C_{64}H_{48}N_2OS$ = 893.16) | P-18 | m/z = 850.27($C_{60}H_{38}N_2O_2S$ = 851.04) |
| P-19 | m/z = 942.27($C_{66}H_{42}N_2OS_2$ = 943.20) | P-20 | m/z = 976.31($C_{70}H_{44}N_2O_2S$ = 977.19) |
| P-21 | m/z = 810.27($C_{58}H_{38}N_2OS$ = 811.02) | P-22 | m/z = 1002.33($C_{72}H_{46}N_2O_2S$ = 1003.23) |
| P-23 | m/z = 1091.35($C_{78}H_{49}N_3O_2S$ = 1092.33) | P-24 | m/z = 960.34($C_{70}H_{44}N_2O_3$ = 961.13) |
| P-25 | m/z = 1066.32($C_{76}H_{46}N_2O_3S$ = 1067.28) | P-26 | m/z = 953.31($C_{67}H_{43}N_3O_2S$ = 954.16) |
| P-27 | m/z = 1090.36($C_{79}H_{50}N_2O_2S$ = 1091.34) | P-28 | m/z = 1088.38($C_{80}H_{52}N_2OS$ = 1089.37) |
| P-29 | m/z = 1002.33($C_{72}H_{46}N_2O_2S$ = 1003.23) | P-30 | m/z = 1114.40($C_{82}H_{54}N_2OS$ = 1115.41) |
| P-31 | m/z = 1077.38($C_{78}H_{51}N_3OS$ = 1078.35) | P-32 | m/z = 1108.32($C_{78}H_{48}N_2O_2S_2$ = 1109.37) |
| P-33 | m/z = 1152.41($C_{85}H_{56}N_2OS$ = 1153.46) | P-34 | m/z = 1397.44($C_{101}H_{63}N_3OS_2$ = 1398.76) |
| P-35 | m/z = 1128.37($C_{82}H_{52}N_2O_2S$ = 1129.39) | P-36 | m/z = 1124.29($C_{78}H_{48}N_2OS_3$ = 1125.44) |
| P-37 | m/z = 1128.47($C_{84}H_{60}N_2O_2$ = 1129.42) | P-38 | m/z = 1012.40($C_{75}H_{52}N_2O_2$ = 1013.25) |
| P-39 | m/z = 1124.43($C_{84}H_{56}N_2O_2$ = 1125.38) | P-40 | m/z = 1072.40($C_{80}H_{52}N_2O_2$ = 1073.31) |
| P-41 | m/z = 1012.35($C_{74}H_{48}N_2OS$ = 1013.27) | P-42 | m/z = 1029.34($C_{73}H_{47}N_3O_2S$ = 1030.26) |
| P-43 | m/z = 1138.40($C_{84}H_{54}N_2OS$ = 1139.43) | P-44 | m/z = 1064.38($C_{78}H_{52}N_2OS$ = 1065.35) |
| P-45 | m/z = 917.35($C_{66}H_{39}D_5N_2OS$ = 918.18) | P-46 | m/z = 932.32($C_{66}H_{42}F_2N_2O_2$ = 933.07) |
| P-47 | m/z = 942.33($C_{67}H_{46}N_2O_2S$ = 943.18) | P-48 | m/z = 876.28($C_{62}H_{40}N_2O_2S$ = 877.07) |
| P-49 | m/z = 926.30($C_{66}H_{42}N_2O_2S$ = 927.13) | P-50 | m/z = 1006.27($C_{70}H_{42}N_2O_2S_2$ = 1007.24) |
| P-51 | m/z = 1018.31($C_{72}H_46N_2OS_2$ = 1019.29) | P-52 | m/z = 1182.33($C_{84}H_{50}N_2O_2S_2$ = 1183.46) |
| P-53 | m/z = 995.32($C_{70}H_{37}D_5N_2O_3S$ = 996.21) | P-54 | m/z = 115.41($C_{84}H_{53}N_3O_3$ = 1152.37) |
| P-55 | m/z = 760.25($C_{54}H_{36}N_2OS$ = 760.96) | P-56 | m/z = 1254.42($C_{92}H_{58}N_2O_2S$ = 1255.55) |
| P-57 | m/z = 1241.44($C_{91}H_{59}N_3OS$ = 1242.55) | P-58 | m/z = 1147.36($C_{81}H_{53}N_3OS_2$ = 1148.46) |
| P-59 | m/z = 1028.34($C_{74}H_{48}N_2O_2S$ = 1029.27) | P-60 | m/z = 1015.32($C_{72}H_{45}N_3O_2S$ = 1016.23) |
| P-61 | m/z = 1052.34($C_{76}H_{48}N_2O_2S$ = 1053.29) | P-62 | m/z = 1402.49($C_{105}H_{66}N_2OS$ = 1403.76) |
| P-63 | m/z = 1180.35($C_{85}H_{52}N_2OS_2$ = 1181.48) | P-64 | m/z = 1157.35($C_{82}H_{51}N_3OS_2$ = 1158.45) |
| P-65 | m/z = 1134.37($C_{81}H_{54}N_2OS_2$ = 1135.46) | P-66 | m/z = 1108.35($C_{79}H_{52}N_2OS_2$ = 1109.42) |
| P-67 | m/z = 1407.46($C_{103}H_{65}N_3S_2$ = 1408.79) | P-68 | m/z = 1098.22($C_{70}H_{39}F_5N_2S_3$ = 1099.27) |
| P-69 | m/z = 1266.40($C_{93}H_{58}N_2S_2$ = 1267.62) | P-70 | m/z = 1141.35($C_{82}H_{51}N_3S_2$ = 1142.45) |
| P-71 | m/z = 1196.33($C_{85}H_{52}N_2S_3$ = 1197.55) | P-72 | m/z = 1211.34($C_{85}H_{53}N_3S_3$ = 1212.56) |
| P-73 | m/z = 932.34($C_{66}H_{48}N_2O_2S$ = 933.18) | P-74 | m/z = 1003.37($C_{70}H_{45}D_5N_2OS_2$ = 1004.33) |
| P-75 | m/z = 1154.34($C_{83}H_{50}N_2OS_2$ = 1155.45) | P-76 | m/z = 1144.35($C_{82}H_{52}N_2OS_2$ = 1145.45) |
| P-77 | m/z = 839.27($C_{57}H_{37}N_5OS$ = 840.02) | P-78 | m/z = 1120.37($C_{76}H_{48}N_8OS$ = 1121.34) |
| P-79 | m/z = 1066.37($C_{76}H_{50}N_4OS$ = 1067.32) | P-80 | m/z = 1003.33($C_{70}H_{45}N_5OS$ = 1004.22) |

TABLE 3-continued

| compound | FD-MS | compound | FD-MS |
|---|---|---|---|
| P-81 | m/z = 810.27($C_{58}H_{38}N_2OS$ = 811.02) | P-82 | m/z = 886.30($C_{64}H_{42}N_2OS$ = 887.11) |
| P-83 | m/z = 810.27($C_{58}H_{38}N_2OS$ = 811.02) | P-84 | m/z = 1026.33($C_{74}H_{46}N_2O_2S$ = 1027.25) |
| P-85 | m/z = 1124.38($C_{83}H_{52}N_2OS$ = 1125.40) | P-86 | m/z = 836.29($C_{60}H_{40}N_2OS$ = 837.05) |
| P-87 | m/z = 1032.28($C_{72}H_{44}N_2O_2S_2$ = 1033.28) | P-88 | m/z = 1016.31($C_{72}H_{44}N_2O_3S$ = 1017.22) |
| P-89 | m/z = 850.27($C_{60}H_{38}N_2O_2S$ = 851.04) | P-90 | m/z = 884.29($C_{64}H_{40}N_2OS$ = 885.10) |
| P-91 | m/z = 884.29($C_{64}H_{40}N_2OS$ = 885.10) | P-92 | m/z = 1088.38($C_{80}H_{52}N_2OS$ = 1089.37) |
| P-93 | m/z = 1183.42($C_{82}H_{61}N_3O_2S_2$ = 1184.53) | P-94 | m/z = 1033.33($C_{72}H_{47}N_3O_3S$ = 1034.25) |
| P-95 | m/z = 1108.38($C_{78}H_{52}N_4O_2S$ = 1109.36) | P-96 | m/z = 1066.37($C_{76}H_{50}N_4OS$ = 1067.32) |
| P-97 | m/z = 1159.36($C_{82}H_{53}N_3OS_2$ = 1160.47) | P-98 | m/z = 1152.41($C_{85}H_{56}N_2OS$ = 1153.46) |
| P-99 | m/z = 1319.48($C_{97}H_{65}N_3OS$ = 1320.67) | P-100 | m/z = 1285.41($C_{92}H_{59}N_3OS_2$ = 1286.62) |
| P-101 | m/z = 1215.44($C_{89}H_{57}N_3O_3$ = 1216.45) | P-102 | m/z = 1077.39($C_{78}H_{51}N_3O_3$ = 1078.28) |
| P-103 | m/z = 1154.39($C_{84}H_{54}N_2O_2S$ = 1155.43) | P-104 | m/z = 1530.44($C_{108}H_{66}N_4OS_3$ = 1531.92) |
| P-105 | m/z = 852.26($C_{60}H_{40}N_2S_2$ = 853.11) | P-106 | m/z = 1103.39($C_{80}H_{53}N_3OS$ = 1104.38) |
| P-107 | m/z = 1346.50($C_{98}H_{66}N_4OS$ = 1347.69) | P-108 | m/z = 1295.45($C_{94}H_{61}N_3O_2S$ = 1296.60) |
| P-109 | m/z = 1013.36($C_{73}H_{47}N_3O_3$ = 1014.20) | P-110 | m/z = 910.36($C_{67}H_{46}N_2O_2$ = 911.12) |
| P-111 | m/z = 1010.35($C_{74}H_{46}N_2O_3$ = 1011.19) | P-112 | m/z = 908.34($C_{67}H_{44}N_2O_2$ = 909.10) |
| P-113 | m/z = 852.26($C_{60}H_{40}N_2S_2$ = 853.11) | P-114 | m/z = 988.29($C_{71}H_{44}N_2S_2$ = 989.27) |
| P-115 | m/z = 882.22($C_{60}H_{38}N_2S_3$ = 883.16) | P-116 | m/z = 1170.23($C_{78}H_{46}N_2S_5$ = 1171.54) |
| P-117 | m/z = 910.30($C_{66}H_{42}N_2OS$ = 911.14) | P-118 | m/z = 886.30($C_{64}H_{42}N_2OS$ = 887.11) |
| P-119 | m/z = 784.25($C_{56}H_{36}N_2OS$ = 784.98) | P-120 | m/z = 734.24($C_{52}H_{34}N_2OS$ = 734.92) |
| P-121 | m/z = 884.29($C_{64}H_{40}N_2OS$ = 885.10) | P-122 | m/z = 996.23($C_{68}H_{40}N_2OS_3$ = 997.26) |
| P-123 | m/z = 1030.27($C_{72}H_{42}N_2O_2S_2$ = 1031.26) | P-124 | m/z = 886.30($C_{84}H_{42}N_2OS$ = 887.11) |
| P-125 | m/z = 1032.28($C_{72}H_{44}N_2O_2S_2$ = 1033.28) | P-126 | m/z = 1050.33($C_{76}H_{46}N_2O_2S$ = 1051.28) |
| P-127 | m/z = 1170.37($C_{84}H_{54}N_2OS_2$ = 1171.49) | P-128 | m/z = 1206.40($C_{88}H_{58}N_2S_2$ = 1207.57) |
| P-129 | m/z = 668.25($C_{48}H_{32}N_2O_2$ = 668.80) | P-130 | m/z = 760.25($C_{54}H_{36}N_2OS$ = 760.96) |
| P-131 | m/z = 684.22($C_{48}H_{32}N_2OS$ = 684.86) | P-132 | m/z = 760.25($C_{54}H_{36}N_2OS$ = 760.96) |
| P-133 | m/z = 684.22($C_{48}H_{32}N_2OS$ = 684.86) | P-134 | m/z = 760.25($C_{54}H_{38}N_2OS$ = 760.96) |
| P-135 | m/z = 700.20($C_{48}H_{32}N_2S_2$ = 700.92) | P-136 | m/z = 912.32($C_{66}H_{44}N_2OS$ = 913.15) |
| P-137 | m/z = 744.28($C_{54}H_{36}N_2O_2$ = 744.89) | P-138 | m/z = 776.23($C_{54}H_{36}N_2S_2$ = 777.02) |
| P-139 | m/z = 760.25($C_{54}H_{36}N_2OS$ = 760.96) | P-140 | m/z = 684.22($C_{48}H_{32}N_2OS$ = 864.86) |
| P-141 | m/z = 740.29($C_{52}H_{40}N_2OS$ = 740.97) | P-142 | m/z = 852.26($C_{80}H_{40}N_2S_2$ = 853.11) |
| P-143 | m/z = 760.25($C_{54}H_{36}N_2OS$ = 760.96) | P-144 | m/z = 760.25($C_{54}H_{36}N_2OS$ = 760.96) |
| P-145 | m/z = 684.22($C_{48}H_{32}N_2OS$ = 684.86) | P-146 | m/z = 820.31($C_{60}H_{40}N_2O_2$ = 820.99) |
| P-147 | m/z = 760.25($C_{54}H_{36}N_2OS$ = 760.96) | P-148 | m/z = 760.25($C_{54}H_{36}N_2OS$ = 760.96) |
| P-149 | m/z = 720.20($C_{48}H_{30}F_2N_2OS$ = 720.84) | P-150 | m/z = 700.20($C_{48}H_{32}N_2S_2$ = 700.92) |
| P-151 | m/z = 754.34($C_{54}H_{26}D_{10}N_2O_2$ = 754.96) | | |

Manufacturing Evaluation of Organic Electronic Element

[Example 1] Red Organic Light Emitting Device (Emitting-Auxiliary Layer)

An organic electroluminescent device was manufactured according to a conventional method using the compound of the present invention as an emitting-auxiliary layer material. First, after vacuum deposition of 4,4',4"-Tris[2-naphthyl (phenyl)amino] triphenylamine (abbreviated as 2-TNATA) to a thickness of 60 nm on the ITO layer (anode) formed on a glass substrate to form a hole injection layer, on the hole injection layer, N,N'-bis(1-naphthalenyl)-N,N'-bis-phenyl-(1,1'-biphenyl)-4,4'-diamine (abbreviated as NPB) as a hole transport compound was vacuum-deposited to a thickness of 60 nm to form a hole transport layer. Then, after vacuum deposition of the compound P-1 of the present invention to a thickness of 40 nm on the hole transport layer to form an emitting auxiliary layer, by using 4,4'-N,N'-dicarbazole-biphenyl (abbreviated as CBP) as a host material and bis-(1-phenylisoquinolyl) iridium (III) acetylacetonate (hereinafter (piq)2lr(acac)) as a dopant material on the emitting-auxiliary layer, doping at a 95:5 weight ratio was vacuum-deposited on the emitting auxiliary layer to a thickness of 30 nm to form an emitting layer. Next, vacuum deposition of (1,1'-biphenyl-4-olato)bis(2-methyl-8-quinolinolato)aluminum (hereinafter BAlq) to a thickness of 5 nm on the emitting layer to form a hole blocking layer, and bis(10-hydroxybenzo[h]quinolinato) beryllium (hereinafter $BeBq_2$) was vacuum-deposited to a thickness of 35 nm on the hole blocking layer to form an electron transport layer. Then, as an electron injection layer, LiF, an alkali metal halide was deposited to a thickness of 0.2 nm on the electron transport layer, then, on the electron injection layer, Al was deposited to a thickness of 150 nm and used as a cathode to prepare an organic electroluminescent device.

[Example 2] to [Example 23]

An organic electroluminescent device was manufactured in the same manner as in Example 1, except that the compound of the present invention described in Table 4 was used instead of the compound P-1 of the present invention as an emitting-auxiliary layer material.

Comparative Example 1

An organic electroluminescent device was manufactured in the same manner as in Example 1, except that the emitting auxiliary layer was not formed.

[Comparative example 2] to Comparative example 6]

An organic electroluminescent device was manufactured in the same manner as in Example 1, except that the comparative compounds A to E were used instead of the compound P-1 of the present invention as an emitting auxiliary layer material.

[Comparative example A]

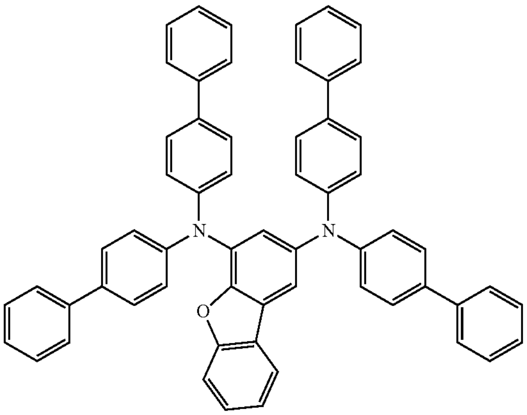

[Comparative example B]

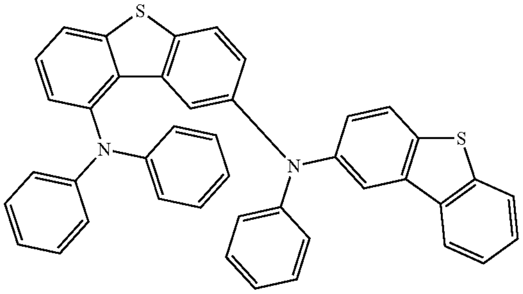

[Comparative example C]

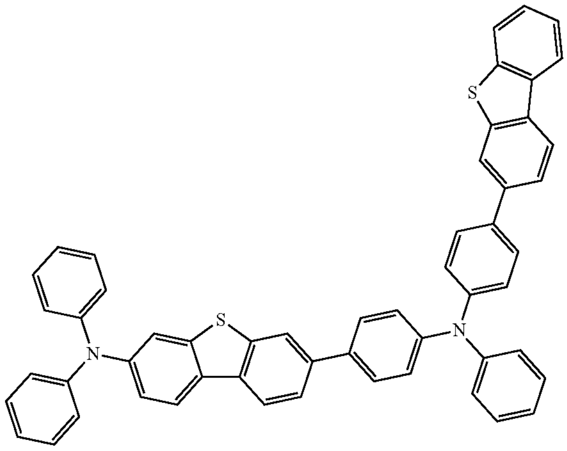

-continued

[Comparative example D]

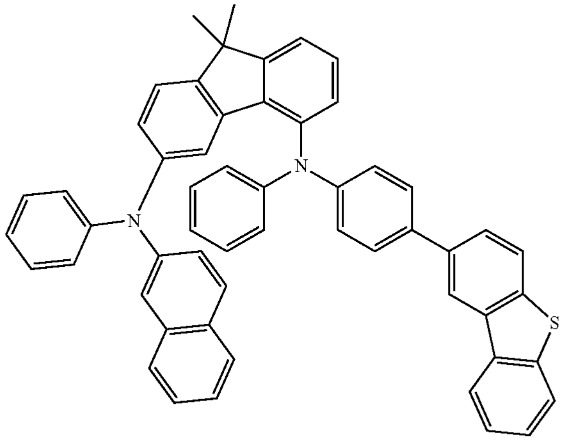

[Comparative example E]

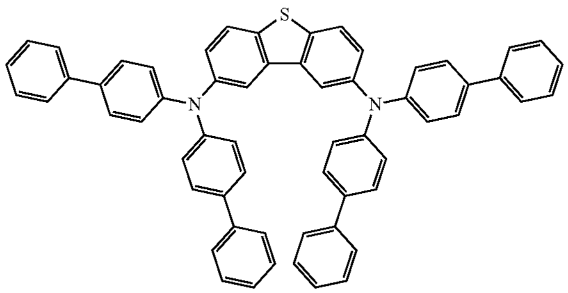

By applying a forward bias DC voltage to the organic electroluminescent devices prepared in Examples and Comparative Examples prepared in this way, Electroluminescence (EL) characteristics were measured with PR-650 from photo research, and as a result of the measurement, the T95 lifetime was measured using a lifetime measuring device manufactured by McScience at 2500 cd/m$^2$ standard luminance. Table 4 below shows the device fabrication and evaluation results.

TABLE 4

| | compound | Voltage | Current Density (mA/cm$^2$) | Brightness (cd/m$^2$) | Efficiency (cd/A) | T(95) |
|---|---|---|---|---|---|---|
| comparative example (1) | — | 6.7 | 32.5 | 2500 | 7.7 | 62.7 |
| comparative example (2) | comparative compound A | 5.9 | 13.6 | 2500 | 20.4 | 113.3 |
| comparative example (3) | comparative compound B | 5.7 | 10.3 | 2500 | 24.2 | 123.2 |
| comparative example (4) | comparative compound C | 6.1 | 16.4 | 2500 | 15.2 | 121.0 |
| comparative example (5) | comparative compound D | 5.9 | 10.8 | 2500 | 23.2 | 107.5 |
| comparative example (6) | comparative compound E | 6.2 | 24.8 | 2500 | 10.1 | 82.3 |

TABLE 4-continued

| | compound | Voltage | Current Density (mA/cm$^2$) | Brightness (cd/m$^2$) | Efficiency (cd/A) | T(95) |
|---|---|---|---|---|---|---|
| example (1) | compound (P-1) | 5.2 | 8.7 | 2500 | 28.9 | 147.9 |
| example (2) | compound (P-2) | 5.4 | 8.9 | 2500 | 28.0 | 130.1 |
| example (3) | compound (P-49) | 5.3 | 8.0 | 2500 | 31.2 | 146.1 |
| example (4) | compound (P-55) | 5.0 | 7.6 | 2500 | 33.1 | 150.7 |
| example (5) | compound (P-83) | 5.4 | 8.6 | 2500 | 29.1 | 133.7 |
| example (6) | compound (P-97) | 5.2 | 8.5 | 2500 | 29.4 | 139.3 |
| example (7) | compound (P-105) | 5.0 | 8.1 | 2500 | 30.8 | 143.6 |
| example (8) | compound (P-114) | 5.2 | 8.5 | 2500 | 29.5 | 130.4 |
| example (9) | compound (P-118) | 5.1 | 8.5 | 2500 | 29.3 | 143.8 |
| example (10) | compound (P-129) | 5.2 | 8.6 | 2500 | 29.2 | 145.3 |
| example (11) | compound (P-130) | 5.2 | 8.8 | 2500 | 28.3 | 137.0 |
| example (12) | compound (P-131) | 5.3 | 7.9 | 2500 | 31.8 | 138.4 |
| example (13) | compound (P-133) | 5.1 | 8.2 | 2500 | 30.6 | 150.6 |
| example (14) | compound (P-134) | 5.0 | 8.1 | 2500 | 30.9 | 152.2 |
| example (15) | compound (P-137) | 5.1 | 8.4 | 2500 | 29.7 | 152.3 |
| example (16) | compound (P-139) | 5.1 | 8.6 | 2500 | 29.2 | 143.9 |
| example (17) | compound (P-143) | 5.2 | 8.0 | 2500 | 31.1 | 141.2 |
| example (18) | compound (P-145) | 5.2 | 8.7 | 2500 | 28.7 | 134.4 |
| example (19) | compound (P-146) | 5.3 | 8.7 | 2500 | 28.8 | 133.1 |
| example (20) | compound (P-148) | 5.1 | 7.9 | 2500 | 31.5 | 146.4 |
| example (21) | compound (P-149) | 5.4 | 7.6 | 2500 | 32.7 | 131.8 |
| example (22) | compound (P-150) | 5.0 | 8.0 | 2500 | 31.3 | 146.2 |
| example (23) | compound (P-152) | 5.0 | 8.1 | 2500 | 33.2 | 150.8 |

Referring to Table 4, when a red organic light emitting device is manufactured using the material for an organic electroluminescent device of the present invention as an emitting-auxiliary layer material, the driving voltage, luminous efficiency and lifespan of the organic electroluminescent device were remarkably improved compared to Comparative Examples in which no emitting auxiliary layer was formed or in which Comparative Compounds A to E were used.

In other words, in Comparative Examples 2 to 6 using Comparative Compounds A to E as an emitting auxiliary layer rather than Comparative Example 1 in which the emitting auxiliary layer was not formed, the driving voltage, efficiency, and lifespan of the device were improved, when the compound of the present invention was used as a material for the emitting auxiliary layer, compared to when Comparative Compounds A to E were used as the emitting auxiliary layer, the driving voltage of the organic electroluminescent device was lowered, and the luminous efficiency and lifespan were improved.

Comparing the comparative compound A or E and the compound of the present invention, it is the same as the structure in which dibenzofuran or dibenzothiophene is bonded between the amine and the amine, but the compound of the present invention has a structure in which dibenzofuran or dibenzothiophene is further substituted with an amine group. Therefore, when dibenzofuran or dibenzothiophene is bonded to an amine group, the refractive index is significantly higher than when a general aryl group substituent is substituted, and Tg also increases, so that efficiency and thermal stability are excellent.

Also, the compound of the present invention is the same as in Comparative Compound B in that an amine group is substituted for dibenzofuran or dibenzothiophene, but is different in that a linking group between dibenzofuran or dibenzothiophene and an amine group is necessarily present.

Accordingly, the compound of the present invention is different from the comparative compound by introducing a linking group between the dibenzofuran or dibenzothiophene and the amine group, so that the conjugation length becomes longer than that of the comparative compound B, as a result, the hole characteristics are improved, and as a result, the driving and efficiency are significantly increased compared to the comparative compound, and the chemical stability for the unshared electron pair is increased, and the lifespan is also increased.

Figure 6:
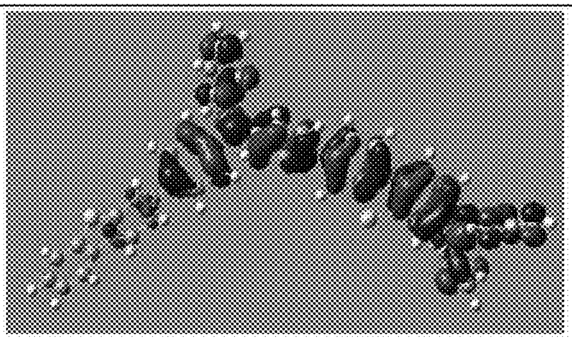
FIG. 6 shows the HOMO electron clouds of the comparative compound C and the compound P-55 of the present invention.
Figure 6:
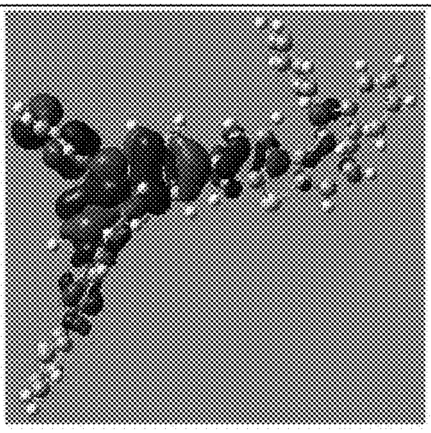

Comparing the comparative compound C and the compound of the present invention, the structure is the same as that of the present invention, but the bonding position of dibenzothiophene between the amine and the amine is the 3rd and 7th positions, and the position of the dibenzothiophene bonded to the amine is substituted with the 3rd position. FIG. 6 shows the HOMO electron clouds of the comparative compound C and the compound P-55 of the present invention.

Referring to FIG. 6, in the case of Comparative Compound C, the electron cloud is widely spread over the two amine moieties, but it can be seen that the compound of the present invention forms an electron cloud in a narrower region than that of the comparative compound, and through this, the hole mobility is improved and it is determined that the device characteristics are affected.

In addition, in order to confirm that the hole mobility is improved, an organic electronic device was fabricated with ITO layer (anode)/2-TNATA 60 nm/NPB 60 nm/Comparative compound C or compound P-55 of the present invention/HATCN 10 nm/Al (cathode) 150 nm and HOD (Hole Only Device) was measured, and the results can be confirmed through FIG. 5 and Table 5 below.

TABLE 6

| Device | Δ Op.V @ 0.1 mA/cm2 | Op.V @ 0.1 mA/cm2 | Δ Op.V @ 10 mA/cm2 | Op.V @ 10 mA/cm2 |
|---|---|---|---|---|
| P-55 | 0.00 | 0.61 | 0.00 | 1.35 |
| Ref. C | 1.58 | 2.19 | 1.62 | 2.97 |

Figure 5:
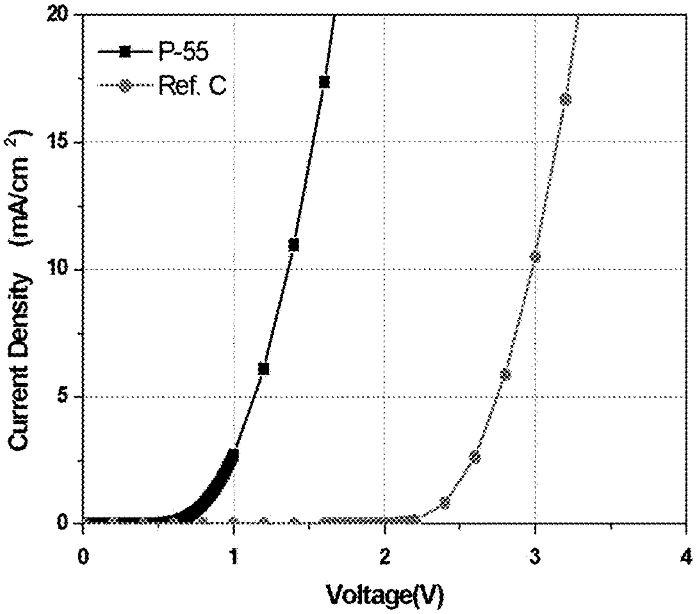
FIG. 5 shows a driving voltage measurement result for hole mobility analysis of an organic electroluminescent device according to an aspect of the present invention.

Referring to FIG. 5 and Table 5, it can be seen that at a current density of 0.1 mA/cm$^2$, the driving voltage is 2.19 V for Comparative Compound C and 0.61 V for Compound P-55 of the present invention, and the difference between the comparative compound C and the compound P-55 of the present invention is 1.58 V. Also, at a current density of 10 $mA/cm^2$, the driving voltage is 2.97 V for Comparative Compound C and 1.35 V for Compound P-55 of the present invention, and It can be seen that the difference between Comparative Compound C and Compound P-55 of the present invention is 1.62 V. Through this, it can be seen that the compound of the present invention has more improved hole mobility compared to Comparative Compound C.

That is, it is judged that the compound of the present invention exhibits superior device characteristics compared to the comparative compound C based on the above-mentioned points.

Comparing the comparative compound D and the compound of the present invention, Comparative Compound D has a structure in which a fluorenyl group is introduced between an amine and an amine, and the compound of the present invention has a structure in which dibenzofuran or dibenzothiophene is bonded between the amine and the amine. It can be confirmed that when dibenzofuran or dibenzothiophene is introduced, the refractive index is significantly higher than when a fluorenyl group is introduced, and Tg is also increased, so that efficiency and thermal stability are improved.

In conclusion, although Comparative Compounds A to E and the compounds of the present invention consist of similar components, a linking group is introduced between dibenzofuran or dibenzothiophene and an amine group, so that the properties of the compound, such as hole characteristics, light efficiency characteristics, hole injection & mobility characteristics, charge balance of holes and electrons, are more suitable for the red emitting auxiliary layer, thereby the device results of Examples 1 to 23 are significantly superior to those of Comparative Examples 2 to 6.

In the case of the emitting-auxiliary layer, since it is necessary to understand the correlation between the hole transport layer and the emitting layer (host), even if a similar core is used, it will be very difficult to infer the characteristics of the emitting-auxiliary layer using the compound of the present invention even for those of ordinary skill in the art.

Also, in the evaluation results of the above-described device fabrication, the device characteristics in which the compound of the present invention is applied only to the emitting-auxiliary layer has been described, but the compound of the present invention may be applied to the hole transport layer or both the hole transport layer and the emitting auxiliary layer may be applied.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound represented by Formula 1:

Formula 1

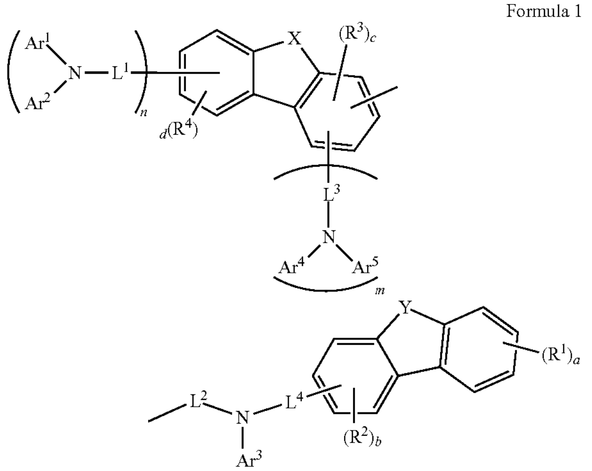

Formula 3-4

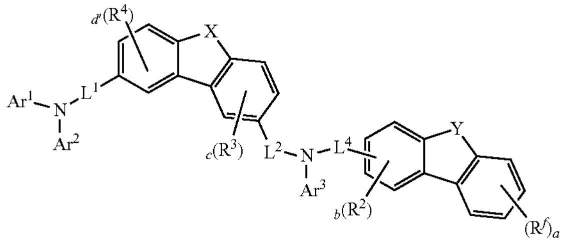

Formula 3-13

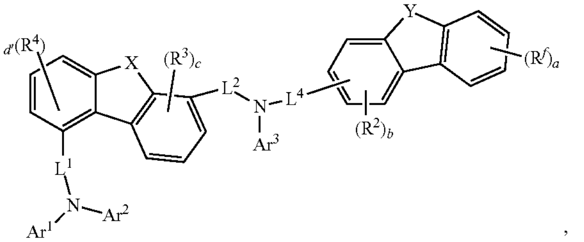

, wherein:

1) $R^1$, $R^2$, $R^3$ and $R^4$ are the same or different from each other, and are each independently selected from the group consisting of hydrogen; deuterium; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and an adjacent plurality of $R^1$s, or a plurality of $R^2$s, or a plurality of $R^3$s, or a plurality of $R^4$s may be bonded to each other to form a ring, 2) X and Y are independently of each other O or S, 3) $L^1$, $L^2$ and $L^3$ are each independently a single bond or any of Formulas b-1 to b-13, with the proviso that (i) at least one of $L^1$ and $L^2$ is any one of Formulas b-1 to b-13 in the case where Formula 1 is Formula 3-4 or Formula 3-13 above, and (ii) at least one of $L^1$ to $L^3$ is any one of Formulas b-1 to b-13 in the case where m+n is 2:
Formula b-1
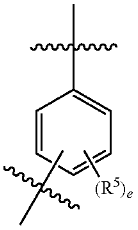
Formula b-2
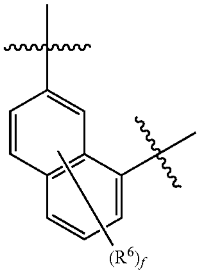
Formula b-3
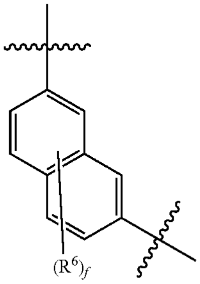
Formula b-4
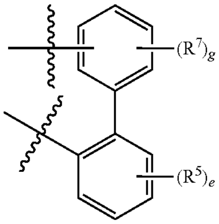
Formula b-5
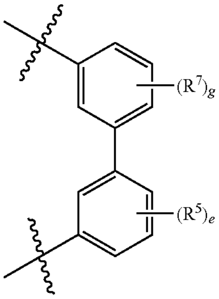
-continued
Formula b-6
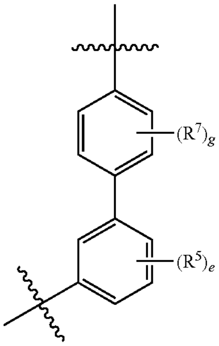
Formula b-7
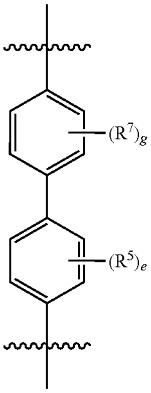
Formula b-8
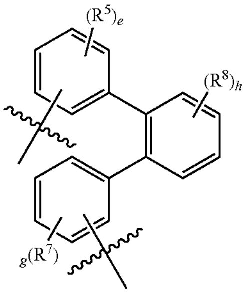
Formula b-9
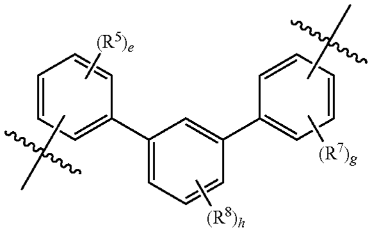
Formula b-10
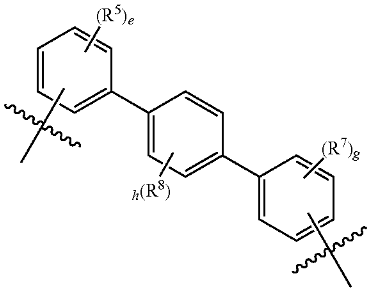

-continued

Formula b-11

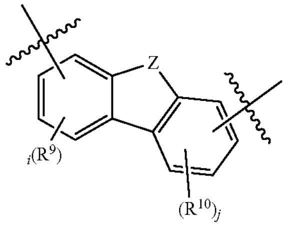

Formula b-12

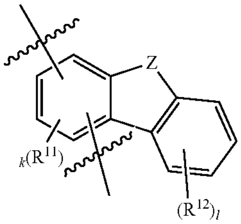

Formula b-13

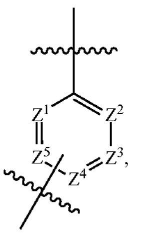

wherein:

Z is O, S, $C(R^{13})(R^{14})$ or $N-L^5-Ar^6$, $Z^1$, $Z^2$, $Z^3$, $Z^4$ and $Z^5$ are each independently N or $C(R^{15})$, provided that at least one of $Z^1$, $Z^2$, $Z^3$, $Z^4$ and $Z^5$ is $C(R^{15})$ and at least one thereof is N, $R^5$, $R^6$, $R^7$, $R^8$, $R^9$, $R^{10}$, $R^{11}$, $R^{12}$, $R^{13}$, $R^{14}$ and $R^{15}$ are the same as the definition of $R^1$ above, or adjacent groups may combine with each other to form a ring, e, g, h and l are each independently an integer of 0 to 4, f is an integer of 0 to 6, i and j are each independently an integer of 0 to 3, k is an integer of 0 to 2, $Ar^6$ is the same as the definition of $Ar^1$ below, $L^5$ is a single bond; a $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring, and (wavy line) indicates the bonding position, 4) $L^4$ is selected from the group consisting of Formulas b-1 to b-13 above, 5) $Ar^1$, $Ar^2$, $Ar^3$, $Ar^4$ and $Ar^5$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; an $C_2$~$C_{30}$ alkenyl group; a $C_2$-$C_{20}$ alkynyl group; a $C_1$-$C_{30}$ alkoxy group; a $C_6$-$C_{30}$ aryloxy group, 6) A and d are each independently an integer of 0 to 4, b and c are each independently an integer of 0 to 3, m and n are each independently 0 or 1, provided that $m+n \geq 1$, 7) d' is an integer from 0 to 3, 8) Wherein the aryl group, arylene group, heterocyclic group, fluorenyl group, fluorenylene group, aliphatic ring group, fused ring group, alkyl group, alkenyl group, alkoxyl group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; $C_8$-$C_{20}$ arylalkenyl group; and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof, and 9) Wherein a compound of Formula 7 is excluded from the compound of Formula 1:

Formula 7

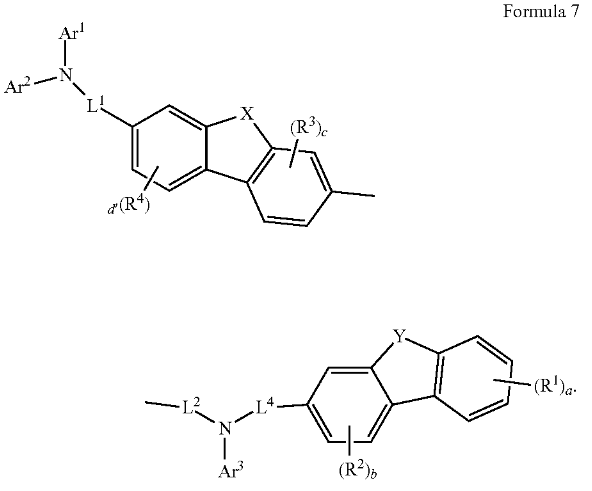

2. The compound of claim 1, wherein the compound of Formula 1 is represented by one of Formulas 1-1 to 1-3:

Formula 1-1

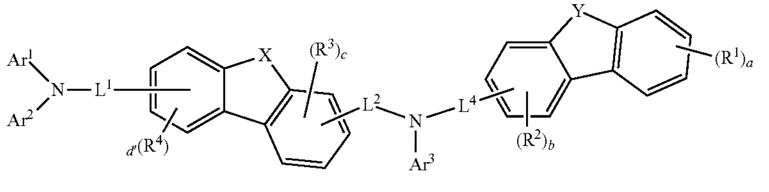

-continued
Formula 1-2
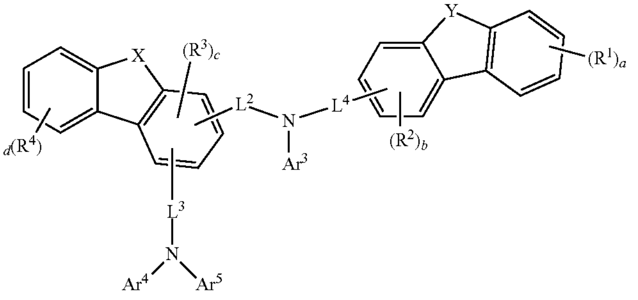
Formula 1-3
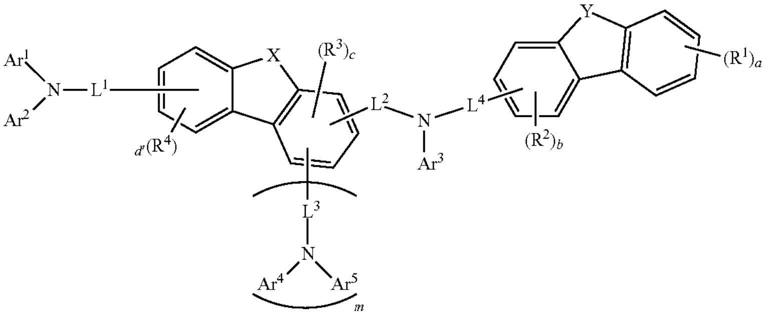
wherein:
1) $R^1$, $R^2$, $R^3$, $R^4$, X, Y, $L^1$, $L^2$, $L^3$, $L^4$, $Ar^1$, $Ar^2$, $Ar^3$, $Ar^4$, $Ar^5$, a, b, c and d are the same as defined in claim 1,
2) c' is an integer from 0 to 2, and d' is an integer from 0 to 3.
3. The compound of claim 1, wherein the compound of Formula 1 is represented by one of Formulas 2-1 to 2-4:
Formula 2-1
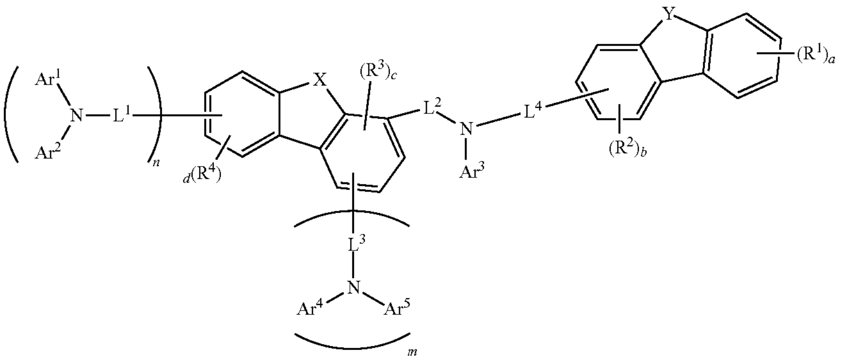
Formula 2-2
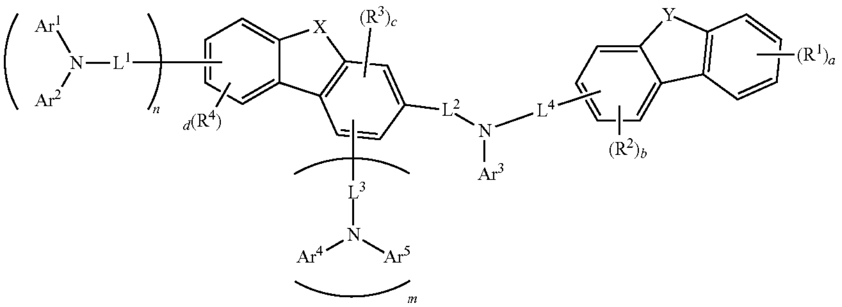

-continued
Formula 2-3
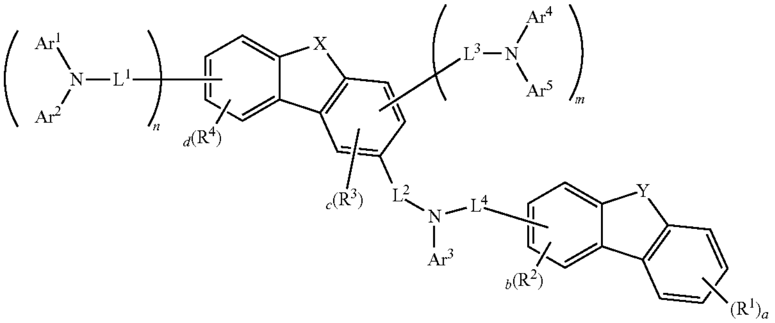
Formula 2-4
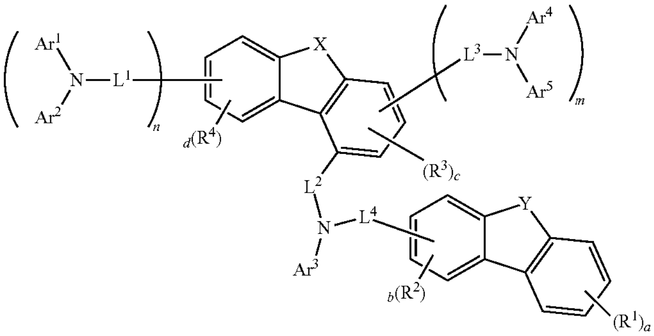
wherein:
$R^1, R^2, R^3, R^4$, X, Y, $L^1, L^2, L^3, L^4, Ar^1, Ar^2, Ar^3, Ar^4, Ar^5$, a, b, c, d, m and n are the same as defined in claim 1.
4. The compound of claim 1, wherein the compound of Formula 1 is represented by one of Formulas 3-1 to 3-14:
Formula 3-1
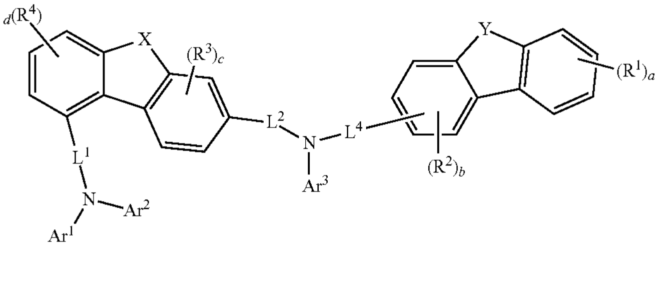
Formula 3-2
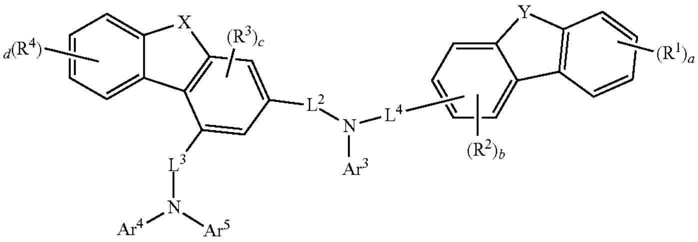

-continued
Formula 3-3
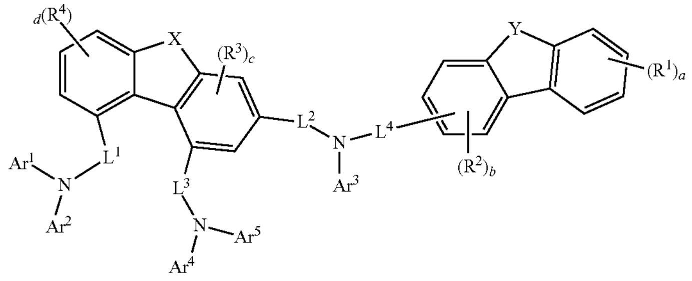
Formula 3-4
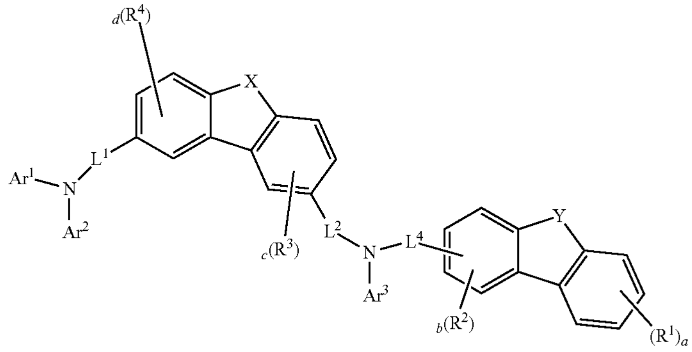
Formula 3-5
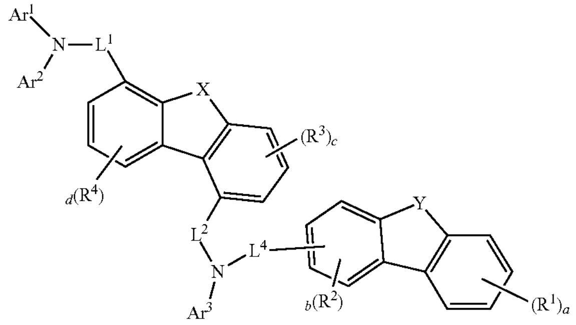
Formula 3-6
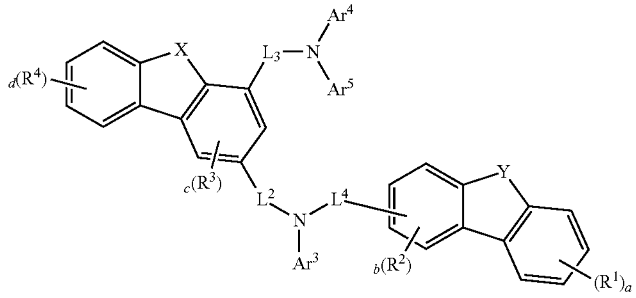
Formula 3-7
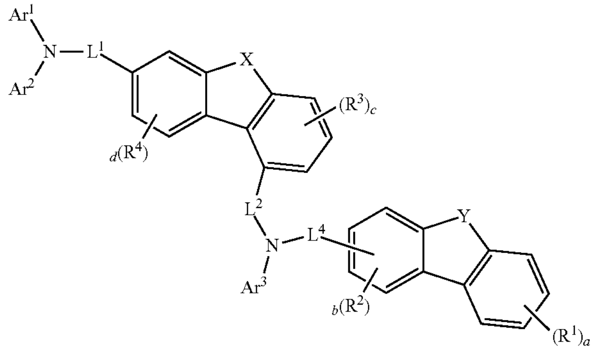

-continued
Formula 3-8
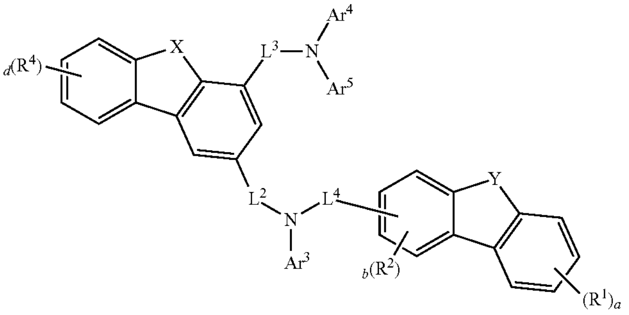
Formula 3-9
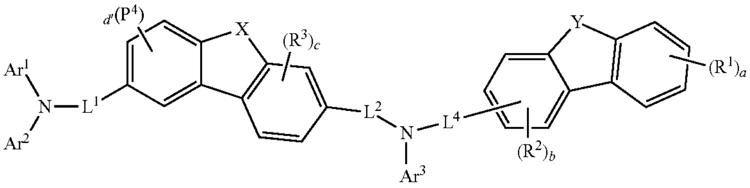
Formula 3-10
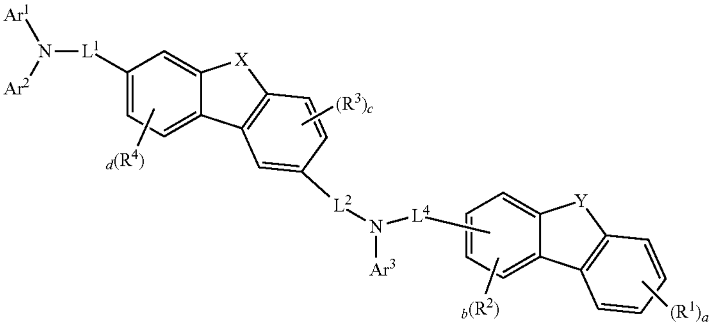
Formula 3-11
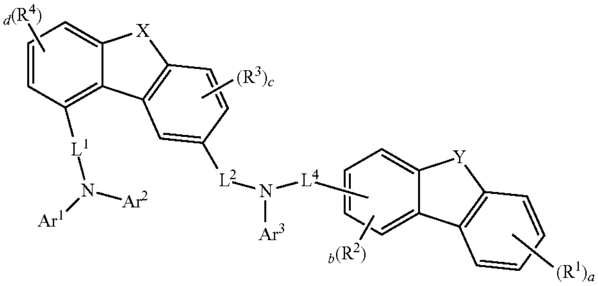
Formula 3-12
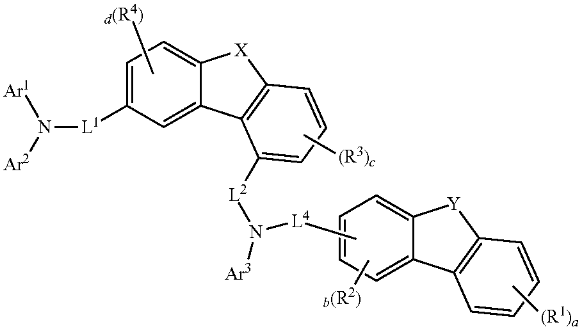

-continued
Formula 3-13
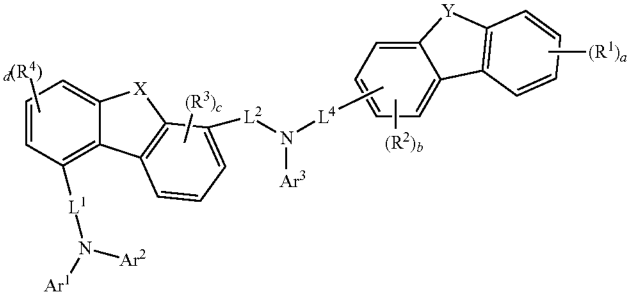
Formula 3-14
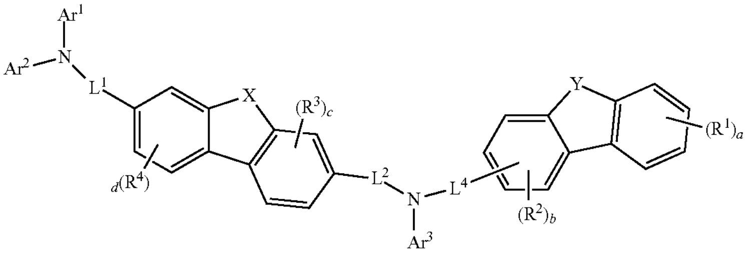
wherein:
1) $R^1$, $R^2$, $R^3$, $R^4$, X, Y, $L^1$, $L^2$, $L^3$, $L^4$, $Ar^1$, $Ar^2$, $Ar^3$, $Ar^4$, $Ar^5$, a, b, c and d are the same as defined in claim 1,
2) c' is an integer from 0 to 2, and d' is an integer from 0 to 3.
5. The compound of claim 1, wherein the compound of Formula 1 is represented by one of Formulas 4-1 to 4-6:
Formula 4-1
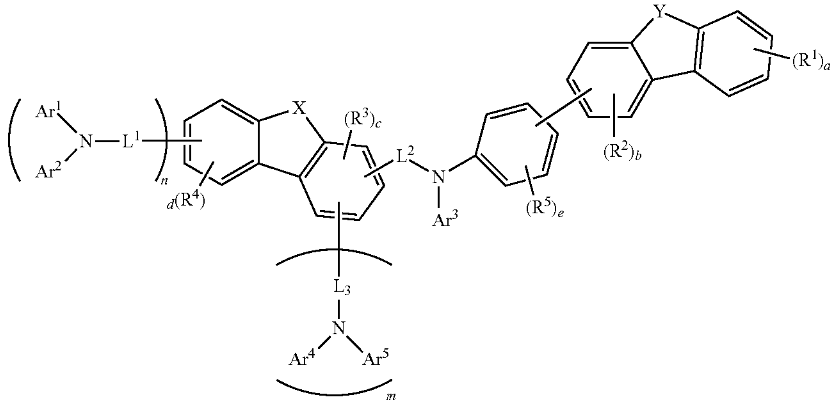
Formula 4-2
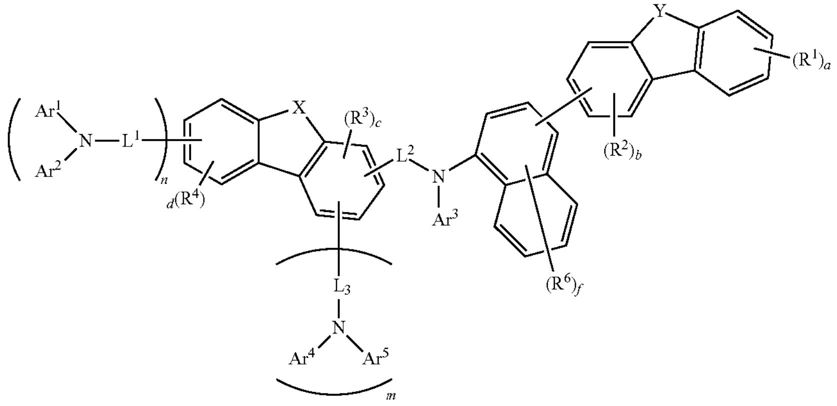

-continued
Formula 4-3
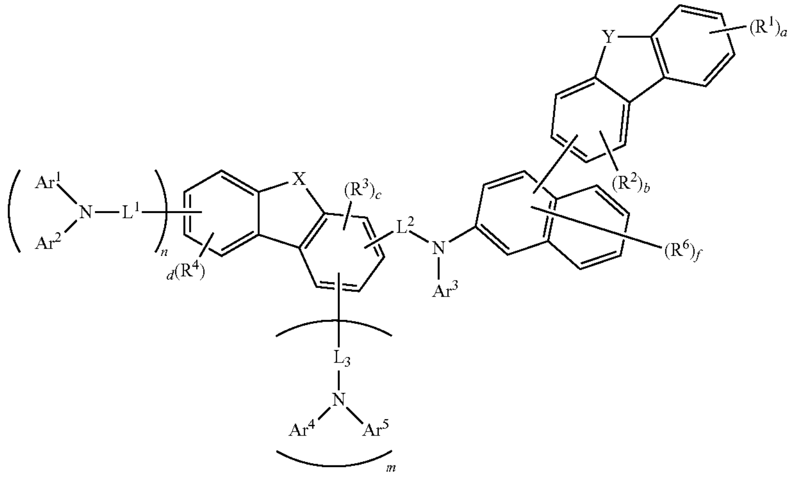
Formula 4-4
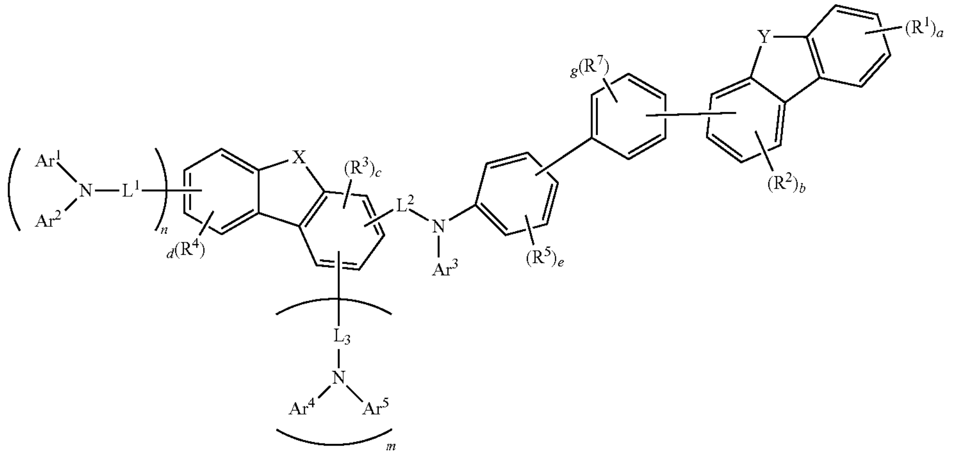
Formula 4-5
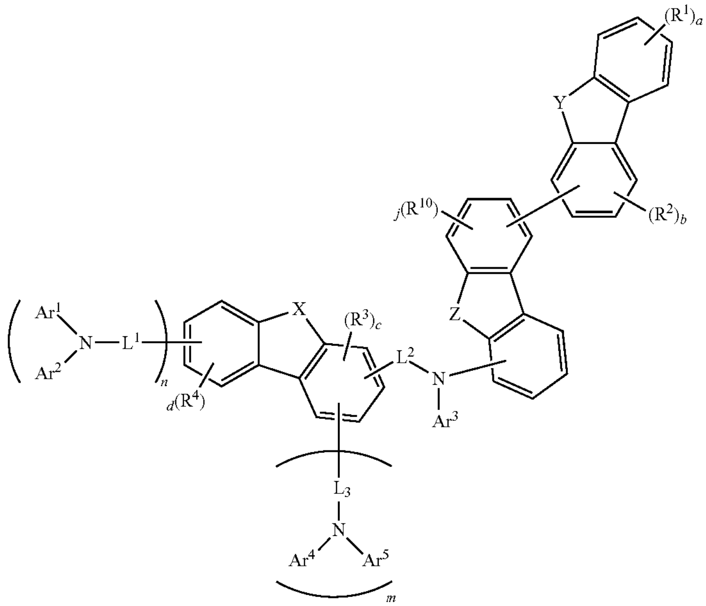

-continued
Formula 4-6
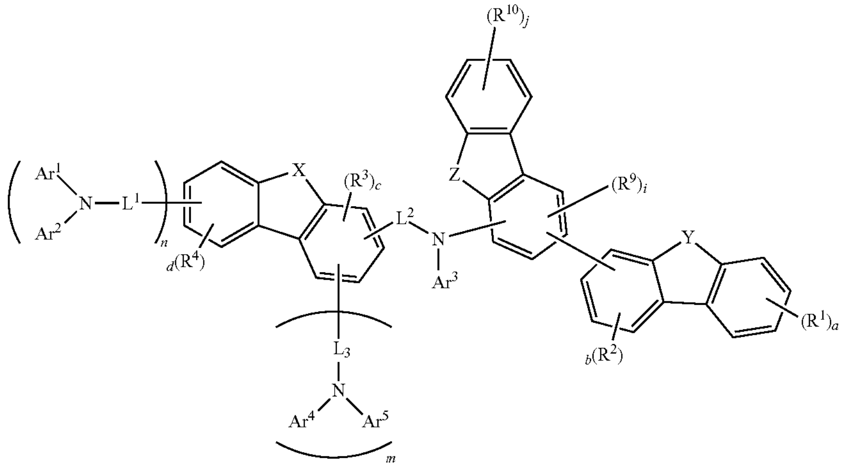
wherein:
1) $R^1$, $R^2$, $R^3$, $R^4$, X, Y, $L^1$, $L^2$, $L^3$, $Ar^1$, $Ar^2$, $Ar^3$, $Ar^4$, $Ar^5$, a, b, c, d, m and n are the same as defined in claim 1,
2) $R^5$, $R^6$, $R^7$, $R^9$, $R^{10}$, $R^{11}$, $R^{12}$, e, f, g, i, j, k, l and Z are the same as defined in claim 1.
6. The compound of claim 1, wherein the compound of Formula 1 is represented by one of Formulas 5-1 to 5-4:
Formula 5-1
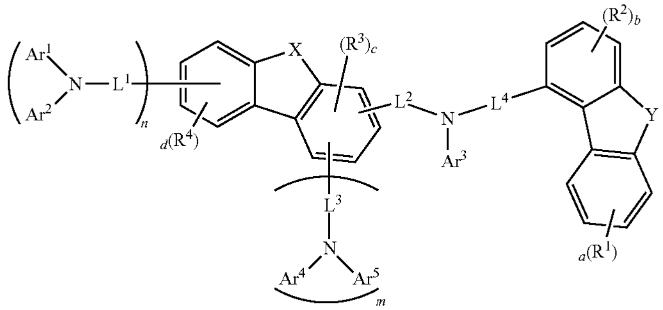
Formula 5-2
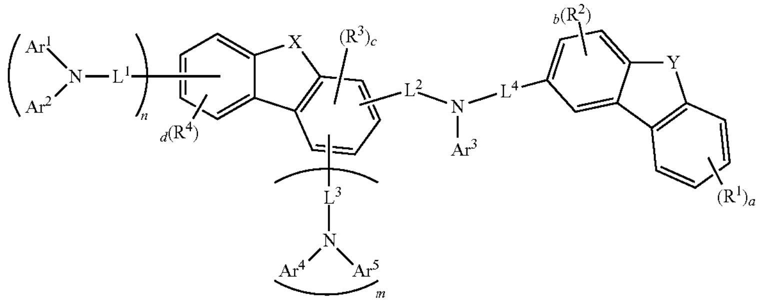

-continued
Formula 5-3
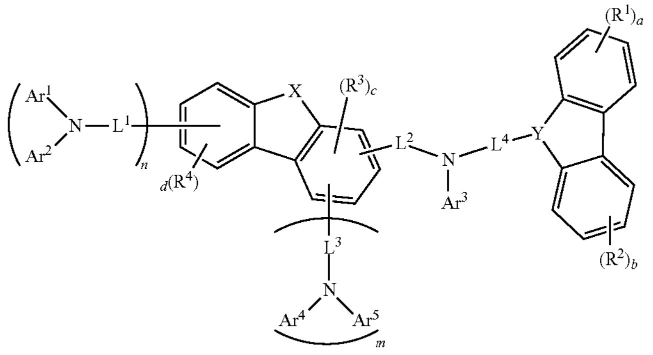
Formula 5-4
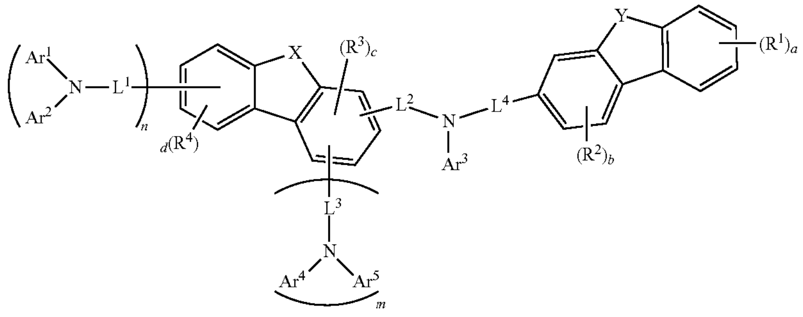
wherein $R^1$, $R^2$, $R^3$, $R^4$, X, Y, $L^1$, $L^2$, $L^3$, $L^4$, $Ar^1$, $Ar^2$, $Ar^3$, $Ar^4$, $Ar^5$, a, b, c, d, m and n are the same as defined in claim 1.
7. The compound of claim 1, wherein the compound represented by Formula 1 is selected from the group consisting of compounds P-1 to P-45, P-47 to P-67, P-69 to P-112, P-114 to P-118, P-120 to P-148 and P-150 to P-152:
P-1
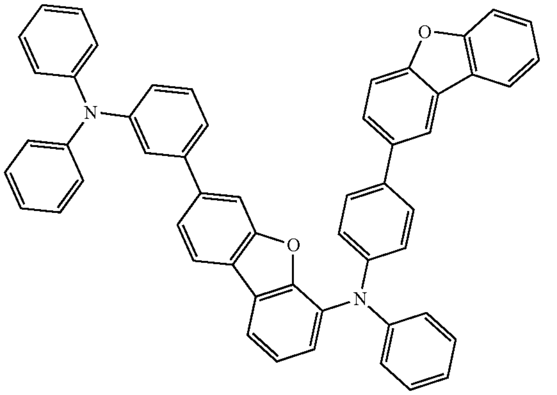

-continued
P-2
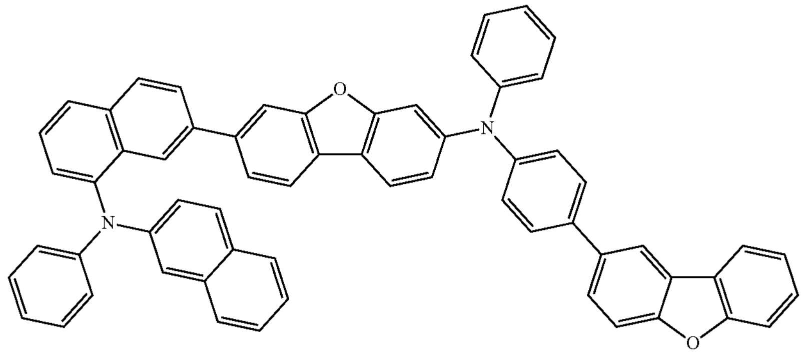
P-3
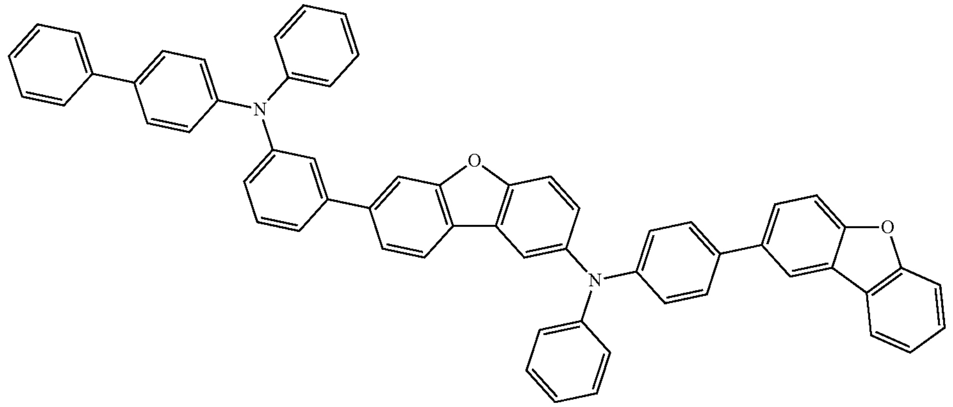
P-4
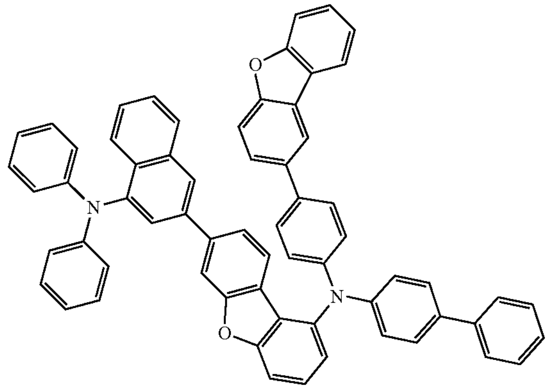
P-5
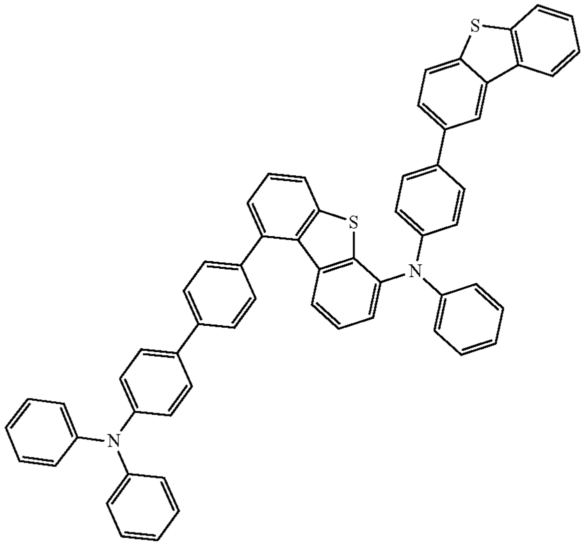

-continued
P-6
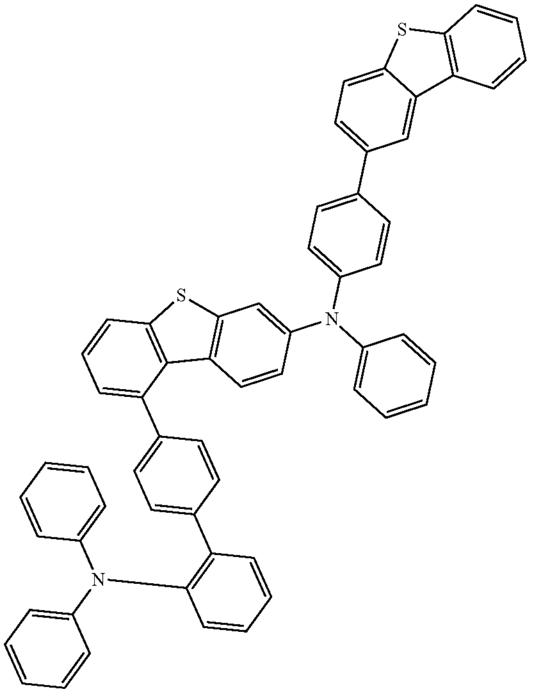
P-7
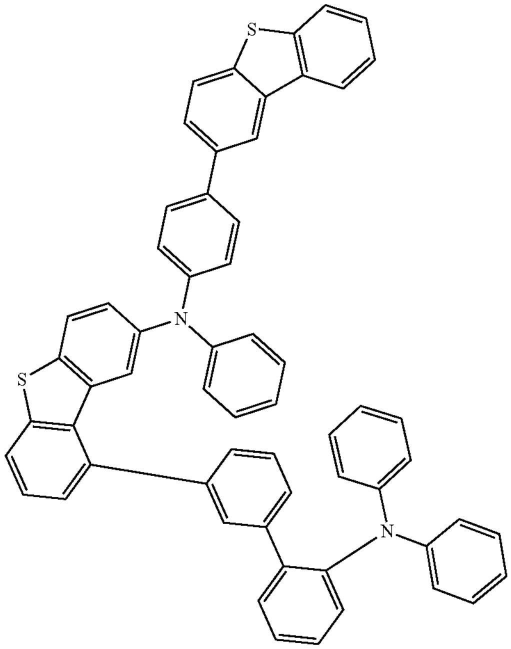
P-8
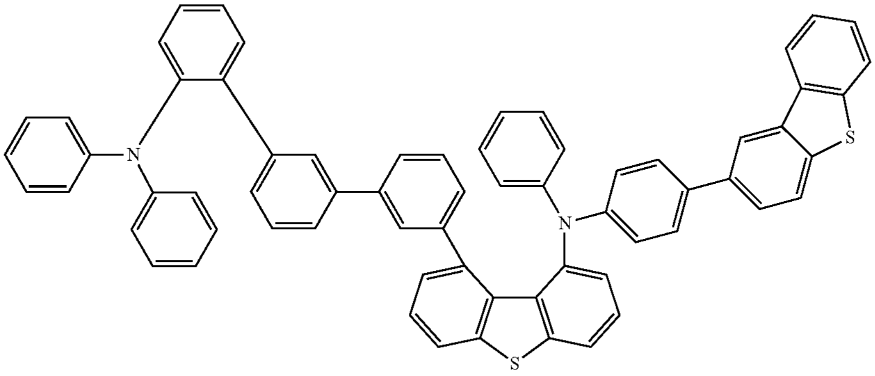
P-9
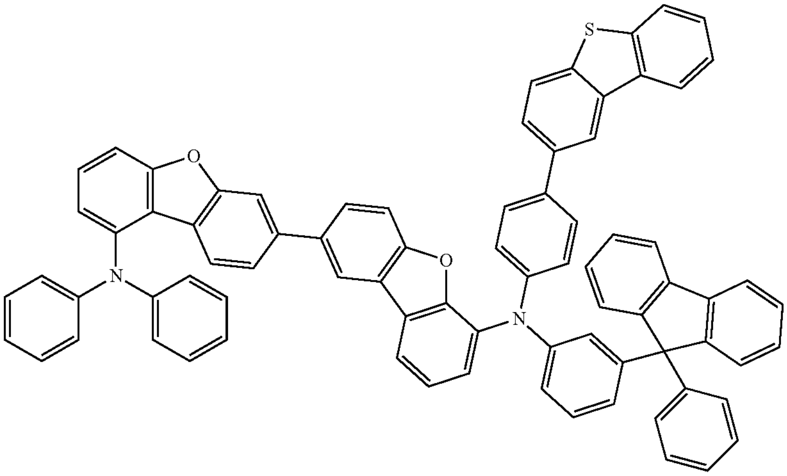

-continued
P-10
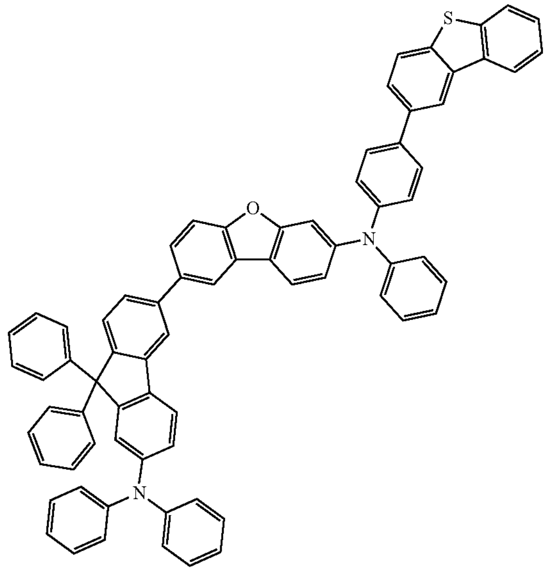
P-11
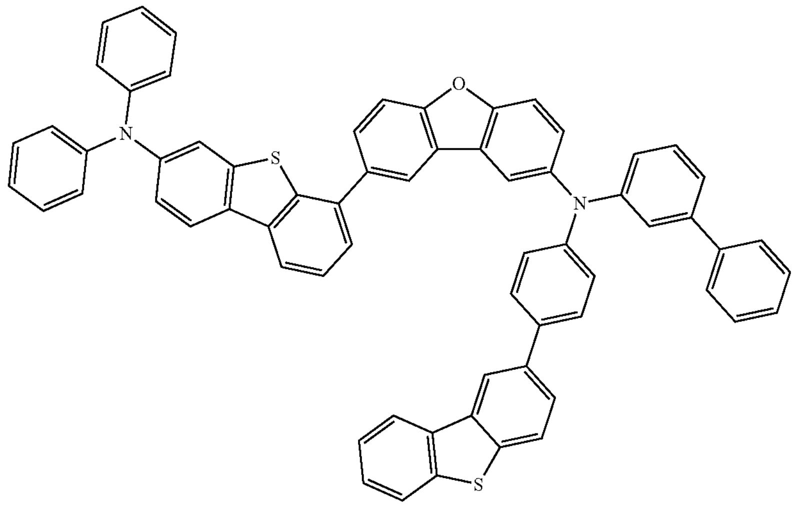
P-12
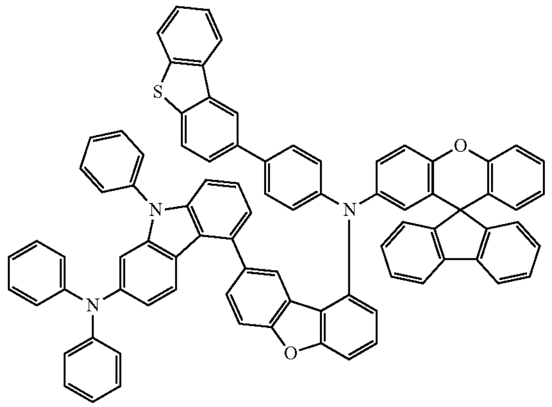
P-13
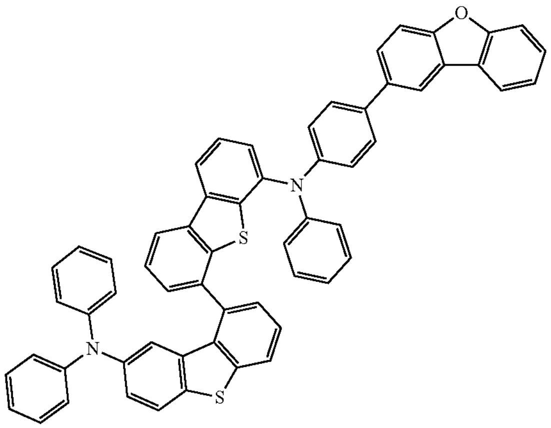

-continued
P-14
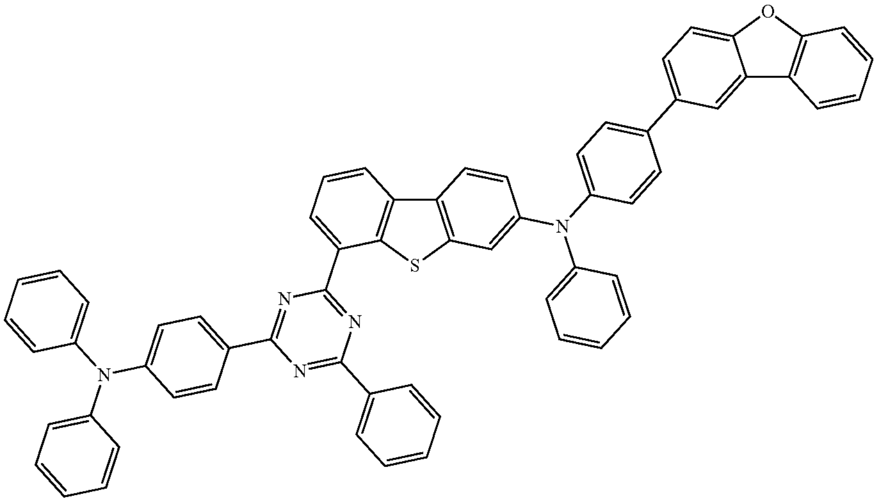
P-15
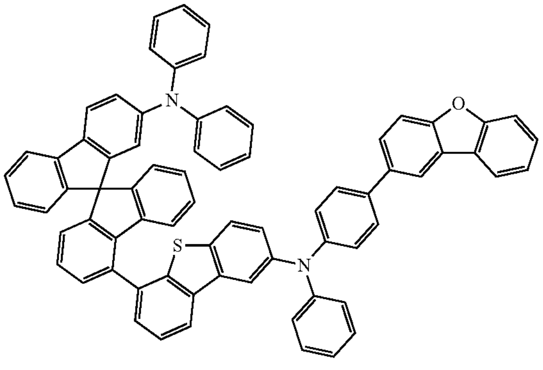
P-16
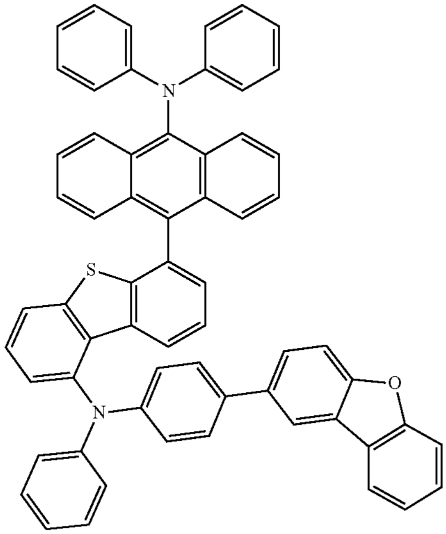

-continued
P-17
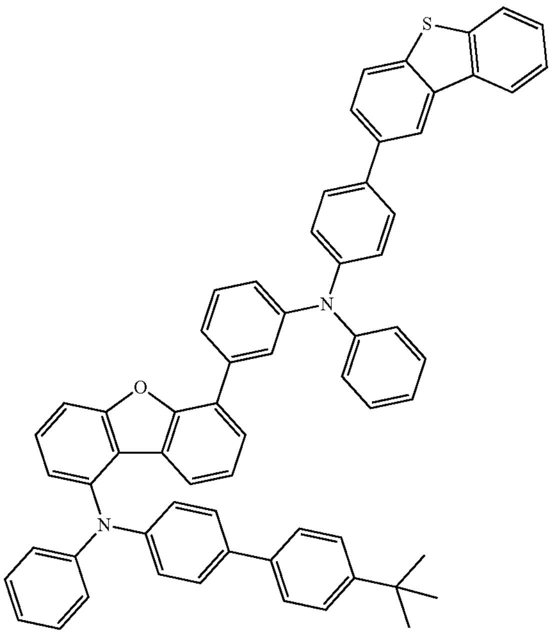
P-18
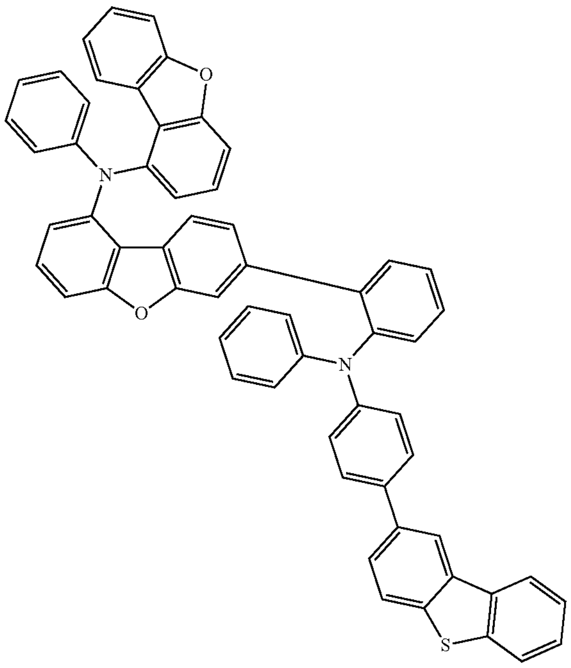
P-19
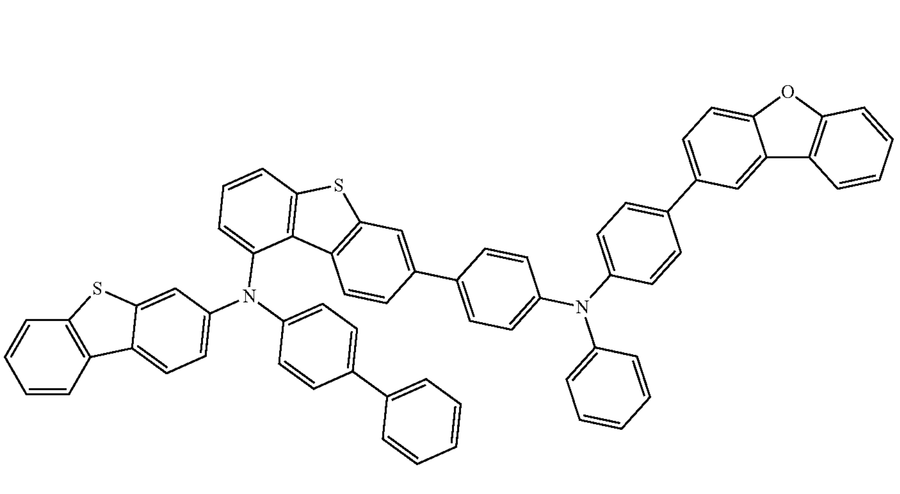

-continued
P-20
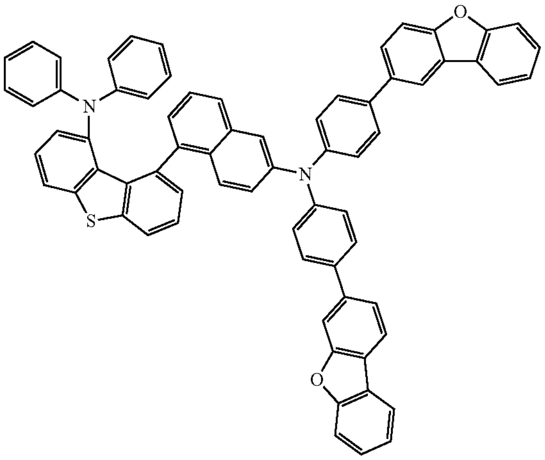
P-21
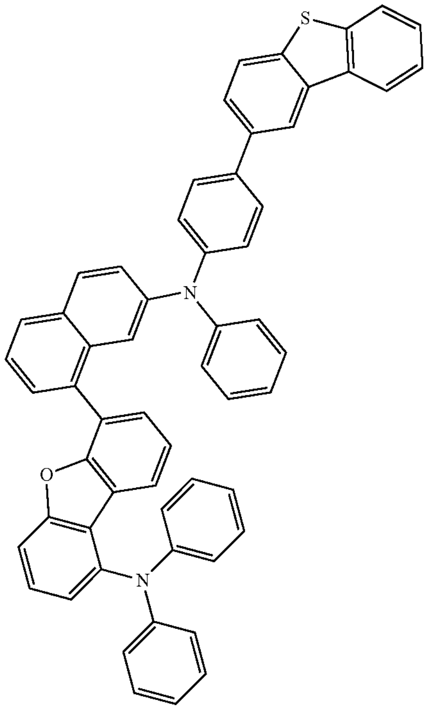
P-22
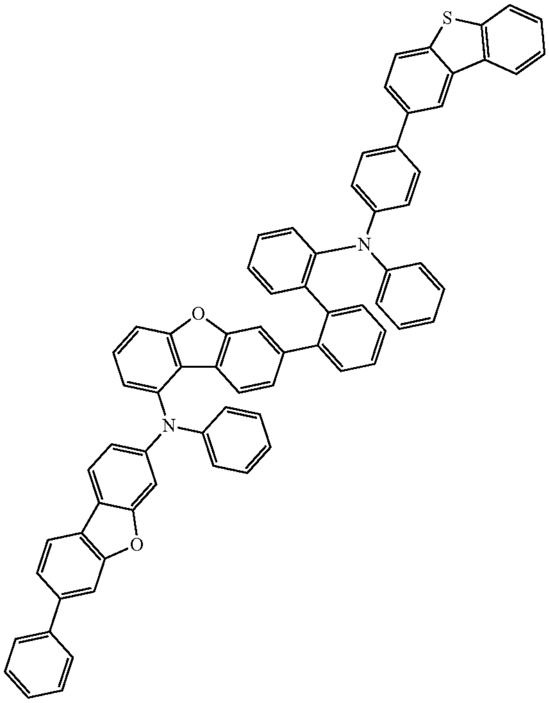

-continued
P-23
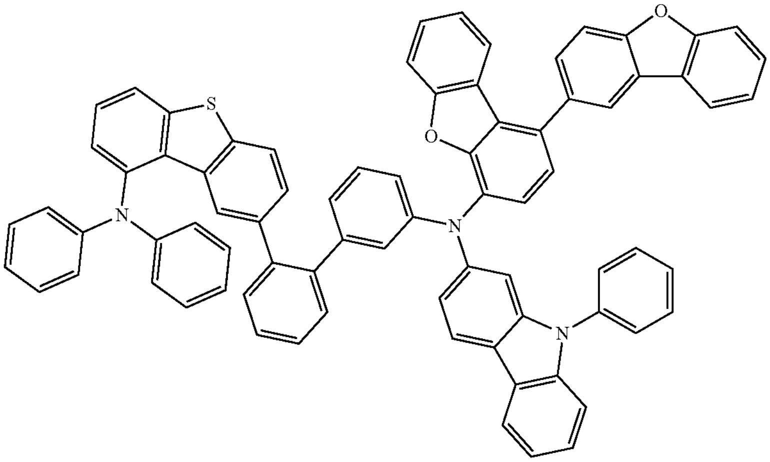
P-24
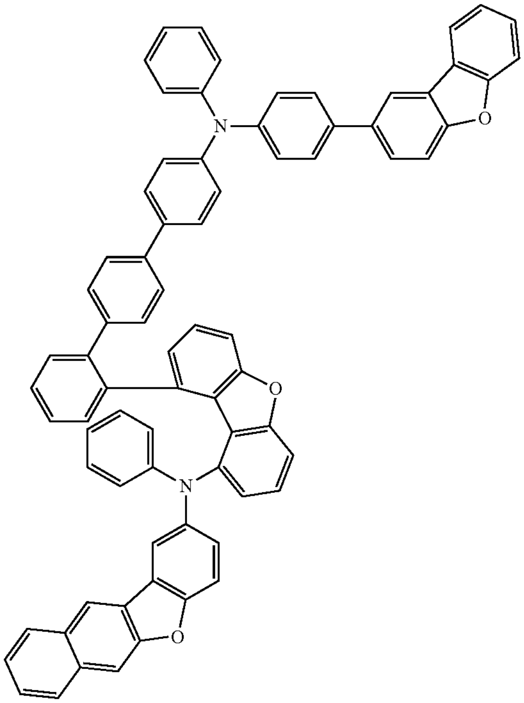
P-25
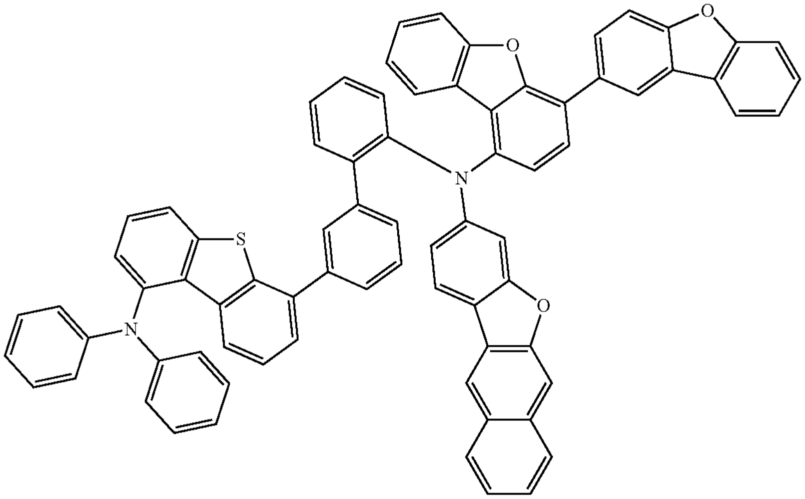

-continued
P-26
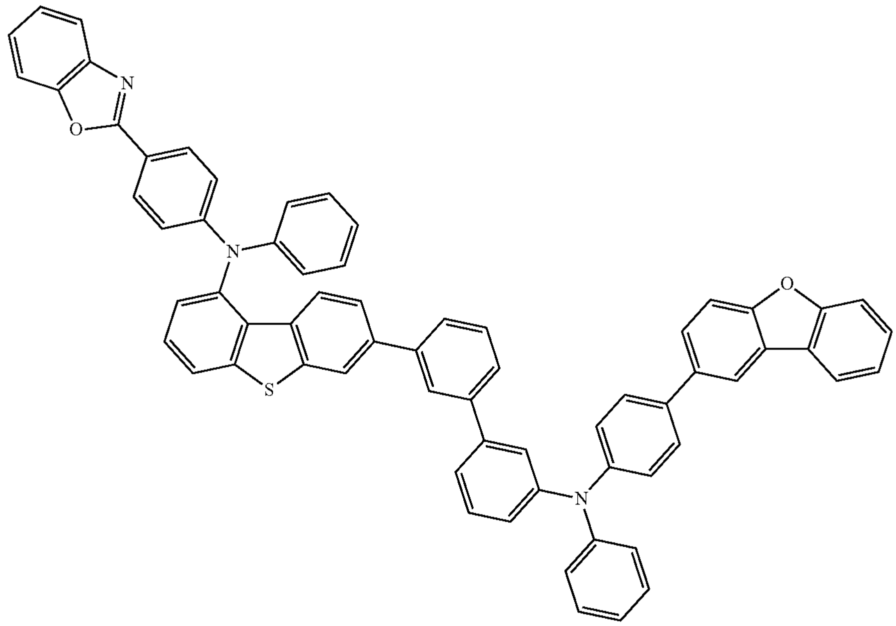
P-27
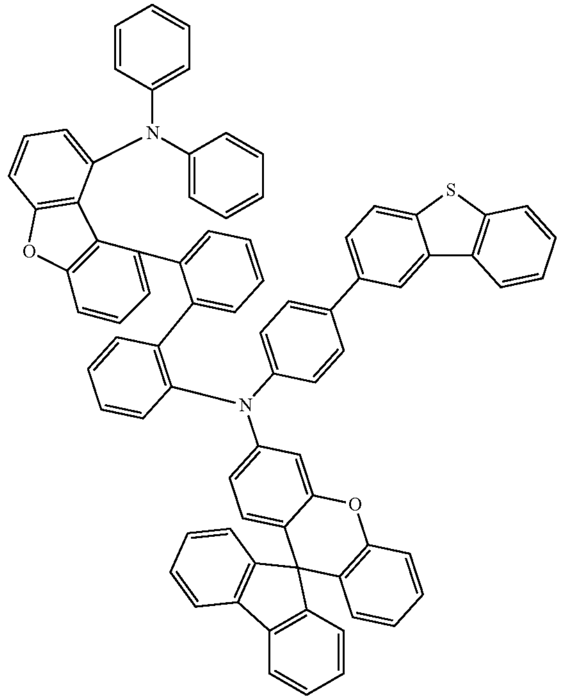
P-28
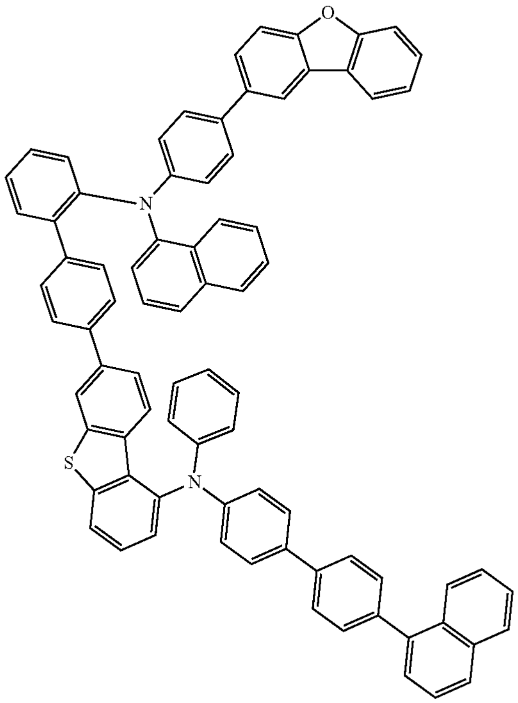

-continued
P-29
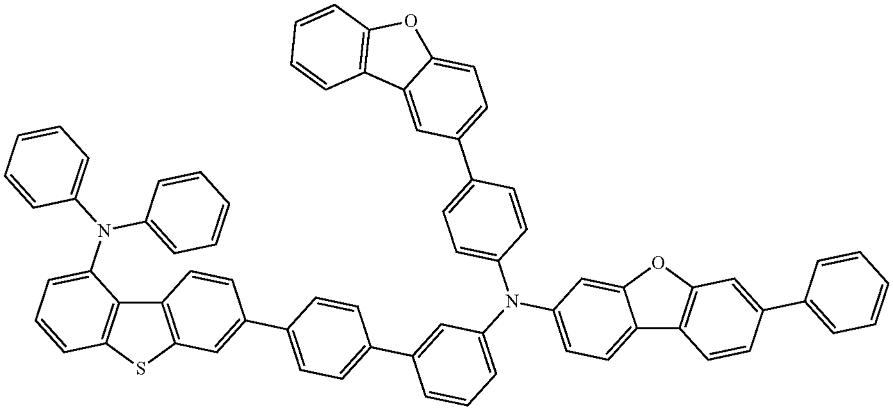
P-30
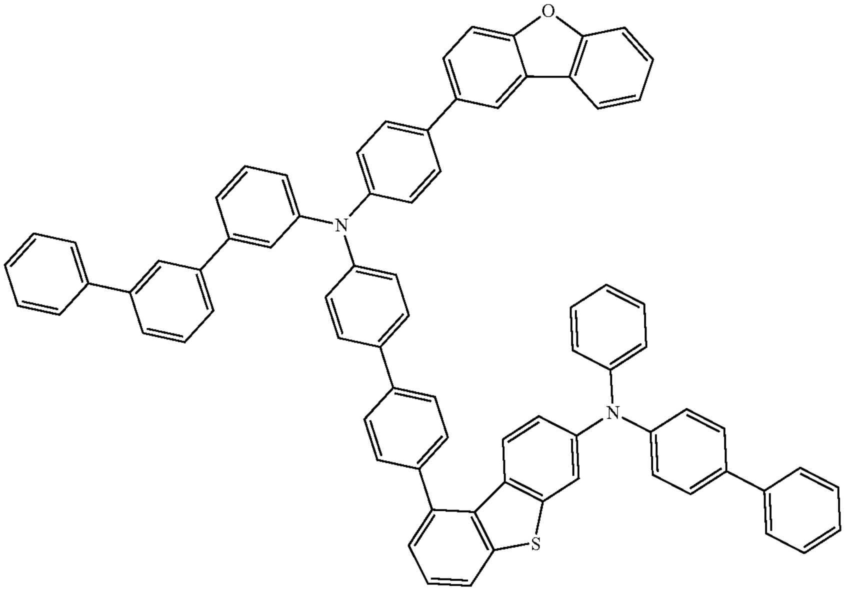
P-31
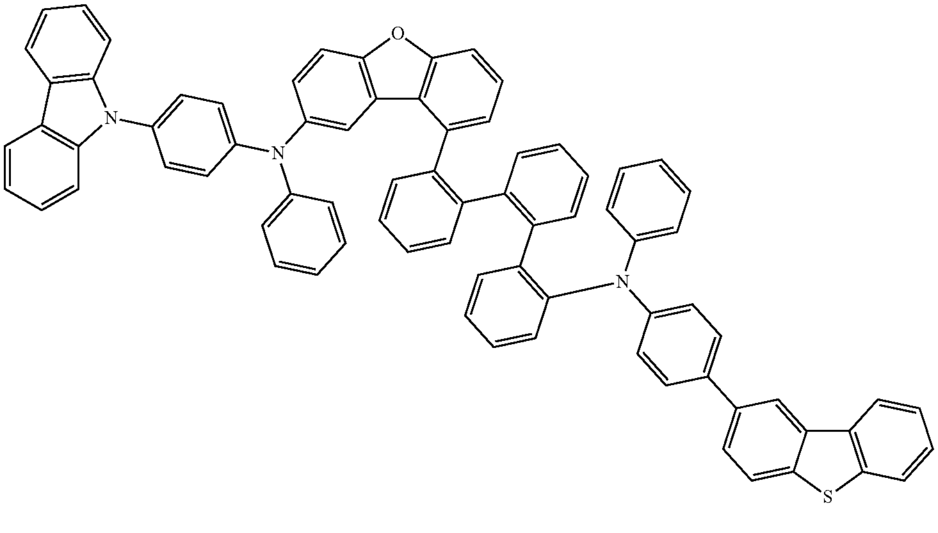

-continued
P-32
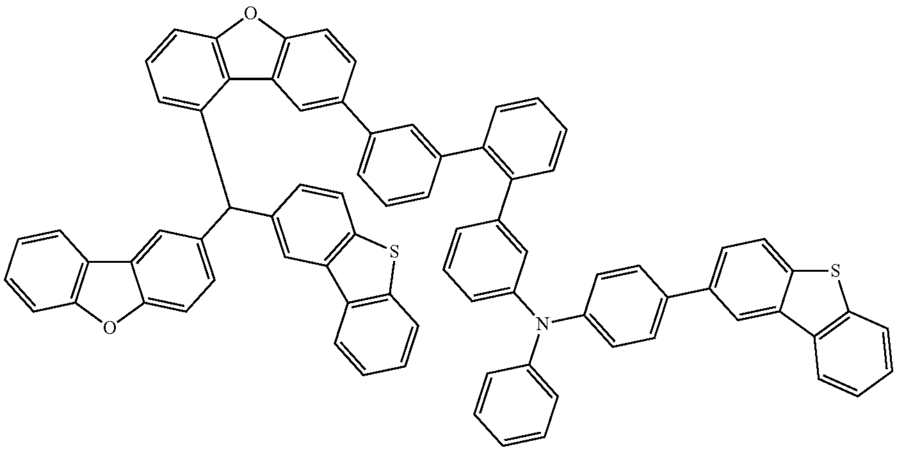
P-33
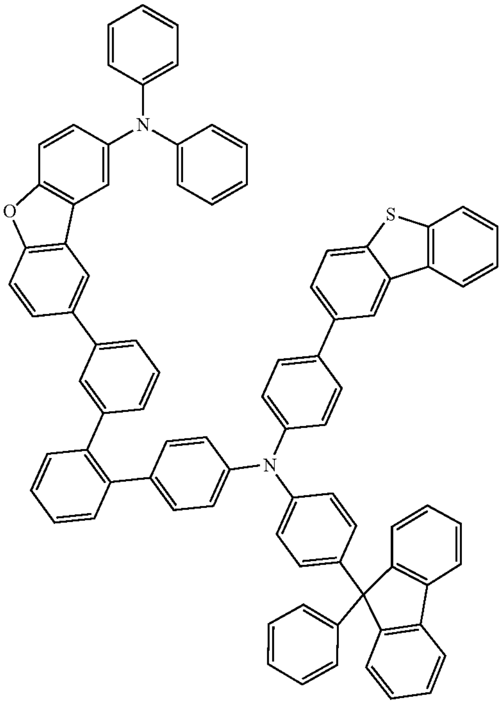
P-34
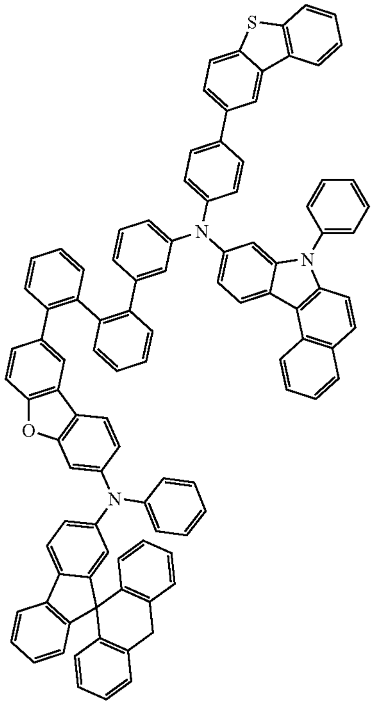
P-35
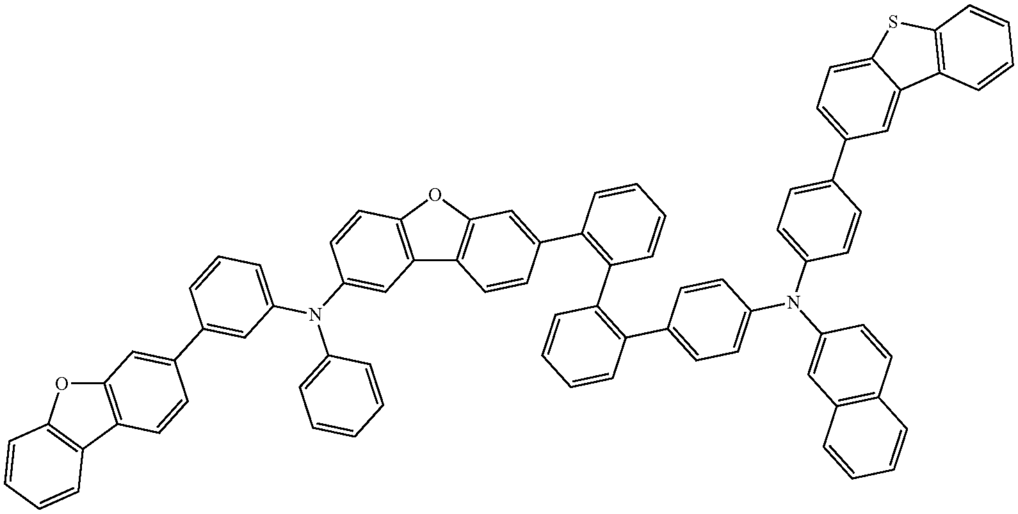

-continued
P-36
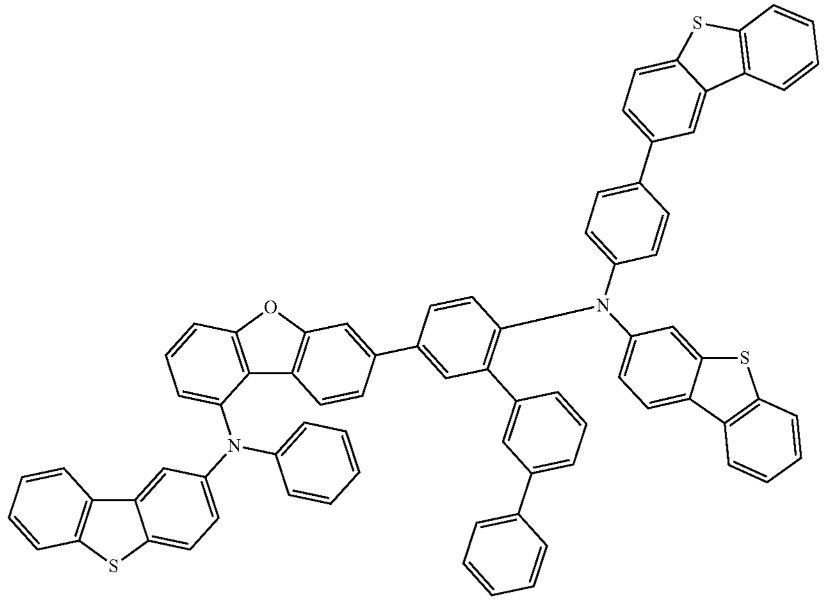
P-37
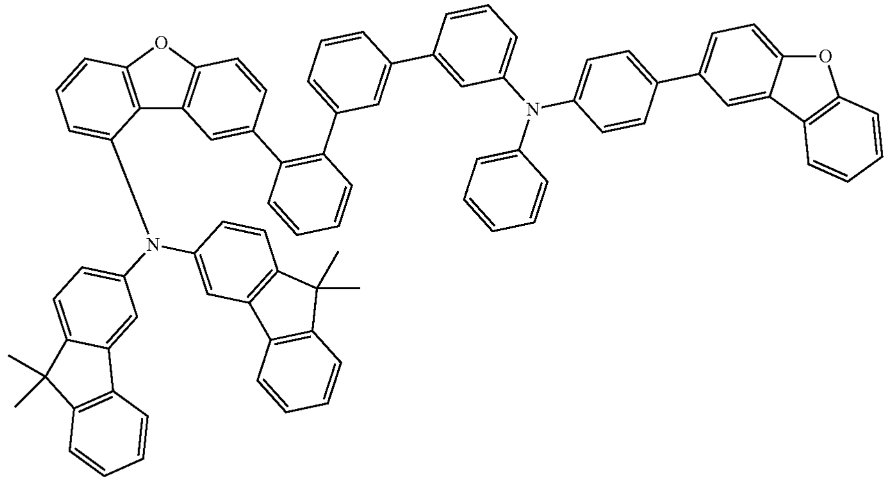

-continued
P-38
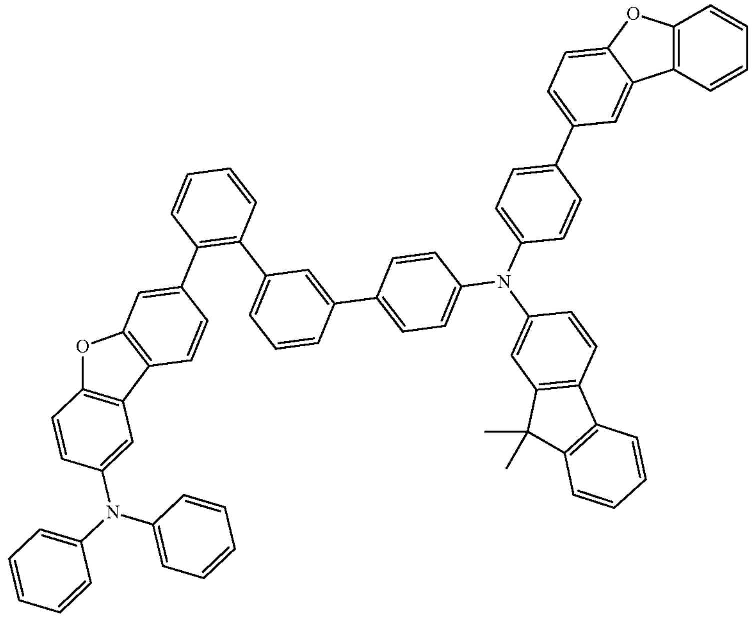
P-39
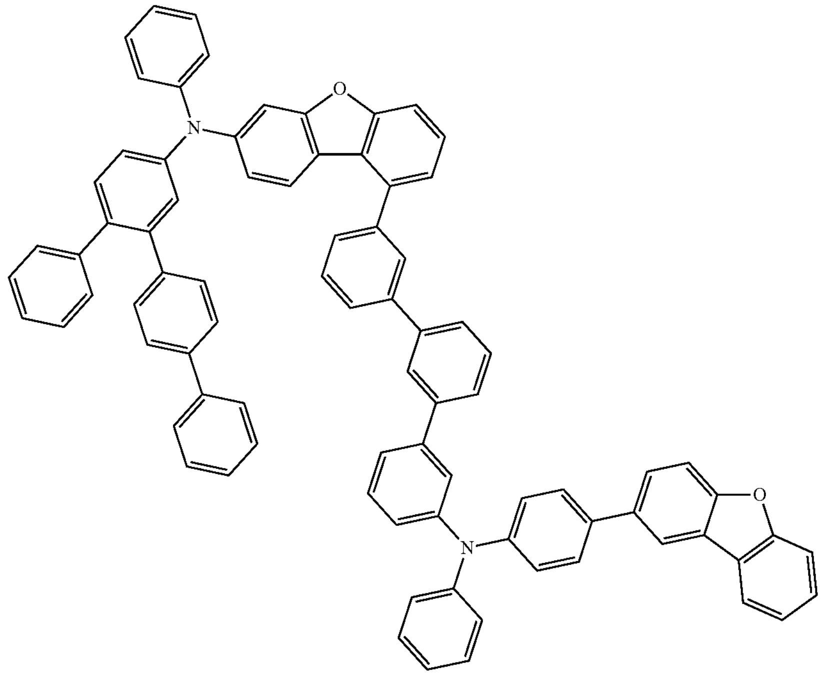

-continued
P-40
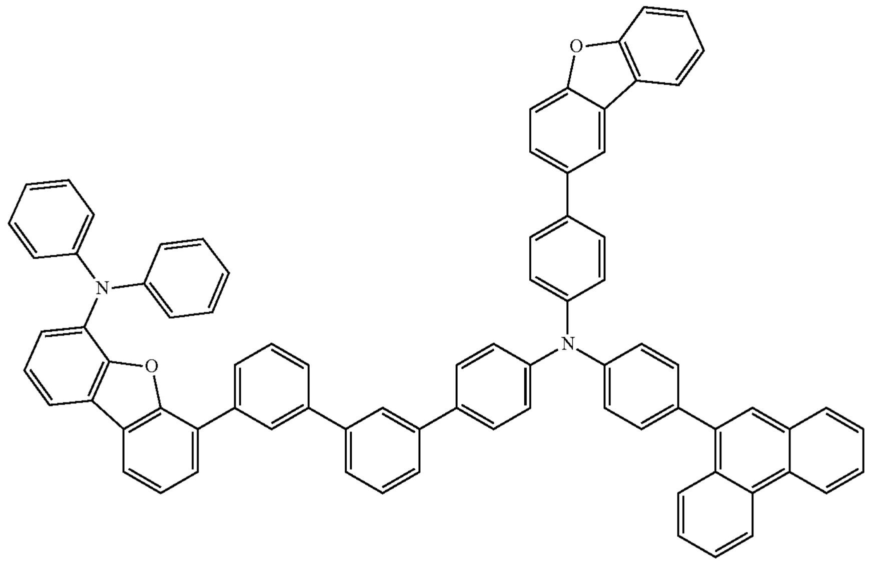
P-41
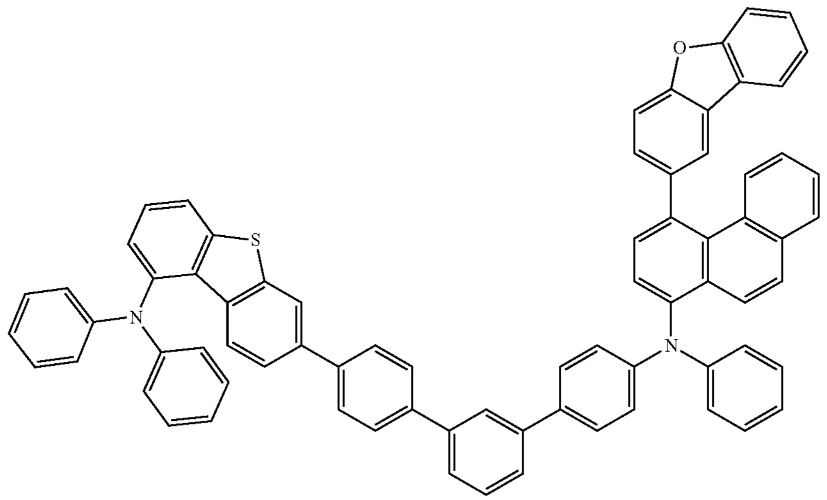

-continued
P-42
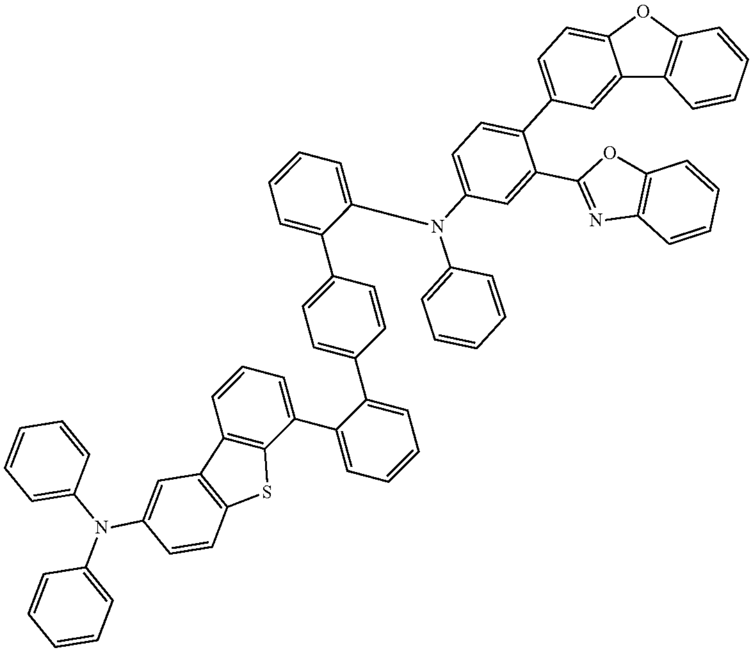
P-43
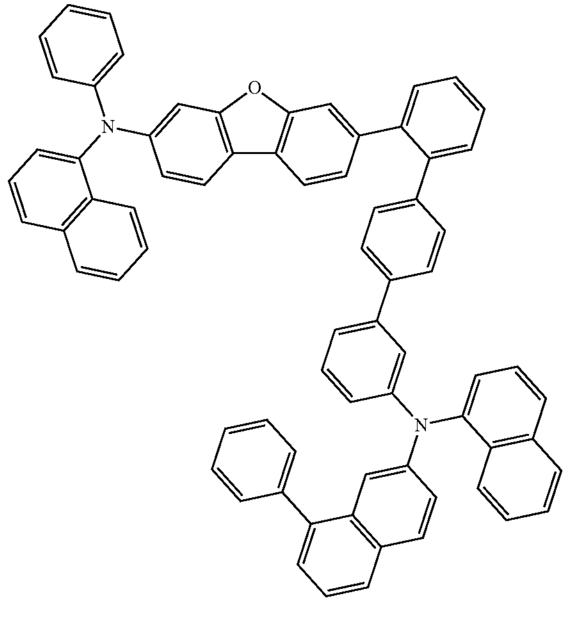
P-44
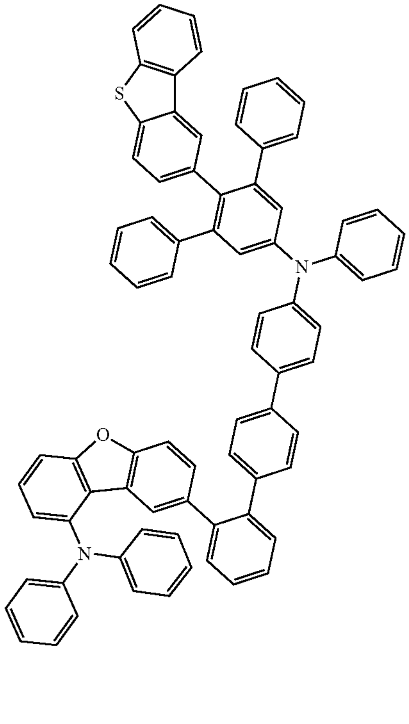

-continued
P-45
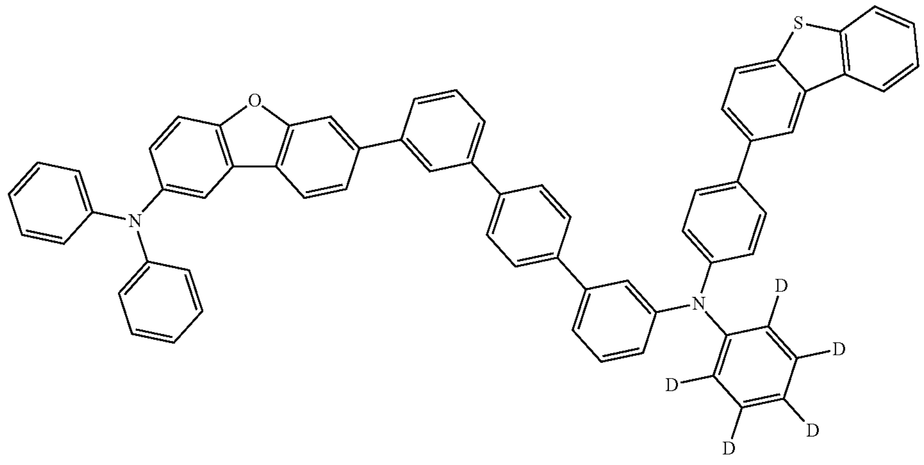
P-46
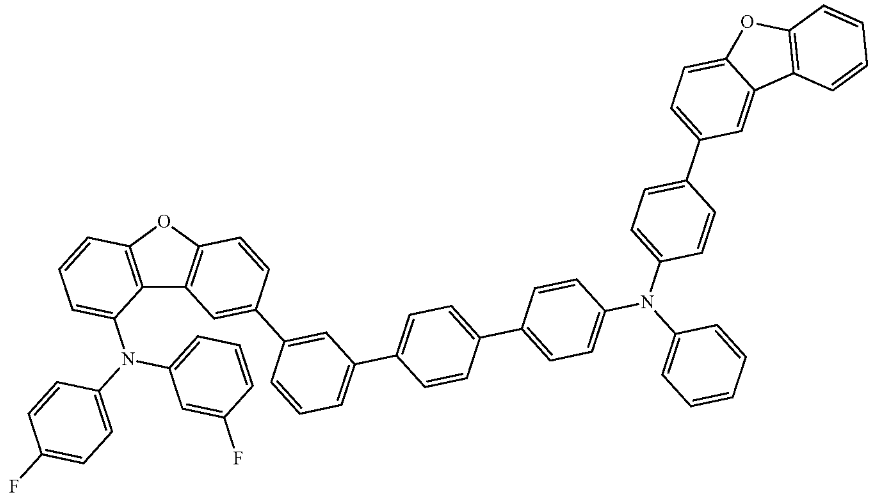
P-47
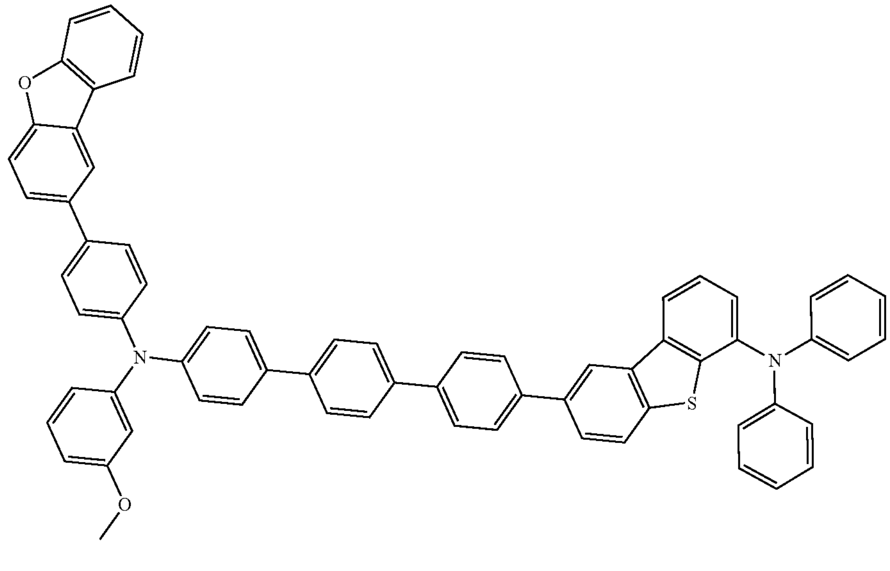

-continued
P-48
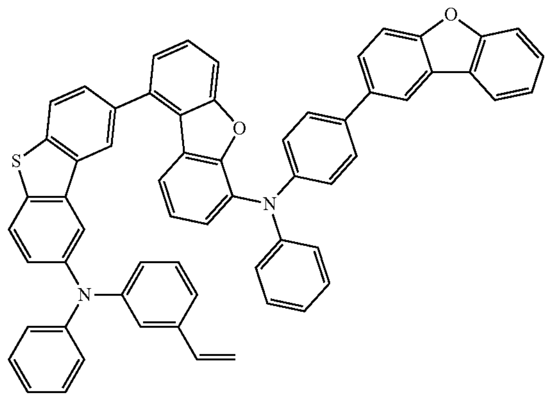
P-49
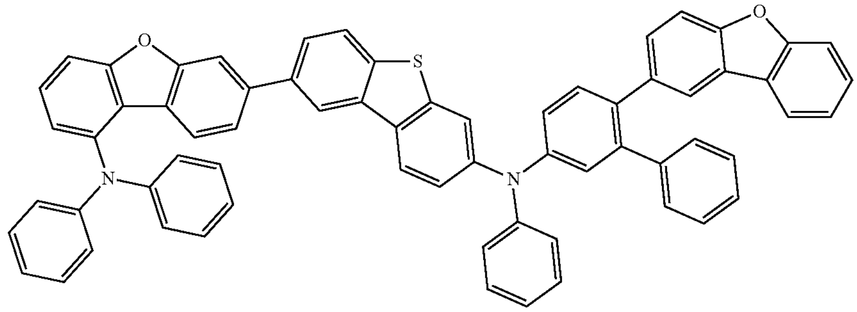
P-50
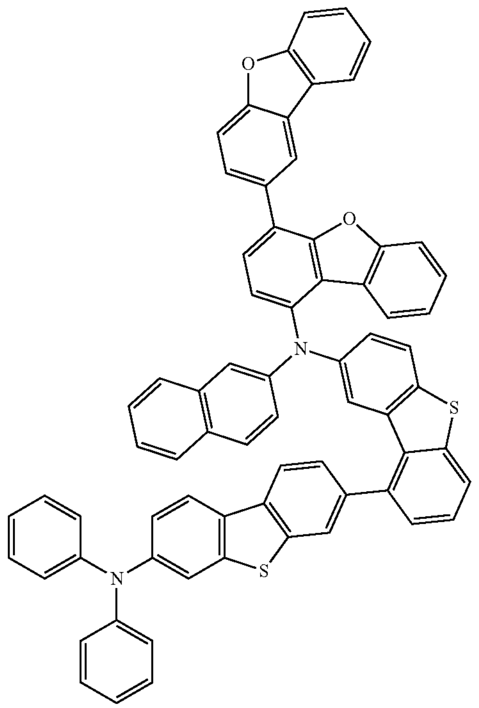
P-51
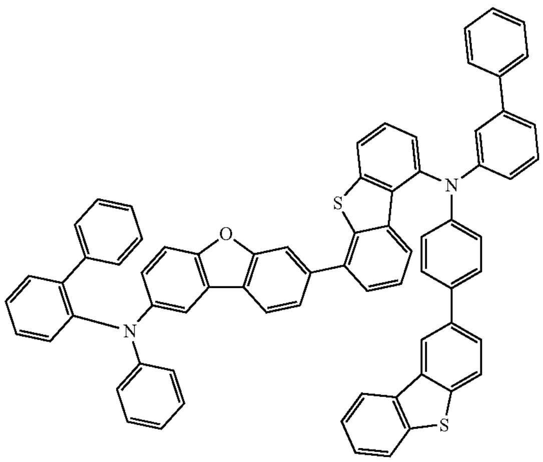

-continued
P-52
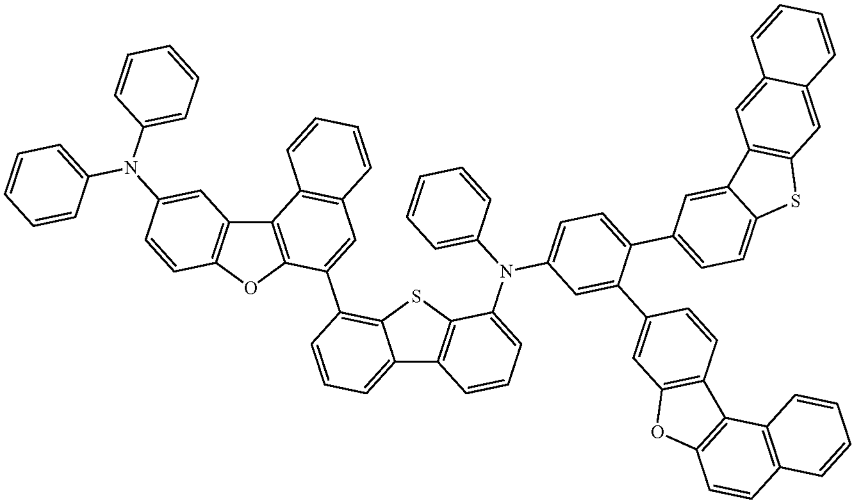
P-53
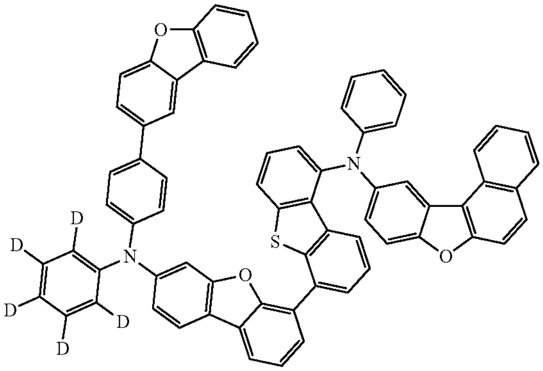
P-54
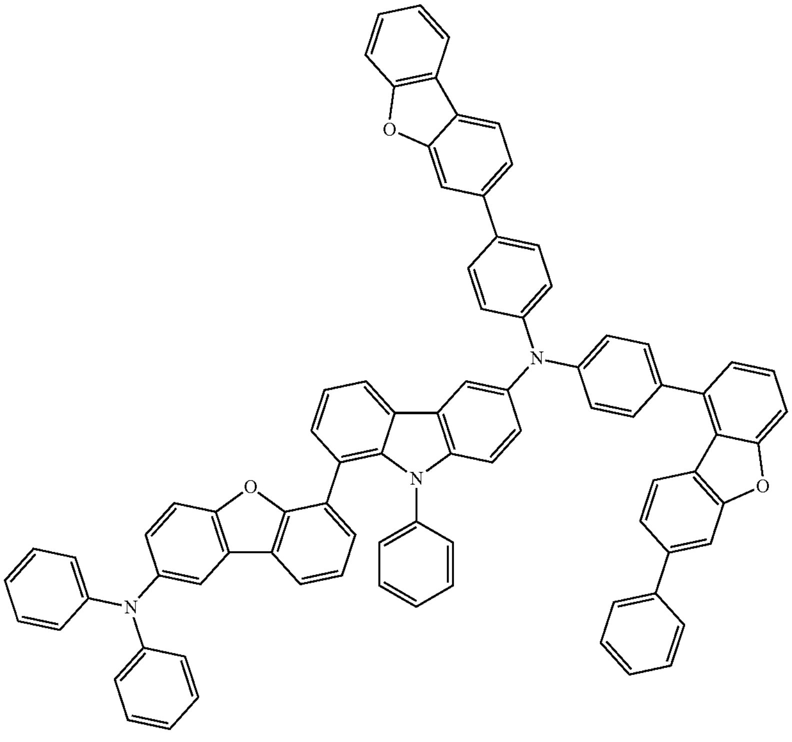

-continued
P-55
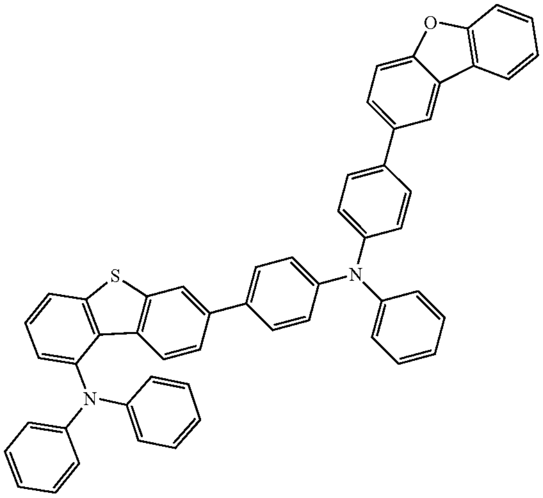
P-56
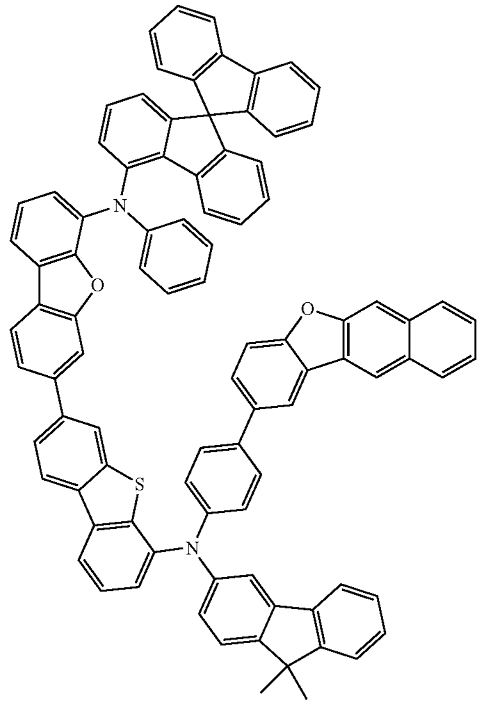
P-57
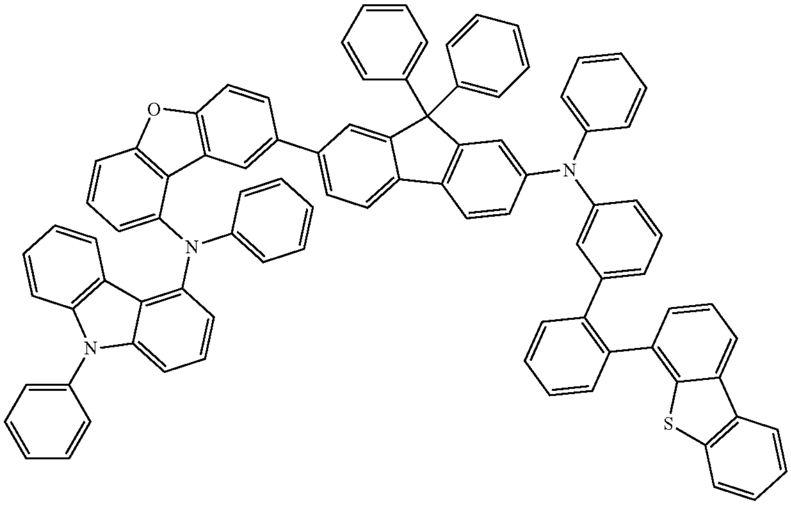

-continued
P-58
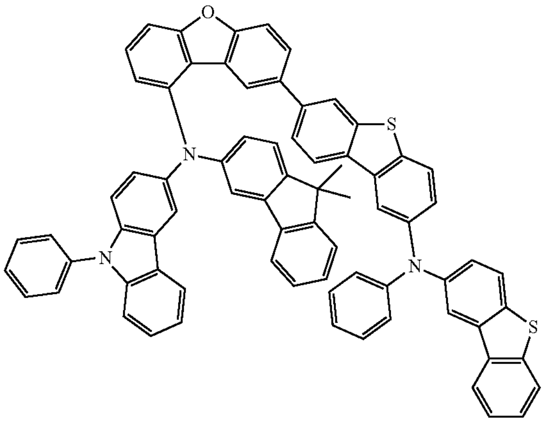
P-59
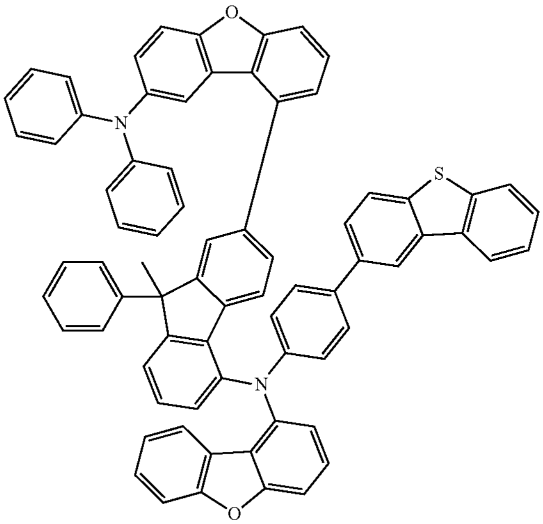
P-60
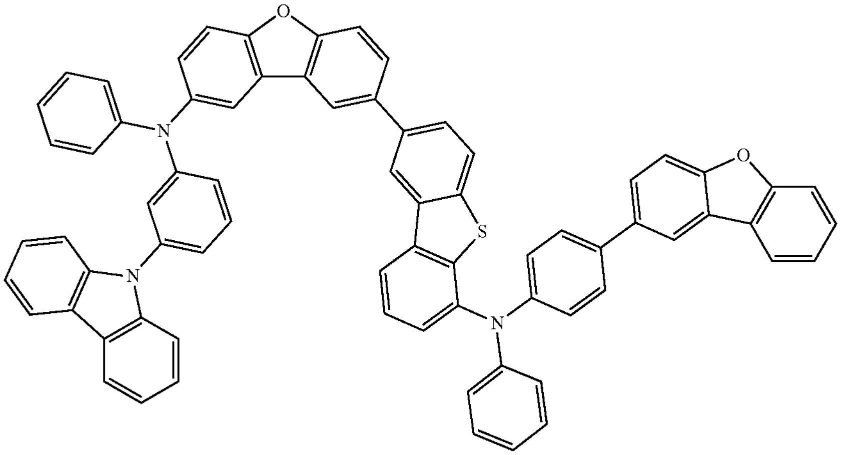
P-61
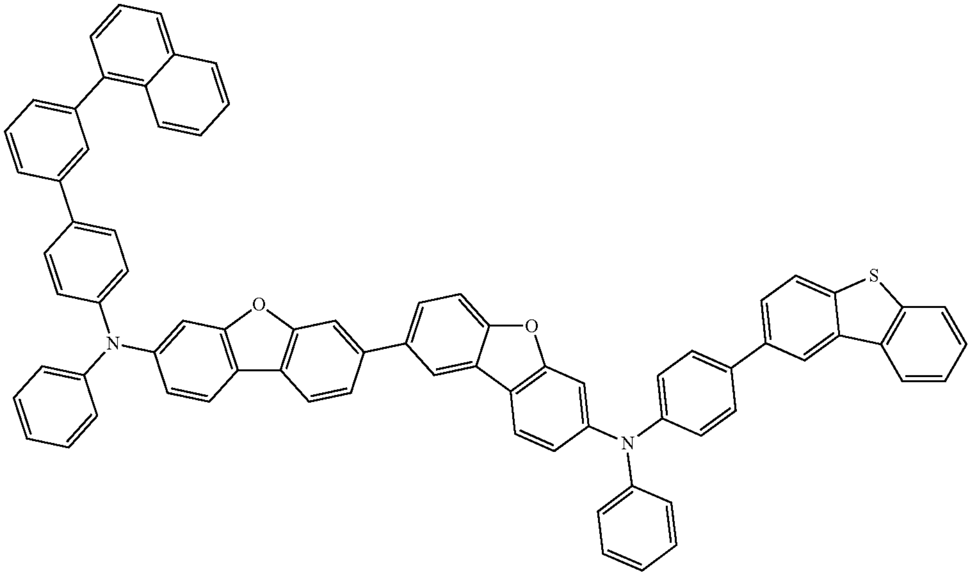

-continued
P-62
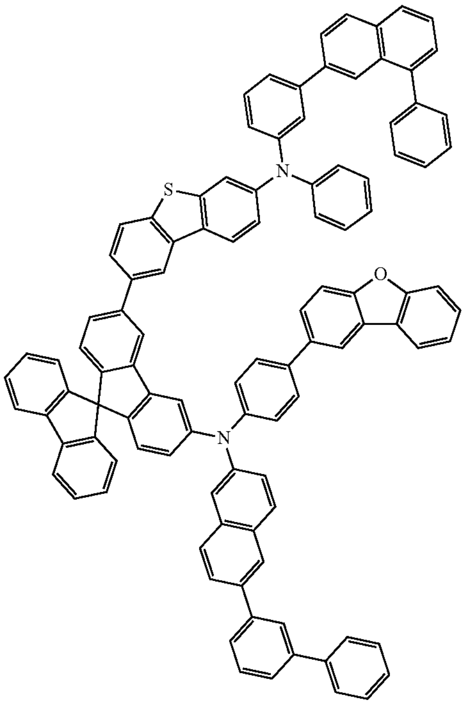
P-63
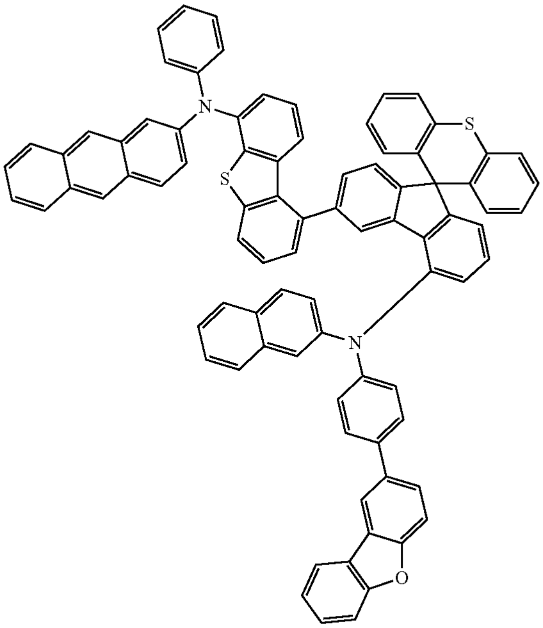
P-64
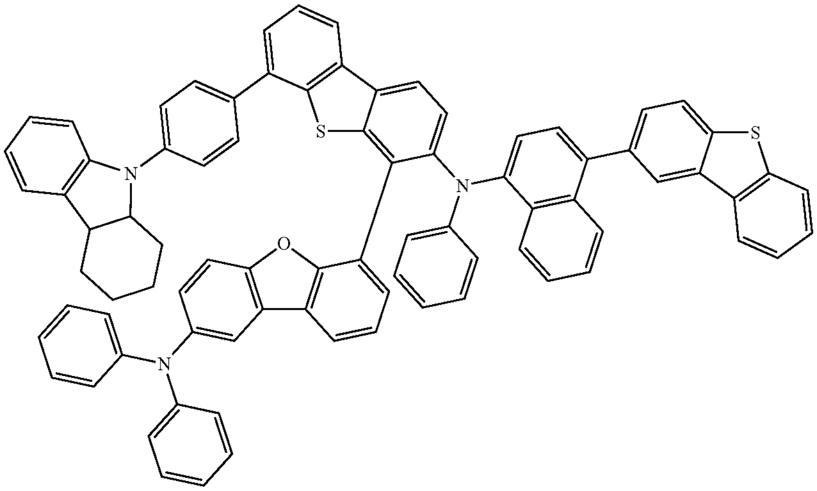

-continued
P-65
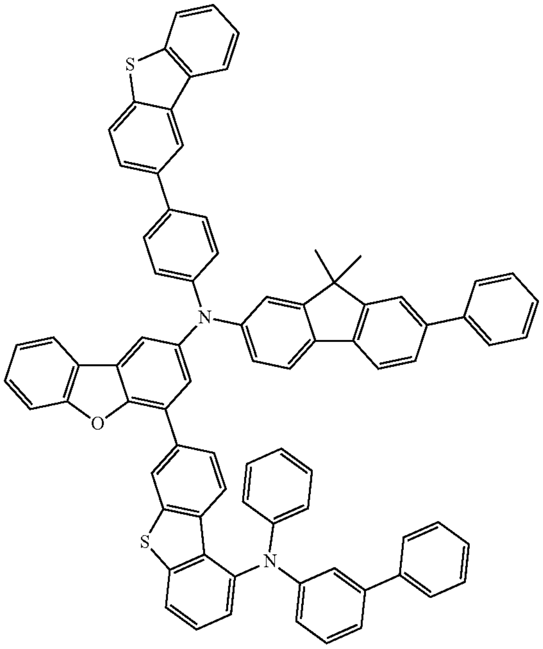
P-66
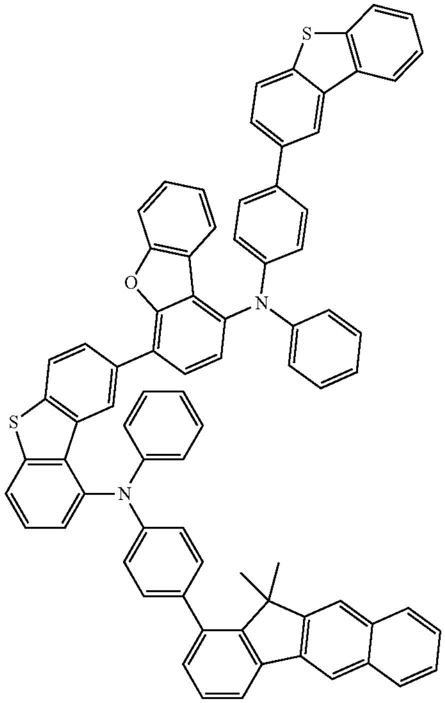
P-67
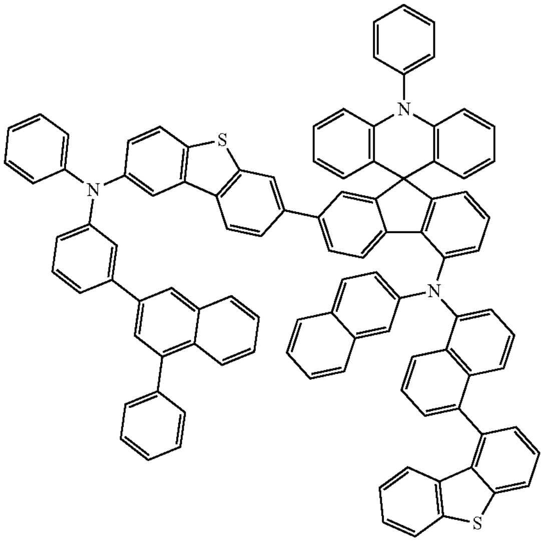
P-68
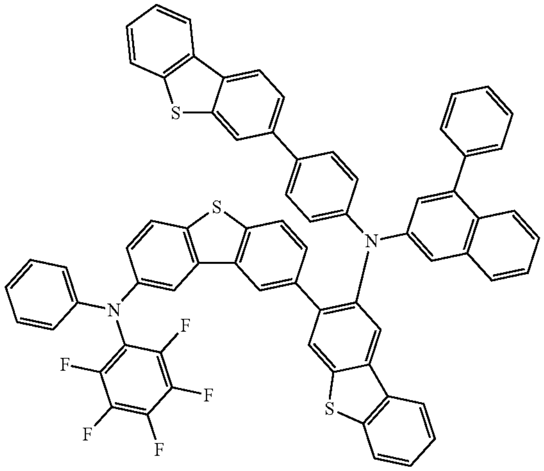

-continued
P-69
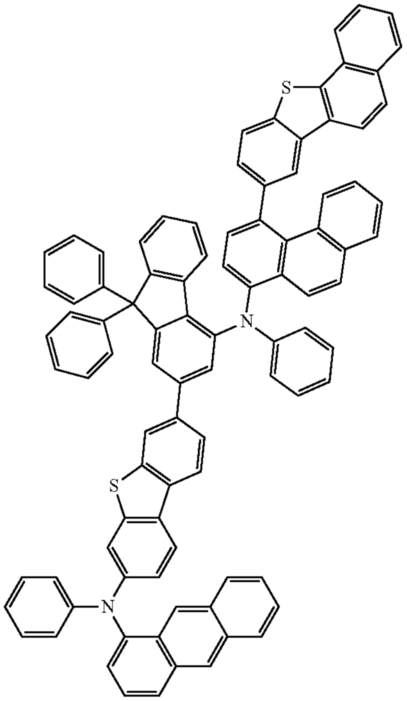
P-70
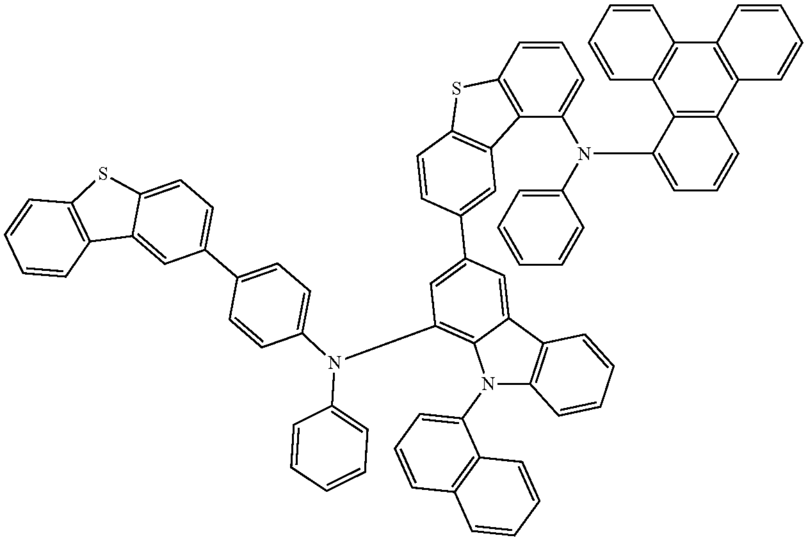

-continued
P-71
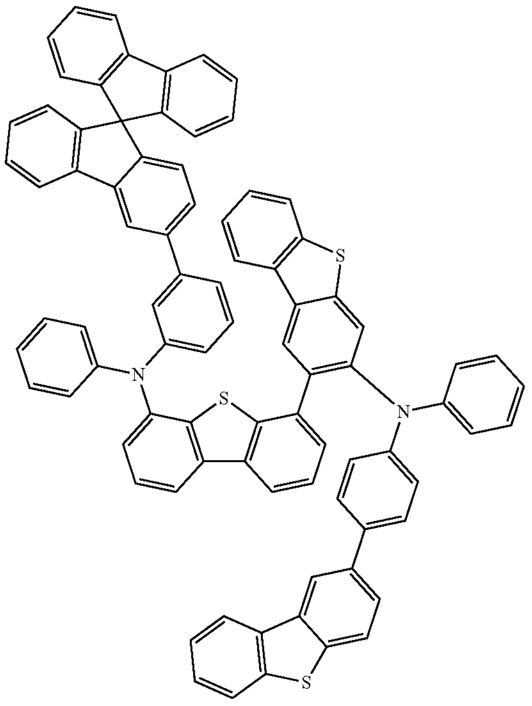
P-72
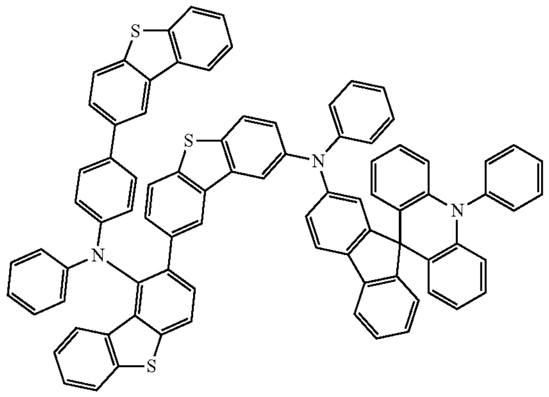
P-73
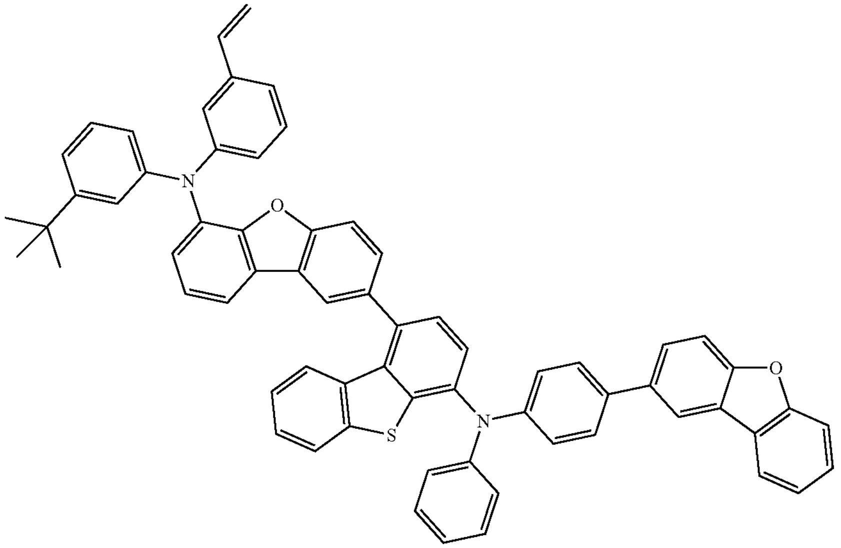

-continued
P-74
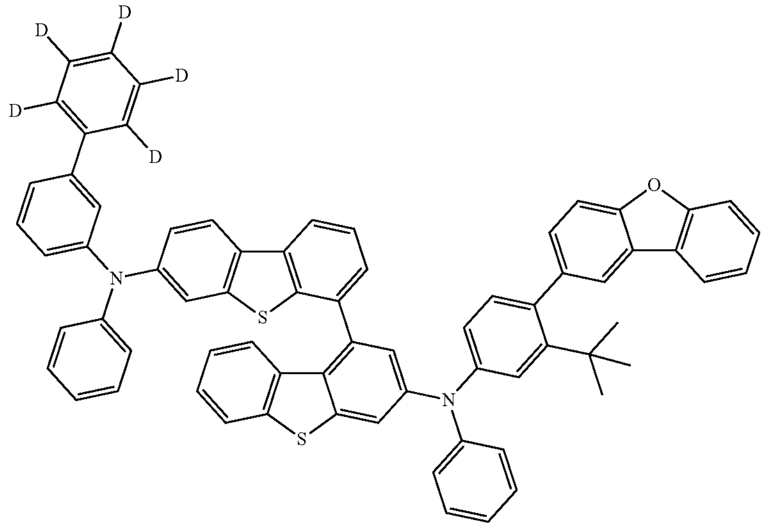
P-75
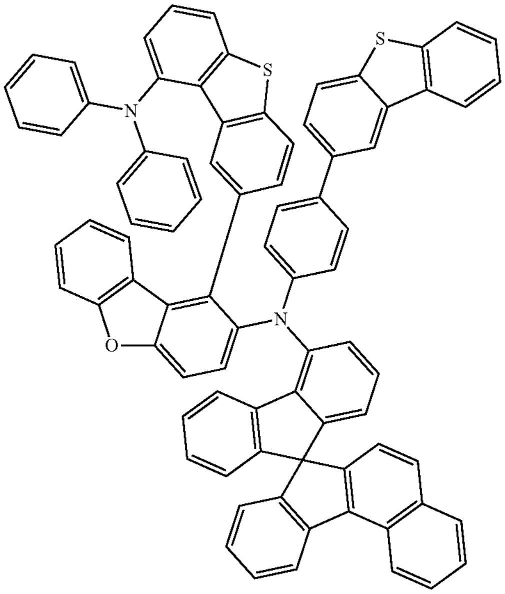

-continued
P-76
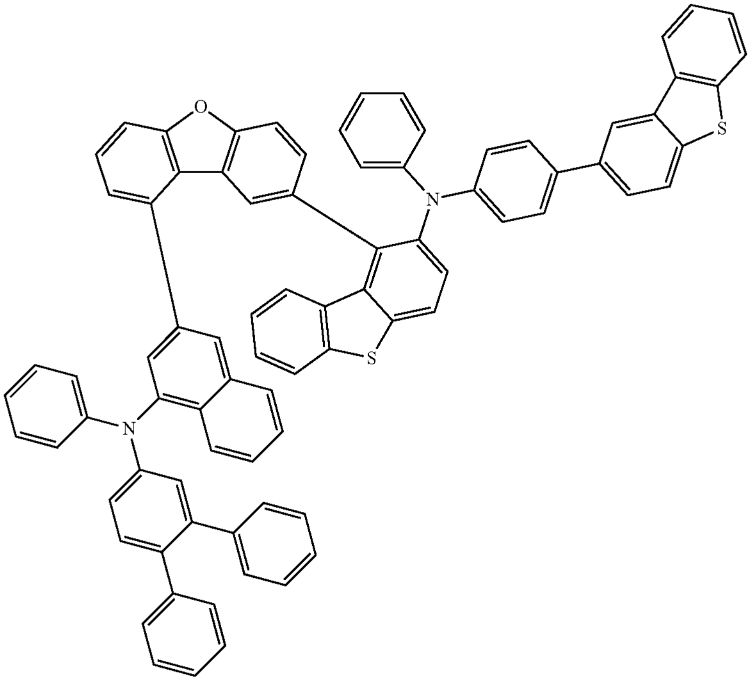
P-77
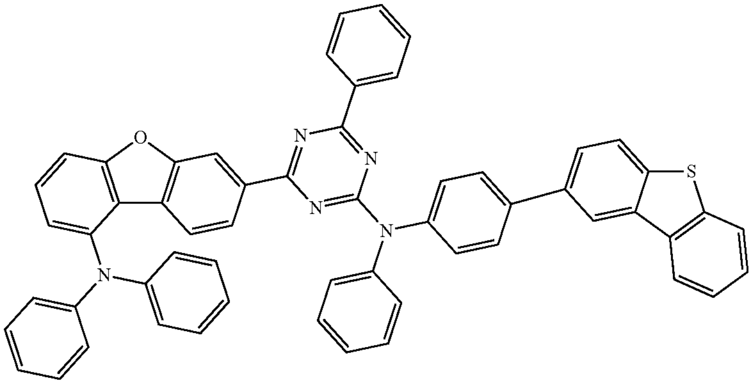
P-78
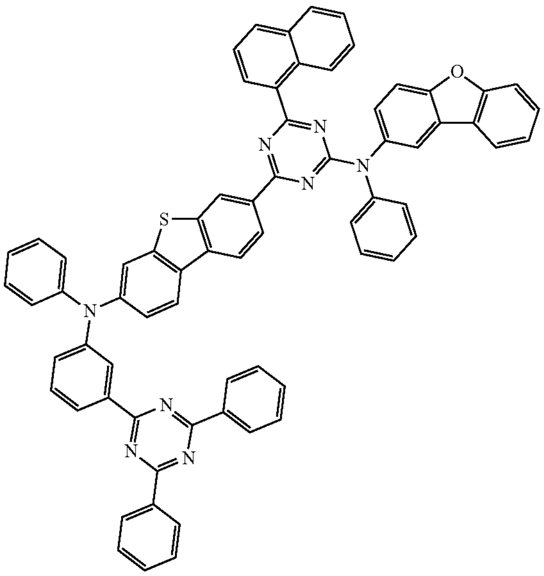
P-79
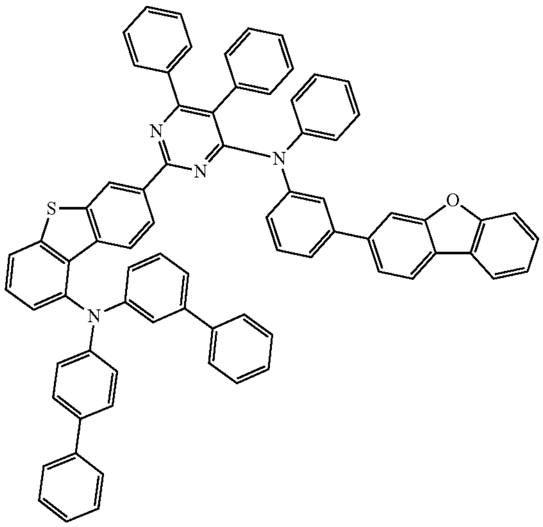

-continued
P-80
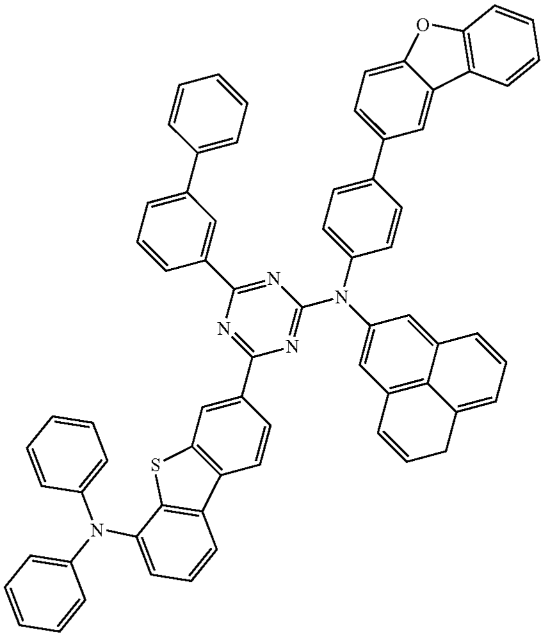
P-81
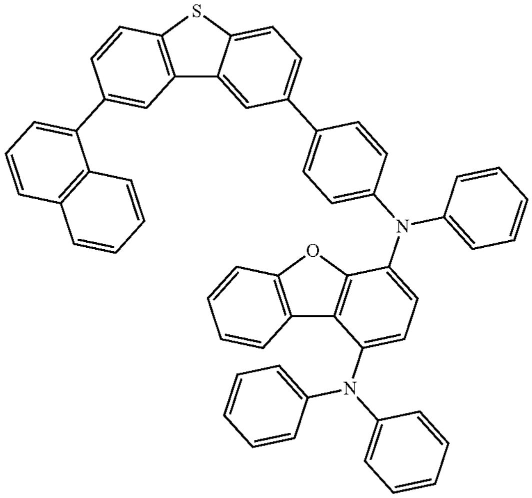
P-82
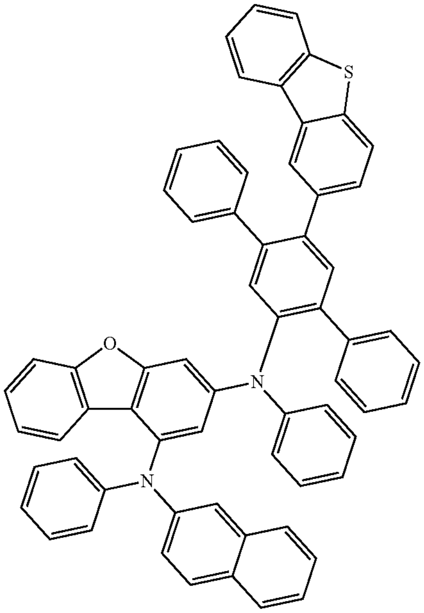
P-83
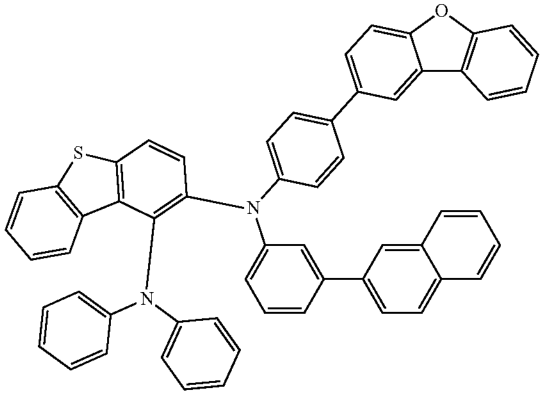

-continued
P-84
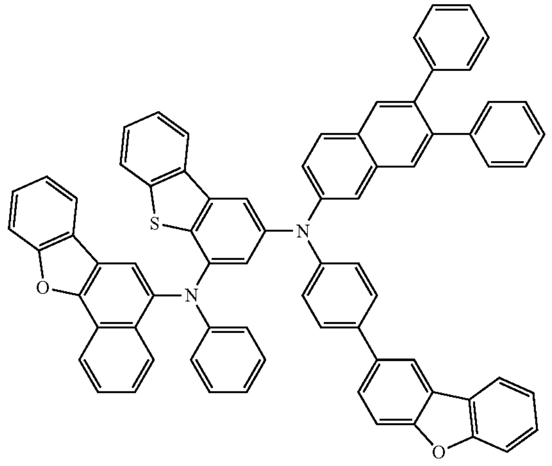
P-85
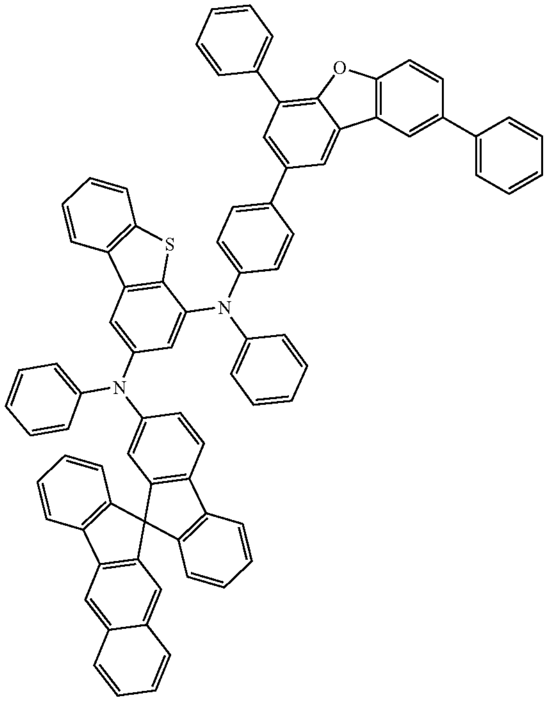
P-86
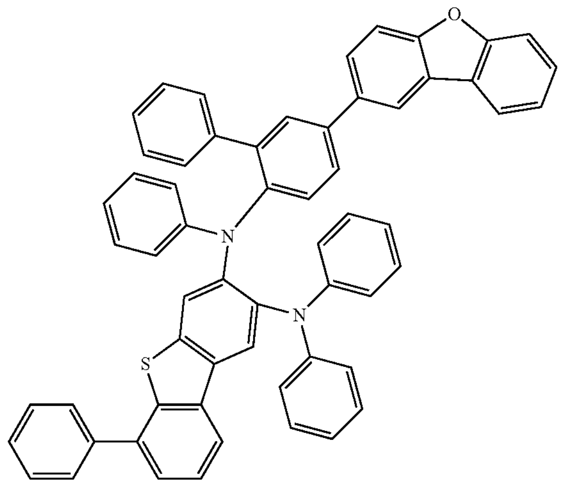
P-87
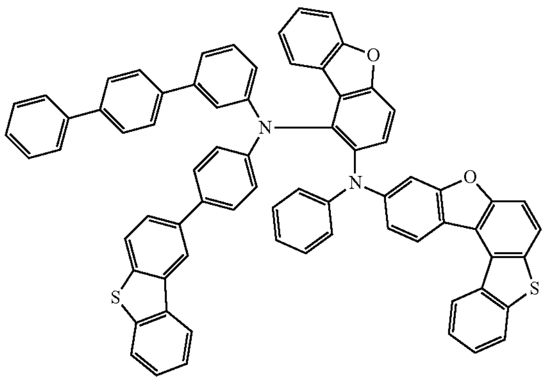

-continued
P-88
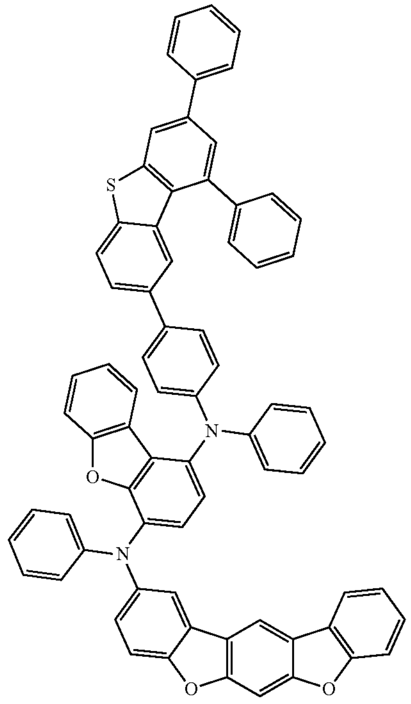
P-89
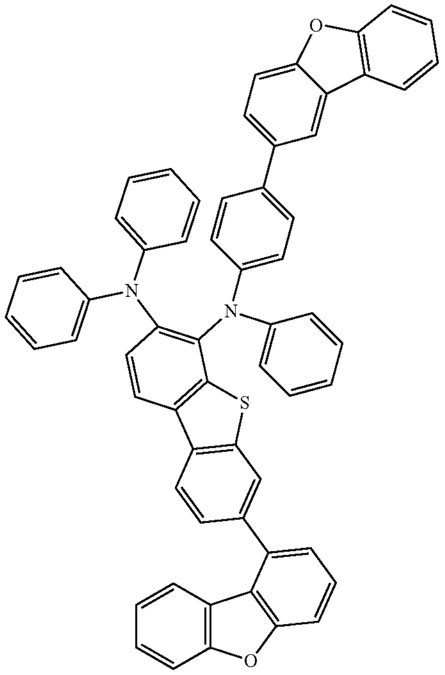
P-90
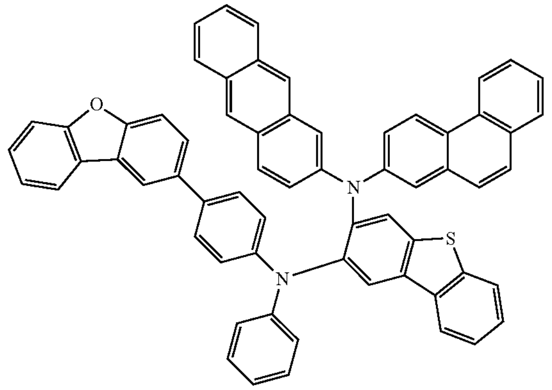
P-91
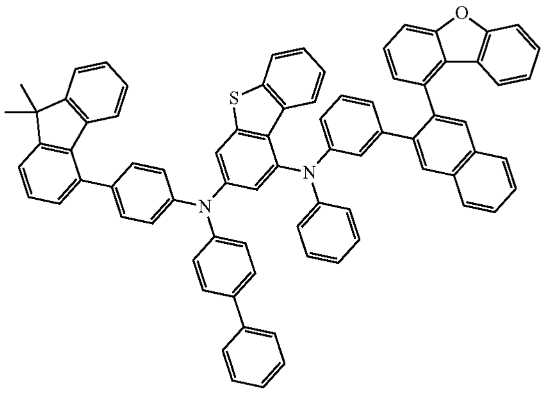

-continued
P-92
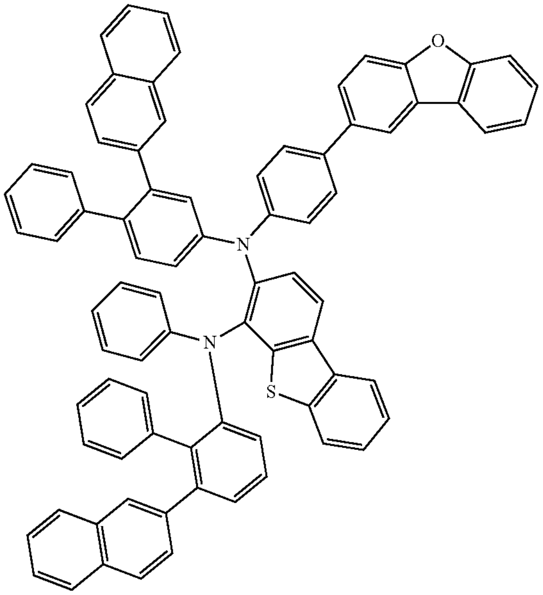
P-93
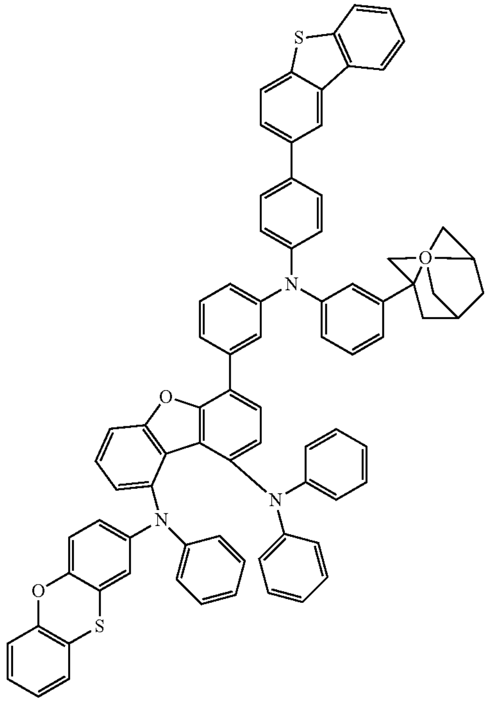
P-94
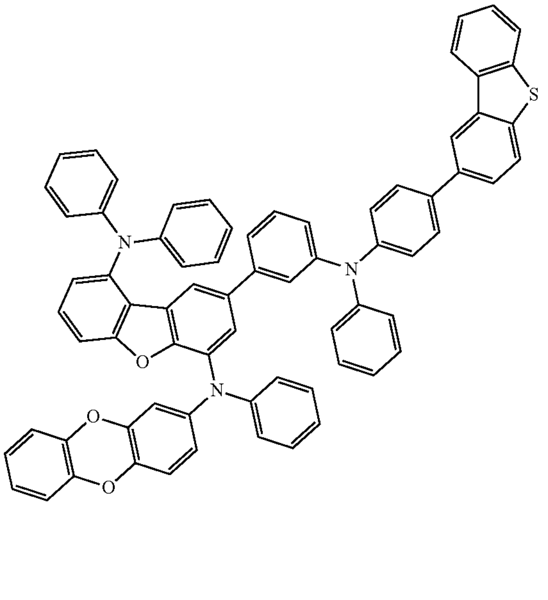
P-95
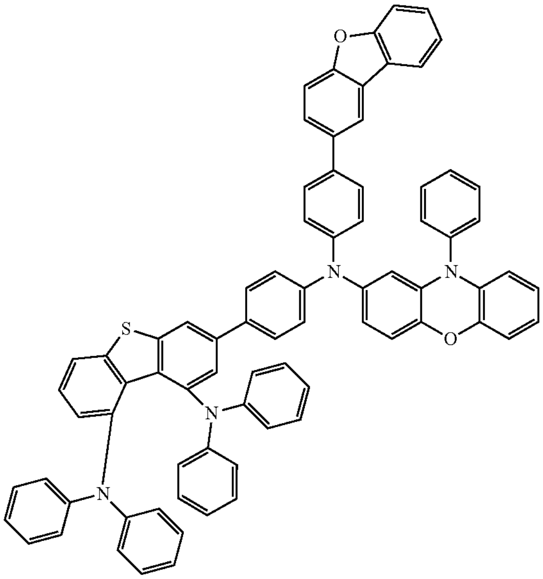

-continued
P-96
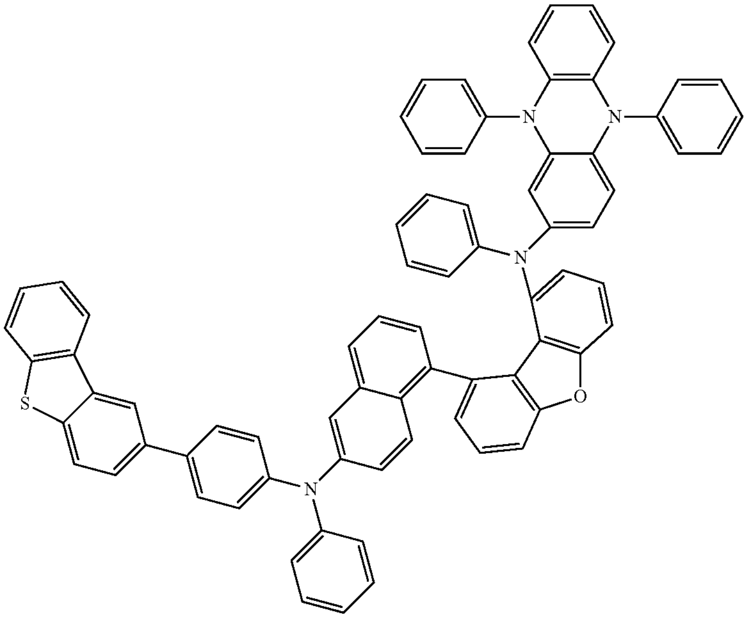
P-97
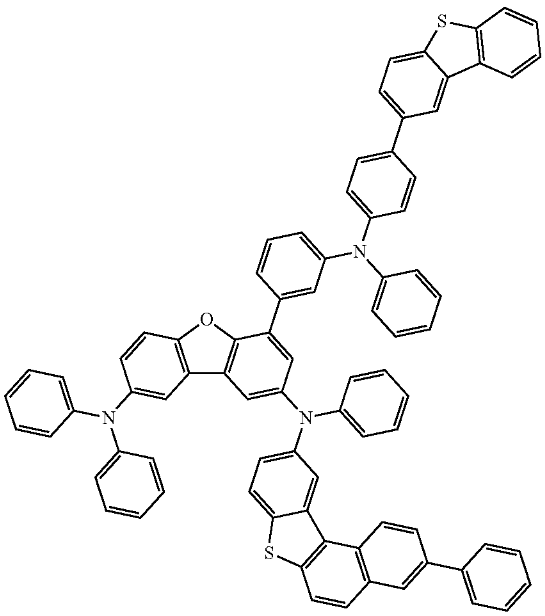
P-98
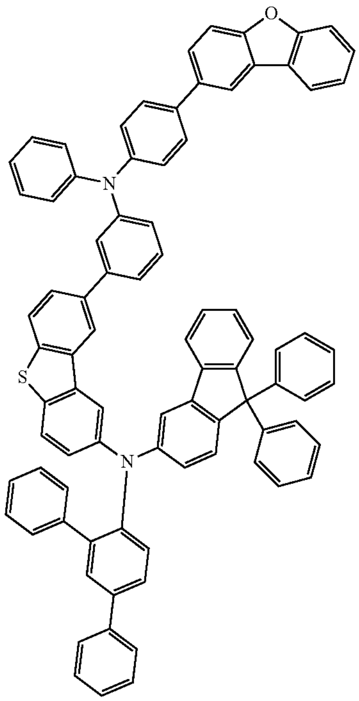

-continued
P-99
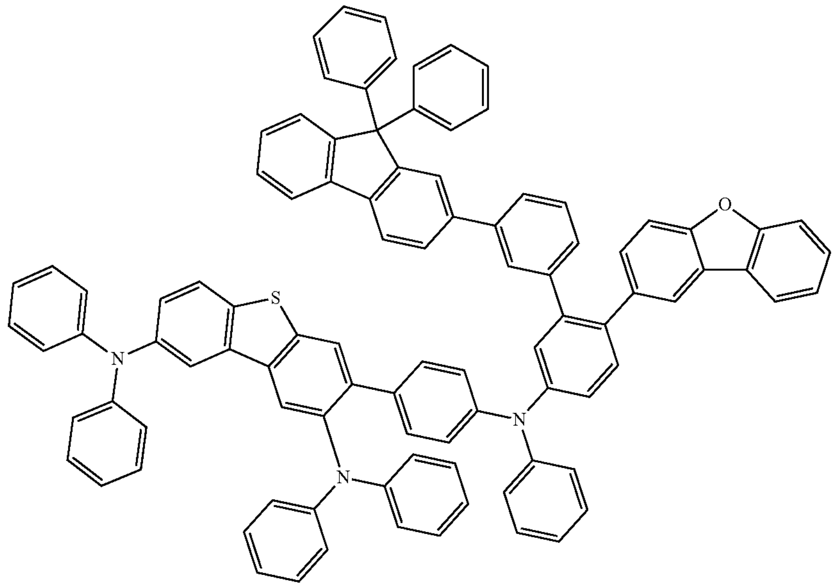
P-100
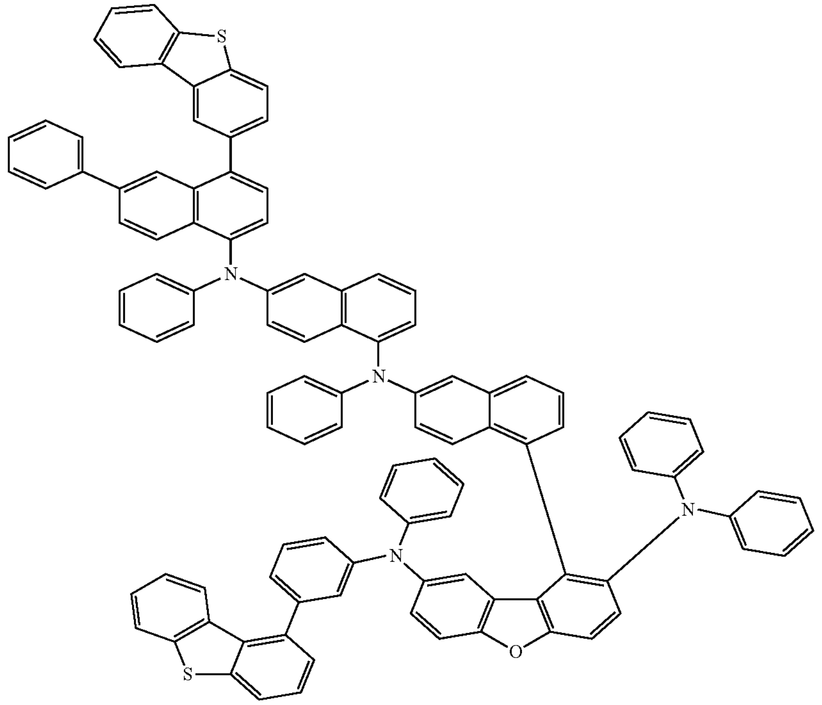

-continued
P-101
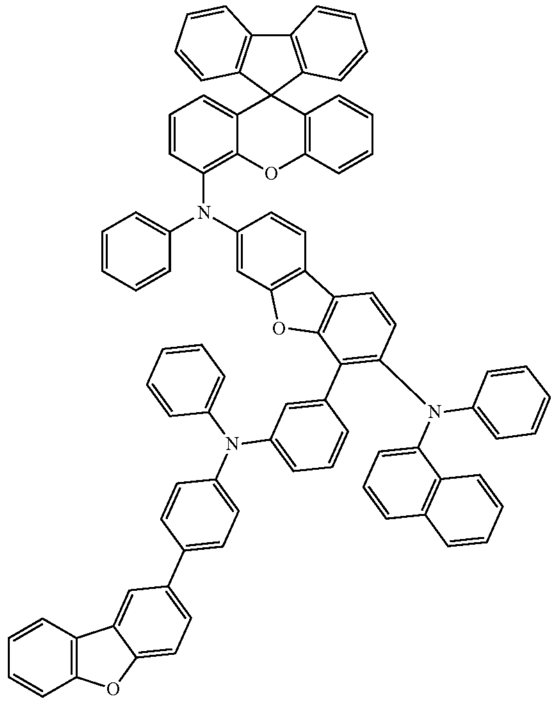
P-102
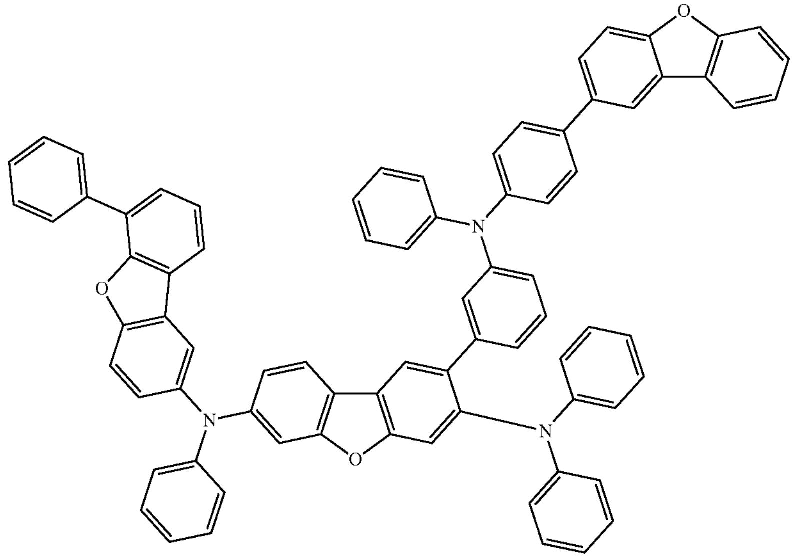

-continued
P-103
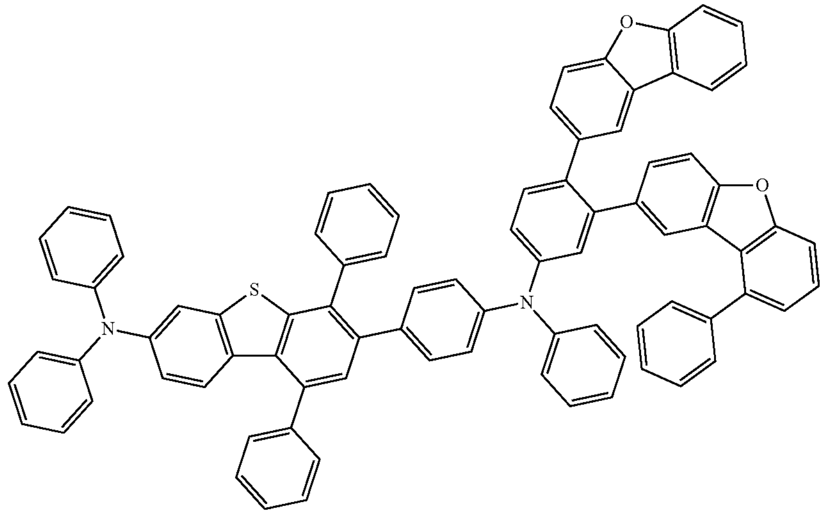
P-104
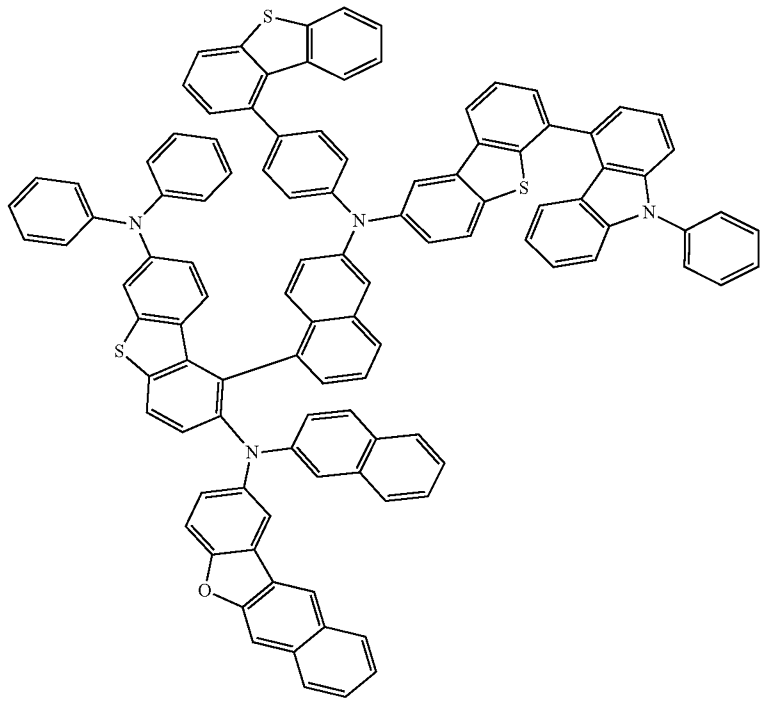

-continued
P-105
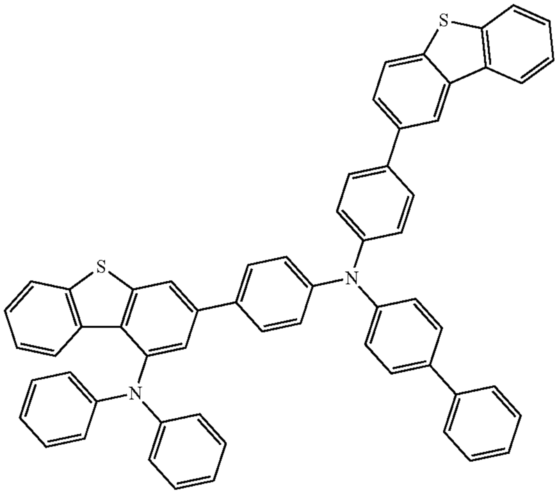
P-106
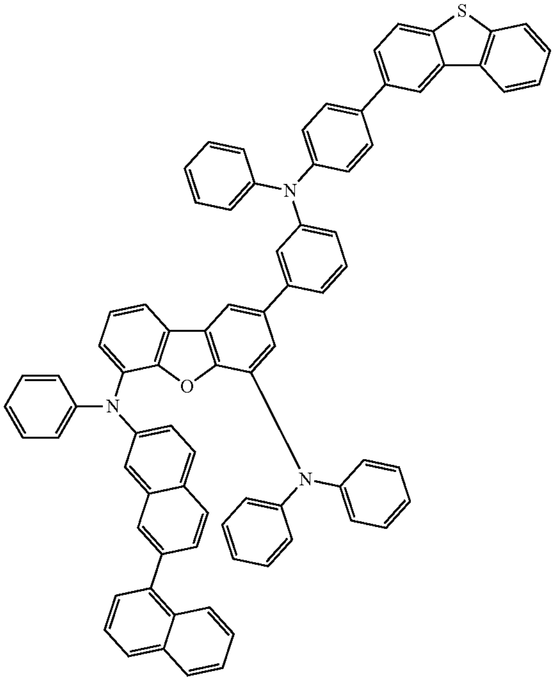
P-107
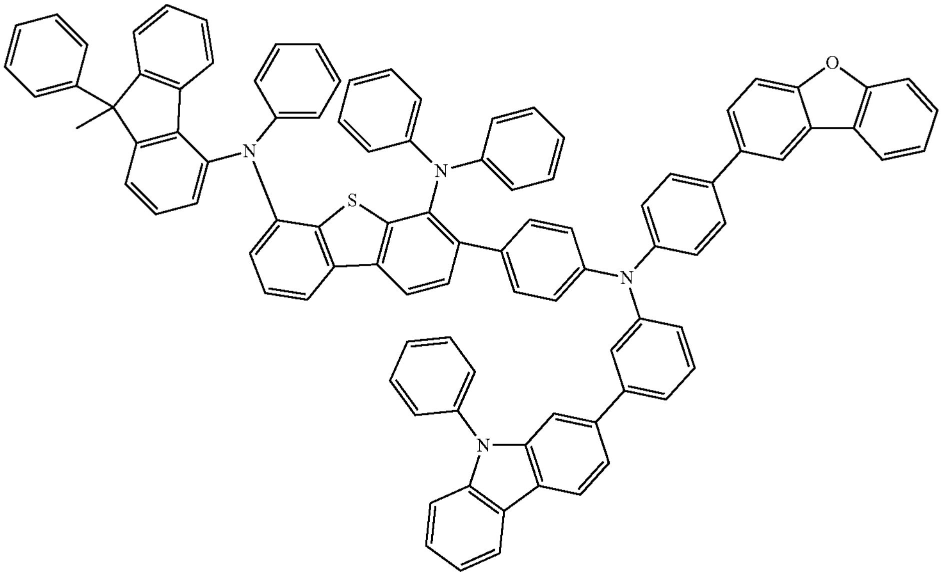

-continued
P-108
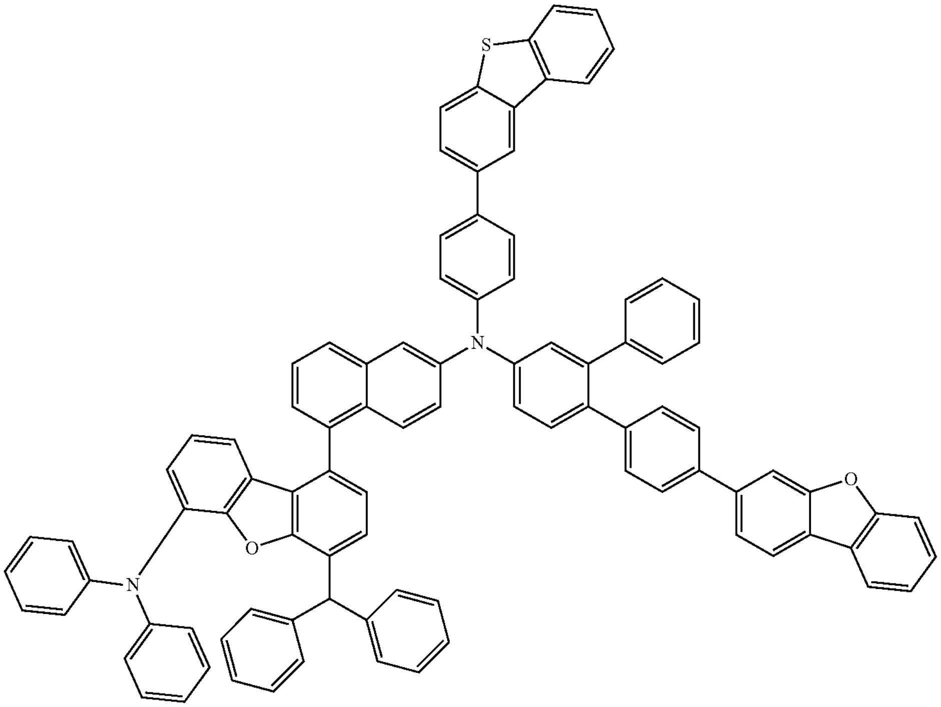
P-109
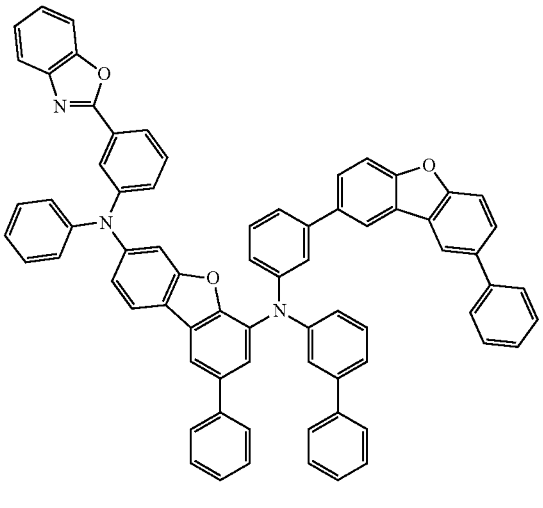
P-110
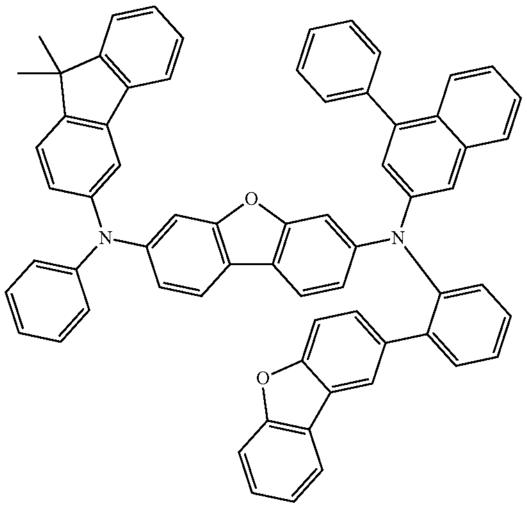

-continued
P-111
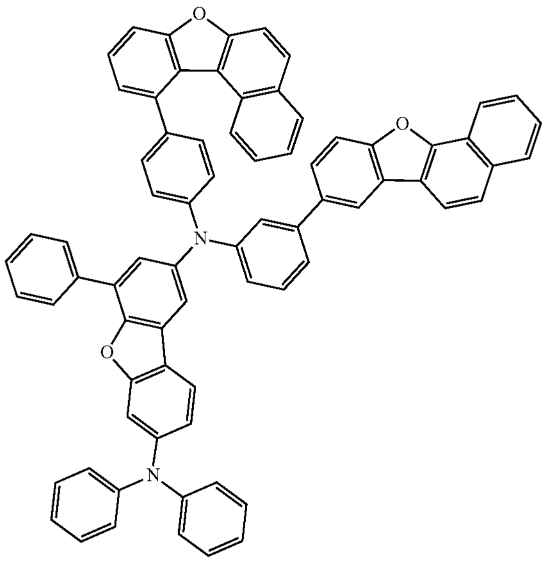
P-112
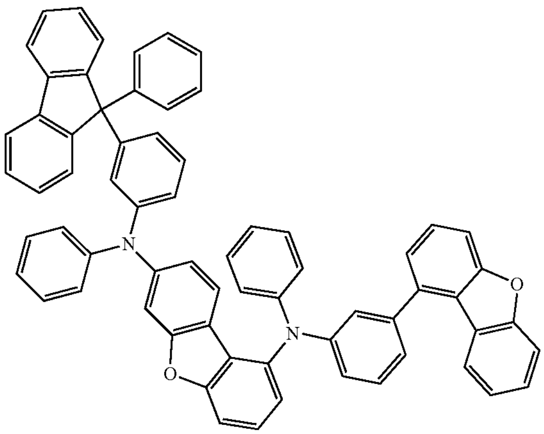
P-113
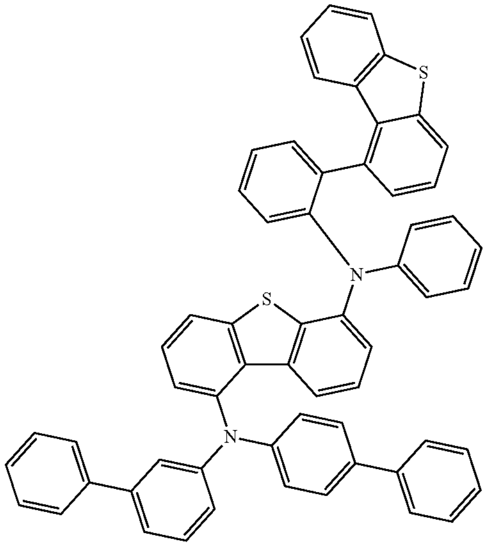
P-114
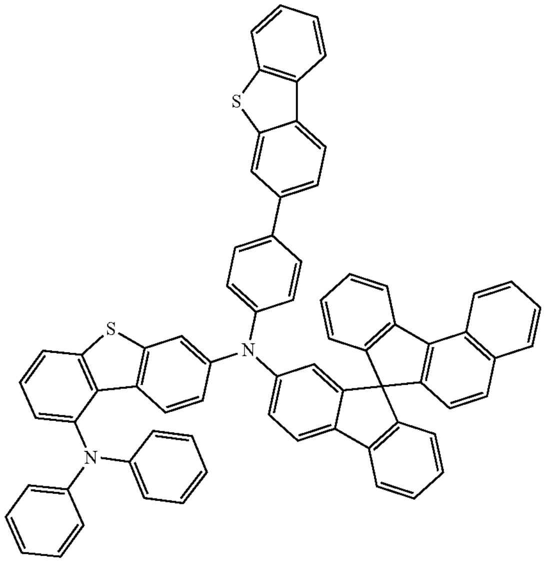
P-115
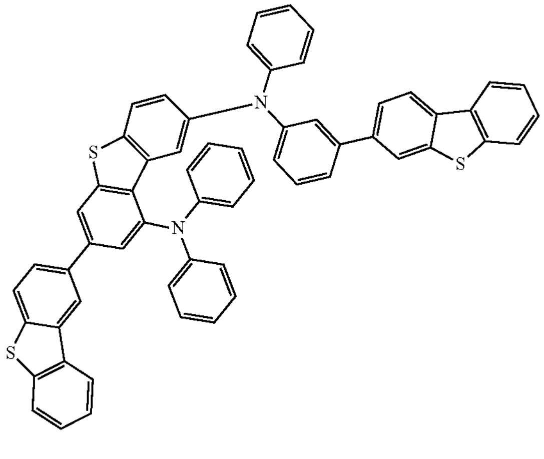

-continued
P-116
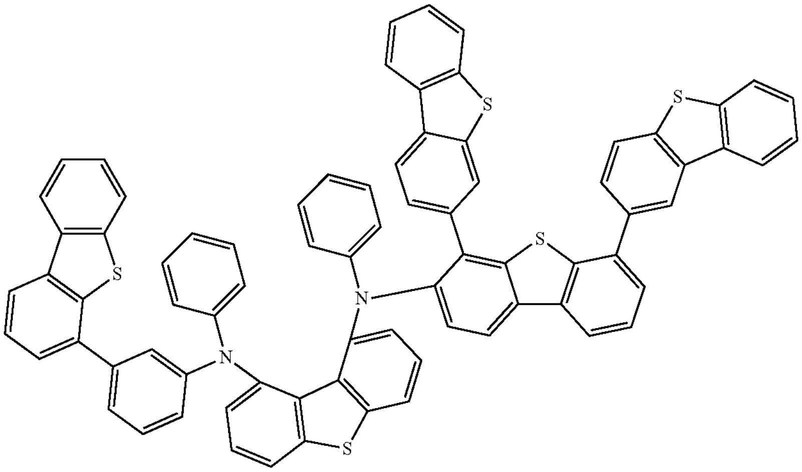
P-117
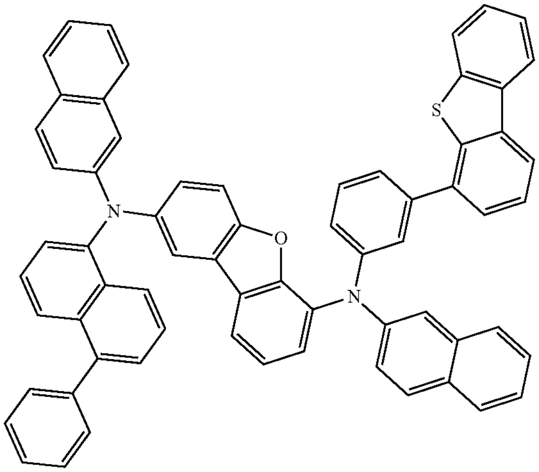
P-118
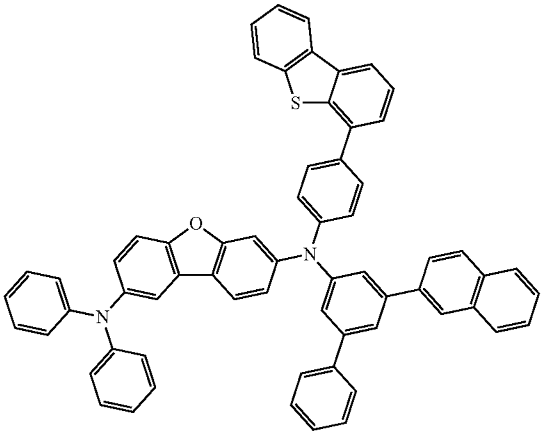
P-119
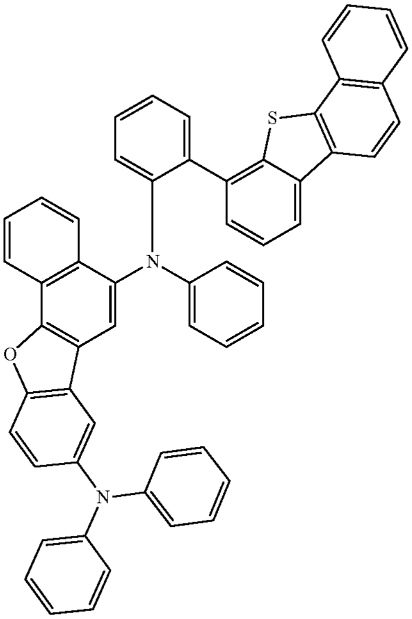
P-120
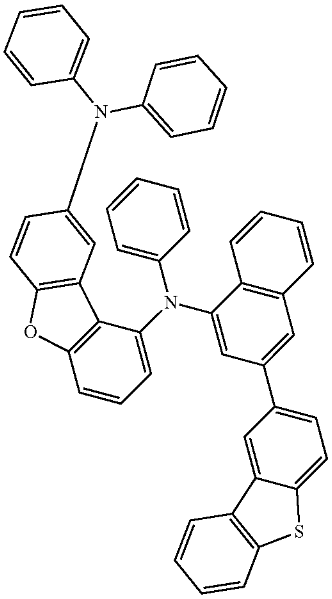

-continued
P-121
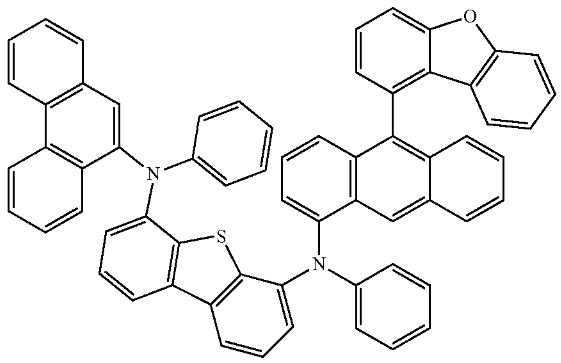
P-122
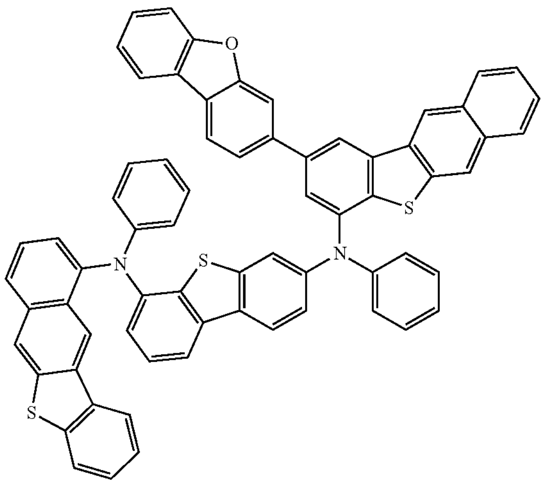
P-123
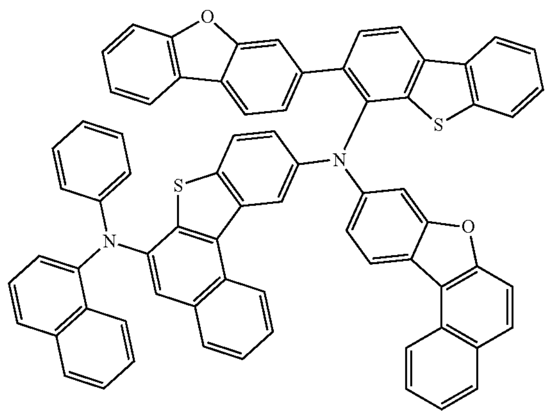
P-124
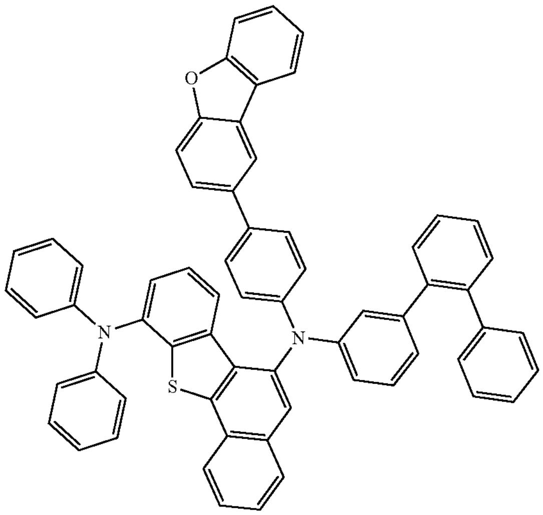
P-125
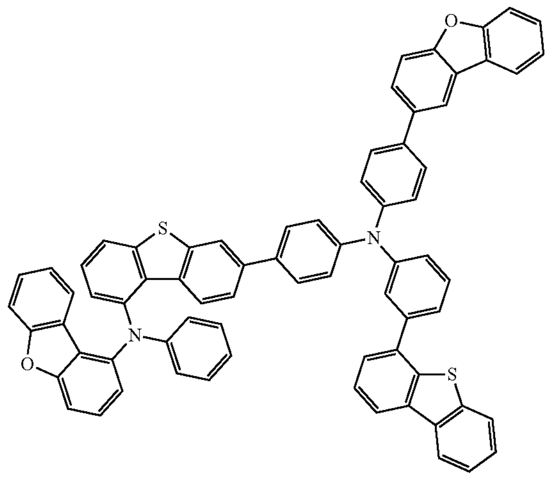
P-126
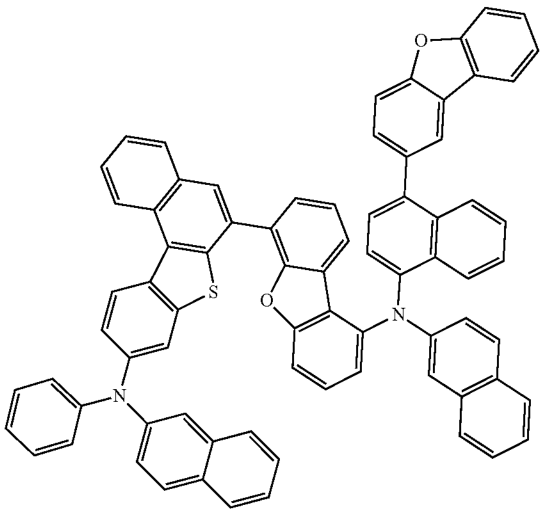

-continued
P-127
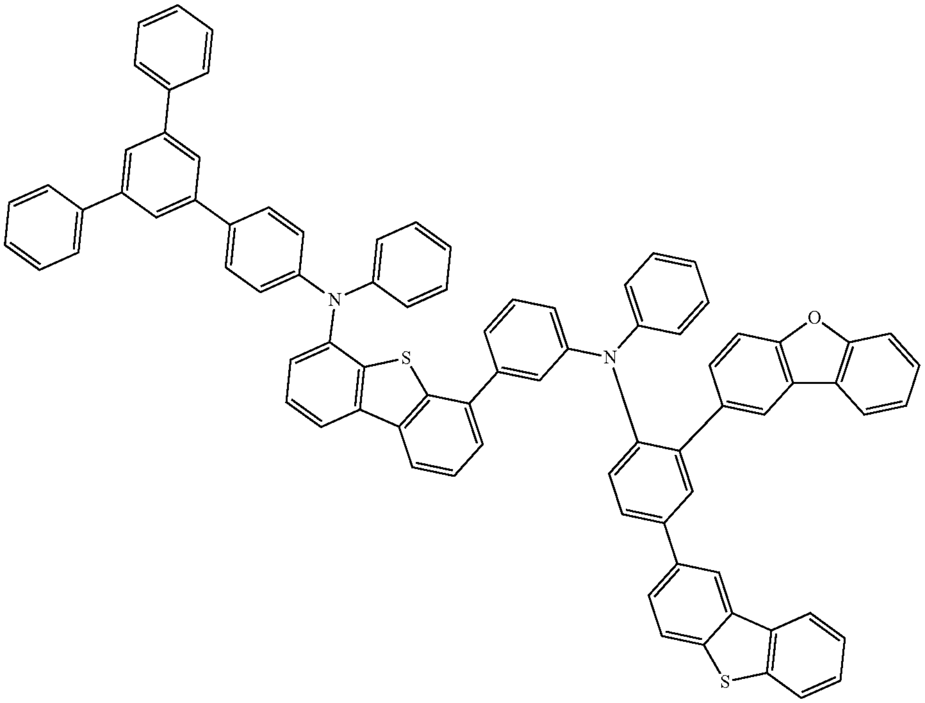
P-128
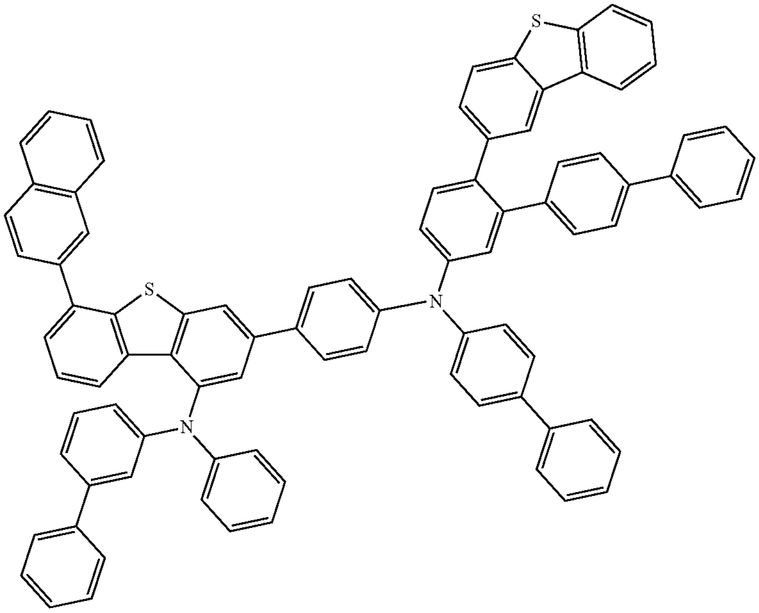

-continued
P-129
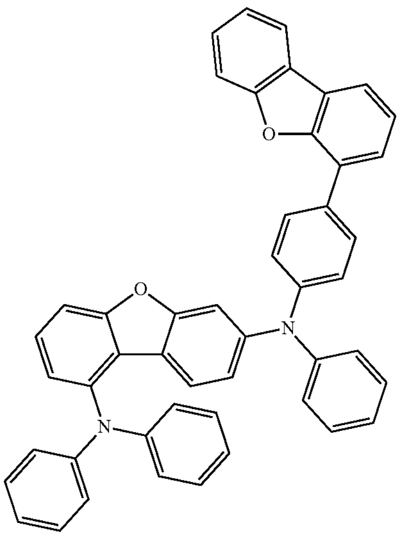
P-130
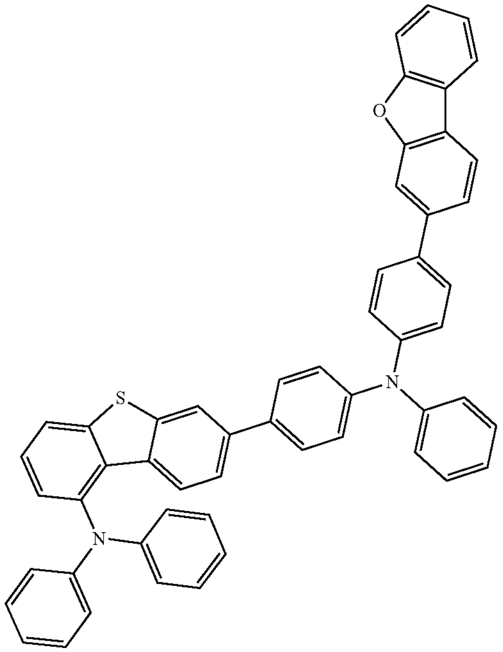
P-131
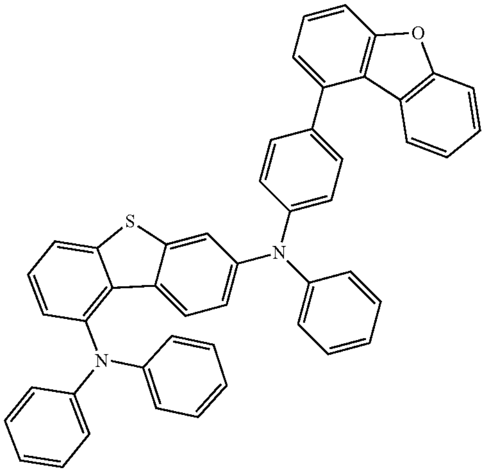
P-132
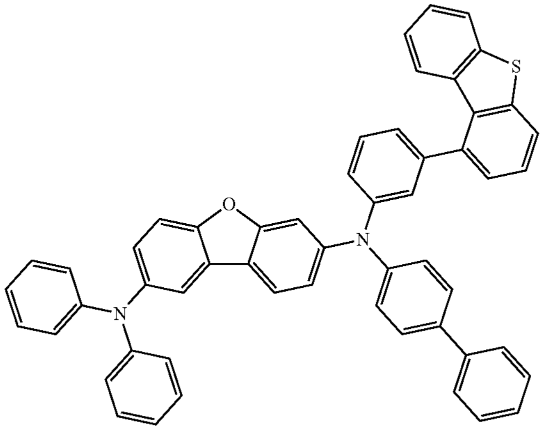

-continued
P-133
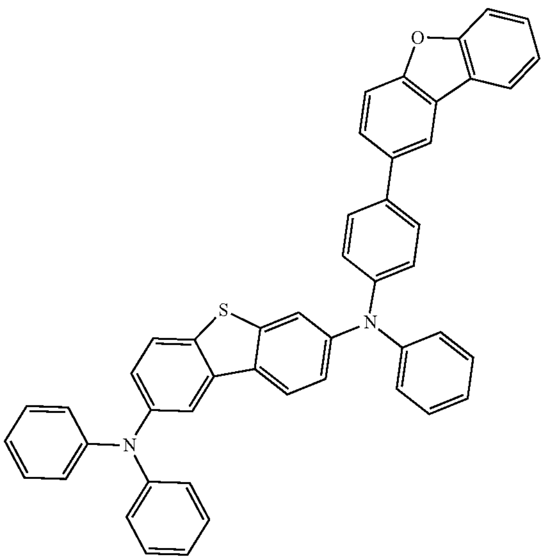
P-134
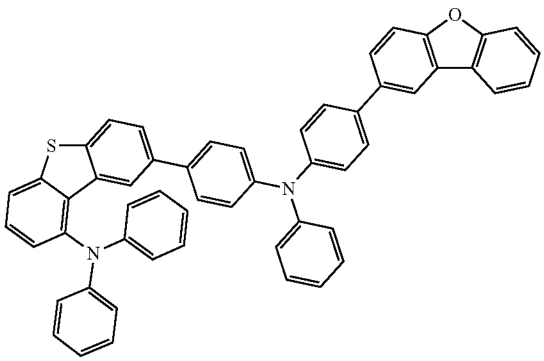
P-135
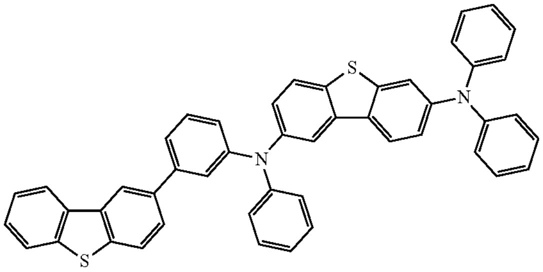
P-136
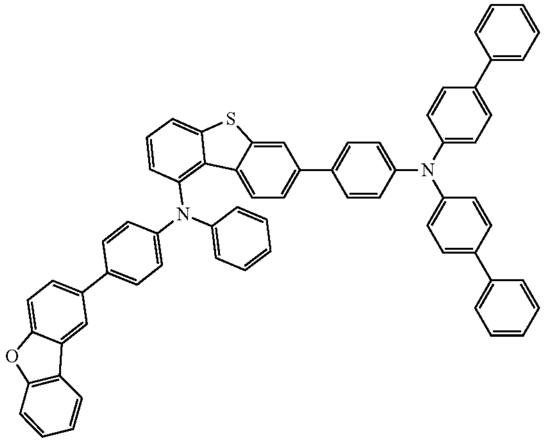
P-137
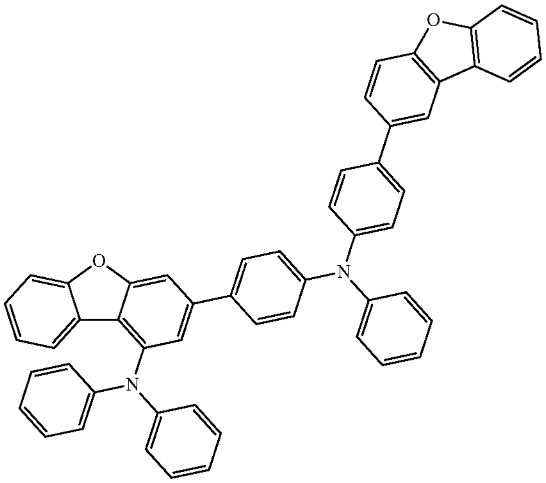
P-138
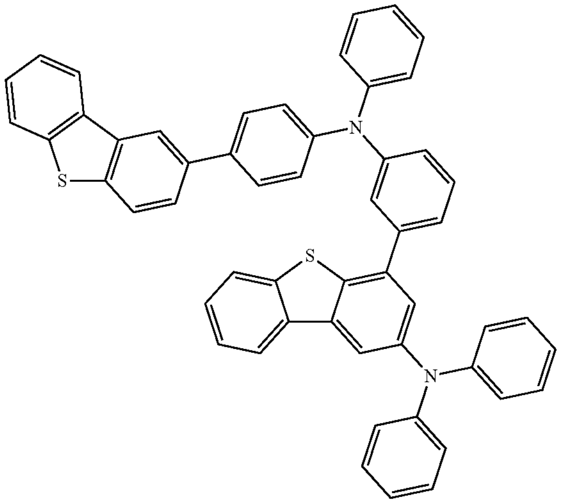

-continued
P-139
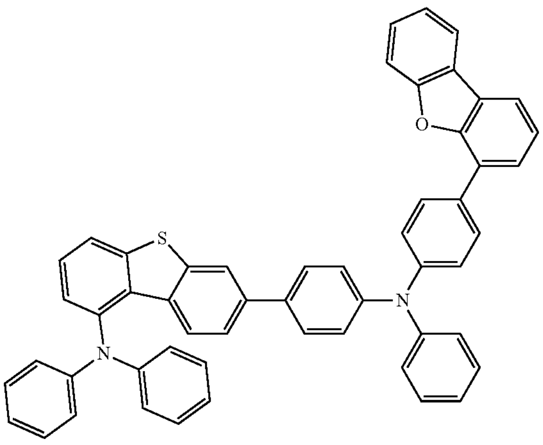
P-140
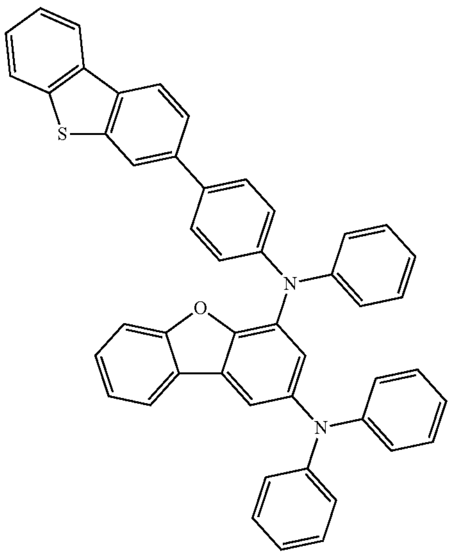
P-141
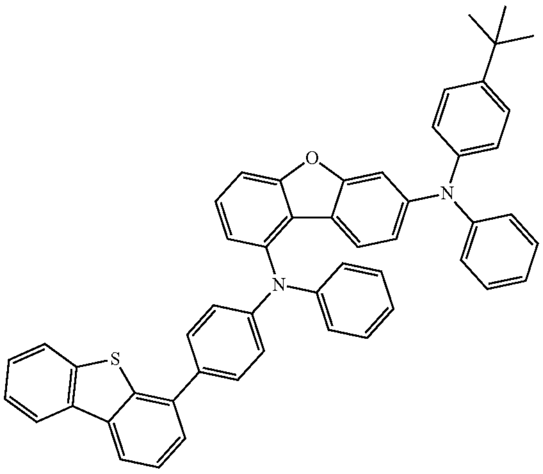
P-142
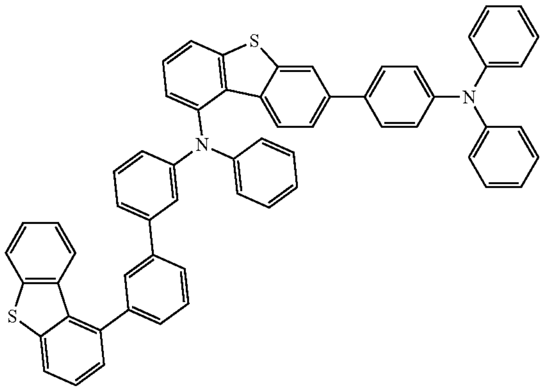
P-143
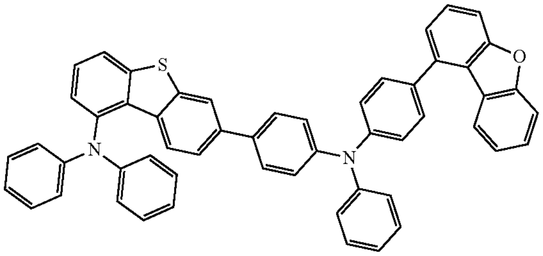
P-144
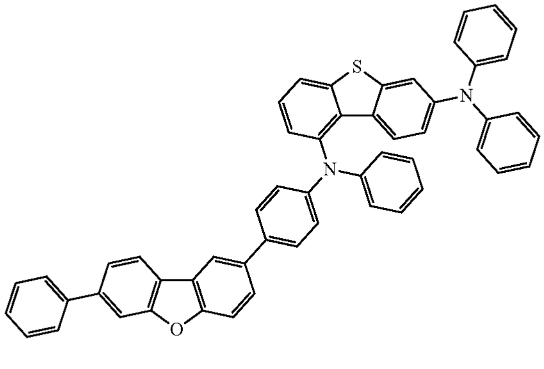

-continued
P-145
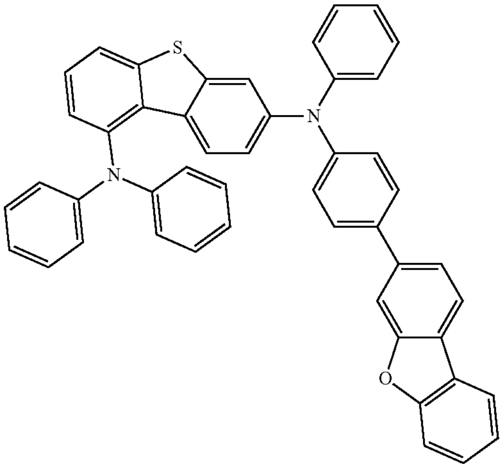
P-146
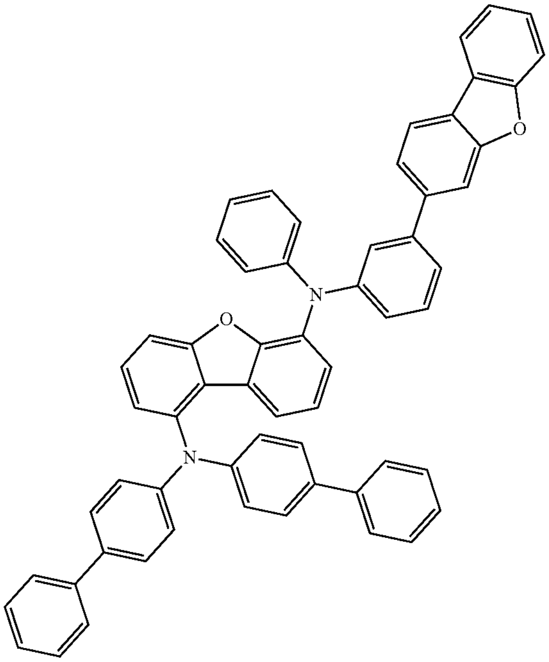
P-147
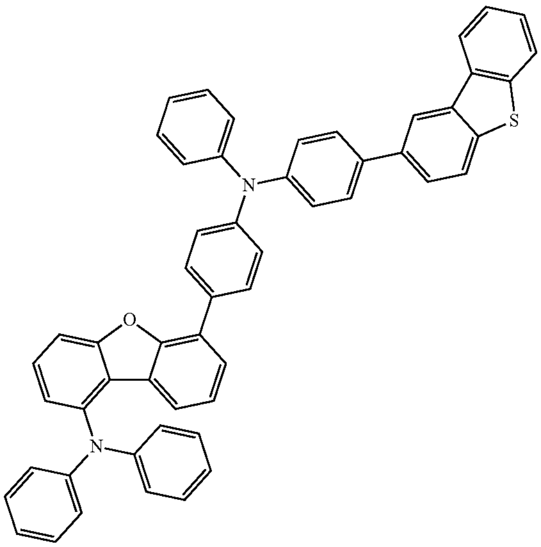
P-148
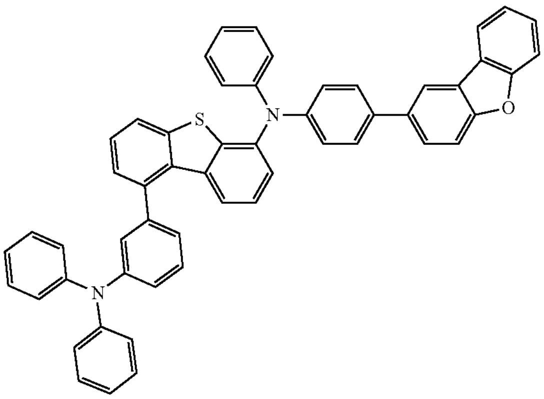

-continued

P-149

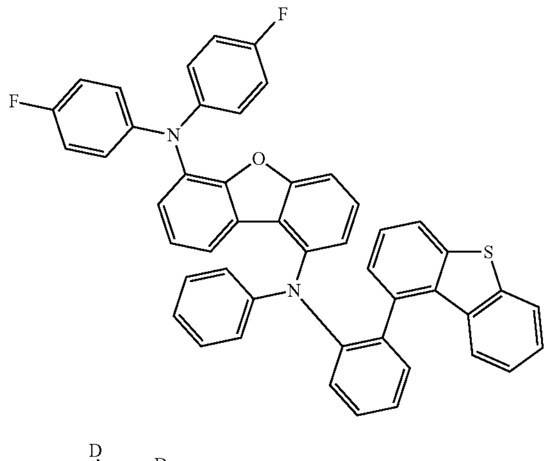

P-150

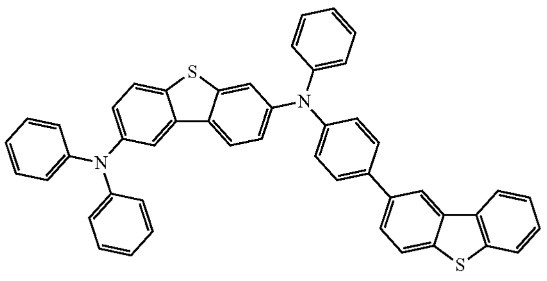

P-151

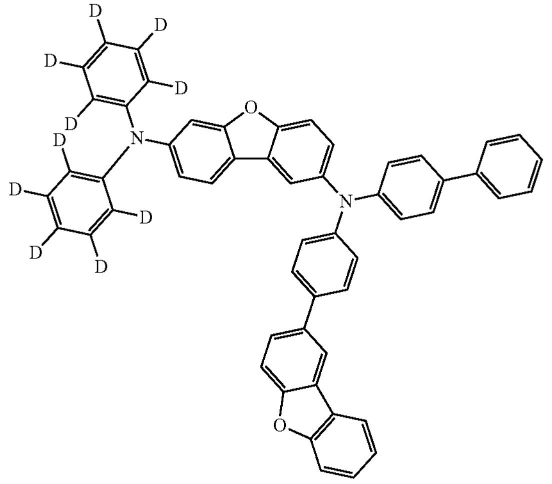

P-152

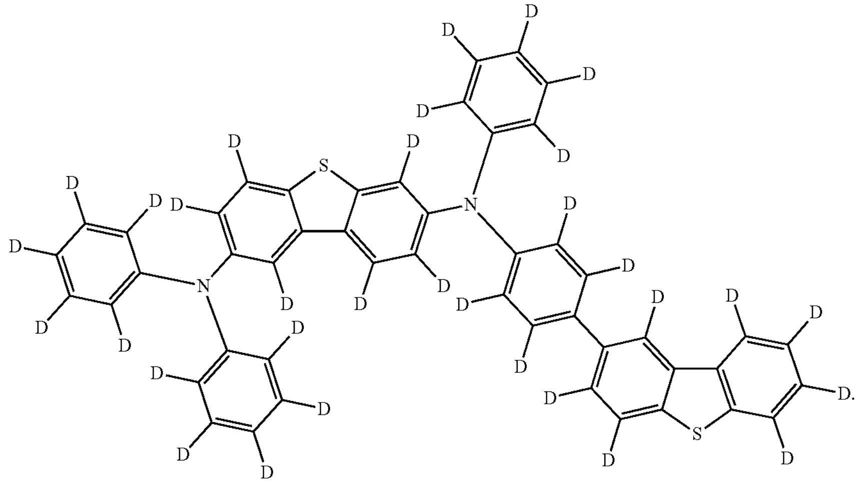

8. An organic electronic element comprising an anode, a cathode, and an organic material layer formed between the anode and the cathode, wherein the organic material layer comprises a single compound or 2 or more compounds represented by Formula 1 of claim 1.

9. The organic electronic element of claim 8, wherein the organic material layer comprises at least one of a hole injection layer, a hole transport layer, an emitting layer, an emitting-auxiliary layer, an electron transport auxiliary layer, an electron transport layer, and an electron injection layer.

10. The organic electronic element of claim 8, wherein the organic material layer is an emitting-auxiliary layer.

11. The organic electronic element of claim 8, wherein the organic material layer is a hole transport layer.

12. The organic electronic element of claim 8, further comprising a light efficiency enhancing layer formed on at least one surface opposite to the organic material layer among one surface of the anode and the cathode.

13. The organic electronic element of claim 8, wherein the organic material layer is a light efficiency enhancing layer.

14. The organic electronic element of claim 8, wherein the organic material layer comprises 2 or more stacks including a hole transport layer, an emitting layer, and an electron transport layer sequentially formed on the anode.

15. The organic electronic element of claim 14, wherein the organic material layer further comprises a charge generating layer formed between the 2 or more stacks.

16. An electronic device comprising: a display device including the organic electronic element of claim 8; and a control unit for driving the display device.

17. The organic electronic element of claim 16, wherein the organic electronic element is any one of an organic electroluminescent device (OLED), an organic solar cell, an organic photoreceptor (OPC), an organic transistor (organic TFT), and an element for monochromic or white illumination.

* * * * *